(12) United States Patent
Roh et al.

(10) Patent No.: US 11,931,118 B1
(45) Date of Patent: Mar. 19, 2024

(54) ROBOTIC SURGICAL SYSTEM FOR REMOTELY MONITORING SURGICAL ROBOTS

(71) Applicant: IX Innovation LLC, Seattle, WA (US)

(72) Inventors: Jeffrey Roh, Seattle, WA (US); Justin Esterberg, Mesa, AZ (US); John Cronin, Jericho, VT (US); Seth Cronin, Essex Junction, VT (US); Michael John Baker, Georgia, VT (US)

(73) Assignee: IX Innovation LLC, Seattle, WA (US)

( * ) Notice: Subject to any disclaimer, the term of this patent is extended or adjusted under 35 U.S.C. 154(b) by 0 days.

(21) Appl. No.: 18/321,990

(22) Filed: May 23, 2023

(51) Int. Cl.
  *A61B 34/00* (2016.01)
  *A61B 34/37* (2016.01)
  *B25J 13/06* (2006.01)

(52) U.S. Cl.
  CPC .............. *A61B 34/25* (2016.02); *A61B 34/37* (2016.02); *B25J 13/06* (2013.01)

(58) Field of Classification Search
  CPC ........... A61B 34/25; A61B 34/37; B25J 13/06
  USPC ............................................................ 606/1
  See application file for complete search history.

*Primary Examiner* — Aaron F Roane
(74) *Attorney, Agent, or Firm* — Perkins Coie LLP

(57) ABSTRACT

Methods, apparatuses, and systems for providing updates to a surgical robot in which a surgical robot receives a notification that there is an update available or detects a new hardware component that has been attached to the surgical robot. The surgical robot then determines if it is currently in use or is inactive and if inactive the surgical robot downloads the latest update. Additionally, the system provides a process of remote monitoring of telesurgical robots for safety and redundancy, in which the surgical robot collects data representing at least one assistance parameter of the surgical robot during a surgical procedure. The data is assessed, and it is determined if non-surgical assistance is required and connecting the medical professional to a technician to resolve the potential issue.

20 Claims, 32 Drawing Sheets

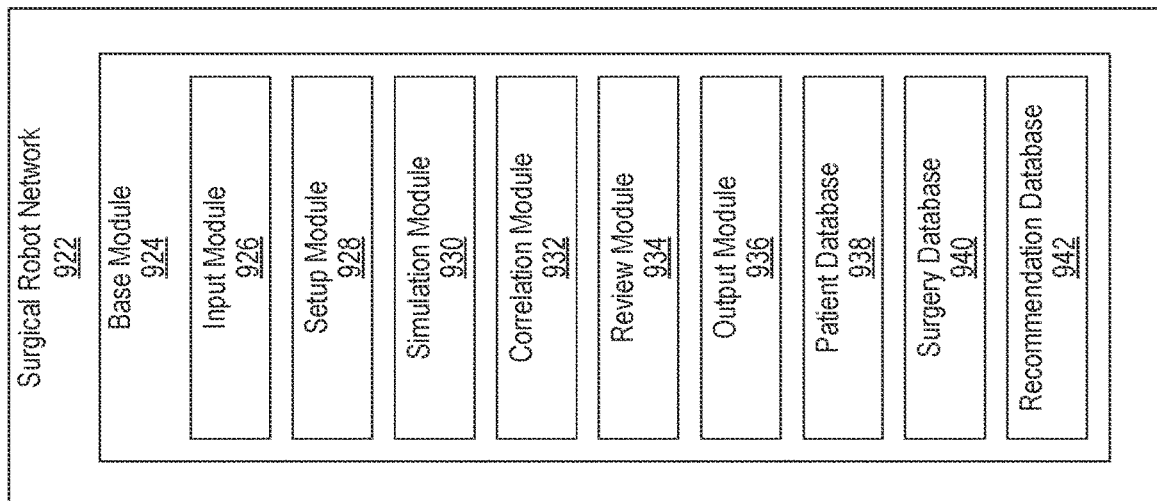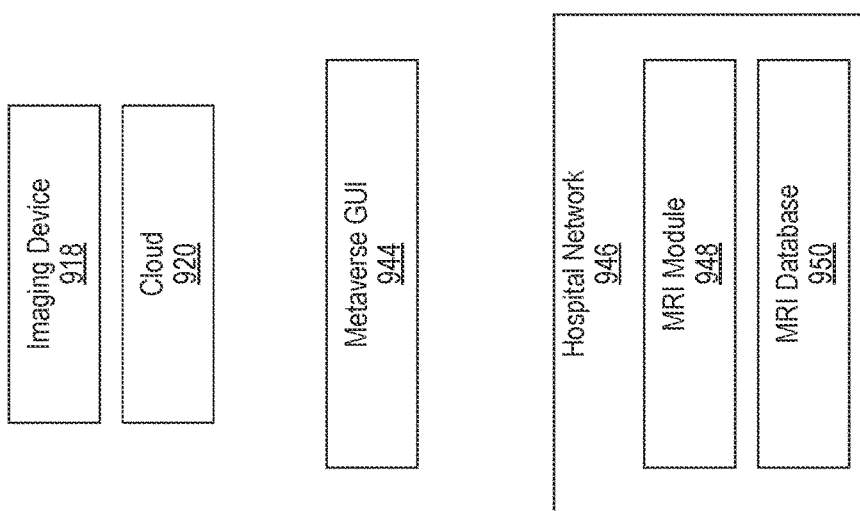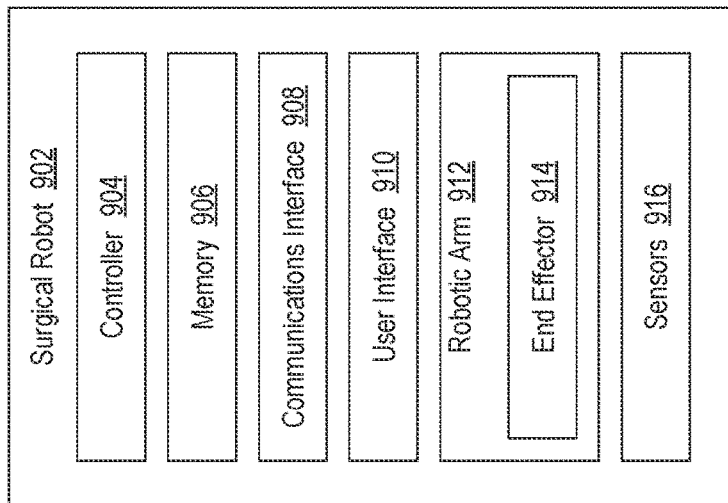
FIG. 9

| Date | Update ID | Version |
|---|---|---|
| 10/20/2022 | SP7896 | 10.003 |
| 10/17/2022 | EE5236 | 10.002 |
| 10/17/2022 | EEC5235 | 10.001 |
| 10/1/2022 | AP1594 | 9.065 |
| --- | --- | --- |
| --- | --- | --- |
| --- | --- | --- |

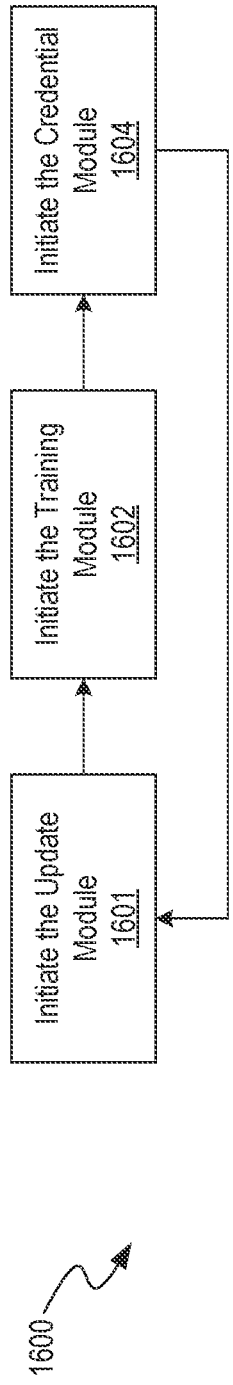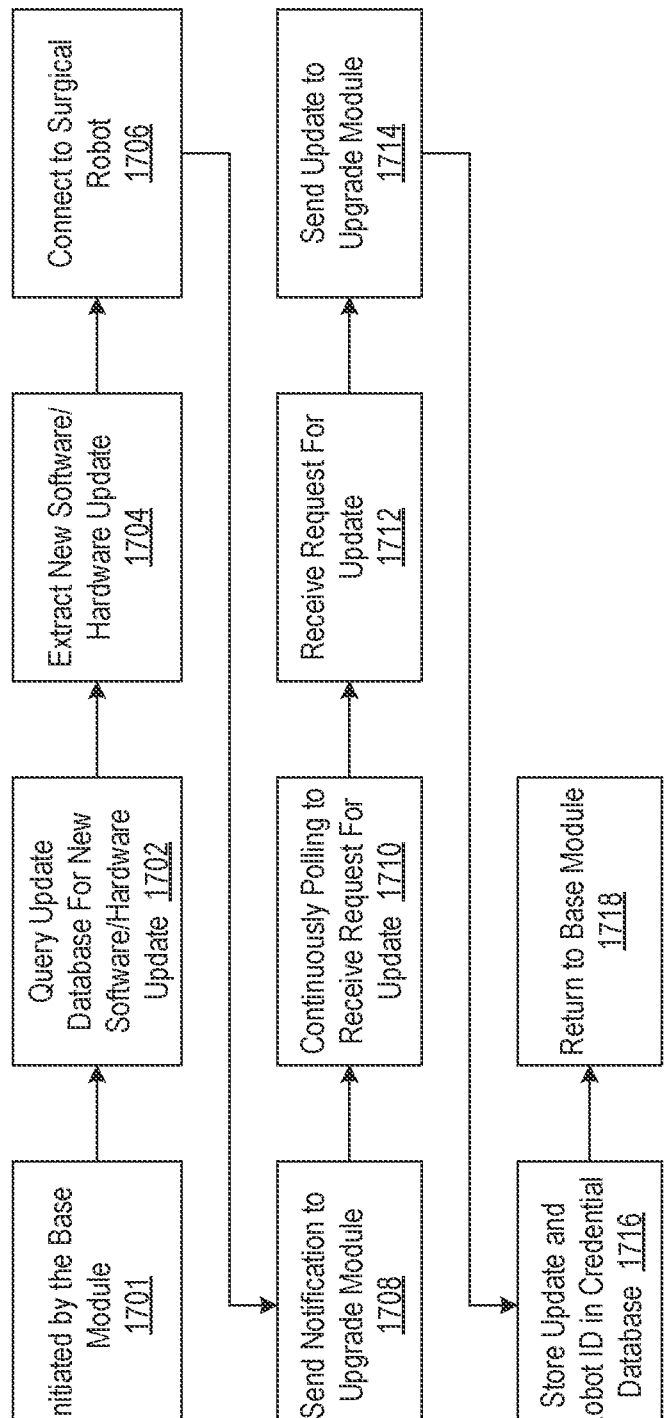

| Date | Update ID | Type | Characteristic | Version | Data File |
|---|---|---|---|---|---|
| 10/20/2022 | SP7896 | Software | Suture Pattern | 10.003 | 10.003.Data |
| 10/17/2022 | EE5236 | Hardware | End Effector | 10.002 | 10.002.Data |
| 10/17/2022 | EEC5235 | Software | End Effector Control | 10.001 | 10.001.Data |
| 10/1/2022 | AP1594 | Software | Anchor Placement | 9.065 | 9.065.Data |
| --- | --- | --- | --- | --- | --- |
| --- | --- | --- | --- | --- | --- |

*FIG. 20*

| Date | Update ID | Version | Medical Professional | Training | Certified |
|---|---|---|---|---|---|
| 10/20/2022 | SP7896 | 10.003 | John Smith | Complete | Yes |
| | | | Tim Johnson | Incomplete | No |
| | | | Betty Halls | Complete | Yes |
| | | | Lindsey Carter | Incomplete | No |
| --- | --- | --- | --- | --- | --- |
| 10/17/2022 | EE5236 | 10.002 | John Smith | Complete | Yes |
| | | | Tim Johnson | Complete | Yes |
| | | | Betty Halls | Complete | Yes |
| | | | Lindsey Carter | Complete | Yes |
| --- | --- | --- | --- | --- | --- |
| 10/17/2022 | EEC5235 | 10.001 | John Smith | Complete | Yes |
| | | | Tim Johnson | Complete | Yes |
| | | | Betty Halls | Complete | Yes |
| | | | Lindsey Carter | Complete | Yes |
| --- | --- | --- | --- | --- | --- |

FIG. 21

| Date | Time | Patient | Procedure | Surgeon | Emergency Surgeon | Medical Observers 1-N | Technician | Emergency Technician |
|---|---|---|---|---|---|---|---|---|
| 11/2/2022 | 7:00am | John Smith | Discectomy | Greg Johnson | Matt Rivers | Brad Street, Laura Gould | Betty Jenkins | Ronald Hall |
| 11/2/2022 | 9:00am | Tom Landry | Brostrom Gould Procedure | Mari Plank | Nate Obando | Bob Sutherland, Jen Olsen | Claire Smith | Eric Glennon |
| 11/2/2022 | 1:00pm | Bryce Jones | Knee Replacement | Joasia Slane | Sam Gil | Rob Park, Tom Chan | Ryan Donnelly | Victor O'Neil |
| --- | --- | --- | --- | --- | --- | --- | --- | --- |
| --- | --- | --- | --- | --- | --- | --- | --- | --- |

| Name | ID | Date | Start Time | Estimated End Time |
|---|---|---|---|---|
| Betty Jenkins | BJ123 | 11/2/2022 | 12:00pm | 3:00pm |
| Betty Jenkins | BJ123 | 11/2/2022 | 4:00pm | 7:00pm |
| Claire Smith | CS456 | 11/2/2022 | 7:00am | 10:00am |
| Claire Smith | CS456 | 11/2/2022 | 11:00am | 2:00pm |
| Claire Smith | RD789 | 11/2/2022 | 8:00am | 11:00am |
| Claire Smith | RD789 | 11/2/2022 | 12:00pm | 3:00pm |
| -- | -- | -- | -- | -- |
| -- | -- | -- | -- | -- |

*FIG. 29*

| Patient Name | Surgical Procedure | Participants | Participant Involvement | Surgical Robot Control | Robotic Arms | End Effectors | User Interface | Communication Interface | Controllers | Surgical Robot Code | Patient EHR | Imaging Devices | Procedure Updates |
|---|---|---|---|---|---|---|---|---|---|---|---|---|---|
| John Smith | Discectomy | Greg Johnson | Surgeon | Yes | Yes | Yes | Yes | Yes | No | No | Yes | Yes | No |
| | | Matt Rivers | Emergency Surgeon | Yes | Yes | Yes | Yes | Yes | No | No | Yes | Yes | No |
| | | Brad Street, Laura Gould | Medical Observers | No | No | No | No | No | No | No | No | Yes | Yes |
| | | Betty Jenkins | Technician | Yes | Yes | Yes | Yes | Yes | Yes | Yes | No | Yes | No |
| | | Ronald Hall | Emergency Technician | Yes | Yes | Yes | Yes | Yes | Yes | Yes | No | Yes | No |
| | | Susan Hall | Patient Wife | No | No | No | No | No | No | No | No | No | Yes |
| | | Vicki Johnson | Patient Mother | No | No | No | No | No | No | No | No | No | Yes |
| | | Joe Johnson | Patient Father | No | No | No | No | No | No | No | No | No | Yes |
| | | Greg Johnson Jr. | Patient Son | No | No | No | No | No | No | No | No | No | Yes |
| | | Ann Johnson | Patient Daughter | No | No | No | No | No | No | No | No | No | Yes |
| ... | ... | ... | ... | ... | ... | ... | ... | ... | ... | ... | ... | ... | ... |
| ... | ... | ... | ... | ... | ... | ... | ... | ... | ... | ... | ... | ... | ... |

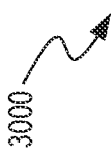

FIG. 30

ROBOTIC SURGICAL SYSTEM FOR REMOTELY MONITORING SURGICAL ROBOTS

TECHNICAL FIELD

The present disclosure is generally related to automated and robotic medical and surgical procedures and specifically to remotely monitoring of surgical robots for safety and providing updates to surgical robots.

BACKGROUND

More than 200 million surgeries are performed worldwide each year, and recent reports reveal that adverse event rates for surgical conditions remain unacceptably high, despite traditional patient safety initiatives. Adverse events resulting from surgical interventions can be related to errors occurring before or after the procedure, as well as technical surgical errors during the operation. For example, adverse events can occur due to (i) a breakdown in communication within and among the surgical team, care providers, patients, and their families; (ii) delays in diagnosis or failure to diagnose; and (iii) delays in treatment or failure to treat. The risk of complications during surgery can include anesthesia complications, hemorrhaging, high blood pressure, a rise or fall in body temperature, etc. Such adverse events can further occur due to medical errors, infections, underlying physical or health conditions of the patient, reactions to anesthetics or other drugs, etc. Conventional methods for preventing wrong-site, wrong-person, wrong-procedure errors, or retained foreign objects are typically based on communication between the patient, the surgeon(s), and other members of the health care team. However, conventional methods are typically insufficient to prevent surgical errors and adverse events during surgery.

BRIEF DESCRIPTION OF THE DRAWINGS

FIG. 9 illustrates a surgical metaverse system, according to an embodiment.

FIG. 14 is a table illustrating example data stored by a software database, in accordance with one or more embodiments.

FIG. 16 is a flow diagram illustrating an example process for a base module, in accordance with one or more embodiments.

FIG. 17 is a flow diagram illustrating an example process for an update module, in accordance with one or more embodiments.

FIG. 20 is a table illustrating example data stored by an update database, in accordance with one or more embodiments.

FIG. 21 is a table illustrating example data stored by a credential database, in accordance with one or more embodiments.

FIG. 28 is a table illustrating example data stored by a surgery database, in accordance with one or more embodiments.

FIG. 29 is a table illustrating example data stored by a tech database, in accordance with one or more embodiments.

FIG. 30 is a table illustrating example data stored by a access database, in accordance with one or more embodiments.

DETAILED DESCRIPTION

Figure 1:
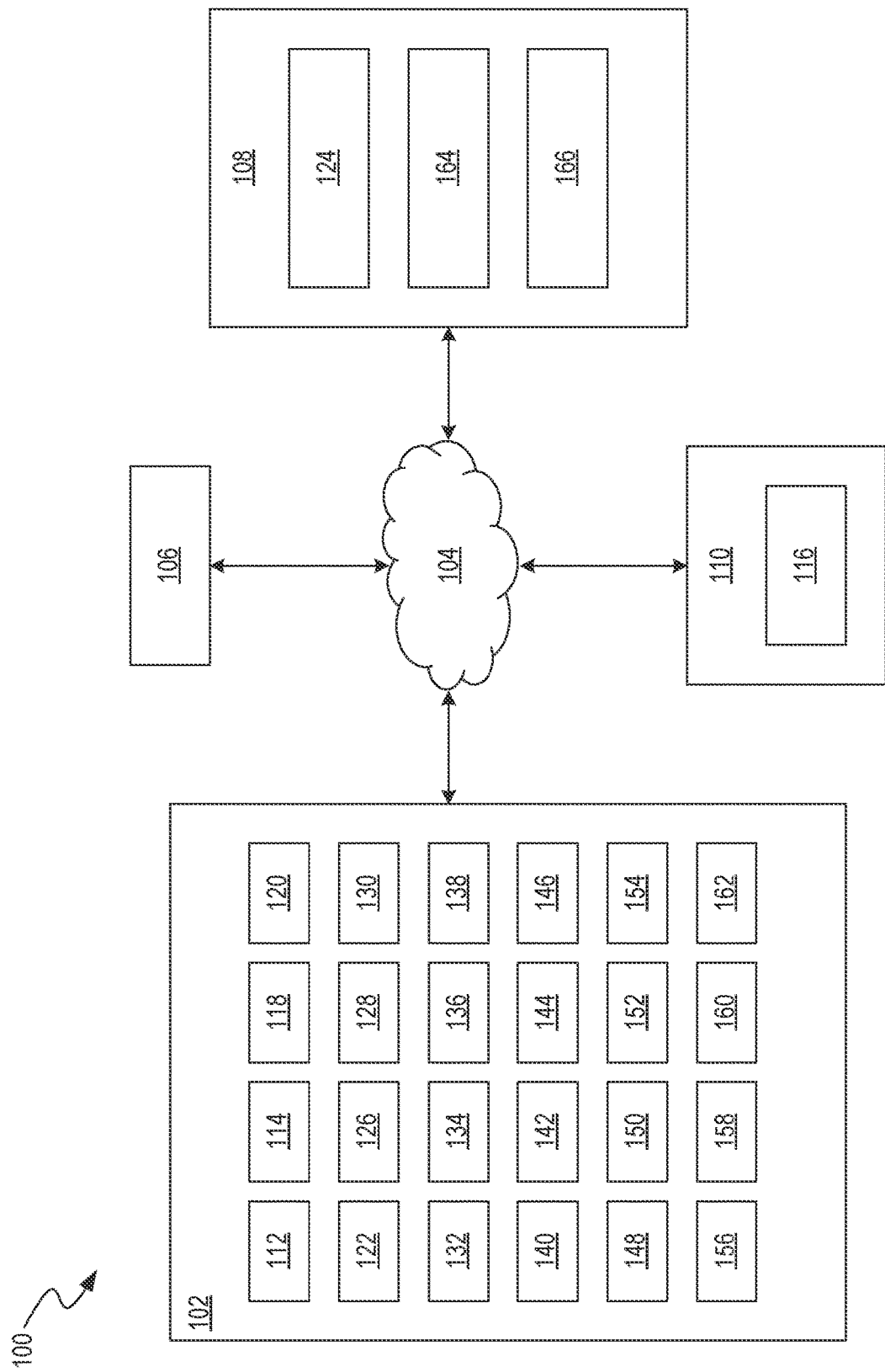
FIG. 1 is a block diagram illustrating an example surgical system, in accordance with one or more embodiments.

Embodiments of the present disclosure will be described more thoroughly from now on with reference to the accompanying drawings. Like numerals represent like elements throughout the several figures, and in which example embodiments are shown. However, embodiments of the claims can be embodied in many different forms and should not be construed as limited to the embodiments set forth herein. The examples set forth herein are non-limiting examples and are merely examples, among other possible examples. Throughout this specification, plural instances (e.g., "610") can implement components, operations, or structures (e.g., "610*a*") described as a single instance. Further, plural instances (e.g., "610") refer collectively to a set of components, operations, or structures (e.g., "610*a*") described as a single instance. The description of a single component (e.g., "610*a*") applies equally to a like-numbered component (e.g., "610*b*") unless indicated otherwise. These and other aspects, features, and implementations can be expressed as methods, apparatuses, systems, components, program products, means or steps for performing a function, and in other ways. These and other aspects, features, and implementations will become apparent from the following descriptions, including the claims.

The robotic surgical system can provide a process for providing one or more updates to a surgical robot. The surgical robot can receive a notification that there is an update available, detect a new hardware component that has been attached to the surgical robot, and/or determine an update is needed. The surgical robot system can determine when to receive and install the update. The surgical robot can determine if it is currently in use or is inactive, and if inactive the surgical robot downloads the latest update. When a medical professional begins a procedure with the surgical robot, the surgical robot receives a training status or certification status of the medical professional for the new update. If the medical professional is trained and/or certified, the medical professional may use the surgical robot with the latest update. If the medical professional is not trained and/or certified, the medical professional may use the surgical robot with a previous version or in some instances may be denied using the surgical robot. In some embodiments, the robotics surgical system can notify the medical professional that they are not trained and/or certified. The robotics surgical system can then perform training and/or certification to a medical professional. This allows the medical professional to decide whether to use a previous version or the updated version of the software. The robotic surgical system can also manage software, software modules, drivers (e.g., software drivers for hardware, sensors, surgical robots), or the like. For example, the robotic surgical system can install, remove, modify, or otherwise manage software.

In some embodiments, a surgical system can manage multiple versions of software for which medical professionals may be trained, certified, or the like. Robotics surgical system can also manage new software (e.g., a new software module to be installed, new device drivers, etc.), updates to software, or other software related activities for surgical robots, patient monitors, etc. The robotic surgical system can manage access to software selected for the medical professionals based on, for example, medical professional's training, certification (e.g., software certification, surgical robot certification, etc.). In some embodiments, tools, surgical robots, other components of a surgical robot may malfunction or other an adverse event. The robotic surgical system can determine whether a new software update is needed to address the adverse event. In some embodiments, the robotics surgical system can coordinate software installation, multiple updates, such as software installation or updates for the surgical robot and a hardware component that has been attached or will be attached to a surgical robot. This allows synchronization of software to improve performance. For example, a new hardware component installed on an end effector of surgical robot may require a particular movement of robotic arm. The surgical system can install software (e.g., new software or software update) to enable the surgical robot to perform that movement. The surgical system can perform software version pre-operative or intra-operative simulations to determine which version of software should be utilized in a procedure. This allows coordination between software for components used in a surgical procedure.

The software can be selected based on users. In some embodiments, the user can select the software to be used and/or the software selection can be linked to the profile of the user. In some embodiments, the surgical system selects software for which the user is trained and/or certified. If the surgical system does not have suitable software, the surgical system can retrieve software from a database for installation, thereby providing flexibility for different users. The software can be linked to the user profile such that the selected software is automatically used by the user. Software can be retrieved intra-operatively to enable the surgical system to perform unplanned steps, utilize new equipment, and/or provide the user with a newly available functionality and/or data in response to one or more unplanned adverse events. The surgical system can manage the software without input from the user to allow the user's attention to be focused on the surgical procedure rather than software management. The surgical system can determine whether to request user input based on an attention score threshold.

In some embodiments a medical professional or consultant can be located at a remote location. The robotics surgical system can provide real-time training to certify the remote user for participating in telesurgery. In some embodiments, the robotic surgical system can analyze surgical plans to determine the surgical steps to be performed. The robotic surgical system will then determine whether any software modifications are needed to perform the surgical plan. The robotics surgical system can also determine whether medical professionals are approved to perform or monitor the surgical procedure based on the software. The robotics surgical system can manage databases of software based on the user profile (e.g., certification status, training, etc.), surgical equipment, etc.

In some embodiments, the robotic surgical system provides remote monitoring and technician support for safety and redundancy. The surgical robot can collect data representing at least one assistance parameter of the surgical robot during a surgical procedure. The data is assessed, and it is determined if non-surgical assistance is required and connecting the medical professional to a technician to resolve a potential issue. The technician may test the data representing at least one assistance parameter to resolve the potential issue the medical professional may be experiencing. The technician can modify hardware, replace hardware, modify software, or the like. The robotic surgical system can automatically manage software based on the changes that were implemented by the technician.

In some embodiments, the robotic surgical system can determine whether new software or a software update can resolve the potential issue. For example, the robotic surgical system can determine that an update to a hardware component or the surgical robot itself can enable the surgical robot to resolve the potential issue. The robotic surgical system can then notify a remote server that the new software update is needed. When newly available software is received, the robotic surgical system can authenticate and then install the software via, for example, and over-the-air installation process, or other update or installation procedure. The newly available software can enable new functionality of the robotic surgical system. In some procedures, the robotic surgical system can automatically notify the technician when an adverse event occurs. This can reduce the response time to resolve to resolve potential issues. The robotic surgical system can generate recommended software modifications for review and approval by the technician prior to implementation.

A surgical implant refers to a medical device manufactured to replace a missing biological structure, support a damaged biological structure, or enhance an existing biological structure. Traditional surgical tools are primarily assistive devices to help surgeons by compensating for tremors, increasing the precision of movement, and providing access to the patient in a less invasive manner which would otherwise not be possible. However, traditional surgical tools are typically unable to perform critical surgical actions, instead relying on a surgeon to take the most significant actions. For example, when inserting a screw into a bone, a surgeon relies on human clinical judgement to determine whether the screw has been implanted completely or they are receiving an unacceptable amount of resistance where continuing may risk harming the patient. Traditional methods therefore result in a wide range of variability among surgeons.

Moreover, surgeons require a significant amount of training in addition to experience before becoming proficient, and often require a similar level of dedication for each type of procedure they master. As such, generalized surgeons are rare and some procedures only have a small handful of people worldwide capable of performing them due to the rarity of some procedures.

In some embodiments, a method performed by a surgical system includes detecting at least one error in an operation of a surgical robot. The error can include component malfunction (e.g., end effector malfunction, robotic arm malfunction, controller malfunction, etc.), operational data varying from target data by a threshold error amount, etc. In response to detecting the at least one error, the surgical system can determine one or more components of the surgical robot associated with the at least one error based on operational data of the surgical robot. The surgical system can select at least one technician to resolve the at least one error based on the one or more components. In some embodiments, the technician can be selected based on which component or equipment malfunctioned, whether software contributed to the error, or the like. For example, the technician can modify effectors or tools of the surgical system.

The surgical system can send a notification to a device associated with the technician. The notification can provide access to a communication channel to the surgical robot to allow the at least one technician to remotely evaluate and/or modify the surgical system. In some embodiments, the surgical system or surgical team can receive, a resolution notification that the at least one error was resolved from the technician. In response to receiving the resolution notification, the surgical system can proceed with the surgical procedure. The surgical system can send additional notifications to consultants or healthcare providers throughout the process.

The embodiments disclosed herein describe methods, apparatuses, and systems for robotic insertion of surgical implants. In some embodiments, by one or more imaging devices of a surgical system image a patient's body for inserting a surgical implant in the patient's body. The surgical implant includes at least one surgical implant component. One or more processors of the surgical system generate a virtual model of the patient's body. The virtual model represents at least an implantation site for the surgical implant. The one or more processors generate an implantation plan based on the virtual model. The implantation plan includes insertion parameters for controlling a surgical robot of the surgical system. The one or more processors modify the insertion parameters based on a comparison of the insertion parameters to stored insertion parameters retrieved from a surgical procedure database using a regression model. The surgical robot inserts the at least one surgical implant component in the patient's body in accordance with the insertion parameters.

This specification also describes extended reality (XR) methods, apparatuses, and systems for robotic medicine, including monitoring of telesurgery robotic medicine. Robotic surgical system can manage software (e.g., new software, software updates, patches, software modules, operating systems, etc.) for extended reality devices. In embodiments, a digital anatomical model is obtained representing the anatomical features of a patient. An XR surgical simulation environment is generated that includes the digital anatomical model. The digital anatomical model is viewable by at least one user using an augmented-reality (AR) device. The XR surgical simulation environment is configured to enable the at least one user to virtually perform one or more surgical steps on the digital anatomical model. Anatomical mapping information is received from the at least one user via the AR device. The robotic surgical system can select and use anatomical mapping software selected based on, for example, the surgical procedure, the user's expertise, usage or training with the extended-reality device, certification of the user, and/or user-specific settings, such as user-selected extended-reality environment settings, available extended-reality input devices, etc. Confidence-score AR mapping is performed to meet a confidence threshold for the one or more surgical steps to be performed on the anatomy of the patient. A portion of the anatomical mapping information for the AR mapping to the anatomy is selected. The selected anatomical mapping information is mapped to the anatomical features of the patient. Via the AR device, an AR environment is displayed to the at least one user. The AR environment includes the mapping of the selected anatomical mapping information to the anatomical features. The AR environment, mappings, and other features can, for example, added, removed, and/or modified via software updates. This allows extended reality to implement newly available information and functionality.

The XR systems disclosed include representative forms such as augmented reality (AR), mixed reality (MR), virtual reality (VR), and the areas interpolated among them. The levels of virtuality range from partially sensory inputs to immersive virtuality, also called VR. In embodiments, any of MR, VR, AR, or a combination thereof is used. In embodiments, one or more images and sensor data for a patient are obtained using one or more sensors. An XR environment is generated, associating one or more virtual models of one or more surgical tools and the surgical robot with the one or more images and the sensor data. The XR environment comprises a 3D digital twin of the anatomy of the patient for performing a virtual simulation of the surgical procedure. Surgical actions performed by a user on the digital twin using the XR environment are identified. The user is typically a medical professional, e.g., a surgeon, a nurse, a surgeon's assistant, or a doctor.

In embodiments, a wearable XR device can be used locally in the surgery room or remotely for telesurgery. The wearable XR device can perform operations to update ocular information for a surgeon's eye by presenting stimuli at field locations of a visual field of the eye. The wearable device obtains spatial information indicating a position, orientation, or other spatial information of a set of electronic displays relative to the wearable device. Some embodiments include instructions to test an operating room location and determine whether the surgeon's eye can see stimuli presented at the operating room location. After selecting an operating room location, a wearable device or a computer connected to the wearable device uses the obtained spatial information to select an electronic display to present a first stimulus at a display location mapped to the field location. Either at the same time or at a different time, the wearable device presents a second stimulus on a display of the wearable device, where the display includes a waveguide or another type of display to present the second stimulus to the surgeon. During or after the presentation of the stimuli, the wearable device collects eye-related characteristics or other feedback information with an eye-tracking sensor or other types of sensors.

In some embodiments, a head-mounted display (HMD) device measures eye responses during a dark adaptation test or other tests that involve exposing an eye to different stimuli. Measured physiological changes may be paired with user-provided inputs that indicate when a user has detected a target stimulus.

In embodiments, medical imaging is performed using different wavelengths of electromagnetic energy, ultrasounds, magnetic resonance, etc. The different wavelengths when directed towards a subject, such as bone tissue, soft tissue, or any other subject or substance, image different types of tissues with varying depths of penetration. For example, when visible light of a predefined wavelength is directed at bone tissue, a part of the incident light can be absorbed by the bone tissue. As a result, the intensity of the reflected/refracted light is less than that of the incident light. The decrease in the intensity of the incident light can be measured and used to generate an image. In embodiments, different medical devices having capabilities including, but not limited to, X-ray imaging, magnetic resonance imaging (MRI), ultrasound, angiography, or computed tomography (CT) are used. In embodiments, omni-tomographic imaging or grand fusion imaging, such as large-scale fusion of simultaneous data acquisition from multiple imaging modalities (e.g., CT, MRI, positron emission tomography (PET), SPECT, USG, or optical imaging), is used. Composite images, including image data from multiple modalities, are sometimes referred to as "multi-modality images" or "multiple-modality images" herein.

In some embodiments, one or more computer processors of a surgical system obtain a digital anatomical model representing anatomical features of a patient's body and an implantation site for inserting a surgical implant in the patient's body. The one or more computer processors generate an extended-reality (XR) surgical simulation environment that includes the digital anatomical model. The XR surgical simulation environment is configured to enable at least one user to simulate inserting the surgical implant using the digital anatomical model. The one or more computer processors generate an implantation plan based on simulating inserting the surgical implant in the XR surgical simulation environment. The one or more computer processors cause the surgical robot to insert the surgical implant in the patient's body in accordance with the implantation plan.

In some implementations, surgical workflow is generated for a surgical robot. The surgical workflow comprises workflow objects for the surgical procedure based on the surgical actions. The surgical workflow is adjusted based on a comparison of the surgical workflow to stored historical workflows. The surgical robot is configured with the adjusted workflow comprising the workflow objects and information describing the surgical actions. The surgical robot performs the surgical actions on the patient using the adjusted workflow.

In some embodiments, a surgical robot receives user inputs, workflow objects, and data files containing surgical actions for robotic movements from a surgery network. Information describing surgical tools required for performing the robotic arthroscopic surgery are displayed on a user interface for the surgical tools to be enabled or disabled. Information describing the robotic arthroscopic surgical steps are displayed on the user interface in a sequence to enable execution of the data files containing the robotic movements. The robotic movements are used to perform surgical steps or assist a surgeon in performing surgical steps.

In embodiments, arthroscopy (also called arthroscopic or keyhole surgery) is performed. Arthroscopy is a minimally invasive surgical procedure performed on a joint in which an examination and sometimes treatment of damage is performed using an arthroscope, which is an endoscope that is inserted into the joint through a small incision. For example, arthroscopic procedures can be performed during anterior cruciate ligament (ACL) reconstruction. The surgical instruments used by the embodiments disclosed herein are smaller than traditional instruments. A surgeon can view the joint area on a video monitor, and can direct a robot to diagnose or repair torn joint tissue, such as ligaments. The arthroscopic embodiments disclosed herein can be used for the knee, shoulder, elbow, wrist, ankle, foot, and hip.

The embodiments disclosed herein describe methods, apparatuses, and systems for performing robotic joint arthroscopic surgery. The disclosed systems use a surgical robot to perform robotic joint arthroscopic surgery for the lateral extensor digitorum longus (EDL) tendon portion of the anatomy. The disclosed systems enable a surgeon or physician to perform a virtual surgical procedure in a virtual environment, storing robotic movements, workflow objects, user inputs, or a description of tools used. The surgical robot filters the stored data to determine a surgical workflow from the stored data. The surgical robot displays information describing a surgical step in the surgical workflow, enabling the surgeon or physician to optionally adjust the surgical workflow. The surgical robot stores the optional adjustments and performs the surgical procedure on a patient by executing surgical actions of the surgical workflow.

In embodiments, the disclosed systems use a surgical robot network that receives medical images of a patient and generates a three-dimensional (3D) rendering of the various medical images. A surgeon or physician is enabled to select workflow objects (such as various tools). The workflow objects can be selected in a sequence for performing actions on the 3D rendering. Data related to the workflow objects and actions in relation to the 3D rendering are stored. The surgeon or physician is enabled to select and perform various threading techniques and input calculations of the actions performed. The user inputs, workflow objects, and actions with respect to the 3D rendering are sent to a surgical robot for performing robotic joint arthroscopic surgery.

In embodiments, a robotic surgical system uses machine learning (ML) to provide recommendations and methods for automated robotic ankle arthroscopic surgery. Historical patient data is filtered to match particular parameters of a patient. The parameters are correlated to the patient. A robotic surgical system or a surgeon reviews the historical patient data to select or adjust the historical patient data to generate a surgical workflow for a surgical robot for performing the robotic arthroscopic surgery.

In some embodiments, a computer-implemented method for performing a robotic arthroscopic surgical procedure includes extracting computer instructions to be executed by a surgical robot from a surgical database. The computer instructions are for performing the robotic arthroscopic surgical procedure. Images of an anatomy of a patient are obtained using an imaging sensor of the surgical robot for performing the robotic arthroscopic surgical procedure based on the computer instructions. A lacerated tendon of the patient is identified within the anatomy using the images. The robotic arthroscopic surgical procedure is for repairing the lacerated tendon.

The surgical robot performs the robotic arthroscopic surgical procedure based on the computer instructions. One or more end effectors of the surgical robot secure a first side of the lacerated tendon. The one or more end effectors secure a second side of the lacerated tendon. A surgical knife coupled to the one or more end effectors cuts lacerated ends of the tendon to remove frayed material from the lacerated ends. The one or more end effectors suture the lacerated ends to repair the tendon.

In some embodiments, the disclosed systems can perform an arthroscopic surgical procedure on a joint of a patient. The system can acquire data (e.g., user input, patient data, etc.) from user interfaces and storage devices. An ML algorithm can analyze the patient data to determine one or more ligament-attachment joint stabilization steps for the joint. The system can generate a robotic-enabled surgical plan for the joint based on the user input and the one or more ligament-attachment joint stabilization steps. In some implementations, the robotic-enabled surgical plan includes a sequence of surgical steps with corresponding surgical tools for attaching one or more connectors to at least one ligament of the joint and another structure of the patient to promote stabilization of the joint. A graphical user interface (GUI) can display the robotic-enabled surgical plan for intraoperative viewing by a user (e.g., healthcare provider) while the robotic surgical system robotically operates on the patient. The system can receive, from the user, intraoperative user input associated with one or more of the surgical steps of the robotic-enabled surgical plan. The system determines information to be displayed, via the GUI, based on the received intraoperative user input while controlling one or more of the tools operated by the robotic surgical system according to a selection.

The advantages and benefits of the methods, systems, and apparatuses disclosed herein include compatibility with best practice guidelines for performing surgery in an operating room, e.g., from regulatory bodies and professional standards organizations such as the Association for Surgical Technologists. The robotic surgical systems disclosed can use multiple transducers and other measurement instrumentation to monitor the insertion of a screw with a higher degree of precision that is beyond the capabilities of a surgeon. Further, the robotic surgical system disclosed is not overwhelmed by receiving multiple measurement readings whereas a surgeon having to monitor multiple readings, such as axial force, tool speed, etc., while inserting a screw is likely to be overwhelmed or distracted. The robotic surgical system disclosed can automates steps of surgical procedures to compensate for a lack of a surgeon's experience with a specific procedure and make surgery more accessible. Moreover, the automated methods for inserting surgical implant components in a patient facilitate more precise placement of implant hardware while reducing opportunities for human error. The disclosed automation methods can serve as a prerequisite for achieving remote surgery capabilities where a surgeon may not be present in an operating room with a patient. Further benefits include improved control of insertion parameters such as preventing too much force from being used that can cause complications during an insertion procedure.

The robotic surgery technologies disclosed further offer valuable enhancements to medical or surgical processes through improved precision, stability, and dexterity. The disclosed methods relieve medical personnel from routine tasks and make medical procedures safer and less costly for patients. The embodiments disclosed enable performing more accurate surgery in more minute locations on or within the human body. The embodiments also and address the use of dangerous substances. The adoption of robotic systems, according to the embodiments disclosed herein, provides several additional benefits, including efficiency and speed improvements, lower costs, and higher accuracy. The equipment tracking system integrated into the disclosed embodiments offers flexibility and other advantages, such as requiring no line-of-sight, reading multiple radio frequency identification (RFID) objects at once, and scanning at a distance. The advantages offered by the surgical tower according to the embodiments disclosed herein are smaller incisions, less pain, lower risk of infection, shorter hospital stays, quicker recovery time, less scarring, and reduced blood loss.

The imaging systems disclosed use computer networks, the Internet, intranets, and supporting technologies to implement a cost-effective technology to collect, transmit, store, analyze, and use imaging information in electronic formats. As a result, surgical robots can use the embodiments to collect and analyze vast amounts of information, resulting in early diagnoses. The disclosed methods reduce the amount of noise and increase the resolution, replicability, efficiency, and accuracy in collecting and analyzing information. Further, the embodiments disclosed herein enable meta-analyses for more-elaborate diagnostic procedures and reduce the need for repetitive invasive diagnostic testing. In addition, the disclosed systems enable continuous monitoring and analysis of the health of the patient in order to provide real-time assistance to a surgical robot or surgeon during a surgical procedure.

The disclosed systems provide varied options for medical professionals to practice and learn how to perform certain procedures in a virtual environment. The disclosed methods enable a surgeon to practice a procedure in a virtual environment and use the same workflow in the actual operating room. The disclosed apparatuses enable practice scenarios in which surgeons can use historical data to improve surgeries or adjust a surgical workflow to improve the procedure. The embodiments herein enable medical professionals to simulate and practice in a virtual environment that creates a surgical workflow to, for example, be trained, complete certification requirements, or practice surgical procedures. The systems can store and run different software for training, certificate, or practice. In some embodiments, the system can determine surgical equipment to use in a procedure. The system can then retrieve or run software for providing a virtual environment in which the user can simulate and practice surgical procedures steps or procedure. If the system does not have suitable software, it can retrieve additional software and install it for performing the simulation and/or practice.

The technologies disclosed provide benefits over traditional open surgery in that a joint does not have to be opened up fully. For knee arthroscopy using the robotic methods disclosed, only two small incisions are made, one for the arthroscope and one for the surgical instruments to be used in the knee cavity. The embodiments reduce recovery time and can increase the rate of success due to less trauma to the connective tissue. The robotic apparatus disclosed results in shorter recovery times with less scarring, because of the smaller incisions. The disclosed methods for robotic surgery use historical data from surgical robots to generate more precise recommendations for patients compared to traditional methods. The disclosed surgical apparatuses perform an ML system using historical data from surgical robots to generate the recommendations. The disclosed systems provide workflows for a surgeon or physician to review and adjust surgical procedures based on historical patient data to generate surgical procedures for patients using an interactive user interface. The embodiments disclosed herein thus provide improved ankle surgery compared to conventional surgery.

Moreover, the disclosed apparatuses provide computer-aided design (CAD) ability to surgeons and physicians to enable them to manipulate a 3D rendering of a region of a patient's anatomy to virtually perform surgery. The disclosed methods provide a workflow process based on CAD software to improve chances of success of detailed steps of a surgical procedure. The disclosed systems enable surgeons to perform virtual surgeries using a robotic system to generate optimal results for a patient, especially for robotic joint arthroscopic surgery for the lateral EDL tendon area of the anatomy. Further, the robotic joint repair surgery technologies disclosed benefit ligament and tendon repair surgery. The surgical robot disclosed performs skillful removal of tissues, precise placement of sutures and bone anchors, and delicate tensioning of the sutures.

Further, the embodiments provide automated and more efficient systems for using multiple imaging modalities, especially those using different wavelengths of electromagnetic waves. Quicker diagnosis of patients is achieved compared to traditional methods via simultaneous or sequential imaging. The automated methods of aligning images taken using different imaging modalities disclosed provided improved analysis of the images to identify medical conditions. In addition, the advantages of the convolutional neural network (CNN) used for ML in the disclosed embodiments include the obviation of feature extraction and the use of shared weight in convolutional layers, which means that the same filter (weights bank) is used for each node in the layer; this both reduces memory footprint and improves performance.

The surgical systems can provide solutions to one or more existing issues. For example, presently an issue with surgical robots or medical robots is that the software and hardware that is installed when they are manufactured can get outdated and it is difficult to keep up with new and innovative medical procedures. Also, it is difficult to constantly track the medical professionals that are trained with certain features, functions, and capabilities of the surgical robots, extended reality-devices, and other equipment since there are newer models that provide different capabilities. Lastly, there is an issue with providing surgical robots software or hardware updates and tracking which medical professionals are up to date on the training needed to fully use the new capabilities of the surgical robot. The importance of having a validated training curriculum not only stems from the responsibility towards patient safety, but also from the ensuing issues with credentialing and associated liability. Proficiency-based training curricula that comprehensively address the skills necessary to perform robotic operations have shown construct and content validity as well as feasibility. Unfortunately, multiple versions of such a training curriculum are often provided to individual, a center, or group of centers. Training curriculum has often ranged from 2 days to 10 weeks of training, has been shown to be feasible and did show a measurable improvement in skills; however, they lacked uniformity in credentialing. Although validated for technical skills, these did not account for the development of non-technical/team skills essential for a novice surgeon. Thus, there is a need to provide updates to surgical robots and other equipment as well as confirm that medical professionals are trained on the updates.

FIG. 1 is a block diagram illustrating an example surgical system 100, in accordance with one or more embodiments. The system 100 includes various surgical and medical equipment (e.g., a patient monitor 112) located within an operating room 102 or a doctor's office 110, a console 108 for performing surgery or other patient care, and a database 106 for storing electronic health records. The system 100 can manage usage of and software for the surgical and medical equipment. The console 108 is the same as or similar to the console 420 illustrated and described in more detail with reference to FIG. 4A. The system 100 is implemented using the components of the example computer system 300 illustrated and described in more detail with reference to FIG. 3. Likewise, embodiments of the system 100 can include different and/or additional components or can be connected in different ways.

The operating room 102 is a facility, e.g., within a hospital, where surgical operations are carried out in an aseptic environment. Proper surgical procedures require a sterile field. In some embodiments, the sterile field is maintained in the operating room 102 in a medical care facility such as a hospital, the doctor's office 110, or an outpatient surgery center.

In some embodiments, the system 100 includes one or more medical or surgical patient monitors 112. The monitors 112 can include a vital signs monitor (a medical diagnostic instrument), which can be a portable, battery-powered, multi-parametric, vital signs monitoring device used for both ambulatory and transport applications as well as bedside monitoring. The vital signs monitor can be used with an isolated data link to an interconnected portable computer or the console 108, allowing snapshot and trended data from the vital signs monitor to be printed automatically at the console 108, and also allowing default configuration settings to be downloaded to the vital signs monitor. The vital signs monitor is capable of use as a stand-alone unit as well as part of a bi-directional wireless communications network that includes at least one remote monitoring station (e.g., the console 108). The vital signs monitor can measure multiple physiological parameters of a patient wherein various sensor output signals are transmitted either wirelessly or by means of a wired connection to at least one remote site, such as the console 108.

In some embodiments, the monitors 112 include a heart rate monitor, which is a sensor and/or a sensor system applied in the context of monitoring heart rates. The heart rate monitor measures, directly or indirectly, any physiological condition from which any relevant aspect of heart rate can be gleaned. For example, some embodiments of the heart rate monitor measure different or overlapping physiological conditions to measure the same aspect of heart rate. Alternatively, some embodiments measure the same, different, or overlapping physiological conditions to measure different aspects of heart rate, e.g., number of beats, strength of beats, regularity of beats, beat anomalies, etc.

In some embodiments, the monitors 112 include a pulse oximeter or SpO2 monitor, which is a plethysmograph or any instrument that measures variations in the size of an organ or body part of the patient on the basis of the amount of blood passing through or present in the body part. The pulse oximeter is a type of plethysmograph that determines the oxygen saturation of the blood by indirectly measuring the oxygen saturation of the patient's blood (as opposed to measuring oxygen saturation directly through a blood sample) and changes in blood volume in the skin. The pulse oximeter can include a light sensor that is placed at a site on the patient, usually a fingertip, toe, forehead, or earlobe, or in the case of a neonate, across a foot. Light, which can be produced by a light source integrated into the pulse oximeter, containing both red and infrared wavelengths, is directed onto the skin of the patient, and the light that passes through the skin is detected by the pulse oximeter. The intensity of light in each wavelength is measured by the pulse oximeter over time. The graph of light intensity versus time is referred to as the photoplethysmogram (PPG) or, more commonly, simply as the "pleth." From the waveform of the PPG, it is possible to identify the pulse rate of the patient and when each individual pulse occurs. In addition, by comparing the intensities of two wavelengths when a pulse occurs, it is possible to determine blood oxygen saturation of hemoglobin in arterial blood. This relies on the observation that highly oxygenated blood will relatively absorb more red light and less infrared light than blood with a lower oxygen saturation.

In some embodiments, the monitors 112 include an end-tidal CO2 monitor or capnography monitor used for measurement of the level of carbon dioxide that is released at the end of an exhaled breath (referred to as end-tidal carbon dioxide, ETCO2). An end-tidal CO2 monitor or capnography monitor is widely used in anesthesia and intensive care. ETCO2 can be calculated by plotting expiratory CO2 with time. Further, ETCO2 monitors are important for the measurement of applications such as cardiopulmonary resuscitation (CPR), airway assessment, procedural sedation and analgesia, pulmonary diseases such as obstructive pulmonary disease, pulmonary embolism, etc., heart failure, metabolic disorders, etc. The end-tidal CO2 monitor can be configured as side stream (diverting) or mainstream (non-diverting). A diverting end-tidal CO2 monitor transports a portion of a patient's respired gases from the sampling site to the end-tidal CO2 monitor, while a non-diverting end-tidal CO2 monitor does not transport gas away. Also, measurement by the end-tidal CO2 monitor is based on the absorption of infrared light by carbon dioxide where exhaled gas passes through a sampling chamber containing an infrared light source and photodetector on both sides. Based on the amount of infrared light reaching the photodetector, the amount of carbon dioxide present in the gas can be determined.

In some embodiments, the monitors 112 include a blood pressure monitor that measures blood pressure, particularly in arteries. The blood pressure monitor uses a non-invasive technique (by external cuff application) or an invasive technique (by a cannula needle inserted in an artery, used in the operating room 102) for measurement. The non-invasive method (referred to as a sphygmomanometer) works by measurement of force exerted against arterial walls during (i) ventricular systole (i.e., systolic blood pressure occurs when the heart beats and pushes blood through the arteries) and (ii) ventricular diastole (i.e., diastolic blood pressure occurs when the heart rests and is filling with blood) thereby measuring systole and diastole, respectively. The blood pressure monitor can be of three types: automatic/digital, manual (aneroid-dial), and manual (mercury-column). The sphygmomanometer can include a bladder, a cuff, a pressure meter, a stethoscope, a valve, and a bulb. The cuff inflates until it fits tightly around the patient's arm, cutting off the blood flow, and then the valve opens to deflate it. The blood pressure monitor operates by inflating a cuff tightly around the arm; as the cuff reaches the systolic pressure, blood begins to flow in the artery, creating a vibration, which is detected by the blood pressure monitor, which records the systolic pressure. The techniques used for measurement can be auscultatory or oscillometric.

In some embodiments, the monitors 112 include a body temperature monitor. The body temperature monitor measures the temperature invasively or non-invasively by placement of a sensor into organs such as the bladder, rectum, esophagus, tympanum, etc., and mouth, armpit, etc., respectively. The body temperature monitor is of two types: contact and non-contact. Temperature can be measured in two forms: core temperature and peripheral temperature. Temperature measurement can be done by thermocouples, resistive temperature devices (RTDs, thermistors), infrared radiators, bimetallic devices, liquid expansion devices, molecular change-of-state, and silicon diodes. A body temperature monitor commonly used for the measurement of temperature includes a temperature sensing element (e.g., temperature sensor) and a means for converting to a numerical value.

In some embodiments, the monitors 112 measure respiration rate or breathing rate—the rate at which breathing occurs—and which is measured by the number of breaths the patient takes per minute. The rate is measured when a person is at rest and simply involves counting the number of breaths for one minute by counting how many times the chest rises. Normal respiration rates for an adult patient at rest are in the range: 12 to 16 breaths per minute. A variation can be an indication of an abnormality/medical condition or the patient's demographic parameters. The monitors 112 can indicate hypoxia, a condition with low levels of oxygen in the cells, or hypercapnia, a condition in which high levels of carbon dioxide are in the bloodstream. Pulmonary disorders, asthma, anxiety, pneumonia, heart diseases, dehydration, and drug overdose are some abnormal conditions, which can cause a change to the respiration rate, thereby increasing or reducing the respiration rate from normal levels.

In some embodiments, the monitors 112 measure an electrocardiogram (EKG or ECG), a representation of the electrical activity of the heart (graphical trace of voltage versus time) by placement of electrodes on the skin/body surface. The electrodes capture the electrical impulse, which travels through the heart causing systole and diastole or the pumping of the heart. This impulse provides information related to the normal functioning of the heart and the production of impulses. A change can occur due to medical conditions such as arrhythmias (tachycardia, where the heart rate becomes faster, and bradycardia, where the heart rate becomes slower), coronary heart disease, heart attacks, or cardiomyopathy. The instrument used for measurement of the electrocardiogram is called an electrocardiograph, which measures the electrical impulses by the placement of electrodes on the surface of the body and represents the ECG by a PQRST waveform. A PQRST wave is read as: P wave, which represents the depolarization of the left and right atrium and corresponds to atrial contraction; QRS complex, which indicates ventricular depolarization and represents the electrical impulse as it spreads through the ventricles; and T wave, which indicates ventricular repolarization and follows the QRS complex.

In some embodiments, the monitors 112 perform neuromonitoring, also called intraoperative neurophysiological monitoring (IONM). For example, the monitors 112 assess functions and changes in the brain, brainstem, spinal cord, cranial nerves, and peripheral nerves during a surgical procedure on these organs. Monitoring includes both continuous monitoring of neural tissue as well as the localization of vital neural structures. IONM measures changes in these organs where the changes are indicative of irreversible damage or injuries in the organs, aiming at reducing the risk of neurological deficits after operations involving the nervous system. Monitoring is effective in localization of anatomical structures, including peripheral nerves and the sensorimotor cortex, which helps in guiding a surgical robot during dissection. Electrophysiological modalities employed in neuromonitoring are an extracellular single unit and local field recordings (LFP), somatosensory evoked potential (SSEP), transcranial electrical motor evoked potentials (TCeMEP), electromyography (EMG), electroencephalography (EEG), and auditory brainstem response (ABR). The use of neurophysiological monitoring during surgical procedures requires anesthesia techniques to avoid interference and signal alteration due to anesthesia.

In some embodiments, the monitors 112 measure motor evoked potential (MEP), electrical signals that are recorded from descending motor pathways or muscles following stimulation of motor pathways within the brain. MEP is determined by measurement of the action potential elicited by non-invasive stimulation of the motor cortex through the scalp. MEP is for intraoperative monitoring and neurophysiological testing of the motor pathways specifically during spinal procedures. The technique of monitoring for measurement of MEP is defined based on parameters, such as a site of stimulation (motor cortex or spinal cord), method of stimulation (electrical potential or magnetic field), and site of recording (spinal cord or peripheral mixed nerve and muscle). The target site is stimulated by the use of electrical or magnetic means.

In some embodiments, the monitors 112 measure somatosensory evoked potential (SSEP or SEP): the electrical signals generated by the brain and the spinal cord in response to sensory stimulus or touch. SSEP is used for intraoperative neurophysiological monitoring in spinal surgeries. The measurements are reliable, which allows for continuous monitoring during a surgical procedure. The sensor stimulus commonly given to the organs can be auditory, visual, or somatosensory SEPs and applied on the skin, peripheral nerves of the upper limbs, lower limbs, or scalp. The stimulation technique can be mechanical, electrical (provides larger and more robust responses), or intraoperative spinal monitoring modality.

In some embodiments, the monitors 112 provide electromyography (EMG): the evaluation and recording of electrical signals or electrical activity of the skeletal muscles. An electromyography instrument, electromyograph, or electromyogram for the measurement of the EMG activity records electrical activity produced by skeletal muscles and evaluates the functional integrity of individual nerves. The nerves monitored by an EMG instrument can be intracranial, spinal, or peripheral nerves. The electrodes used for the acquisition of signals can be invasive or non-invasive electrodes. The technique used for measurement can be spontaneous or triggered. Spontaneous EMG refers to the recording of myoelectric signals such as compression, stretching, or pulling of nerves during surgical manipulation. Spontaneous EMG is recorded by the insertion of a needle electrode. Triggered EMG refers to the recording of myoelectric signals during stimulation of a target site such as a pedicle screw with incremental current intensities.

In some embodiments, the monitors 112 provide electroencephalography (EEG), measuring the electrical signals in the brain. Brain cells communicate with each other through electrical impulses. EEG can be used to help detect potential problems associated with this activity. An electroencephalograph is used for the measurement of EEG activity. Electrodes ranging from 8 to 16 pairs are attached to the scalp, where each pair of electrodes transmits a signal to one or more recording channels. EEG is a modality for intraoperative neurophysiological monitoring and assessing cortical perfusion and oxygenation during a variety of vascular, cardiac, and neurosurgical procedures. The waves produced by EEG are alpha, beta, theta, and delta.

In some embodiments, the monitors 112 include sensors, such as microphones or optical sensors, that produce images or video captured from at least one of multiple imaging devices, for example, cameras attached to manipulators or end effectors, cameras mounted to the ceiling or other surface above the surgical theater, or cameras mounted on a tripod or other independent mounting device. In some embodiments, the cameras are body worn by a surgical robot or other surgical staff, cameras are incorporated into a wearable device, such as an AR device like Google Glass™, or cameras are integrated into an endoscopic, microscopic, or laparoscopic device. In some embodiments, a camera or other imaging device (e.g., ultrasound) present in the operating room 102 is associated with one or more areas in the operating room 102. The sensors can be associated with measuring a specific parameter of the patient, such as respiratory rate, blood pressure, blood oxygen level, heart rate, etc.

In some embodiments, the system 100 includes a medical visualization apparatus 114 used for visualization and analysis of objects (preferably two-dimensional (2D) or three-dimensional (3D) objects) in the operating room 102. The medical visualization apparatus 114 provides the selection of points at surfaces, selection of a region of interest, or selection of objects. The medical visualization apparatus 114 can also be used for diagnosis, treatment planning, intraoperative support, documentation, or educational purposes. The medical visualization apparatus 114 can further include microscopes, endoscopes/arthroscopes/laparoscopes, fiber optics, surgical lights, high-definition monitors, operating room cameras, etc. Two-dimensional (2D) or three-dimensional (3D) visualization software provides visual representations of scanned body parts via virtual models, offering significant depth and nuance to static two-dimensional medical images. The software facilitates improved diagnoses, narrowed surgical operation learning curves, reduced operational costs, and shortened image acquisition times.

In some embodiments, the system 100 includes an instrument 118 such as an endoscope, arthroscope, or laparoscope for minimally invasive surgery (MIS), in which procedures are performed by cutting a minimal incision in the body. An endoscope refers to an instrument used to visualize, diagnose, and treat problems inside hollow organs where the instrument is inserted through natural body openings such as the mouth or anus. An endoscope can perform a procedure as follows: a scope with a tiny camera attached to a long, thin tube is inserted. A surgical robot moves it through a body passageway or opening to see inside an organ. It can be used for diagnosis and surgery (such as for removing polyps from the colon). An arthroscope refers to an instrument used to visualize, diagnose, and treat problems inside a joint by a TV camera inserted through small portals/incisions and to perform procedures on cartilage, ligaments, tendons, etc. An arthroscope can perform the procedure as follows: a surgical robot makes a small incision in a patient's skin and inserts a pencil-sized instrument with a small lens and lighting system to magnify the target site (joint) and viewing of the interior of the joint by means of a miniature TV camera and then performs the procedure. A laparoscope refers to an instrument used to visualize, diagnose, and treat problems inside soft organs like the abdomen and pelvis by a TV camera inserted through small portals/incisions and to perform procedures.

In some embodiments, the system 100 includes fiber optics 120, which refer to flexible, transparent fiber made by drawing glass (silica) or plastic to a diameter slightly thicker than that of a human hair. Fiber optics 120 are arranged in bundles called optical cables and used to transmit light signals across long distances. Fiber optics 120 are used most often as a means to transmit light between the two ends of the fiber and find wide usage in the medical field. Traditional surgery requires sizable and invasive incisions to expose internal organs and operate on affected areas, but with fiber optics 120 much smaller surgical incisions can be performed. Fiber optics 120 contain components such as a core, cladding, and buffer coating. Fiber optics 120 can be inserted in hypodermic needles and catheters, endoscopes, operation theater tools, ophthalmological tools, and dentistry tools. Fiber optic sensors include a light source, optical fiber, external transducer, and photodetector. Fiber optic sensors can be intrinsic or extrinsic. Fiber optic sensors can be categorized into four types: physical, imaging, chemical, and biological.

In some embodiments, the system 100 includes surgical lights 122 (referred to as operating lights) that perform illumination of a local area or cavity of the patient. Surgical lights 122 play an important role in illumination before, during, and after a medical procedure. Surgical lights 122 can be categorized by lamp type as conventional (incandescent) and LED (light-emitting diode). Surgical lights 122 can be categorized by mounting configuration as ceiling-mounted, wall-mounted, or floor stand. Surgical lights 122 can be categorized by type as tungsten, quartz, xenon halogens, and/or LEDs. Surgical lights 122 include sterilizable handles 126, which allow a surgical robot to adjust light positions. Some important factors affecting surgical lights 122 can be illumination, shadow management (cast shadows and contour shadows), the volume of light, heat management, or fail-safe surgical lighting.

In some embodiments, the system 100 includes a surgical tower 128, e.g., used in conjunction with the robotic surgical system 160 disclosed herein, for MIS. The surgical tower 128 includes instruments used for performing MIS or surgery, which is performed by creating small incisions in the body. The instruments are also referred to as minimally invasive devices or minimally invasive access devices. The procedure of performing MIS can also be referred to as a minimally invasive procedure. MIS is a safer, less invasive, and more precise surgical procedure. Some medical procedures where the surgical tower 128 is useful and widely used are procedures for lung, gynecological, head and neck, heart, and urological conditions. MIS can be robotic or non-robotic/endoscopic. MIS can include endoscopic, laparoscopic, arthroscopic, natural orifice intraluminal, and natural orifice transluminal procedures. A surgical tower access device can also be designed as an outer sleeve and an inner sleeve that telescopingly or slidably engage with one another. When a telescope is used to operate on the abdomen, the procedure is called laparoscopy. The surgical tower 128 typically includes access to a variety of surgical tools, such as for electrocautery, radiofrequency, lasers, sensors, etc.

In some embodiments, radiofrequency (RF) is used in association with MIS devices. The RF can be used for the treatment of skin by delivering it to the skin through a minimally invasive surgical tool (e.g., fine needles), which does not require skin excision. The RF can be used for real-time tracking of MIS devices such as laparoscopic instruments. The RF can provide radiofrequency ablation to a patient suffering from atrial fibrillation through smaller incisions made between the ribs. The RF can be used to perform an endoscopic surgery on the body such as the spine by delivery of RF energy.

In some embodiments, the system 100 includes an instrument 130 to perform electrocautery for burning a part of the body to remove or close off a part of it. Various physiological conditions or surgical procedures require the removal of body tissues and organs, a consequence of which is bleeding. In order to achieve hemostasis and for removing and sealing all blood vessels that are supplied to an organ after surgical incision, the electrocautery instrument 130 can be used. For example, after removing part of the liver for removal of a tumor, etc., blood vessels in the liver must be sealed individually. The electrocautery instrument 130 can be used for sealing living tissue such as arteries, veins, lymph nodes, nerves, fats, ligaments, and other soft tissue structures. The electrocautery instrument 130 can be used in applications such as surgery, tumor removal, nasal treatment, or wart removal. Electrocautery can operate in two modes, monopolar or bipolar. The electrocautery instrument 130 can consist of a generator, a handpiece, and one or more electrodes.

In some embodiments, the system 100 includes a laser 132 used in association with MIS devices. The laser 132 can be used in MIS with an endoscope. The laser 132 is attached to the distal end of the endoscope and steered at high speed by producing higher incision quality than with existing surgical tools thereby minimizing damage to surrounding tissue. The laser 132 can be used to perform MIS using a laparoscope in the lower and upper gastrointestinal tract, eye, nose, and throat. The laser 132 is used in MIS to ablate soft tissues, such as a herniated spinal disc bulge.

In some embodiments, sensors 134 are used in association with MIS devices and the robotic surgical system 160 described herein. The sensors 134 can be used in MIS for tactile sensing of surgical tool-tissue interaction forces. During MIS, the field of view and workspace of surgical tools are compromised due to the indirect access to the anatomy and lack of surgeon's hand-eye coordination. The sensors 134 provide a tactile sensation to the surgeon by providing information regarding shape, stiffness, and texture of organ or tissue (different characteristics) to the surgeon's hands through a sense of touch. This detects a tumor through palpation, which exhibits a "tougher" feel than that of healthy soft tissue, pulse felt from blood vessels, and abnormal lesions. The sensors 134 can output shape, size, pressure, softness, composition, temperature, vibration, shear, and normal forces. The sensors 134 can be electrical or optical, consisting of capacitive, inductive, piezoelectric, piezoresistive, magnetic, and auditory. The sensors 134 can be used in robotic or laparoscopic surgery, palpation, biopsy, heart ablation, and valvuloplasty.

In some embodiments, the system 100 includes an imaging system 136 (instruments are used for the creation of images and visualization of the interior of a human body for diagnostic and treatment purposes). The imaging system 136 is used in different medical settings and can help in the screening of health conditions, diagnosing causes of symptoms, or monitoring of health conditions. The imaging system 136 can include various imaging techniques such as X-ray, fluoroscopy, MRI, ultrasound, endoscopy, elastography, tactile imaging, thermography, medical photography, and nuclear medicine, e.g., PET. Some factors which can drive the market are cost and clinical advantages of medical imaging modalities, a rising share of ageing populations, increasing prevalence of cardiovascular or lifestyle diseases, and increasing demand from emerging economies.

In some embodiments, the imaging system 136 includes X-ray medical imaging instruments that use X-ray radiation (i.e., X-ray range in the electromagnetic radiation spectrum) for the creation of images of the interior of the human body for diagnostic and treatment purposes. An X-ray instrument is also referred to as an X-ray generator. It is a non-invasive instrument based on different absorption of X-rays by tissues based on their radiological density (radiological density is different for bones and soft tissues). For the creation of an image by the X-ray instrument, X-rays produced by an X-ray tube are passed through a patient positioned to the detector. As the X-rays pass through the body, images appear in shades of black and white, depending on the type and densities of tissue the X-rays pass through. Some of the applications where X-rays are used can be bone fractures, infections, calcification, tumors, arthritis, blood vessel blockages, digestive problems, or heart problems. The X-ray instrument can consist of components such as an X-ray tube, operating console, collimator, grid, detector, radiographic film, etc.

In some embodiments, the imaging system 136 includes MRI medical imaging instruments that use powerful magnets for the creation of images of the interior of the human body for diagnostic and treatment purposes. Some of the applications where MRI can be used are brain/spinal cord anomalies, tumors in the body, breast cancer screening, joint injuries, uterine/pelvic pain detection, or heart problems. For the creation of the image by an MRI instrument, magnetic resonance is produced by powerful magnets, which produce a strong magnetic field that forces protons in the body to align with that field. When a radiofrequency current is then pulsed through the patient, the protons are stimulated, and spin out of equilibrium, straining against the pull of the magnetic field. Turning off the radiofrequency field allows detection of energy released by realignment of protons with the magnetic field by MRI sensors. The time taken by the protons for realignment with the magnetic field and energy release is dependent on environmental factors and the chemical nature of the molecules. MRI is more widely suitable for imaging of non-bony parts or soft tissues of the body. MRI can be less harmful as it does not use damaging ionizing radiation as in the X-ray instrument. MRI instruments can consist of magnets, gradients, radiofrequency systems, or computer control systems. Some areas where imaging by MRI should be prohibited can be people with implants.

In some embodiments, the imaging system 136 uses CT imaging that uses an X-ray radiation (i.e., X-ray range in the electromagnetic radiation spectrum) for the creation of cross-sectional images of the interior of the human body. CT refers to a computerized X-ray imaging procedure in which a narrow beam of X-rays is aimed at a patient and quickly rotated around the body, producing signals that are processed by the machine's computer to generate cross-sectional images—or "slices"—of the body. A CT instrument is different from an X-ray instrument as it creates 3-dimensional cross-sectional images of the body while the X-ray instrument creates 2-dimensional images of the body; the 3-dimensional cross-sectional images are created by taking images from different angles, which is done by taking a series of tomographic images from different angles. The diverse images are collected by a computer and digitally stacked to form a 3-dimensional image of the patient. For creation of images by the CT instrument, a CT scanner uses a motorized X-ray source that rotates around the circular opening of a donut-shaped structure called a gantry while the X-ray tube rotates around the patient shooting narrow beams of X-rays through the body. Some of the applications where CT can be used can be blood clots; bone fractures, including subtle fractures not visible on X-ray; or organ injuries.

In some embodiments, the imaging system 136 includes ultrasound imaging, also referred to as sonography or ultrasonography, that uses ultrasound or sound waves (also referred to as acoustic waves) for the creation of cross-sectional images of the interior of the human body. Ultrasound waves in the imaging system 136 can be produced by a piezoelectric transducer, which produces sound waves and sends them into the body. The sound waves that are reflected are converted into electrical signals, which are sent to an ultrasound scanner. Ultrasound instruments can be used for diagnostic and functional imaging or for therapeutic or interventional procedures. Some of the applications where ultrasound can be used are diagnosis/treatment/guidance during medical procedures (e.g., biopsies, internal organs such as liver/kidneys/pancreas, fetal monitoring, etc.), in soft tissues, muscles, blood vessels, tendons, or joints. Ultrasound can be used for internal imaging (where the transducer is placed in organs, e.g., vagina) and external imaging (where the transducer is placed on the chest for heart monitoring or the abdomen for fetal monitoring). An ultrasound machine can consist of a monitor, keyboard, processor, data storage, probe, and transducer.

In some embodiments, the system 100 includes a stereotactic navigation system 138 that uses patient imaging (e.g., CT, MRI) to guide surgical robots in the placement of specialized surgical instruments and implants. The patient images are taken to guide a surgical robot before or during the medical procedure. The stereotactic navigation system 138 includes a camera having infrared sensors to determine the location of the tip of the probe being used in the surgical procedure. This information is sent in real-time so that the surgical robot has a clear image of the precise location where it is working in the body. The stereotactic navigation system 138 can be framed (requires attachment of a frame to the patient's head using screws or pins) or frameless (does not require the placement of a frame on the patient's anatomy). The stereotactic navigation system 138 can be used for diagnostic biopsies, tumor resection, bone preparation/implant placement, placement of electrodes, otolaryngologic procedures, or neurosurgical procedures.

In some embodiments, the system 100 includes an anesthesiology machine 140 that is used to generate and mix medical gases, such as oxygen or air, and anesthetic agents to induce and maintain anesthesia in patients. The anesthesiology machine 140 delivers oxygen and anesthetic gas to the patient and filters out expiratory carbon dioxide. The anesthesiology machine 140 can perform functions such as providing oxygen (O2), accurately mixing anesthetic gases and vapors, enabling patient ventilation, and minimizing anesthesia-related risks to patients and staff. The anesthesiology machine 140 can include the following essential components: a source of O2, O2 flowmeter, vaporizer (anesthetics include isoflurane, halothane, enflurane, desflurane, sevoflurane, and methoxyflurane), patient breathing circuit (tubing, connectors, and valves), and scavenging system (removes any excess anesthetics gases). The anesthesiology machine 140 can be divided into three parts: the high pressure system, the intermediate pressure system, and the low pressure system. The process of anesthesia starts with oxygen flow from a pipeline or cylinder through the flowmeter; the O2 flows through the vaporizer and picks up the anesthetic vapors; the O2-anesthetic mix then flows through the breathing circuit and into the patient's lungs, usually by spontaneous ventilation or normal respiration.

In some embodiments, the system 100 includes a surgical bed 142 equipped with mechanisms that can elevate or lower the entire bed platform; flex, or extend individual components of the platform; or raise or lower the head or the feet of the patient independently. The surgical bed 142 can be an operation bed, cardiac bed, amputation bed, or fracture bed. Some essential components of the surgical bed 142 can be a bed sheet, woolen blanket, bath towel, and bed block. The surgical bed 142 can also be referred to as a post-operative bed, which refers to a special type of bed made for the patient who is coming from the operation theater or from another procedure that requires anesthesia. The surgical bed 142 is designed in a manner that makes it easier to transfer an unconscious or weak patient from a stretcher/wheelchair to the bed. The surgical bed 142 should protect bed linen from vomiting, bleeding, drainage, and discharge; provide warmth and comfort to the patient to prevent shock; provide necessary positions, which are suitable for operation; protect patient from being chilled; and be prepared to meet any emergency.

In some embodiments, the system 100 includes a Jackson frame 144 (or Jackson table), which refers to a frame or table that is designed for use in spinal surgeries and can be used in a variety of spinal procedures in supine, prone, or lateral positions in a safe manner. Two peculiar features of the Jackson table 144 are the absence of central table support and an ability to rotate the table through 180 degrees. The Jackson table 144 is supported at both ends, which keeps the whole of the table free. This allows the visualization of a patient's trunk and major parts of extremities as well. The Jackson frame 144 allows the patient to be slid from the cart onto the table in the supine position with appropriate padding placed. The patient is then strapped securely on the Jackson table 144.

In some embodiments, the system 100 includes a disposable air warmer 146 (sometimes referred to as a Bair™ or Bair Hugger™). The disposable air warmer 146 is a convective temperature management system used in a hospital or surgery center to maintain a patient's core body temperature. The disposable air warmer 146 includes a reusable warming unit and a single-use disposable warming blanket for use during surgery. It can also be used before and after surgery. The disposable air warmer 146 uses convective warming consisting of two components: a warming unit and a disposable blanket. The disposable air warmer 146 filters air and then forces warm air through disposable blankets, which cover the patient. The blanket can be designed to use pressure points on the patient's body to prevent heat from reaching areas at risk for pressure sores or burns. The blanket can also include drainage holes where fluid passes through the surface of the blanket to linen underneath, which will reduce the risk of skin softening and reduce the risk of unintended cooling because of heat loss from evaporation.

In some embodiments, the system 100 includes a sequential compression device (SCD) 148 used to help prevent blood clots in the deep veins of legs. The SCD 148 uses cuffs around the legs that fill with air and squeeze the legs. This increases blood flow through the veins of the legs and helps prevent blood clots. A deep vein thrombosis (DVT) is a blood clot that forms in a vein deep inside the body. Some of the risks of using the SCD 148 can be discomfort, warmth, sweating beneath the cuff, skin breakdown, nerve damage, or pressure injury.

In some embodiments, the system 100 includes a bed position controller 150, which refers to an instrument for controlling the position of the patient bed. Positioning a patient in bed is important for maintaining alignment and for preventing bedsores (pressure ulcers), foot drop, and contractures. Proper positioning is also vital for providing comfort for patients who are bedridden or have decreased mobility related to a medical condition or treatment. When positioning a patient in bed, supportive devices such as pillows, rolls, and blankets, along with repositioning, can aid in providing comfort and safety. The patient can be in the following positions in a bed: supine position, prone position, lateral position, Sims' position, Fowler's position, semi-Fowler's position, orthopedic or tripod position, or Trendelenburg position.

In some embodiments, the system 100 includes environmental controls 152. The environmental controls 152 can be operating room environmental controls for control or maintenance of the environment in the operating room 102 where procedures are performed to minimize the risk of airborne infection and to provide a conducive environment for everyone in the operating room 102 (e.g., surgeon, anesthesiologist, nurses, and patient). Some factors that can contribute to poor quality in the environment of the operating room 102 are temperature, ventilation, and humidity, and those conditions can lead to profound effects on the health and work productivity of people in the operating room 102. As an example: surgeons prefer a cool, dry climate since they work under bright, hot lights; anesthesia personnel prefer a warmer, less breezy climate; patient condition demands a relatively warm, humid, and quiet environment. The operating room environmental controls can control the environment by taking care of the following factors: environmental humidity, infection control, or odor control. Humidity control can be performed by controlling the temperature of anesthesia gases; infection can be controlled by the use of filters to purify the air.

In some embodiments, the environmental controls 152 include a heating, ventilation, and air conditioning (HVAC) system for regulating the environment of indoor settings by moving air between indoor and outdoor areas, along with heating and cooling. HVAC can use a different combination of systems, machines, and technologies to improve comfort. HVAC can be necessary to maintain the environment of the operating room 102. The operating room 102 can be a traditional operating room (which can have a large diffuser array directly above the operating table) or a hybrid operating room (which can have monitors and imaging equipment 136 that consume valuable ceiling space and complicate the design process). HVAC can include three main units, for example, a heating unit (e.g., furnace or boiler), a ventilation unit (natural or forced), and an air conditioning unit (which can remove existing heat). HVAC can be made of components such as air returns, filters, exhaust outlets, ducts, electrical elements, outdoor units, compressors, coils, and blowers. The HVAC system can use central heating and AC systems that use a single blower to circulate air via internal ducts.

In some embodiments, the environmental controls 152 include an air purification system for removing contaminants from the air in the operating room 102 to improve indoor air quality. Air purification can be important in the operating room 102 as surgical site infection can be a reason for high mortality and morbidity. The air purification system can deliver clean, filtered, contaminant-free air over the surgical bed 142 using a diffuser, airflow, etc., to remove all infectious particles down and away from the patient. The air purification system can be an air curtain, multi-diffuser array, or single large diffuser (based on laminar diffuser flow) or High-Efficiency Particulate Air filter (HEPA filter). A HEPA filter protects a patient from infection and contamination using a filter, which is mounted at the terminal of the duct. A HEPA filter can be mounted on the ceiling and deliver clean, filtered air in a flow to the operating room 102 that provides a sweeping effect that pushes contaminants out via the return grilles that are usually mounted on the lower wall.

In some embodiments, the system 100 includes one or more medical or surgical tools 154. The surgical tools 154 can include orthopedic tools (also referred to as orthopedic instruments) used for treatment and prevention of deformities and injuries of the musculoskeletal system or skeleton, articulations, and locomotive system (i.e., set formed by skeleton, muscles attached to it, and the part of the nervous system that controls the muscles). A major percentage of orthopedic tools are made of plastic. The orthopedic tools can be divided into the following specialties: hand and wrist, foot and ankle, shoulder, and elbow, arthroscopic, hip, and knee. The orthopedic tools can be fixation tools, relieving tools, corrective tools, or compression-distraction tools. A fixation tool refers to a tool designed to restrict movements partially or completely in a joint, e.g., hinged splints (for preserving a certain range of movement in a joint) or rigid splints. A relieving tool refers to a tool designed to relieve pressure on an ailing part by transferring support to healthy parts of an extremity, e.g., Thomas splint and the Voskoboinikova apparatus. A corrective tool refers to a surgical tool designed to gradually correct a deformity, e.g., corsets, splints, orthopedic footwear, insoles, and other devices to correct abnormal positions of the foot. A compression-distraction tool refers to a surgical tool designed to correct acquired or congenital deformities of the extremities, e.g., curvature, shortening, and pseudarthrosis such as Gudushauri. A fixation tool can be an internal fixation tool (e.g., screws, plates) or external fixation tools used to correct a radius or tibia fracture. The orthopedic tools can be bone-holding forceps, drill bits, nail pins, hammers, staples, etc.

In some embodiments, the surgical tools 154 include a drill for making holes in bones for insertion of implants like nails, plates, screws, and wires. The drill tool functions by drilling cylindrical tunnels into bone. Drills can be used in orthopedics for performing medical procedures. If the drill does not stop immediately when used, the use of the drill on bones can have some risks, such as harm caused to bone, muscle, nerves, and venous tissues, which are wrapped by surrounding tissue. Drills vary widely in speed, power, and size. Drills can be powered as electrical, pneumatic, or battery. Drills generally can work on speeds below 1000 rpm in orthopedic settings. Temperature control of drills is an important aspect in the functioning of the drill and is dependent on parameters such as rotation speed, torque, orthotropic site, sharpness of the cutting edges, irrigation, and cooling systems. The drill can include a physical drill, power cord, electronically motorized bone drill, or rotating bone shearing incision work unit and can output operation data, such as speed data (e.g., rotational speed, RPMs, linear speed), force data (e.g., torque data, pressure data, etc.), drill bit temperature, drill temperature, etc. In some embodiments, the surgical tools 154 can output operation data including, for example, pumping data, fluid data (e.g., flow rate data, viscosity data, etc.), sampling data (e.g., sampling rate data, sampling schedule data, etc.), temperature, etc. The operational data can be selected based on the configuration of the surgical tool 154.

In some embodiments, the surgical tools 154 include a scalpel for slicing, cutting, or osteotomy of bone during orthopedic procedure. The scalpel can be designed to provide clean cuts through osseous structures with minimal loss of viable bone while sparing adjacent elastic soft tissues largely unaffected while performing a slicing procedure. This is suited for spine applications where bone must be cut adjacent to the dura and neural structures. The scalpel does not rotate but performs cutting by an ultrasonically oscillating or forward/backward moving metal tip. Scalpels can prevent injuries caused by a drill in a spinal surgery such as complications such as nerve thermal injury, grasping soft tissue, tearing dura mater, and mechanical injury.

In some embodiments, stitches (also referred to as sutures) or a sterile, surgical thread is used to repair cuts or lacerations and is used to close incisions or hold body tissues together after a surgery or an injury. Stitches can involve the use of a needle along with an attached thread. Stitches can be either absorbable (the stitches automatically break down harmlessly in the body over time without intervention) or non-absorbable (the stitches do not automatically break down over time and must be manually removed if not left indefinitely). Stitches can be based on material monofilament, multifilament, and barb. Stitches can be classified based on size. Stitches can be based on synthetic or natural material. Stitches can be coated or un-coated.

In some embodiments, the surgical tools 154 include a stapler used for fragment fixation when inter-fragmental screw fixation is not easy. When there is vast damage and a bone is broken into fragments, staples can be used between these fragments for internal fixation and bone reconstruction. For example, they can be used around joints in ankle and foot surgeries, in cases of soft tissue damage, or to attach tendons or ligaments to the bone for reconstruction surgery. Staplers can be made of surgical grade stainless steel or titanium, and they are thicker, stronger, and larger.

In some embodiments, other medical or surgical equipment, such as a set of articles, surgical tools, or objects, is used to implement or achieve an operation or activity. A medical equipment refers to an article, instrument, apparatus, or machine used for diagnosis, prevention, or treatment of a medical condition or disease, or to the detection, measurement, restoration, correction, or modification of structure/function of the body for some health purpose. The medical equipment can perform functions invasively or non-invasively. In some embodiments, the medical equipment includes components such as a sensor/transducer, a signal conditioner, a display, or a data storage unit, etc. In some embodiments, the medical equipment includes a sensor to receive a signal from instruments measuring a patient's body, a transducer for converting one form of energy to electrical energy, a signal conditioner such as an amplifier, filter, etc., to convert the output from the transducer into an electrical value, a display to provide a visual representation of the measured parameter or quantity, or a storage system to store data, which can be used for future reference. A medical equipment can perform diagnosis or provide therapy; for example, the equipment delivers air into the lungs of a patient who is physically unable to breathe, or breathes insufficiently, and moves it out of the lungs.

In some embodiments, the system includes a machine 156 to aid in breathing. The machine 156 can be a ventilator (also referred to as a respirator) that provides a patient with oxygen when they are unable to breathe on their own. A ventilator is required when a person is not able to breathe on their own. A ventilator can perform a function of gently pushing air into the lungs and allow it to come back out. The ventilator functions by delivery of positive pressure to force air into the lungs, while usual breathing uses negative pressure by the opening of the mouth, and air flows in. The ventilator can be required during surgery or after surgery. The ventilator can be required in case of respiratory failure due to acute respiratory distress syndrome, head injury, asthma, lung diseases, drug overdose, neonatal respiratory distress syndrome, pneumonia, sepsis, spinal cord injury, cardiac arrest, etc., or during surgery. The ventilator can be used with a face mask (non-invasive ventilation, where the ventilation is required for a shorter duration of time) or with a breathing tube also referred to as an endotracheal tube (invasive ventilation, where the ventilation is required for a longer duration of time). Ventilator use can have some risks such as infections, fluid build-up, muscle weakness, lung damage, etc. The ventilator can be operated in various modes, such as assist-control ventilation (ACV), synchronized intermittent-mandatory ventilation (SIMV), pressure-controlled ventilation (PCV), pressure support ventilation (PSV), pressure-controlled inverse ratio ventilation (PCIRV), airway pressure release ventilation (APRV), etc. The ventilator can include a gas delivery system, power source, control system, safety feature, gas filter, and monitor.

In some embodiments, the machine 156 is a continuous positive airway pressure (CPAP) used for the treatment of sleep apnea disorder in a patient. Sleep apnea refers to a disorder in which breathing repeatedly stops and starts while a patient is sleeping, often because throat/airways briefly collapse or something temporarily blocks them. Sleep apnea can lead to serious health problems, such as high blood pressure and heart trouble. A CPAP instrument helps the patient with sleep apnea to breathe more easily during sleep by sending a steady flow of oxygen into the nose and mouth during sleep, which keeps the airways open and helps the patient to breathe normally. The CPAP machine can work by a compressor/motor, which generates a continuous stream of pressurized air that travels through an air filter into a flexible tube. The tube delivers purified air into a mask sealed around the nose/mouth of the patient. The airstream from the instrument pushes against any blockages, opening the airways so lungs receive plenty of oxygen, and breathing does not stop as nothing obstructs oxygen. This helps the patient to not wake up to resume breathing. CPAP can have a nasal pillow mask, nasal mask, or full mask. A CPAP instrument can include a motor, a cushioned mask, a tube that connects the motor to the mask, a headgear frame, and adjustable straps. The essential components can be a motor, a cushioned mask, and a tube that connects the motor to the mask.

In some embodiments, the system 100 includes surgical supplies, consumables 158, or necessary supplies for the system 100 to provide care within the hospital or surgical environment. The consumables 158 can include gloves, gowns, masks, syringes, needles, sutures, staples, tubing, catheters, or adhesives for wound dressing, in addition to other surgical tools needed by surgical robots, doctors, and nurses to provide care. Depending on the device, mechanical testing can be carried out in tensile, compression, or flexure; in dynamic or fatigue; via impact; or with the application of torsion. The consumables 158 can be disposable (e.g., time-saving, have no risk of healthcare-associated infections, and cost-efficient) or sterilizable (to avoid cross-contamination or risk of surgical site infections).

In some embodiments, the system 100 includes a robotic surgical system 160 (sometimes referred to as a medical robotic system or a robotic system) that provides intelligent services and information to the operating room 102 and the console 108 by interacting with the environment, including human beings, via the use of various sensors, actuators, and human interfaces. The robotic surgical system 160 can be employed for automating processes in a wide range of applications, ranging from industrial (manufacturing), domestic, medical, service, military, entertainment, space, etc. The medical robotic system market is segmented by product type into surgical robotic systems, rehabilitative robotic systems, non-invasive radiosurgery robots, and hospital and pharmacy robotic systems. Robotic surgeries can be performed using tele-manipulators (e.g., input devices 166 at the console 108), which use the surgeon's actions on one side to control one or more "effectors" on the other side. The medical robotic system 160 provides precision and can be used for remotely controlled, minimally invasive procedures. The robotic surgical system 160 includes computer-controlled electromechanical devices that work in response to controls (e.g., input devices 166 at the console 108) manipulated by the surgeons.

In some embodiments, the system 100 includes equipment tracking systems 162, such as RFID, which is used to tag an instrument with an electronic tag and tracks it using the tag. Typically, this could involve a centralized platform that provides details such as location, owner, contract, and maintenance history for all equipment in real-time. A variety of techniques can be used to track physical assets, including RFID, global positioning system (GPS), Bluetooth low energy (BLE), barcodes, near-field communication (NFC), Wi-Fi, etc. The equipment tracking system 162 includes hardware components, such as RFID tags, GPS trackers, barcodes, and QR codes. The hardware component is placed on the asset, and it communicates with the software (directly or via a scanner), providing the software with data about the asset's location and properties. In some embodiments, the equipment tracking system 162 uses electromagnetic fields to transmit data from an RFID tag to a reader. Reading of RFID tags can be done by portable or mounted RFID readers. The read range for RFID varies with the frequency used. Managing and locating important assets is a key challenge for tracking medical equipment. Time spent searching for critical equipment can lead to expensive delays or downtime, missed deadlines and customer commitments, and wasted labor. The problem has previously been solved by using barcode labels or manual serial numbers and spreadsheets; however, these require manual labor. The RFID tag can be passive (smaller and less expensive, read ranges are shorter, have no power of their own, and are powered by the radio frequency energy transmitted from RFID readers/antennas) or active (larger and more expensive, read ranges are longer, have a built-in power source and transmitter of their own).

In some embodiments, the system 100 includes medical equipment, computers, software, etc., located in the doctor's office 110 that is communicably coupled to the operating room 102 over the network 104. For example, the medical equipment in the doctor's office 110 can include a microscope 116 used for viewing samples and objects that cannot be seen with an unaided eye. The microscope 116 can have components such as eyepieces, objective lenses, adjustment knobs, a stage, an illuminator, a condenser, or a diaphragm. The microscope 116 works by manipulating how light enters the eye using a convex lens, where both sides of the lens are curved outwards. When light reflects off of an object being viewed under the microscope 116 and passes through the lens, it bends toward the eye. This makes the object look bigger than it is. The microscope 116 can be compound (light-illuminated and the image seen with the microscope 116 is two-dimensional), dissection or stereoscope (light-illuminated and the image seen with the microscope 116 is three-dimensional), confocal (laser-illuminated and the image seen with the microscope 116 is on a digital computer screen), scanning electron (SEM) (electron-illuminated and the image seen with the microscope 116 is in black and white), or transmission electron microscope (TEM) (electron-illuminated and the image seen with the microscope 116 is the high magnification and high resolution).

The system 100 includes an electronic health records (EHR) database 106 that contains patient records. The EHR is a digital version of patients' paper charts. The EHR database 106 can contain more information than a traditional patient chart, including, but not limited to, a patient's medical history, diagnoses, medications, treatment plans, allergies, diagnostic imaging, lab results, etc. In some embodiments, the steps for each procedure disclosed herein are stored in the EHR database 106. Electronic health records can also include data collected from the monitors 112 from historical procedures. The EHR database 106 is implemented using components of the example computer system 300 illustrated and described in more detail with reference to FIG. 3.

In some embodiments, the EHR database 106 includes a digital record of patients' health information, collected, and stored systematically over time. The EHR database 106 can include demographics, medical history, history of present illness (HPI), progress notes, problems, medications, vital signs, immunizations, laboratory data, or radiology reports. Software (in memory 164) operating on the console 108 or implemented on the example computer system 300 (e.g., the instructions 304, 308 illustrated and described in more detail with reference to FIG. 3) are used to capture, store, and share patient data in a structured way. The EHR database 106 can be created and managed by authorized providers and can make health information accessible to authorized providers across practices and health organizations, such as laboratories, specialists, medical imaging facilities, pharmacies, emergency facilities, etc. The timely availability of EHR data enables healthcare providers to make more accurate decisions and provide better care to the patients by effective diagnosis and reduced medical errors. Besides providing opportunities to enhance patient care, the EHR database 106 can also be used to facilitate clinical research by combining patients' demographics into a large pool. For example, the EHR database 106 can support a wide range of epidemiological research on the natural history of disease, drug utilization, and safety, as well as health services research.

The console 108 is a computer device, such as a server, computer, tablet, smartphone, smart speaker, etc., implemented using components of the example computer system 300 illustrated and described in more detail with reference to FIG. 3. In some embodiments, the steps for each procedure disclosed herein are stored in memory 164 on the console 108 for execution.

In some embodiments, the operating room 102 or the console 108 includes high-definition monitors 124, which refer to displays in which a clearer picture is possible than with low-definition, low-resolution screens. The high-definition monitors 124 have a higher density of pixels per inch than past standard TV screens. Resolution for the high-definition monitors 124 can be 1280×720 pixels or more (e.g., Full HD, 1920×1080; Quad HD, 2560×1440; 4K, 3840×2160; 8K, 7680×4320 pixels). The high-definition monitor 124 can operate in progressive or interlaced scanning mode. High-definition monitors used in medical applications can offer improved visibility; allow for precise and safe surgery with rich color reproduction; provide suitable colors for each clinical discipline; provide better visibility, operability with a large screen and electronic zoom, higher image quality in low light conditions, better visualization of blood vessels and lesions, and high contrast at high spatial frequencies; be twice as sensitive as conventional sensors; and make it easier to determine tissue boundaries (fat, nerves, vessels, etc.).

In some embodiments, the console 108 includes an input interface or one or more input devices 166. The input devices 166 can include a keyboard, a mouse, a joystick, any hand-held controller, or a hand-controlled manipulator, e.g., a tele-manipulator used to perform robotic surgery.

In some embodiments, the console 108, the equipment in the doctor's office 110, and the EHR database 106 are communicatively coupled to the equipment in the operating room 102 by a direct connection, such as ethernet, or wirelessly by the cloud over the network 104. The network 104 is the same as or similar to the network 314 illustrated and described in more detail with reference to FIG. 3. For example, the console 108 can communicate with the robotic surgical system 160 using the network adapter 312 illustrated and described in more detail with reference to FIG. 3.

In embodiments, the system 100 uses quantum computing. Quantum computing refers to the use of a computational device or method that uses properties of quantum states defined by quantum mechanics such as superposition, entanglement, etc., to perform computations. Quantum devices use qubits, which are the quantum equivalent of bits in a classical computing system. Qubits have at least two quantum states or probable outcomes. These outcomes, combined with a coefficient representing the probability of each outcome, describes the possible states, or bits of data, which can be represented by the qubits according to the principle of quantum superposition. These states can be manipulated to shift the probability of each outcome, or additionally, add additional possible outcomes to perform computations, the final state of which can be measured to achieve the result.

Quantum computing provides significant benefits in the areas of encryption and the simulation of natural systems. Encryption is aided by the uncertain nature of quantum computing in that data is represented by an indeterminate state of probable outcomes, therefore making decryption virtually impossible. The simulation of natural systems, such as chemical and biological interactions, benefit from the fact that the nature of quantum computing is the same as the systems being simulated. In medical fields, quantum computing shows the greatest promise for drug discovery and simulating the interaction of drugs with biologic systems, however the same technology can also be used to predict the interaction of a biologic system with an implanted device, preventing rejection of an implant by a patient's body. Quantum computing can be used to investigate long-term functioning of an implant. Further, quantum computing can be used to study the reaction of a patient to a surgical procedure, during a simulation, before a procedure, or actively during a procedure.

Figure 2:
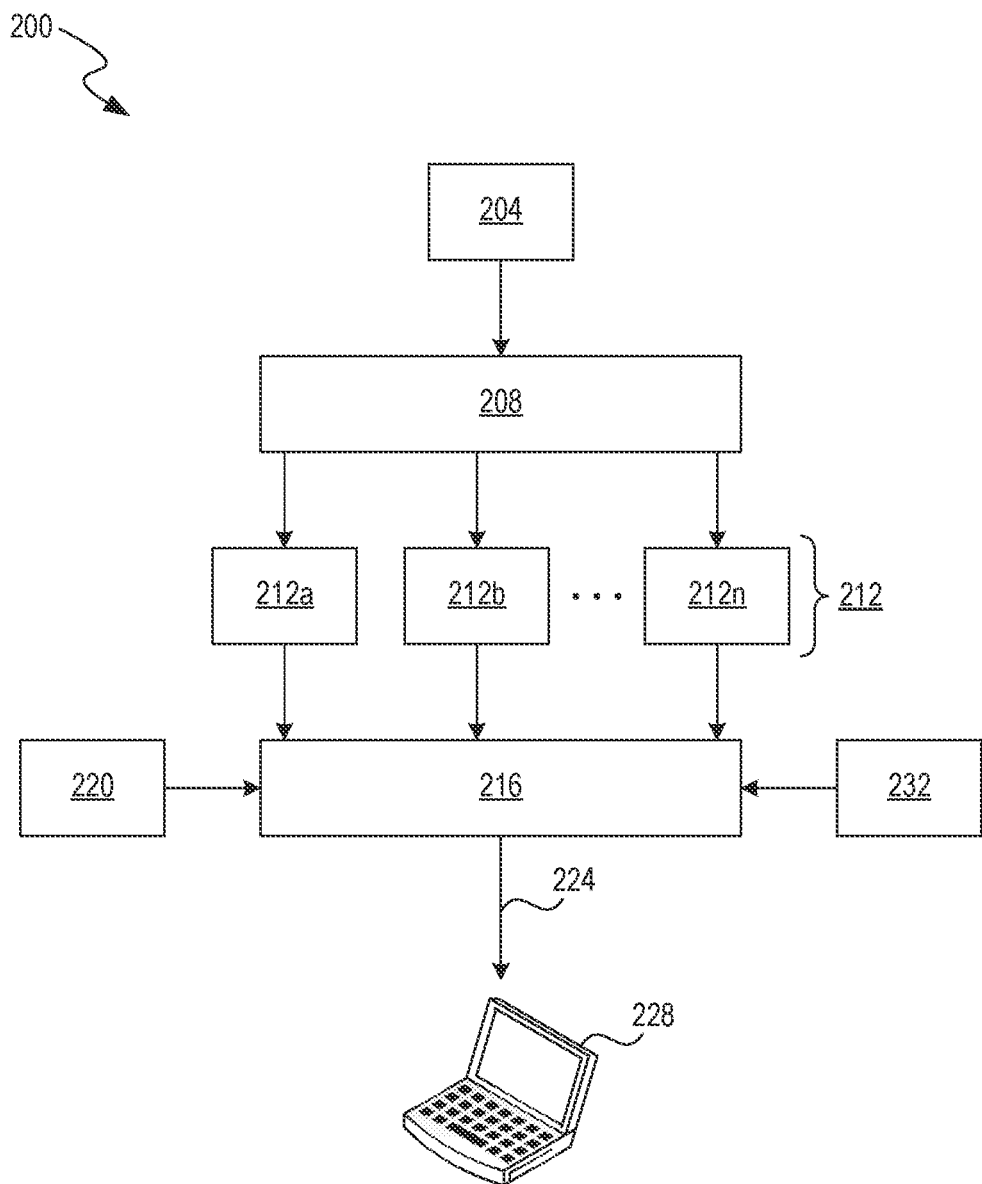
FIG. 2 is a block diagram illustrating an example machine learning (ML) system, in accordance with one or more embodiments.

FIG. 2 is a block diagram illustrating an example ML system 200, in accordance with one or more embodiments. The ML system 200 is implemented using components of the example computer system 300 illustrated and described in more detail with reference to FIG. 3. For example, the ML system 200 can be implemented on the console 108 using instructions programmed in the memory 164 illustrated and described in more detail with reference to FIG. 1. Likewise, embodiments of the ML system 200 can include different and/or additional components or be connected in different ways. The ML system 200 is sometimes referred to as a ML module.

The ML system 200 includes a feature extraction module 208 implemented using components of the example computer system 300 illustrated and described in more detail with reference to FIG. 3. In some embodiments, the feature extraction module 208 extracts a feature vector 212 from input data 204. For example, the input data 204 can include one or more physiological parameters measured by the monitors 112 illustrated and described in more detail with reference to FIG. 1. The feature vector 212 includes features 212a, 212b, ..., 212n. The feature extraction module 208 reduces the redundancy in the input data 204, e.g., repetitive data values, to transform the input data 204 into the reduced set of features 212, e.g., features 212a, 212b, ..., 212n. The feature vector 212 contains the relevant information from the input data 204, such that events or data value thresholds of interest can be identified by the ML model 216 by using this reduced representation. In some example embodiments, the following dimensionality reduction techniques are used by the feature extraction module 208: independent component analysis, Isomap, kernel principal component analysis (PCA), latent semantic analysis, partial least squares, PCA, multifactor dimensionality reduction, nonlinear dimensionality reduction, multilinear PCA, multilinear subspace learning, semidefinite embedding, autoencoder, and deep feature synthesis.

In alternate embodiments, the ML model 216 performs deep learning (also known as deep structured learning or hierarchical learning) directly on the input data 204 to learn data representations, as opposed to using task-specific algorithms. In deep learning, no explicit feature extraction is performed; the features 212 are implicitly extracted by the ML system 200. For example, the ML model 216 can use a cascade of multiple layers of nonlinear processing units for implicit feature extraction and transformation. Each successive layer uses the output from the previous layer as input. The ML model 216 can thus learn in supervised (e.g., classification) and/or unsupervised (e.g., pattern analysis) modes. The ML model 216 can learn multiple levels of representations that correspond to different levels of abstraction, wherein the different levels form a hierarchy of concepts. In this manner, the ML model 216 can be configured to differentiate features of interest from background features.

In alternative example embodiments, the ML model 216, e.g., in the form of a CNN generates the output 224, without the need for feature extraction, directly from the input data 204. The output 224 is provided to the computer device 228 or the console 108 illustrated and described in more detail with reference to FIG. 1. The computer device 228 is a server, computer, tablet, smartphone, smart speaker, etc., implemented using components of the example computer system 300 illustrated and described in more detail with reference to FIG. 3. In some embodiments, the steps performed by the ML system 200 are stored in memory on the computer device 228 for execution. In other embodiments, the output 224 is displayed on the high-definition monitors 124 illustrated and described in more detail with reference to FIG. 1.

A CNN is a type of feed-forward artificial neural network in which the connectivity pattern between its neurons is inspired by the organization of a visual cortex. Individual cortical neurons respond to stimuli in a restricted area of space known as the receptive field. The receptive fields of different neurons partially overlap such that they tile the visual field. The response of an individual neuron to stimuli within its receptive field can be approximated mathematically by a convolution operation. CNNs are based on biological processes and are variations of multilayer perceptrons designed to use minimal amounts of preprocessing.

The ML model 216 can be a CNN that includes both convolutional layers and max pooling layers. The architecture of the ML model 216 can be "fully convolutional," which means that variable sized sensor data vectors can be fed into it. For all convolutional layers, the ML model 216 can specify a kernel size, a stride of the convolution, and an amount of zero padding applied to the input of that layer. For the pooling layers, the model 216 can specify the kernel size and stride of the pooling.

In some embodiments, the ML system 200 trains the ML model 216, based on the training data 220, to correlate the feature vector 212 to expected outputs in the training data 220. As part of the training of the ML model 216, the ML system 200 forms a training set of features and training labels by identifying a positive training set of features that have been determined to have a desired property in question, and, in some embodiments, forms a negative training set of features that lack the property in question.

The ML system 200 applies ML techniques to train the ML model 216, that when applied to the feature vector 212, outputs indications of whether the feature vector 212 has an associated desired property or properties, such as a probability that the feature vector 212 has a particular Boolean property, or an estimated value of a scalar property. The ML system 200 can further apply dimensionality reduction (e.g., via linear discriminant analysis (LDA), PCA, or the like) to reduce the amount of data in the feature vector 212 to a smaller, more representative set of data.

The ML system 200 can use supervised ML to train the ML model 216, with feature vectors of the positive training set and the negative training set serving as the inputs. In some embodiments, different ML techniques, such as linear support vector machine (linear SVM), boosting for other algorithms (e.g., AdaBoost), logistic regression, naïve Bayes, memory-based learning, random forests, bagged trees, decision trees, boosted trees, boosted stumps, neural networks, CNNs, etc., are used. In some example embodiments, a validation set 232 is formed of additional features, other than those in the training data 220, which have already been determined to have or to lack the property in question. The ML system 200 applies the trained ML model 216 to the features of the validation set 232 to quantify the accuracy of the ML model 216. Common metrics applied in accuracy measurement include: Precision and Recall, where Precision refers to a number of results the ML model 216 correctly predicted out of the total it predicted, and Recall is a number of results the ML model 216 correctly predicted out of the total number of features that had the desired property in question. In some embodiments, the ML system 200 iteratively re-trains the ML model 216 until the occurrence of a stopping condition, such as the accuracy measurement indication that the ML model 216 is sufficiently accurate, or a number of training rounds having taken place. The validation set 232 can include data corresponding to confirmed anatomical features, tissue states, tissue conditions, diagnoses, or combinations thereof. This allows the detected values to be validated using the validation set 232. The validation set 232 can be generated based on analysis to be performed.

Figure 3:
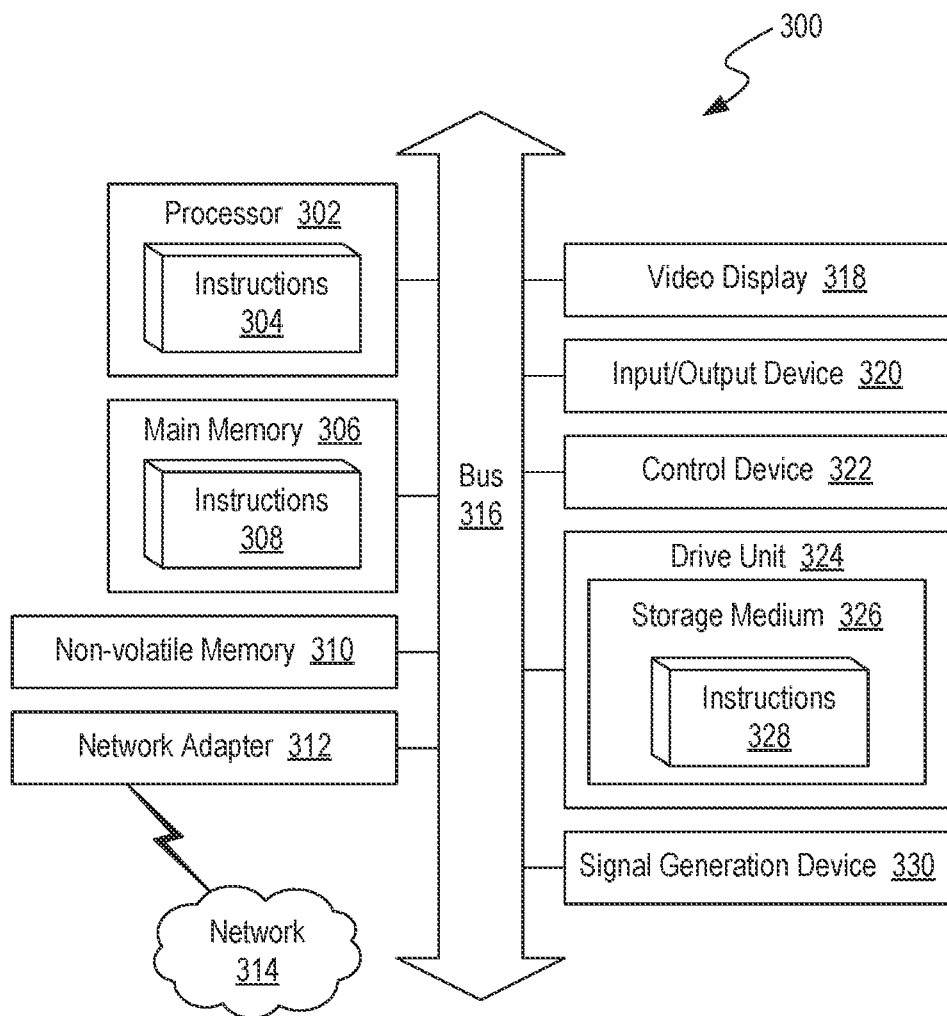
FIG. 3 is a block diagram illustrating an example computer system, in accordance with one or more embodiments.

FIG. 3 is a block diagram illustrating an example computer system, in accordance with one or more embodiments. Components of the example computer system 300 can be used to implement the monitors 112, the console 108, or the EHR database 106 illustrated and described in more detail with reference to FIG. 1. In some embodiments, components of the example computer system 300 are used to implement the ML system 200 illustrated and described in more detail with reference to FIG. 2. At least some operations described herein can be implemented on the computer system 300.

The computer system 300 can include one or more central processing units ("processors") 302, main memory 306, non-volatile memory 310, network adapters 312 (e.g., network interface), video displays 318, input/output devices 320, control devices 322 (e.g., keyboard and pointing devices), drive units 324 including a storage medium 326, and a signal generation device 320 that are communicatively connected to a bus 316. The bus 316 is illustrated as an abstraction that represents one or more physical buses and/or point-to-point connections that are connected by appropriate bridges, adapters, or controllers. The bus 316, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The computer system 300 can share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), VR/AR systems (e.g., a head-mounted display), or another electronic device capable of executing a set of instructions (sequential or otherwise) that specify action(s) to be taken by the computer system 300.

While the main memory 306, non-volatile memory 310, and storage medium 326 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 328. The term "machine-readable medium" and "storage medium" shall also be taken to include any medium that is capable of storing, encoding, or carrying a set of instructions for execution by the computer system 300.

In general, the routines executed to implement the embodiments of the disclosure can be implemented as part of an operating system or a specific application, component, program, object, module, or sequence of instructions (collectively referred to as "computer programs"). The computer programs typically include one or more instructions (e.g., instructions 304, 308, 328) set at various times in various memory and storage devices in a computer device. When read and executed by the one or more processors 302, the instruction(s) cause the computer system 300 to perform operations to execute elements involving the various aspects of the disclosure.

Moreover, while embodiments have been described in the context of fully functioning computer devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 310, floppy and other removable disks, hard disk drives, optical discs (e.g., Compact Disc Read-Only Memory (CD-ROMS), Digital Versatile Discs (DVDs)), and transmission-type media such as digital and analog communication links.

The network adapter 312 enables the computer system 300 to mediate data in a network 314 with an entity that is external to the computer system 300 through any communication protocol supported by the computer system 300 and the external entity. The network adapter 312 can include a network adapter card, a wireless network interface card, a router, an access point, a wireless router, a switch, a multilayer switch, a protocol converter, a gateway, a bridge, a bridge router, a hub, a digital media receiver, and/or a repeater.

The network adapter 312 can include a firewall that governs and/or manages permission to access proxy data in a computer network and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall can additionally manage and/or have access to an access control list that details permissions including the access and operation rights of an object by an individual, a machine, and/or an application, and the circumstances under which the permission rights stand.

Figure 4A:
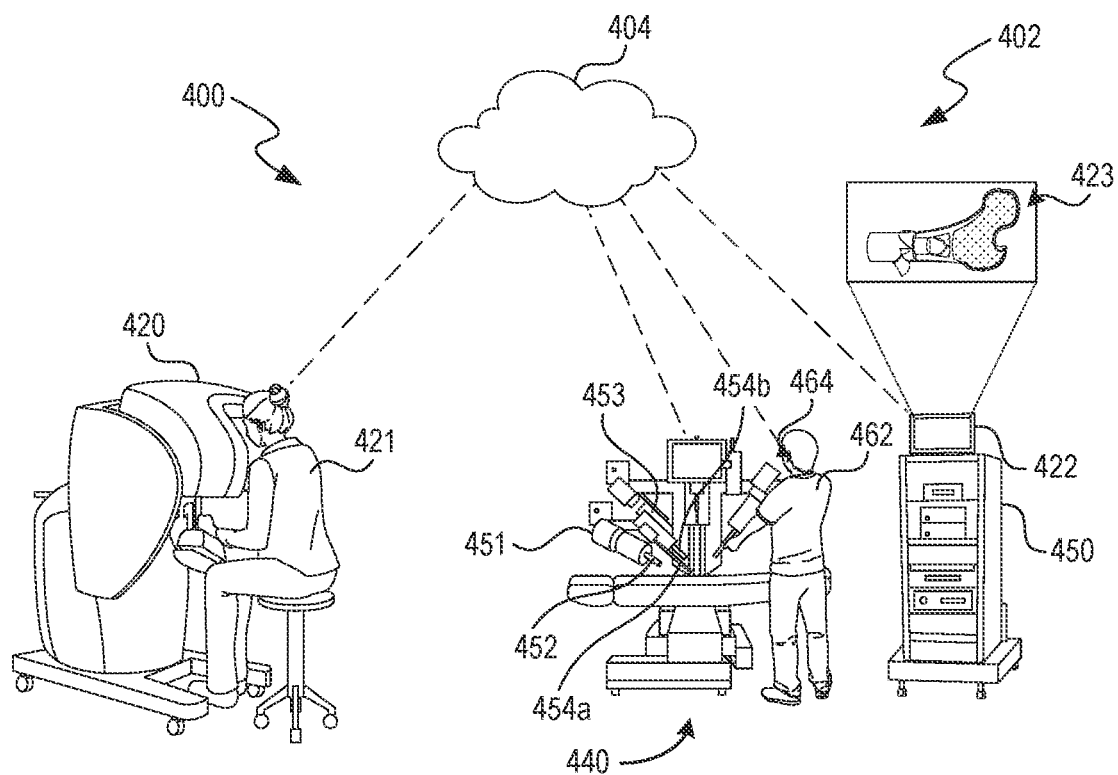
FIG. 4A is a block diagram illustrating an example robotic surgical system, in accordance with one or more embodiments.

FIG. 4A is a block diagram illustrating an example robotic surgical suite or system 400 ("robotic surgical system 400"), in accordance with one or more embodiments. The robotic surgical system 400 is the same as or similar to the robotic surgical system 160 illustrated and described in more detail with reference to FIG. 1. The robotic surgical system 400 can include components and features discussed in connection with FIGS. 1-3 and 4B-5. For example, the robotic surgical system 400 can include a console 420 with features of the console 108 of FIG. 1. Likewise, the components and features of FIG. 4A can be included or used with other embodiments disclosed herein. For example, the description of the input devices of FIG. 4A applies equally to other input devices (e.g., input devices 166 of FIG. 1). The robotic surgical system 400 can be configured to provide telepresence control by one or more consultants at remote locations based on a pre-operative surgical plan, inter-operative surgical event(s) at the surgical suite, etc. Machine learning (ML) algorithms and other techniques disclosed herein can be used to manage surgical suite resources, schedule consultants, manage permission rights, and/or adjust network flow to improve surgical outcomes. For example, flow of network traffic at the surgical suite can be controlled to maintain a threshold level of control of the medical equipment by the user. The user is typically a medical professional, e.g., a surgeon, a nurse, a surgeon's assistant, or doctor.

The robotic surgical system 400 includes a user device or console 420 ("console 420"), a surgical robot 440, and a computer, controller, or data system 450. The console 420 can be on-site or at a remote location and operated by a surgeon and can communicate with components in a surgical suite or an operating room 402 ("operating room 402"), remote devices/servers, a network 404, or databases (e.g., database 106 of FIG. 1) via the network 404. The robotic surgical system 400 can include surgical control software and can include a guidance system (e.g., ML guidance system, artificial intelligence (AI) guidance system, etc.), surgical planning software, event detection software, surgical tool software, etc., or other features disclosed herein to perform surgical step(s) or procedures or implement steps of processes discussed herein.

A consultant device 401 can communicate via the network 404 with components of the robotic surgical system 400, monitoring equipment, or other components of the robotic surgical system 400. The surgical robot 440, or other components disclosed herein, can communicate with and send collected data (e.g., sensor readings, instrument data, surgical robot data, etc.) to at least one database or data system 450, which are accessible to the consultant(s). This information can be used to, for example, create new ML training data sets, generate procedure plans, perform future simulations, post-operatively analyze surgical procedures, or the like. The controller or data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A mobile network test module may measure the latency of the wireless communication established between the robotic surgical system and the consultant device 401 to manage network flow. A measured/determined latency of a wireless network may be the same as a latency of a network that includes the wireless network, where the network may include a starting point/node for data to be transmitted to an ending point/node, and where the data is communicated by one computer/device associated with a surgical site to another computer/device associated with a location of the remote physician/surgeon. Scheduling of consultants can be based, at least in part, on expected latency (e.g., latency within the network 404 or other network) required to perform the telesurgery based on the received one or more surgery data. For example, a scheduling module may be configured to determine the requirement of the bandwidth (e.g., 10 MHz, 20 MHz, 30 MHz, etc.) needed and/or expected latency (e.g., ±50 milliseconds, 70 milliseconds, 100 milliseconds, etc.). The parameters for scheduling participation of the consultant device 401 can be selected by a surgical team, healthcare provider, or the like.

The user 421 can use the console 420 to view and control the surgical robot 440. The console 420 can be communicatively coupled to one or more components disclosed herein and can include input devices operated by one, two, or more users. The input devices can be hand-operated controls, but can alternatively, or in addition, include controls that can be operated by other parts of the user's body, such as, but not limited to, foot pedals. The console 420 can include a clutch pedal to allow the user 421 to disengage one or more sensor-actuator components from control by the surgical robot 440. The console 420 can also include display or output so that the one of more users can observe the patient being operated on, or the product being assembled, for example. In some embodiments, the display can show images, such as, but not limited to, medical images, video, etc. For surgical applications, the images could include, but are not limited to, real-time optical images, real-time ultrasound, real-time OCT images and/or other modalities, or could include pre-operative images, such as MRI, CT, PET, etc. The various imaging modalities can be selectable, programmed, superimposed, and/or can include other information superimposed in graphical and/or numerical or symbolic form.

The robotic surgical system 400 can include multiple consoles 420 to allow multiple users to simultaneously or sequentially perform portions of a surgical procedure. The term "simultaneous" herein refers to actions performed at the same time or in the same surgical step. The number and configuration of consoles 420 can be selected based on the surgical procedure to be performed, number and configurations of surgical robots, surgical team capabilities, or the like.

In embodiments, the robotic surgical system 400 performs robotic joint arthroscopic procedures based on patient data to improve outcomes. For example, the robotic surgical system 400 analyzes patient joint data to identify and evaluate anatomical structures, tissue (e.g., bone, soft tissue, etc.), biomechanics, and other features of the joints. The robotic surgical system 400 can perform one or more simulations to develop a robotic-enabled surgical plan that achieves one or more targeted outcomes. Image processing can be applied to patient images (e.g., scans, video, or the like) to determine elasticity, strength, and other properties of soft tissue, such as cartilage, tendons, synovial fluid, or the like.

The robotic surgical system 400 can assign properties to structures of the joint to accurately represent the functionality of the joint. This allows simulations to accurately represent complex anatomical structures. Advantageously, the robotic-enabled surgical plan can include surgical steps that can be performed with a higher degree of accuracy than manually performed steps. Additionally, the robotic surgical system 400 can dynamically modify surgical steps based on real-time analysis of the surgical site using ML algorithms to improve performance. In some embodiments, the robotic-enabled surgical plan can include both autonomously performed robotic surgical steps and manual surgical steps. This allows a surgical team to participate interactively with the robotic surgical system 400.

Pre-operative simulations can use a virtual patient-specific model that matches the pre-operative anatomy to generate pre-operative surgical plans. Intraoperative data can be used to generate intraoperative virtual models for intraoperative simulations performed to modify pre-operative surgical plans. For example, continuous or periodic intraoperative imaging of a surgical site can be performed to update the virtual model. If a tissue structure is modified (e.g., cut, removed, etc.), the virtual model can be updated accordingly. One or more simulations can then be performed using the modified virtual model to assess predicted outcomes based on the current state of the surgical site. Additionally, the system 900 can determine additional imaging that may be available. For example, when internal tissues are exposed via incisions or ports, the robotic surgical system 400 can automatically image the exposed internal tissue. This allows tissue analyses to be performed using near real-time or real-time acquired data.

The robotic surgical system 400 can be incorporated into or used with technology discussed in connection with FIGS. 1-8B. For example, one or more components of the robotic surgical system 400 can be incorporated into the operating room 102 discussed in connection with FIG. 1. By way of another example, a user interface and/or imaging device of the robotic surgical system 400 can be part of interface 420 discussed in connection with FIG. 4B. Output from the robotic surgical system 400 can be transmitted to controller 450 in FIG. 5 and/or various other components disclosed herein. Accordingly, the robotic surgical system 400 can be incorporated into robotic surgery systems, or utilized to perform manual surgical procedures or to perform other procedures disclosed herein.

With continued reference to FIG. 4A, the robotic surgical system 400 can include a surgical robot 440 configured to perform robotic joint arthroscopic surgery involving the extensor retinaculum. The surgical robot 440 can include the features and components discussed in connection with FIGS. 1-8B. The surgical robot 440 can receive one or more user inputs, workflow objects, and/or data files containing surgical actions for robotic movements. The user inputs can include, without limitation, type of procedure, targeted outcome, physician notes, or other user inputs disclosed herein. The workflow objects can include surgical techniques, surgical steps, surgical processes, etc. The data files can include executable instructions for performing the techniques/processes for specific surgical tools 154. The surgical robot 440 can determine one or more end effectors and/or surgical tools for performing robotic arthroscopic surgery. The end effectors and/or surgical tools can be displayed by a user interface for selective enabling and/or disabling by the user. The data files can be generated using ML algorithms and/or other techniques disclosed herein. In some embodiments, the surgical robot 440 can be designed to assist a surgeon in performing a surgical operation on a patient. The surgical robot 440 can include a controller, memory, and at least one robotic arm with an end effector. Likewise, embodiments of the system of FIG. 9 can include different and/or additional components disclosed herein or can be connected in different ways.

Robotic arthroscopic surgical steps can be displayed on the user interface (e.g., interfaces of displays 401/422, interface or GUI 461) in a sequence to enable execution of the data files containing the robotic movements. The arthroscopic surgical plan can be displayed for pre-operative viewing for surgical planning and/or intraoperative viewing (i.e., while the robotic surgical system robotically operates on the patient) for monitoring the procedure. For intraoperative viewing, the robotic surgical system 400 can determine information to be displayed based on received user input while controlling one or more of the tools operated by the robotic surgical system according to the user input. For example, predicted outcomes can be adjusted based on enabling and/or disabling of a surgical tool. The robotic surgical system 400 can select and display predicted outcomes and can also display surgical steps, surgical plans, patient databases (e.g., patient databases), joint data (e.g., joint data discussed in connection with FIGS. 6B and 7-8B), or other data. For example, a patient database and associated real-time generated predicted joint movement can be simultaneously displayed while the robotic surgical system 400 controls end effectors or surgical tools 154.

The robotic surgical system 400 automatically designs a surgical workflow for and performs robotic joint arthroscopic surgery. The system of FIG. 9 includes surgical robot 440, which is a robotic system designed to perform or assist a surgeon in performing a surgical operation on a patient. In embodiments, surgical robot 440 includes a controller, a memory, and at least one robotic arm having an end effector. Likewise, embodiments of the robotic surgical system 400 can include different and/or additional components or can be connected in different ways.

In embodiments, the robotic surgical system 400 performs one or more multi-modality analyses in which one or more multi-sensing devices (e.g., multi-modality imagers, multiple imaging machines, etc.) perform (sequentially or concurrently) multiple scans/tests, such as CT scans, radiation tests, sound tests, optical tests, acoustic tests, photoacoustic tests, combinations thereof, or the like. In embodiments, a multi-modality image can simultaneously image a target region to capture images with matching perspectives relative to the target region such that features from one image can be overlayed onto another, features from multiple images can be stitched together to form a composite image, and/or cross-image features identification can be performed.

The robotic surgical system 400 can perform multi-modality imaging pre-operatively, intraoperatively, and/or post-operatively. Pre-operative images can be used to generate pre-operative plans. Intraoperative images can be used to modify surgical plans, update virtual models of surgical sites, provide monitoring of the surgical procedure to a surgical team, or combinations thereof. Post-operative multiple images can be generated to evaluate the predicted outcome of the procedure, success of the procedure, or the like. In some embodiments, tests are performed during one or more scans of the target region. In a single scan test, the robotic surgical system 400 can concurrently perform multiple tests while moving along the tissue sample. In multiple scan tests, the robotic surgical system 400 sequentially performs tests during corresponding scans and/or concurrently performs multiple tests during each scan. The tests can include, without limitation, mobility tests, range of motion tests, stability tests (e.g., lateral angle stability tests), and functional tests (e.g., foot lift tests, functional hop tests, Y-balance tests, etc.), and can be performed for one or more regions of interest. The robotic surgical system 400 can generate scanning/testing protocols for specific joints based on the patient's condition. The robotic surgical system 400 can perform different testing, imaging, and/or scanning protocols based on the analysis to be performed. The robotic surgical system 400 can compare pre-operative data and post-operative data to determine prediction accuracy scores for the surgical procedure, rehabilitation protocols, or the like. In response to prediction accuracy scores falling below a threshold score, the ML algorithm can be retrained to increase accuracy scores. The robotic surgical system 400 can generate patient-specific rehabilitation protocols based on the post-operative condition of the patient.

The robotic surgical system 400 can generate a virtual model based on captured images and can perform surgical simulations using the virtual model to predict at least one of joint functionality, stability of the joint, or the like. In embodiments, robotic surgical system 400 determines a next step of a surgical procedure to be performed by surgical robot 440 in accordance with a surgical plan. For example, an arthroscopic surgical plan can be modified based on the surgical simulations to achieve at least one of target post-operative functionality, stability of the joint, or other characteristics of the joints. Pre-operative images can be used to perform pre-operative surgical simulations to generate an initial surgical plan. Intraoperative images can be used to perform intraoperative simulations to allow for adjustments to the surgical plan based on newly captured image data. For example, if an unplanned alteration to tissue occurs, robotic surgical system 400 can identify the alteration and perform new simulations to determine how the alteration may affect the joint. The robotic surgical system 400 generates a modified surgical plan to achieve desired post-operative outcomes.

The robotic surgical system 400 can control imaging equipment to capture images of the altered tissue to generate an alternate or modified surgical plan. In the procedures discussed herein, the robotic surgical system 400 can acquire and analyze images to determine how to robotically apply one or more sutures to anchors. Post-operative simulations (e.g., functionality simulations, stability simulations, range of motion simulations) can use a real-time three-dimensionally generated virtual model. In some procedures, the robotic surgical system 400 can identify, using image processing techniques, one or more damaged tissue structures contributing to instability of a joint. The robotic surgical system 400 can then determine locations of anchoring and tethers for compensating for the one or more damaged tissue structures so as to, for example, increase stability of the joint while maintaining a predetermined threshold joint functionality value. The predetermined threshold joint functionality value for maintaining a minimum range of motion of the joint can be inputted by the user or determined by robotic surgical system 400. Example ranges of motion of joints are discussed in connection with FIGS. 7, 8A, and 8B.

In embodiments, tests are performed during one or more scans of the target region. In a single scan test, the robotic surgical system 400 can concurrently perform multiple tests while moving along the tissue sample. In multiple scan tests, system 600 sequentially performs tests during corresponding scans and/or concurrently performs multiple tests during each scan. The robotic surgical system 400 can perform different testing, imaging, and/or scanning protocols based on the analysis to be performed.

The robotic surgical system 400 can facilitate communication with another robotic surgical system, doctor, surgeon, or other medical professional by providing results (e.g., multi-modality data, raw data, visualizations of the data, and the like) from the test(s) in real-time. Further, the robotic surgical system 400 can combine the results from imaging device(s) to provide a diagnosis of a tissue sample, target region, surgical site, or combinations thereof. In surgical procedures, the results can be automatically transmitted to a surgical robot that analyzes the results to perform one or more surgical steps. Surgical robot 440 can request additional information from the robotic surgical system 400 to, for example, complete a surgical step, confirm completion of a surgical step, plan a surgical step, plan a series of surgical steps, or the like. For example, robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by user 421 of FIG. 4A while, for example, monitoring or performing one or more surgical steps.

The robotic surgical system 400 includes the surgical robot 440 for performing robotic joint arthroscopic surgery for the lateral EDL tendon portion of the anatomy. The EDL is situated at the lateral part of the front of the leg. The EDL arises from the lateral condyle of the tibia, from the upper three-quarters of the anterior surface of the body of the fibula, from the upper part of the interosseous membrane, from the deep surface of the fascia, and from the intermuscular septa between the EDL and the tibialis anterior on the medial, and the peroneal muscles on the lateral side. Between the EDL and the tibialis anterior are the upper portions of the anterior tibial vessels and deep peroneal nerve. The EDL passes under the superior and inferior extensor retinaculum of the foot in company with the fibularis tertius, and divides into four slips, which run forward on the dorsum of the foot and are inserted into the second and third phalanges of the four lesser toes. The extensor retinaculum of the arm is located on the back of the forearm, just proximal to the hand. The extensor retinaculum is continuous with the palmar carpal ligament, which is located on the anterior side of the forearm. The superior extensor retinaculum of the leg is the upper part of the extensor retinaculum of the foot, which extends from the ankle to the heelbone.

The surgical robot 440 can request additional information from the robotic surgical system 400 to, for example, complete a surgical step, confirm completion of a surgical step, plan a surgical step, plan a series of surgical steps, or the like. For example, the robotic surgical system 400 can receive multi-modality results from another system to perform a multi-modality-guided robotic surgical step. In embodiments, the results are displayed via display 422 for viewing by the surgical team, as shown in FIG. 4A. Additionally, or alternatively, the results can be viewable via console 420 by a user 421 of FIG. 4A while, for example, monitoring or performing one or more surgical steps.

The robotic surgical system 400 comprises surgical robot 440, which is a robotic system designed to assist a surgeon in performing a surgical operation on a patient. Surgical robot 440 includes a controller, memory, and at least one robotic arm with an end effector. Surgical robot 440 may further include a user interface for accepting control inputs from a user, such as a surgeon or other medical professional and a communications interface for transmitting and receiving data to and from a cloud for the purpose of training an AI operating within the surgical robot or receiving remote commands from a remote user or an AI existing external to the surgical robot 440. The surgical robot 440 may additionally comprise a plurality of sensors for providing feedback to the user or an AI.

In embodiments, robotic surgical system 400 is used to simulate virtual models. Virtual models can be two-dimensional virtual models, three-dimensional models, and other models for representing anatomical features of the patient. The virtual models can have predefined kinematics, properties (e.g., tissue properties, cartilage properties, bone properties, implant properties, suture properties, anchor properties, etc.), dynamic characteristics, or the like. This allows virtual models to accurately represent pre-operative conditions of complex anatomical structures, such as joints, movement of surgical robots, operation of tools, etc. Preoperative virtual models can represent predicted outcomes for joints, such as improved functionality, stability, or the like. The virtual models can be used to perform simulations to generate simulation data. In some embodiments, virtual models can incorporate or be based on 3D renderings of medical images.

Extended-reality surgical simulation environments can include virtual models that can be manipulated to simulate robotic steps performed by a surgical robot under control of the user, operating autonomously according to a surgical plan, etc. User input (e.g., user input via hand controls, a user interface, voice commands, etc.) can be used to control movements of virtual models of tools, end effectors, manipulators, multiple surgical robots, or the like. The surgical steps can be also be performed on virtual models representing anatomical structures. The system and/or user can analyze the simulated surgical steps to modify surgical plans, determine surgical steps, practice surgical steps, or the like. In some embodiments, the system can receive multiple models from databases, including manufacturer databases (e.g., manufactures of surgical equipment), hospital databases, etc. The models can be transformed into virtual models that can be imported into a single simulation environment. For example, the system can retrieve stored CAD models (e.g., IGES files, STEP files, universal CAD files) from manufactures of surgical instruments. The CAD models can be converted into virtual models that can be imported into the surgical simulation environment. This allows simulations to be performed for equipment from different manufactures. The robotic surgical system 400 can generate three-dimensional movements (e.g., anatomical movements, movements of the surgical tools, movements of the surgical robot, movements of implants, etc.) within the extended-reality (XR) surgical simulation environment to simulate surgical steps performed by the one or more surgical tools.

A 3D rendering is a mathematical representation of an object or surface as such object or surface would appear by width, breadth, and depth dimensions. The 3D rendering that is generated transforms the medical images into high-quality, detailed, and lifelike images. The 3D rendering can be generated by robotic surgical system 400. For example, robotic surgical system 400 uses computer graphics processing to generate 3D data and models. The robotic surgical system 400 creates a lifelike or non-photorealistic image. The 3D rendering output is a digital file of an object created using software or through 3D scanning.

In embodiments, robotic surgical system 400 includes a CAD GUI. The CAD GUI is a user interface for a computer software system to design surgical processes for patients. CAD refers to the use of computers to aid in the creation, modification, analysis, or optimization of a design, such as a surgical procedure. CAD software is used to increase the productivity of the designer or user, such as a doctor or medical professional, to improve the quality of design, to improve communications through documentation, and to create a database for the procedure. CAD output is often in the form of electronic files for print, machining, or other manufacturing operations.

The GUI is an interface(s) that may either accept inputs from users, provide outputs to users, or perform both actions. In one case, a user can interact with the interface(s) using one or more user-interactive objects and devices. The user-interactive objects and devices may include user input buttons, switches, knobs, levers, keys, trackballs, touchpads, cameras, microphones, motion sensors, heat sensors, inertial sensors, touch sensors, or a combination of the above. Further, the interface(s) may be implemented as a command line interface (CLI), a GUI, a voice interface, or a web-based user interface.

The CAD GUI enables a user, such as a surgeon, doctor, medical professional, etc., to view an area of a patient's body that requires surgery in a 3D space. The CAD GUI also allows the user to select various surgical tools 154, materials, and techniques required for the surgery and allows the user to manipulate the surgical tools 154, materials, and techniques, as rendered over the patient's 3D image to perform the processes and steps needed for the surgery in a virtual space. The user's movements and actions may be saved and stored in an operation database to assist the surgeon in performing the surgery or to provide the surgical robot 440 with the approximate (x, y, z) coordinates to perform the surgery.

The CAD GUI allows other users to view or replay the surgery in the 3D space to alter or adjust movements or actions to perform the surgery. In some embodiments, the CAD GUI may provide the user or surgical robot 440 with a list of materials needed, a list of surgical tools 154 required, a workflow process of the surgical procedure, a 3D visual replay of the surgical procedure, etc. A hospital network provides medical information of a patient to the surgical robot network, such as electronic health records, medical images (MRIs, X-rays, etc.), a list of the patient's doctors and health care professionals, the patient's current medications and prescriptions, the patient's medical history, the names of the patient's specialists, etc.

A GUI or guided user interface may be an interface(s) may either accept inputs from users or provide outputs to the users or may perform both the actions. In one case, a user can interact with the interface(s) using one or more user-interactive objects and devices. The user-interactive objects and devices may comprise user input buttons, switches, knobs, levers, keys, trackballs, touchpads, cameras, microphones, motion sensors, heat sensors, inertial sensors, touch sensors, or a combination of the above. Further, the interface(s) may either be implemented as a CLI, a GUI, a voice interface, or a web-based user interface. The CAD GUI 946 allows a user, such as a surgeon, doctor, medical professional, etc., to view an area of a patient's body that requires surgery in a 3D space. In embodiments, at least one surgical step described by a surgical workflow is indicated by a user using CAD GUI 946. For example, CAD GUI 946 enables a user to select various surgical tools 154, materials, and techniques required for the surgery and allows the user to manipulate the surgical tools 154, materials, and techniques, rendered over a patient's 3D image to perform the processes and steps needed for the surgery in a virtual space.

In embodiments, one or more ML systems trained to correlate feature vectors to prior patient data having favorable outcomes are executed. For example, surgical robot 440 includes one or more ML systems trained to correlate feature vectors to expected outputs in the training data. As part of the training of an ML model, the ML system can form a training set of favorable outcomes (e.g., prior patient data with favorable outcomes) and training labels by identifying a positive training set of features that have been determined to have a desired property in question, and, in some embodiments, forms a negative training set of features that lack the property in question. The property in question can include, without limitation, one or more threshold outcomes/scores, therapeutic effect(s), or other criteria selected by, for example, a user or surgical team.

The surgical robot 440 can include a correlation module configured to retrieve data from a surgery database based on the surgery type. The correlation module performs correlations on selected parameter(s) to determine if parameters are highly correlated. The correlation module determines if the correlation coefficient is over the predetermined threshold, for example, over a correlation coefficient (e.g., a predetermined correlation coefficient). If it is determined that the correlation coefficient is over the predetermined threshold, then the correlation module extracts the best match data point from the data set. The correlation module then stores the data entry for the best match data point in a recommendation database. If it is determined that the correlation coefficient is not over the predetermined threshold, or after the data entry for the best match data point is stored in the recommendation database, the correlation module determines if there are more parameters remaining in the surgery database. If it is determined that there are more parameters remaining in the surgery database, the correlation module selects the next parameter in the surgery database and the process returns to performing correlations on the parameters. If it is determined that there are no more parameters remaining in the surgery database, the correlation module returns to the base module.

The recommendation module can begin by being initiated by the base module. The recommendation module filters the recommendation database based on the correlation coefficient (e.g., the highest correlation coefficient). The recommendation module selects the highest correlated data entry in the recommendation database. Other techniques can be used.

For arthroscopic procedures, the training data can include, without limitation, pre-operative data, post-operative data, outcomes (e.g., short-term outcomes, long-term outcomes, etc.), and surgical data (e.g., adverse events, physician input, etc.). For leg-related procedures, the training data can include threshold criteria (e.g., threshold values, threshold scores, etc.), scores (e.g., American Orthopedic Foot and Ankle Society (AOFAS) score, Visual Analogue Scale (VAS) score, Cumberland Ankle Instability Tool (CAIT) scores, quality of life scores, pain scores, etc.), stress radiographs to measure tilt test (e.g., talar tilt test) and anterior drawer tests, or the like. The threshold criteria can be selected as a favorable outcome. The values/scores can be selected as threshold outcomes or therapeutic effect(s) for approving surgical plans, simulations, etc. For arm-related procedures, the training data can include, without limitation, thresholding values/scores, Disabilities of the Arm, Shoulder, and Hand (DASH) questionnaire scores, etc. The surgical robot 440 can set up and train the ML model as discussed in connection with FIG. 2 and can include one or more ML systems (e.g., ML system 200 of FIG. 2).

The surgical robot 440 can also generate surgical procedures or plans with joint stabilization predictions (e.g., post-operative stability scores of joints, long-term stability scores of joints, etc.), joint mechanics predictions (e.g., one or more target characteristics of joint mechanics), predicted restored function of the joint, combinations thereof, or the like. The surgical robot 440 can manage pain by, for example, determining ligament-attachment joint stabilization steps for utilizing connectors to adjust movement of the joint. For example, robotic surgical system 400 can identify attachment sites to be physically connected to other structures (e.g., ligaments, bones, muscle, etc.) of the joints.

In some implementations, robotic surgical system 400 can identify one or more attachment points along an anatomical structure (e.g., extensor retinaculum, dorsal carpal ligament, posterior annular ligament, antebrachial fascia, etc.) that are capable of serving as attachment points for limiting motion of the joint, reinforcing the joint, limiting range of motion of the joint, combinations thereof, or the like. Images of the anatomical structure can be analyzed to determine the contribution of the anatomical structure to properties of the joint. The robotic surgical system 400 can then identify the number and position of attachment points based on the desired forces to be applied to the anatomical structures. The properties of implantable connectors can be selected based on target outcomes. For example, unextendible, flexible sutures can connect a ligament to a bone on the opposite side of a joint to limit or fix a range of motion of a joint. This can allow the joint to have normal range of motion in one direction while limiting the range of motion in an opposite direction.

The surgical robot 440 can use one or more ML systems to analyze real-time data (e.g., video, images, etc.) of a surgery site to determine one or more candidate surgical steps, generate predicted outcomes for candidate surgical steps, and/or generate simulations for physician review. As shown in FIG. 4C, a physician can view a surgical site 465 annotated with, for example, labeled structures of a joint, joint mechanics information, plan surgical steps, surgical tools, or the like.

In embodiments, robotic surgical system 400 analyzes patient joint data to evaluate at least one of anatomical structures, tissue, or biomechanics of joints of the patient. A simulation is performed to generate a surgical plan, wherein the surgical plan is intended to achieve a targeted outcome for the surgical procedure. For example, patient data 472 includes, without limitation, target sites (e.g., attachment sites, anchor sites), joint data, mobility data, and other patient data related to the surgical procedure. Example information for display is discussed in connection with FIGS. 6A, 6B, 7, 8A, and 8B. The robotic surgical system 400 can predict post-operative outcomes based on, for example, properties of ligaments, properties of implantable connectors, etc. to improve joint stabilization, limit disease progression, and/or improve patient biomechanics. The predicted post-operative outcomes can be for a selected time or period of time. For example, robotic surgical system 400 can predict post-operative outcomes one month after surgery, six months after surgery, one year after surgery, two years after surgery, or the like. Age-related changes to anatomical structures, tissue, and other anatomical elements can be used to generate the predicted time-varying post-operative outcomes. By way of example, soft tissue, such as ligaments, may become hardened or lose elasticity over a period of time. The robotic surgical system 400 can predict biomechanics at joints based on such tissue changes. This allows a user to evaluate long-term outcomes of surgical procedures based on typical age-related effects.

In embodiments, patient joint data comprises patient images. Analyzing the patient joint data comprises applying image processing to the patient images to determine elasticity or strength of at least one of cartilage, tendons, or synovial fluid of the patient. For example, robotic surgical system 400 generates post-operative outcomes based on different types of simulations. The simulations can include nonlinear characteristics (e.g., micromechanics, mechanical behavior, etc.) of soft tissue. Linear, nonlinear, and other mechanical properties can be applied to tissue to generate linear finite element models, nonlinear finite element models, joint modeling (e.g., linear joint modeling, nonlinear joint modeling, dynamic joint modeling, etc.), or the like. For example, the robotic surgical system 400 can model and simulate the dynamic behavior of nonlinear anatomical structures of a joint. The dominant characteristics of the joints can be identified and used to determine anatomical features to be modified.

In embodiments, robotic surgical system 400 includes an imaging device, which is any device capable of collecting data which can be used to create an image, or a representation of a physical structure or phenomena. In embodiments, a plurality of surgical tools comprise an imaging sensor. The terms imaging device and imaging sensor are used interchangeably herein. The imaging device can include any device capable of detecting sound or electromagnetic waves and assembling a visual representation of the detected waves. Imaging devices can collect waves from any part of the electromagnetic spectrum or sounds at any range of frequencies, often as a matrix of independently acquired measurements that each represent a pixel of a 2D or 3D image. These measurements may be taken simultaneously or in series via a scanning process or a combination of methods. Some pixels of an image produced by an imaging device may be interpolated from direct measurements representing adjacent pixels in order to increase the resolution of a generated image.

The imaging device can include an algorithm or software module capable of determining qualitative or quantitative data from medical images. The algorithm can be a deep learning algorithm trained on a data set of medical images. The imaging device may further refer to a device used to acquire medical imagery by any means including MRI, CT, or X-ray. The imaging device may further refer to a device used to acquire medical imagery by PET, ultrasound, or arthrography. The imaging device may further refer to a device used to acquire medical imagery by angiography, fluoroscopy, or myelography.

The imaging device can be controlled to acquire images that can be annotated with, for example, patient information, procedure information, or the like. The patient information can include, without limitation, damaged structures of the joint, joint mechanics information (e.g., a range of motion, degrees of freedom, areas contributing to joint instability, motion of FIGS. 7-8B, etc.), ligaments, bone, soft tissue, muscle, synovial sacs, or the like. The procedure information can include, for example, completed surgical steps, planned future surgical steps, information (e.g., calculations, technique information, etc.), attachment sites (e.g., anchor sites, suture sites, etc.), connector information (e.g., number of connectors, dimensions of connectors, properties of connectors, orientation of connectors, routing of connectors, etc.), and other information discussed in connection with FIGS. 1-8B, and other information disclosed herein.

The imaging device refers to any device capable of collecting data which can be used to create an image, or a representation of a physical structure or phenomena. An imaging device may include any device capable of detecting sound or electromagnetic waves and assembling a visual representation of the detected waves. The imaging device may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device can be interpolated from direct measurements representing adjacent pixels in order to increase the resolution of a generated image.

In embodiments, a surgery is designed to address ankle instability to, for example, improve an outcome score, such as the AOFAS score, VAS score, overall joint score, composite joint score (e.g., composite score based on weighted AOFAS and VAS scores), etc. For example, the ankle can be pre-operatively and/or post-operatively evaluated to generate both pre-operative scores (e.g., AOFAS scores, VAS scores, etc.), and/or post-operative scores. Scores can be used to evaluate the ankles, subtalar, talonavicular, and calcaneocuboid joints, as well as arthrodesis, fractures, arthroplasty, and instabilities. The wrists, hands, shoulders, knee, and other anatomical structures can be scored using different scoring protocols.

In embodiments, robotic surgical system 400 determines that a surgical step is complete based on a surgical plan. For example, the surgical plan is generated to achieve a threshold score, increase/decrease a pre-operative score(s) (e.g., threshold increase/decrease of AOFAS score, VAS score, respectively), etc. The Brostrom-Gould repair surgery is primarily used to repair the anterior talofibular ligament (ATFL) in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

Figure 4B:
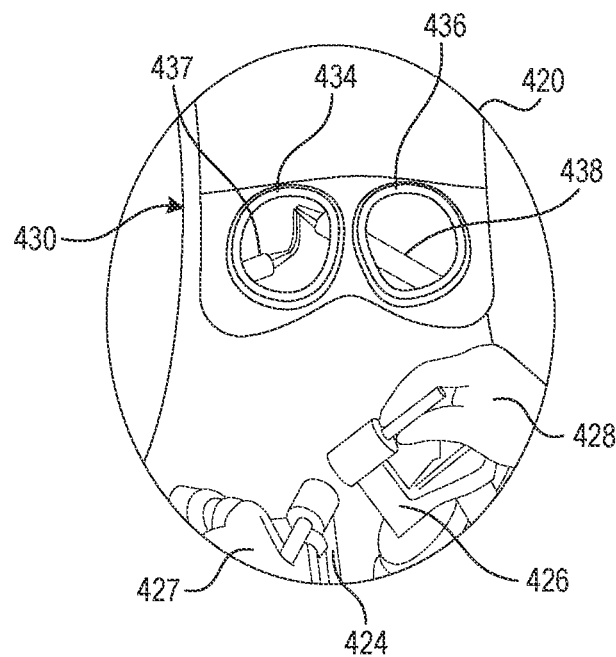
FIG. 4B illustrates an example console of the robotic surgical system of FIG. 4A, in accordance with one or more embodiments.
Figure 4C:
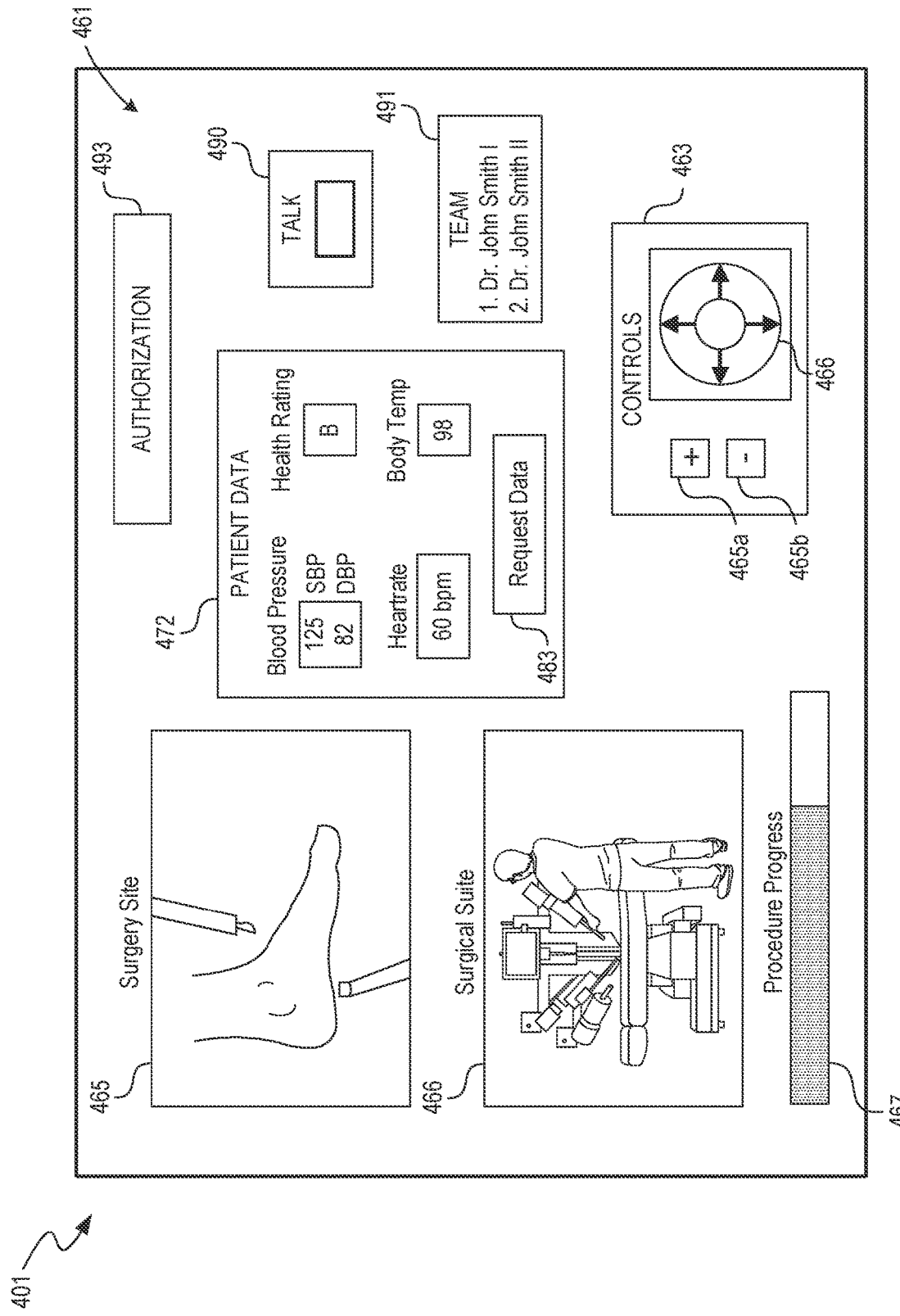
FIG. 4C illustrates an example display of a user device, in accordance with one or more embodiments.

FIG. 4B illustrates an example console 420 of the robotic surgical system 400 of FIG. 4A, in accordance with one or more embodiments. The console 420 includes hand-operated input devices 424, 426, illustrated held by the user's left and right hands 427, 428, respectively. A viewer 430 includes left and right eye displays 434, 436. The user can view, for example, the surgical site, instruments 437, 438, or the like. The user's movements of the input devices 424, 426 can be translated in real-time to, for example, mimic the movement of the user on the viewer 430 and display (e.g., display 124 of FIG. 1) and within the patient's body while the user can be provided with output, such as alerts, notifications, and information. The information can include, without limitation, surgical or implantation plans, patient vitals, modification to surgical plans, values, scores, predictions, simulations, and other output, data, and information disclosed herein. The console 420 can be located at the surgical room or at a remote location.

The viewer 430 can display at least a portion of a surgical plan, including multiwavelength images, image modality information, fused data sets, tissue types, mapped images (e.g., tissue types maps, bone tissue maps, tissue density maps, diseased tissue maps, tissue condition maps, etc.), past and future surgical steps, patient monitor readings (e.g., vitals), surgical room information (e.g., available team members, available surgical equipment, surgical robot status, or the like), images (e.g., pre-operative images, images from simulations, real-time images, instructional images, etc.), and other surgical assist information. In some embodiments, the viewer 430 can be a VR/AR headset, display, or the like. The robotic surgical system 400, illustrated and described in more detail with reference to FIG. 4A, can further include multiple viewers 430 so that multiple members of a surgical team can view the surgical procedure. The number and configuration of the viewers 430 can be selected based on the configuration and number of surgical robots.

In some embodiments, user 462 uses a visualization device 464 to monitor a surgical procedure. The visualization device 464 is a wearable artificial reality or extended reality (XR) device. The visualization device 464 can communicate, via the network 404, with components of the operating room 402 and can be a wearable augmented-reality (AR) device that provides virtually reality simulations for assisting with surgical procedures by, for example, displaying information (e.g., surgical plan information, identifying anatomical features (e.g., tissue, organs, abnormal features, normal features, or non-targeted tissue), or other information. The system 400 can coordinate or synchronize activities of the user. Example visualization devices are discussed in connection with FIGS. 9-12.

Referring again to FIG. 4A, the surgical robot 440 can include one or more controllers, computers, sensors, arms, articulators, joints, links, grippers, motors, actuators, imaging systems, effector interfaces, end effectors, or the like. For example, a surgical robot with a high number of degrees of freedom can be used to perform complicated procedures whereas a surgical robot with a low number of degrees of freedom can be used to perform simple procedures. The configuration (e.g., number of arms, articulators, degrees of freedom, etc.) and functionality of the surgical robot 440 can be selected based on the procedures to be performed.

The surgical robot 440 can operate in different modes selected by a user, set by the surgical plan, and/or selected by the robotic surgical system 400. The user is typically a medical professional, e.g., a surgeon, a nurse, a surgeon's assistant, or doctor. In some procedures, the surgical robot 440 can remain in the same mode throughout a surgical procedure. In other procedures, the surgical robot 440 can be switched between modes any number of times. The configuration, functionality, number of modes, and type of modes can be selected based on the desired functionality and user control of the robotic surgical system 400. The robotic surgical system 400 can switch between modes based on one or more features, such as triggers, notifications, warnings, events, etc. Different example modes are discussed below. A trigger can be implemented in software to execute a jump to a particular instruction or step of a program. A trigger can be implemented in hardware, e.g., by applying a pulse to a trigger circuit.

In a user control mode, a user 421 controls, via the console 420, movement of the surgical robot 440. The user's movements of the input devices can be translated in real-time into movement of end effectors 452 (one identified).

In a semi-autonomous mode, the user 421 controls selected steps and the surgical robot 440 autonomously performs other steps. For example, the user 421 can control one robotic arm to perform one surgical step while the surgical robot 440 autonomously controls one or more of the other arms to concurrently perform another surgical step. In another example, the user 421 can perform steps suitable for physician control. After completion, the surgical robot 440 can perform steps involving coordination between three or more robotic arms, thereby enabling complicated procedures. For example, the surgical robot 440 can perform steps involving four or five surgical arms, each with one or more end effectors 452. The surgical robot 440 can include a multi-modality imager 453 having imaging devices 454*a*, 454*b* (collectively "imaging devices 454"). The imaging devices 454 can be, for example, PET scanners, ultrasound imagers, MRI imagers, CT scanners, cameras (e.g., camera imager hardware, digital cameras, etc.), infrared imagers, etc. In embodiments, the surgical robot 440 retrieves/receives images from stand-alone X-ray machines, MRI machines, CT scanners, etc. Example imaging devices and imaging modalities are discussed in connection with FIGS. 1, 4A, and 6. The number, imaging capabilities, and configurations of the imaging devices 454 can be selected based on the imaging to be performed.

The robotic surgical system 400 can automatically generate multi-modality images based on surgical plans and then perform one or more surgical steps of a planned surgical procedure. In embodiments, the robotic surgical system 400 analyzes a surgical plan for a patient to generate an imaging plan for obtaining patient information for diagnostic purposes, modifying the surgical plan, performing surgical steps (e.g., one surgical step, multiple surgical steps, all surgical steps), etc. The imaging plan can include, without limitation, one or more regions of interest, targeted information, predicted features of interest, information for diagnostic purposes, or the like. The robotic surgical system 400 can generate the imaging plan based on imaging capabilities of the multi-modality imager 453. The robotic surgical system 400 can notify the surgical team to add or replace imaging devices 454 to achieve the desired imaging capability.

The robotic surgical system 400 can retrieve available images of a patient from, for example, electronic medical records, image databases, and/or other imaging sources. The robotic surgical system 400 can identify and retrieve images that can be processed for producing one or more multi-modality images. The robotic surgical system 400 can determine whether additional unavailable images could be useful for generating multi-modality images that (1) meet at least one threshold criteria (e.g., a confidence score), (2) identify features of interest, (3) have diagnostic capability criteria, etc. In some procedures, the robotic surgical system 400 retrieves available images and determines imaging programs or parameters (e.g., positions, imaging settings, etc.) of one or more of the imaging devices 454 corresponding to the available images. In embodiments, an ML system (see FIG. 2) can be used to generate imaging plans based on training sets. The training sets can include, for example, single modality training sets, composite multi-modality training sets, confirmed diagnostic training sets, and other training sets. This allows the robotic surgical system 400 to perform re-training procedures for continuously or periodically training the ML system. Newly captured images can be keyed to or matched with the retrieved images, thereby increasing accuracy of the multi-modality images. During intro-operative imaging, the images can be analyzed in real-time to further control the robotic surgical system 400.

In an autonomous mode, the surgical robot 440 can autonomously perform steps under the control of the data system 450. The robotic surgical system 400 can be pre-programmed with instructions for performing the steps autonomously. For example, command instructions can be generated based on a surgical plan. The surgical robot 440 autonomously performs steps or the entire procedure. The user 421 and surgical team can observe the surgical procedure to modify or stop the procedure. Advantageously, complicated procedures can be autonomously performed without user intervention to enable the surgical team to focus and attend to other tasks. Although the robotic surgical system 400 can autonomously perform steps, the surgical team can provide information in real-time that is used to continue the surgical procedure. The information can include surgical robot input, surgical team observations, and other data input.

The robotic surgical system 400 can also adapt to the user control to facilitate completion of the surgical procedure. In some embodiments, the robotic surgical system 400 can monitor, via one or more sensors, at least a portion of the surgical procedure performed by the surgical robot 440. The robotic surgical system 400 can identify an event, such as a potential adverse surgical event, associated with a robotically performed surgical task. For example, a potential adverse surgical event can be determined based on acquired monitoring data and information for the end effector, such as surgical tool data from a medical device report, database, manufacturer, etc. The robotic surgical system 400 can perform one or more actions based on the identified event. The actions can include, without limitation, modification of the surgical plan to address the potential adverse surgical event, thereby reducing the risk of the event occurring. The adverse surgical event can include one or more operating parameters approaching respective critical thresholds. The adverse surgical events can be identified using an ML model trained using, for example, prior patient data, training sets (e.g., tool data), etc.

In some embodiments, the robotic surgical system 400 determines whether a detected event (e.g., operational parameters outside a target range or exceeding a threshold, etc.) is potentially an adverse surgical event based on one or more criteria set by the robotic surgical system 400, user, or both. The adverse surgical event can be an adverse physiological event of the patient, surgical robotic malfunction, surgical errors, or other event that can adversely affect the patient or the outcome of the surgery. Surgical events can be defined and inputted by the user, surgical team, healthcare provider, manufacturer of the robotic surgery system, or the like.

The robotic surgical system 400 can take other actions in response to identification of an event. If the robotic surgical system 400 identifies an end effector malfunction or error, the robotic surgical system 400 can stop usage of the end effector and replace the malfunctioning component (e.g., surgical tool or equipment) to complete the procedure. The robotic surgical system 400 can monitor hospital inventory, available resources in the surgical room 402, time to acquire equipment (e.g., time to acquire replacement end effectors, surgical tools, or other equipment), and other information to determine how to proceed with surgery. The robotic surgical system 400 can generate multiple proposed surgical plans for continuing with the surgical procedure. The user and surgical team can review the proposed surgical plans to select an appropriate surgical plan. The robotic surgical system 400 can modify a surgical plan with one or more corrective surgical steps based on identified surgical complications, sensor readings, or the like. The surgical steps include, without limitation, cauterizing, cutting tissue, clamping tissue, stapling tissue, excising tissue, implanting items, alternative steps to replace planned surgical steps, manipulating tissue, or other steps disclosed herein. The surgical steps can be selected to keep the patient's vital(s) within a target range, for example, based on one or more surgical criteria (e.g., overall surgical time, length of surgical step, etc.).

The robotic surgical system 400 can retrieve surgical system information from a database to identify events. The database can describe, for example, maintenance of the robotic surgery system, specifications of the robotic surgery system, specifications of end effectors, surgical procedure information for surgical tools, consumable information associated with surgical tools, operational programs and parameters for surgical tools, monitoring protocols for surgical tools, or the like. The robotic surgical system 400 can use other information in databases disclosed herein to generate rules for triggering actions, identifying warnings, defining events, or the like. Databases can be updated with data (e.g., intraoperative data collected during the surgical procedure, simulation data, etc.) to intraoperatively adjust surgical plans, collect data for ML/AI training sets, or the like. Data from on-site and off-site simulations (e.g., pre-, or postoperative virtual simulations, simulations using models, etc.) can be generated and collected.

The surgical robot 440 can include robotic arms 451 (one identified) with robotic links, motors, and integrated or removable end effectors 452 (one identified). The end effectors 452 can include, without limitation, imagers (e.g., cameras, optical guides, etc.), robotic grippers, instrument holders, cutting instruments (e.g., cutters, scalpels, or the like), drills, cannulas, reamers, rongeurs, scissors, clamps, or other equipment or surgical tools disclosed herein. In some embodiments, the end effectors can be reusable or disposable surgical tools. The number and configuration of end effectors can be selected based on the configuration of the robotic system, procedure to be performed, surgical plan, etc. Imaging and viewing technologies can integrate with the surgical robot 440 to provide more intelligent and intuitive results.

The data system 450 can improve surgical planning, monitoring (e.g., via the display 422), data collection, surgical robotics/navigation systems, intelligence for selecting instruments, implants, etc. The data system 450 can execute, for example, surgical control instructions or programs for a guidance system (e.g., ML guidance system, AI guidance system, etc.), surgical planning programs, event detection programs, surgical tool programs, etc. For example, the data system 450 can increase procedure efficiency and reduce surgery duration by providing information insertion paths, surgical steps, or the like. The data system 450 can be incorporated into or include other components and systems disclosed herein. As shown by FIG. 4A, the display 422 can display, for example, a diagnosis of tissue, images, maps, surgical plans, etc. For example, the display 422 can display a diagnostic image or map showing, for example, a bone in image 423 (discussed in more detail below with reference to multi-modality imaging), regions of interest (e.g., zones of diseased tissue, regions of tissue with specific characteristic(s), margins, etc.), features of interest, anatomical elements (e.g., cartilage, soft tissue, etc.), or the like. An example image is discussed in connection with FIG. 5. In some embodiments, a diagnostic image can include tissue density, tissue state, identified disease tissue, or the like. The system 402 can use the displayed data to perform one or more surgical steps. A user can view the display 422 to confirm the position of the tissue during the procedure.

Referring to FIGS. 4A and 4C, the consultant device 401 can display procedure information from the surgery room, equipment controls, and other data disclosed herein. Referring now to FIG. 4C, the consultant device can display a GUI 461 for telepresence consulting. The GUI 461 includes an authorization input 493 for authorizing the consultant for participation in a surgical procedure and displays procedure and patient data 465, 466, 472, 491. Imaging equipment can automatically capture images for surgical side viewing via a display 465. The GUI 461 includes a procedure progress 467 that can be updated to show completed progress for the procedure, and controls 463 can be used to operate machines/applications. The user can customize the GUI 461 by rearranging the displayed items for convenience.

The consultant can use an authorization input 493 to, for example, input user authorization information (e.g., access codes, pins, etc.), employee credential information, surgical procedure information (e.g., serial number or code for the surgical procedure), or the like to access and operate equipment. If the consultant needs additional permission rights, the consultant can request the additional permission rights using the authorization input 493. For example, if an adverse event occurs during the procedure requiring the consultant to provide additional care, the consultant can request access to the additional equipment (e.g., robotic arms of surgical robot, breathing machine, heart rate monitor, etc.) via the authorization input 493. The surgical suite system can receive the requested authorization and perform an authorization protocol routine to determine whether the consultant should be granted permission rights to the additionally requested equipment. The surgical suite system can analyze the surgical plan, planned permission rights (e.g., plan of permission rights assigning permission rights to features or steps of the surgical plan), consultant credentials and/or expertise, and/or other information disclosed herein to determine whether to grant permissions. If requested permission rights are denied, the on-site medical team can be notified of the denied request and consultant input, recommendation, etc. If the request is granted, the system can automatically establish communication and control channels for displaying the additional information for the additional equipment via the consultant device 401. The procedure progress 467 can show completed progress for the modified procedure based on the additional equipment.

Dynamic updating of the equipment controls 463 on the consultant device 401 allows the user to acquire control of additional medical equipment in the same consulting session without disrupting communication channels. This reduces the risk of latency and/or network problems that could affect the medical procedure. The controls 463 can be configured to perform all or some of the controls as discussed in connection with FIG. 4B. For example, the controls 463 can include a touch input control module 466 with input features 465a, 465b that can be used to increase or decrease, respectively, settings of equipment. The touch input control module 466 can be used to control movement of, for example, robotic surgical arms, robotic manipulators, and effectors, or the like. For example, the touch input control module 466 can be configured to provide the same controllability as the hand-operated input devices 424, 426 of FIG. 4B. In some embodiments, the controls 463 of FIG. 4C can be modified to include controls for the additional equipment such that the consultant has access to controls for operating newly available equipment in real-time while continuing to view real-time patient data 472. Data collected by and/or associated with additional equipment can automatically be added to the patient data 472.

The consultant device 401 can include a procedure viewer 465, a surgical suite or room viewer 466, and/or other viewers or windows for providing viewing (e.g., real-time or near real-time viewing) of the surgical suite (e.g., viewing at operating rooms, recovery rooms, etc.), medical team, medical equipment, etc. The consultant device 401 can display patient data 472 that can include, for example, blood pressure, health rating, heart rate, body temperature, vitals, physician notes, and/or additional patient data useful to the consultant. To change or receive additional patient data, the consultant can use a request data button 483 to send a message or notification to the on-site surgical team to provide additional patient data. The consultant can use a talk feature 490 to verbally communicate with the surgical team. The consultant device 401 can also display the surgical team information 491. The surgical team information can list physicians, nurses, staff, consultants, and other staffing information.

In some embodiments, the consultant device 401 can be used by a technician (including multiple technicians) to resolve technical issues with the surgery system 400. If the surgery system 400 of FIG. 4A detects an adverse event, such as an error in operation of the surgical robot 440 it can determine which features (e.g., hardware components, software modules, controllers, processor, subsystems, etc.) are associated with the error. For example, the system 400 can analyze operation data of the robot. In some embodiments, the operation data can include, for example, temperature, operational speeds, subsystem operational data (e.g., data from electrical subsystems, pneumatic subsystems, etc.), operational data of robotic arms, kinematics of robotic arms, and other operation data disclosed herein. The system 400 can select the technician based on an area of expertise, historical outcomes (e.g., successful repair for outcomes, completion of surgical step/procedure within a target period, etc.). For example, the system can analyze available technicians certified or trained to resolve the detected error, work on the surgical robot, or the like. The surgery system 400 can perform simulations based on the technician's profile (e.g., successful repair for outcomes, certification information, geographic location, etc.) to confirm that the adverse event or repair can be completed within a threshold time (e.g., to complete step of surgery, surgical procedure, etc.). The surgical team can be notified of the predicted completion time by the technician for planning the rest of the procedure or other activities. The system 400 can also predict a completion time for software modifications associated with the technician's modifications.

System 400 can send to a device associated with the selected technician (e.g., an individual technician, team of technicians, etc.) a notification that provides access to the surgical sweet. The notification can include access to a communication channel for communication with the surgical robot via the device. Referring now to FIG. 4C, the technician device 400 can be in the form of the device 401 discussed in FIG. 4. The technician can enter in authorization input via authorization element 493. The system 400 can employ token-based authentication, key-based authentication, multi-factor authentication, etc. The authentication information can be stored locally or remotely. The technician can use controls 463 to, for example, operate, diagnose, and/or troubleshoot components associated with adverse events (e.g., whether causing or contributing to malfunctions, operational errors, etc.). The technician can talk to the surgery team via the talk button 490. For example, the technician can ask the surgery team to perform tasks, replace components, modify components, or the like. The communication channel can be established using the techniques discussed in connecting with FIG. 4.

Technician can determine whether the issue has been resolved. Once the technician has decided that the error has been resolved, the technician can send a resolution notification to the system 400 indicating that the error was resolved. In response to the resolution notification, the system 400 can proceed with the surgical procedure. In other embodiments, the system 400 can determine whether the issue has been resolved by, for example, performing diagnostic routines (e.g., self-diagnostic routines), inspections (e.g., visual inspection via cameras, etc.), and/or questioning of the surgical team. The system 400 can retrieve diagnostic software modules, inspection software modules, or other modules for evaluating the system 400.

The robotic surgical system 400, illustrated and described in more detail with reference to FIG. 4A, can further include multiple consultant devices 401 so that multiple members of a surgical team or consultants can view the surgical procedure. The number and configuration of the consultant devices 401 can be selected based on the configuration and number of surgical robots, monitoring equipment, etc. The consultant device 401 can also display procedure data, including a surgical plan (e.g., a surgical plan including completed and future planned surgical steps), patient monitor readings, surgical suite or room information (e.g., available team members, available surgical equipment, surgical robot status, or the like), images (e.g., pre-operative images, images from simulations, real-time images, instructional images, etc.), and other surgical assist information. In some embodiments, the consultant device 401 can be an AR/VR headset, display, or the like.

Referring to FIG. 4A, the robotic surgical system 400 can be used to perform open procedures, minimally invasive procedures, such as laparoscopic surgeries, non-robotic laparoscopic/abdominal surgery, retroperitoneoscopy, arthroscopy, pelviscopy, nephroscopy, cystoscopy, cisternoscopy, sinoscopy, hysteroscopy, urethroscopy, and the like. The methods, components, apparatuses, and systems can be used with many different systems for conducting robotic or MIS. One example of a surgical system and surgical robots which can incorporate methods and technology is the DAVINCI™ system available from Intuitive Surgical, Inc.™ of Mountain View, California. However, other surgical systems, robots, and apparatuses can be used.

The robotic surgical system 400 can perform one or more simulations using selected entry port placements and/or robot positions, to allow a surgeon or other user to practice procedures. The practice session can be used to generate, modify, or select a surgical plan. In some embodiments, the system can generate a set of surgical plans for physician consideration. The physician can perform practice sessions for each surgical plan to determine and select a surgical plan to be implemented. In some embodiments, the systems disclosed herein can perform virtual surgeries to recommend a surgical plan. The physician can review the virtual simulations to accept or reject the recommended surgical plan. The physician can modify surgical plans pre-operatively or intraoperatively.

Embodiments can provide a means for mapping the surgical path for neurosurgery procedures that minimize damage through AI mapping. The software for AI is trained to track the least destructive pathway. A surgical robot can make an initial incision based on a laser marking on the skin that illuminates the optimal site. Next, a robot can make a small hole and insert surgical equipment (e.g., guide wires, cannulas, etc.) that highlights the best pathway. This pathway minimizes the amount of tissue damage that occurs during surgery. Mapping can also be used to identify one or more insertion points associated with a surgical path. Mapping can be performed before treatment, during treatment, and/or after treatment. For example, pretreatment and post-treatment mapping can be compared by the surgeon and/or ML/AI system. The comparison can be used to determine next steps in a procedure and/or further train the ML/AI system. In some embodiments, the system determines the location, number, angle, and depth of arthroscopic ports (e.g., tubes, rods, etc.) to place in a patient. The system can select the location, number, angle, and depth of the arthroscopic ports based on the maneuverability of the surgical robot, maneuverability of the end effectors of the surgical robot and/or the availability of the surgical tool to place the arthroscopic ports in the patient.

Figure 5:
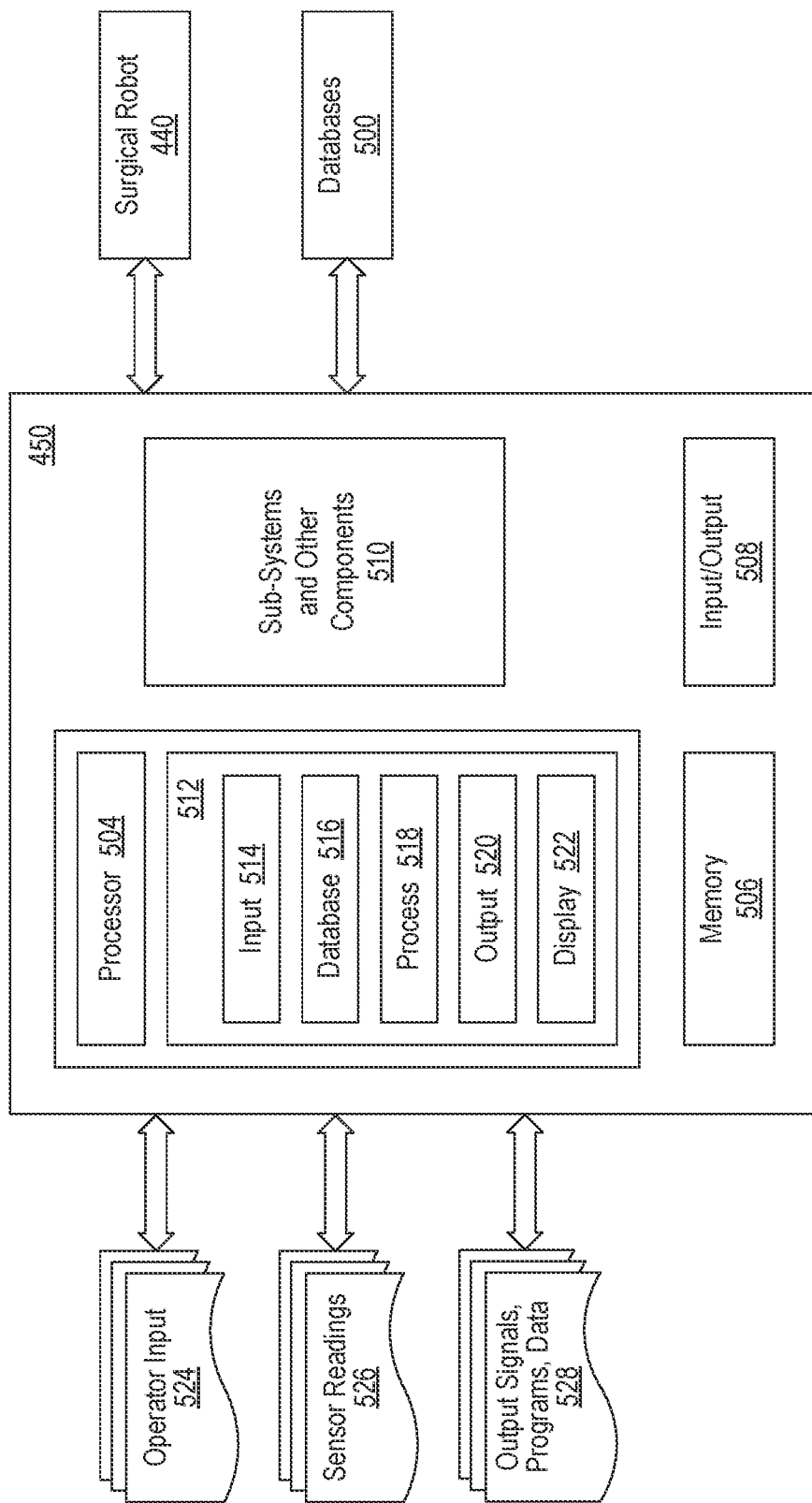
FIG. 5 is a schematic block diagram illustrating subcomponents of the robotic surgical system of FIG. 4A, in accordance with one or more embodiments.

FIG. 5 is a schematic block diagram illustrating subcomponents of the robotic surgical system 400 of FIG. 4A in accordance with embodiment of the present technology. The controller or data system 450 has one or more processors 504, a memory 506, input/output devices 508, and/or subsystems and other components 510. The processor 504 can perform any of a wide variety of computing processing, image processing, robotic system control, plan generation or modification, and/or other functions. Components of the data system 450 can be housed in a single unit (e.g., within a hospital or surgical room) or distributed over multiple, interconnected units (e.g., though a communications network). The components of the data system 450 can accordingly include local and/or devices.

As illustrated in FIG. 5, the processor 504 can include a plurality of functional modules 512, such as software modules, for execution by the processor 504. The various implementations of source code (i.e., in a conventional programming language) can be stored on a computer-readable storage medium or can be embodied on a transmission medium in a carrier wave. The modules 512 of the processor 504 can include an input module 514, a database module 516, a process module 518, an output module 520, and, optionally, a display module 524 for controlling the display.

In operation, the input module 514 accepts an operator input 524 via the one or more input devices (including consultant devices), and communicates the accepted information or selections to other components for further processing. The database module 516 organizes plans (e.g., robotic control plans, surgical plans, etc.), records (e.g., maintenance records, patient records, historical treatment data, etc.), surgical equipment data (e.g., instrument specifications), control programs, and operating records and other operator activities, and facilitates storing and retrieving of these records to and from a data storage device (e.g., internal memory 506, external databases, etc.). Any type of database organization can be utilized, including a flat file system, hierarchical database, relational database, distributed database, etc.

In the illustrated example, the process module 518 can generate control variables based on sensor readings 526 from sensors (e.g., end effector sensors of the surgical robot 440, patient monitoring equipment, etc.), operator input 524 (e.g., input from the surgeon console 420 and/or other data sources), and the output module 520 can communicate operator input to external computing devices and control variables to controllers. The display module 522 can be configured to convert and transmit processing parameters, sensor readings 526, output signals 528, input data, treatment profiles and prescribed operational parameters through one or more connected display devices, such as a display screen, touchscreen, printer, speaker system, etc.

In various embodiments, the processor 504 can be a standard central processing unit or a secure processor. Secure processors can be special-purpose processors (e.g., reduced instruction set processor) that can withstand sophisticated attacks that attempt to extract data or programming logic. The secure processors cannot have debugging pins that enable an external debugger to monitor the secure processor's execution or registers. In other embodiments, the system can employ a secure field-programmable gate array, a smartcard, or other secure devices.

The memory 506 can be standard memory, secure memory, or a combination of both memory types. By employing a secure processor and/or secure memory, the system can ensure that data and instructions are both highly secure and sensitive operations such as decryption are shielded from observation. In various embodiments, the memory 506 can be flash memory, secure serial EEPROM, secure field-programmable gate array, or secure application-specific integrated circuit. The memory 506 can store instructions for causing the surgical robot 440 to perform acts disclosed herein.

The input/output device 508 can include, without limitation, a touchscreen, a keyboard, a mouse, a stylus, a push button, a switch, a potentiometer, a scanner, an audio component such as a microphone, or any other device suitable for accepting user input and can also include one or more video monitors, a medium reader, an audio device such as a speaker, any combination thereof, and any other device or devices suitable for providing user feedback. The user is typically a medical professional, e.g., a surgeon, a nurse, a surgeon's assistant, or doctor. For example, if an applicator moves an undesirable amount during a treatment session, the input/output device 508 can alert the subject and/or operator via an audible alarm. The input/output device 508 can be a touch screen that functions as both an input device and an output device.

The data system 450 can output instructions to command the surgical robot 440 and communicate with one or more databases 500. The surgical robot 440 or other components disclosed herein can communicate to send collected data (e.g., sensor readings, instrument data, surgical robot data, etc.) to the database 500. This information can be used to, for example, create new training data sets, generate plans, perform future simulations, post-operatively analyze surgical procedures, or the like. The data system 450 can be incorporated, used with, or otherwise interact with other databases, systems, and components disclosed herein. In some embodiments, the data system 450 can be incorporated into the surgical robot 440 or other systems disclosed herein. In some embodiments, the data system 450 can be located at a remote location and can communicate with a surgical robot via one or more networks. For example, the data system 450 can communicate with a hospital via a network, such as a wide area network, a cellular network, etc. One or more local networks at the hospital can establish communication channels between pieces of surgical equipment within the surgical room. A network adapter 501 can be an operator authorizing device to manage communications and operation of components, as described with reference to FIG. 3. The network adapter 501 can govern and/or manage permissions to access proxy data in a computer network, track varying levels of trust between different machines and/or applications, and manage control access to surgical equipment, communications between remote devices and the surgical room, etc.

A surgical program or plan ("surgical plan") can include, without limitation, patient data (e.g., pre-operative images, medical history, physician notes, etc.), imaging programs, surgical steps, mode switching programs, criteria, goals, or the like. The imaging programs can include, without limitation, AR/VR programs, identification programs (e.g., fiducial identification programs, tissue identification programs, target tissue identification programs, etc.), image analysis programs, or the like. Surgical programs can define surgical procedures or a portion thereof. For example, surgical programs can include end effector information, positional information, surgical procedure protocols, safety settings, surgical robot information (e.g., specifications, usage history, maintenance records, performance ratings, etc.), order of surgical steps, acts for a surgical step, feedback (e.g., haptic feedback, audible feedback, etc.), or the like. The mode switching programs can be used to determine when to switch the mode of operation of the surgical robot 440. For example, mode switching programs can include threshold or configuration settings for determining when to switch the mode of operation of the surgical robot 440. Example criteria can include, without limitation, thresholds for identifying events, data for evaluating surgical steps, monitoring criteria, patient health criteria, physician preference, or the like. The goals can include intraoperative goals, post-operative goals (e.g., target outcomes, metrics, etc.), goal rankings, etc. Monitoring equipment or the surgical team can determine goal progress, whether a goal has been achieved, etc. If an intraoperative goal is not met, the surgical plan can be modified in real-time so that, for example, the post-operative goal is achieved. The post-operative goal can be redefined intraoperatively in response to events, such as surgical complications, unplanned changes to the patient's vitals, etc.

The surgical plan can also include healthcare information, surgical team information, assignments for surgical team members, or the like. The healthcare information can include surgical room resources, hospital resources (e.g., blood banks, standby services, available specialists, etc.), local or remote consultant availability, insurance information, cost information (e.g., surgical room costs, surgical team costs, etc.).

The systems disclosed herein can generate pre-operative plans and simulation plans. Pre-operative plans can include scheduling of equipment, surgical room, staff, surgical teams, and resources for surgery. The systems can retrieve information from one or more databases to generate the pre-operative plan based on physician input, insurance information, regulatory information, reimbursements, patient medical history, patient data, or the like. Pre-operative plans can be used to generate surgical plans, cost estimates, scheduling of consultants and remote resources, or the like. For example, a surgical plan can be generated based on available resources scheduled by the pre-operative plans. If a resource becomes unavailable, the surgical plan can be adjusted for the change in resources. The healthcare provider can be alerted if additional resources are recommended. The systems disclosed herein can generate simulation plans for practicing surgical procedures. On approval, a surgeon can virtually simulate a procedure using a console or another simulation device. Plans (e.g., surgical plans, implantation plans, etc.) can be generated and modified based on the surgeon's performance and simulated outcome.

The systems disclosed herein can generate post-operative plans for evaluating surgical outcomes, developing physical therapy and/or rehab programs and plans, etc. The post-operative plans can be modified by the surgical team, primary care provider, and others based on the recovery of the patient. In some embodiments, systems generate pre-operative plans, surgical plans, and post-operative plans prior to beginning a surgical procedure. The system then modifies one or more or the plans as additional information is provided. For example, one or more steps of the methods discussed herein can generate data that is incorporated into the plan. ML data sets to be incorporated into the plan generate a wide range of variables to be considered when generating plans. Plans can be generated to optimize patient outcome, reduce or limit the risk of surgical complications, mitigate adverse events, manage costs for surgical procedures, reduce recovery time, or the like. The healthcare provider can modify how plans are generated over time to further optimize based on one or more criteria.

Figure 6A:
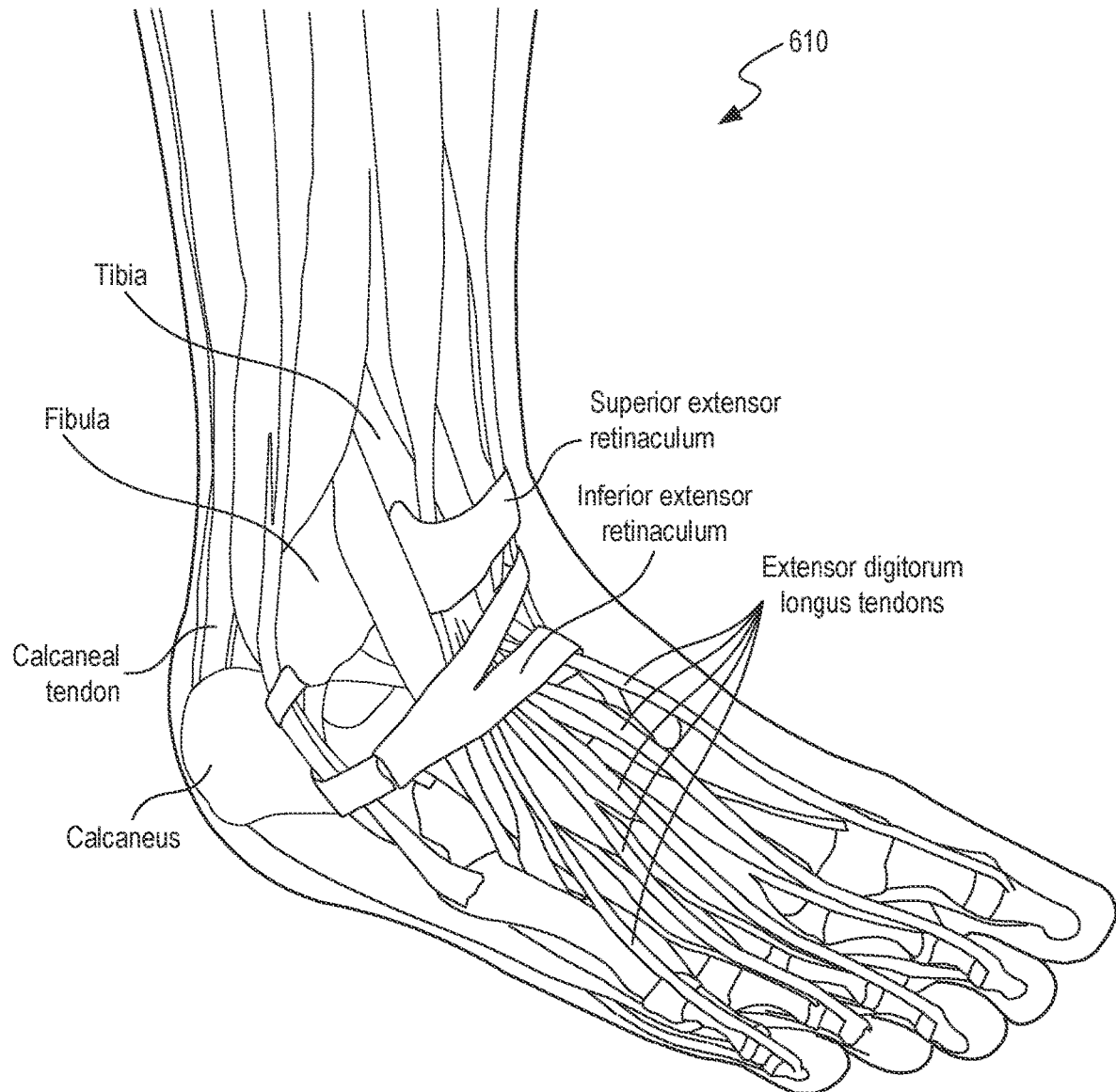
FIG. 6A illustrates an example multi-modality image of a target region, in accordance with one or more embodiments.
Figure 6B:
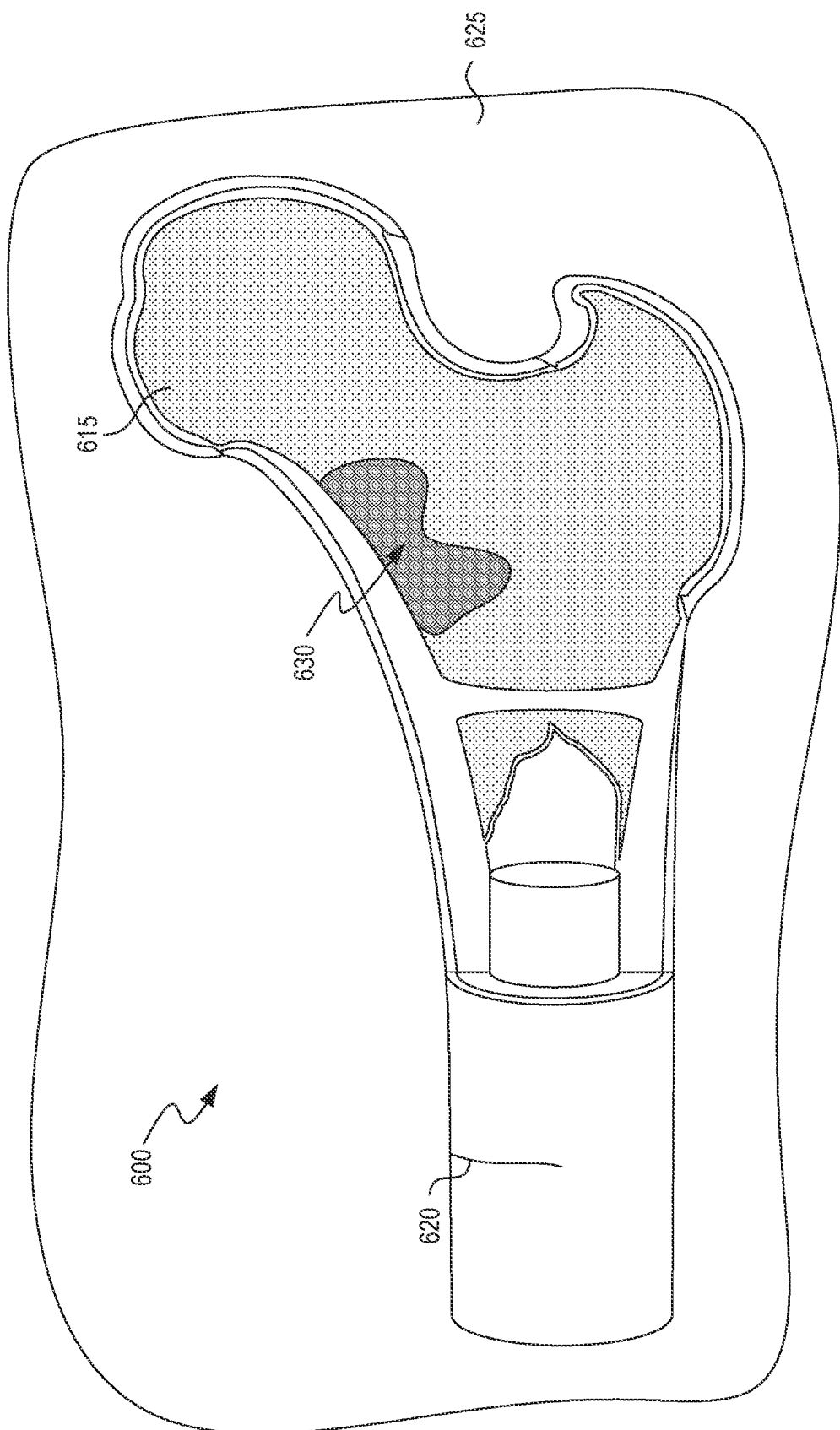
FIG. 6B illustrates an example image of another target region, in accordance with one or more embodiments.

FIG. 6A illustrates an example multi-modality image 600 of a target region, in accordance with one or more embodiments. FIG. 6B illustrates an example of another image 610, in accordance with one or more embodiments. The images 600, 610 can allow a healthcare worker to view a target region 625 to analyze an automated diagnosis, anatomical features, identify tissue of interest, etc. Systems disclosed herein can analyze a surgical plan to identify potential one or more anatomical features of interest. The system can select imaging modalities based on the potential one or more anatomical features of interest and available imaging modalities. The system can obtain at least one image for each imaging modality and generate a multi-modality image based on each of the obtained images. The system can determine one or more imaging characteristics for each potential anatomical feature of interest and correlate imaging characteristics to identify the available imaging modalities used to select the image modalities. The system can identify anatomical features in the image 600 (e.g., a pre-operative image, real-time intraoperative image, etc.). The multi-modality images 600, 610 can be generated based on a surgical plan, physician input, or other input data, and can indicate features (e.g., anatomical elements), margins, tissue type, etc.

Referring to FIG. 6A, to generate the image 600, systems disclosed herein can receive a tissue density image from an MRI device, a bone fracture image from a CT scanner, a bone degeneration or cancerous tissue image from an ultrasound machine, or images from other imagers disclosed herein. In embodiments, the image 600 is generated for a surgical plan for treating a damaged bone and can include, for example, tissue density data 615 (e.g., healthy tissue data from an MRI device), a bone fracture 620 (e.g., identified using a CT scan), diseased tissue 630 (e.g., low-density tissue, cancerous tissue, etc., from ultrasound images), or the like. The system can combine the data to generate the image 600 with features and/or information of interest. In some embodiments, the image 600 highlights regions 625 of a tissue sample according to the diagnoses and/or the values from a multi-modality device or multiple imaging devices. For example, the image 600 can annotate highlight and/or otherwise identify/emphasize features of interest. The emphasis can help direct the doctor's review of the target region 625 and/or further analysis of the patient. In embodiments, images are generated that include raw data and multi-modality images (e.g., composite images, a multilayer overlaid image, etc.) to allow a physician to perform an independent diagnosis. In embodiments, the raw data is indicated via differences in shading, color, fill patterns, express indications, display tables, selectable displays, and/or in any other suitable manner. Similar processes can be used to generate the image 610.

The multi-modality images 600, 610 of FIGS. 6A and 6B can include selectable layers. For example, the multi-modality images can include a first layer created using a first modality, a second layer created using a second modality, and a third layer created using a third modality. A composite layer can include selected data from one or more of the three layers. The number of layers, number of imaging modalities, types of imaging modalities, data sets, fused data sets, and/or image processing (e.g., scaling of images, filtering of images, etc.) can be selected based on target characteristics of the composite layer, surgical plan (e.g., features of interest, anatomical elements, etc.). For example, the image 600 of FIG. 6 can include selectable layers each with one or more anatomical features identified (e.g., via annotation, false colors, etc.).

Figure 7:
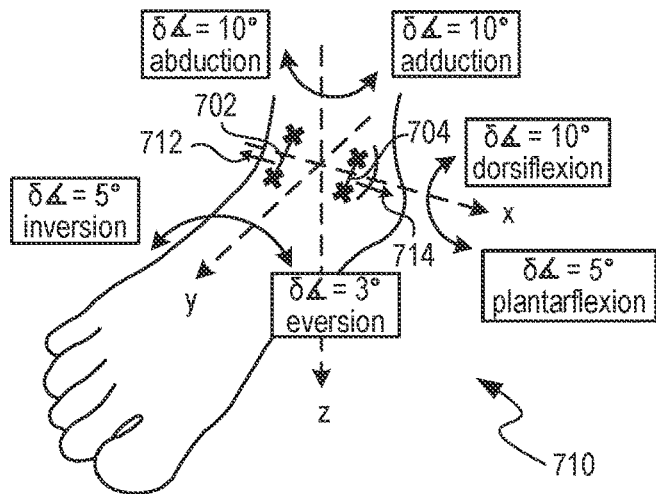
FIG. 7 shows movement of the human ankle, in accordance with one or more embodiments.
Figure 8A:
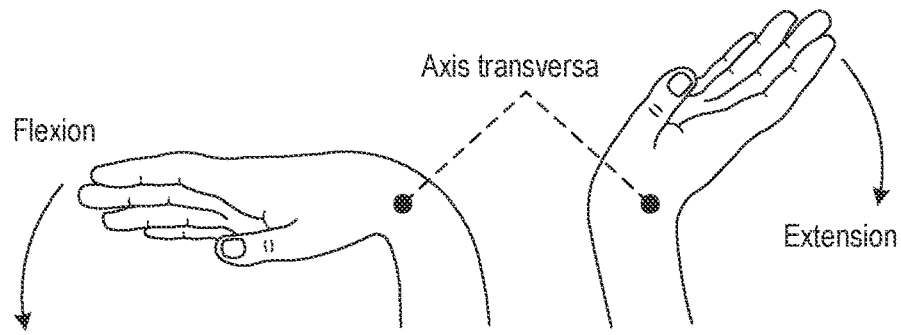
FIGS. 8A and 8B show movement of the human wrist, in accordance with one or more embodiments.
Figure 8B:
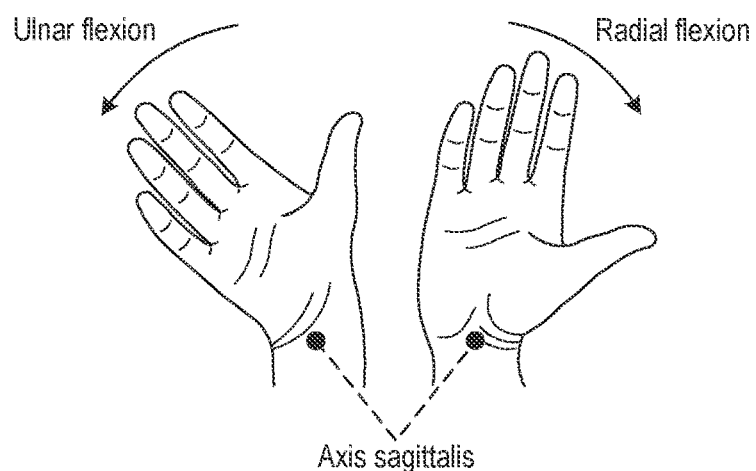

FIG. 7 shows movement of the human ankle, in accordance with one or more embodiments. FIGS. 8A and 8B show movement of the human wrist, in accordance with one or more embodiments. The systems disclosed herein can develop surgical plans to achieve the targeted motion and can simultaneously display pre-operative biomechanics and intraoperative biomechanics, pre-operative renderings of the surgical site and captured images of the surgical site, captured images of the surgical site and metrics, or combinations thereof. This allows a user to evaluate the accuracy of pre-operative predictions, progress of the surgical procedure, and/or real-time monitoring of metrics. The user is typically a medical professional, e.g., a surgeon, a nurse, a surgeon's assistant, or doctor. For example, a user can input one or more target outcome values, such as the number of degrees of freedom, range of motion, maximum/minimum motion/joint angles, or the like. The system can then perform any number of simulations using one or more virtual models to generate a surgical plan that meets the user inputted target outcome values.

Advantageously, surgical steps can be generated and provided to a surgical system to perform the procedure to meet the predicted outcomes based on soft tissue compliance, joint mechanics, loading, activities performed by patient, etc. The system can then update surgical plans to achieve the target outcome values and/or other user input. The number and position of anchor points, connections, and other features of the tethering can be selected to achieve the outcome criteria. For example, prior to conducting a surgery, the systems disclosed herein can simulate the mobility (e.g., sit, stand, walk, etc.) of the patient after the surgery.

FIG. 7 shows tethering 702, 704 (via anchors and sutures) that can stabilize the joint 710. Virtual connections 702, 704 can be used in simulations to generate values or metrics for the ankle. For example, the values can include, for example, angles of abduction, dorsiflexion, plantarflexion, eversion, inversion, and/or other metrics, which can be displayed for evaluating predicted outcomes. The system can move tethering in a virtual model to perform additional simulations. For example, the tethering 702, 704 can be moved to another location, as illustrated by arrows 712, 714, respectively. The change in biomechanics based on a modification can be illustrated for viewing. For example, the change in the abduction, adduction dorsiflexion, plantarflexion, eversion, and/or inversion can be calculated and displayed.

By way of example, the pre-operative range of motion of the ankle can be, for example, dorsiflexion of 20°-30°, plantarflexion of 40°-50°, inversion/eversion of 30°, supination of 5°, or other ranges of motion. The change in tethering positions can result in an angle change of abduction of about 10° in either direction, angle of dorsiflexion of 10°, plantarflexion angle of 5°, eversion angle of 3°, and/or inversion angle of 5°. Bone-ligament tethering of ankle structures can be selected to achieve one or more of target outcome values. A user can move the location of the tethering to see the effects with joint movement in real-time.

Referring to FIGS. 8A and 8B, bone-ligament tethering, or other surgical steps, can be generated to modify the wrist to achieve one or more of target outcome values. A user can input target outcome values, such as a flexion of 80°-90°, extension of 75°-85°, radial flexion of 20°-22°, ulnar flexion of 35°, or other ranges of motion or values.

Virtual models and simulations disclosed herein can be performed to generate the surgical plans for the Figures herein. 3D images generated can be of the virtual model, simulated virtual steps of the procedure, and other images associated with the model/simulation. In some procedures, a CAD GUI receives images of the patient's anatomy and generates virtual two-dimensional or three-dimensional models with surface topologies, tissue properties, boundary conditions, etc. The models can represent anatomical features of interest, including skin, bones, soft tissue, fluids, connective tissue, and ligaments using the embodiments, methods, and features disclosed herein. The embodiments, methods, and features disclosed herein can be used to implement the examples discussed below.

In some virtually simulated leg procedures, an incision is made from a tip of the fibula to the extensor retinaculum of the virtual model. Virtual holes can be drilled in structures, such as the fibula, to place virtual drill guides, anchors, and other features along the anatomy. Multiple positions of fibula anchors can be analyzed to select a target fibula anchor position. One or more sutures can pass through the fibula anchor and be connected to another structure, such as ligaments (e.g., extensor retinaculum). The suture can then be routed back and returned to the anchor. In this manner, the fibula anchor can be used to limit motion of another structure. The system can analyze the characteristics and properties of the extensor retinaculum based on, for example, X-ray images, MRIs, and other patient images. Ankle simulations can be performed to, for example, select the number and locations of the anchors and sutures extending through, under, and/or above the extensor retinaculum.

Anchoring of the extensor retinaculum can cause tendons of the extensor muscles to be pulled inwardly toward the fibula. This can cause tensioning of the tendons of the peroneus tertius and the EDL. The alterations to the tendons can be virtually simulated based on the virtual tensioning of the sutures. This allows for virtual simulations of movement of a joint under loading, performing predefined determined tasks, etc. The tensioning of the extensor retinaculum can be increased or decreased to increase or decrease, respectively, the tensioning of the underlying tendons. Three-dimensional modeling analyses can be performed to accurately determine procedures to be performed based on the tensioning. In some procedures, additional or ancillary procedures can be performed to further adjust the procedure.

Additional anchors can be positioned along the leg. By way of example, a calcaneus anchor can be attached to the calcaneus bone. One or more sutures can be connected to the calcaneus anchor and connected to the extensor retinaculum (e.g., superior extensor retinaculum, inferior extensor retinaculum, etc.) one or more times in, for example, a weaving fashion, an overlapping fashion, or the like. The suture can then be attached to the fibula anchor, the calcaneus anchor, or another anchor. Tensioning of the extensor retinaculum can alter underlying tissue by, for example, tensioning one or more of the longus tendons. The number of anchors, number of times the suture passes through or is connected to the ligament, and other parameters can be selected based on the targeted outcome. Advantageously, overall motion of the joint can be analyzed based on multiple connections between multiple anatomical structures of the joint or structures surrounding the joint. The output from the simulations can be displayed for movements of the anatomy as illustrated in FIGS. 7-8B. A user can modify, adjust, and/or input values for the patient databases to perform additional simulations to generate predicted outcomes and confidence scores.

Inter-operative data can be compared to the predicted data in the patient databases. If differences between the predicted data and the actual data exceed a threshold, one or more warnings can be sent to the user or the robotic system. The surgical procedure can be adjusted to compensate for the changes. In some embodiments, the user can stop the procedure to perform alternative steps or evaluation based on the alert. The thresholds for alerts can be selected using ML models trained based on previous procedures. This allows alerts to be accurately generated.

The virtual robotic surgical procedures disclosed herein can be performed using simulation and CAD. For example, the virtual robotic surgical procedure is performed using the one or more processors to aid in the creation, modification, analysis, or optimization of implants and tools, and to create a database for manufacturing. Further, the virtual robotic surgical procedure can use vector-based graphics to depict the surgical implants, and can also produce raster graphics showing the overall appearance and path of the surgical implant in the virtual robotic surgical procedure. Moreover, the output of the virtual robotic surgical procedure can convey information, such as processes, dimensions, and tolerances, according to application-specific conventions. The virtual robotic surgical procedure can be used to design curves and figures in two-dimensional space or curves, surfaces, and solids in three-dimensional space, and to rotate and move a virtual model of the surgical implant for viewing. For example, virtual joints can be generated for 2D or 3D spaces.

Simulations for the virtual robotic surgical procedure can be performed using virtual models that can include two- or three-dimensional models to evaluate, for example, one or more steps of a surgical procedure (or entire procedure), predicted events, outcomes, etc. The simulations can be used to identify and assess biomechanics, access paths, stresses, strains, deformation characteristics (e.g., load deformation characteristics, load distributions, etc.), fracture characteristics (e.g., fracture toughness), fatigue life, etc. The virtual model can include a model of the patient's anatomy, implant(s), end effectors, instruments, access tools, or the like. The one or more processors can generate a three-dimensional mesh to analyze models. ML techniques can be used to create an optimized mesh based on a dataset of joints, anatomical features, and implants, or other devices. The three-dimensional models, surfaces, and virtual representations can be generated by CAD software, FEA software, and robotic control software/programs based on patient data (e.g., images, scans, etc.), implant design data, or the like. A user can view, manipulate (e.g., rotate, move, etc.), modify, set parameters (e.g., boundary conditions, properties, etc.), and interact with the models. The control parameters, robotic kinematics, and functionality can be used to generate the simulations. In some embodiments, models of end effectors of a robotic system are generated to perform virtual procedures on virtual anatomical models. Virtual simulations of surgical procedures in which a user selected robotic surgical steps and physician steps can be used to generate, modify, and select surgical plans, surgical robot configurations, or the like.

Pre-operative simulations can be performed for different surgical robots using pre-operative patient data (e.g., pre-operative scans, images, etc.). A surgical robot for performing a surgical procedure or portion thereof can be selected based on the simulation(s). This allows a healthcare provider to select a surgical robot suitable for a particular procedure. Additionally, the simulations can be used to generate, modify, and/or verify surgical plans. In some embodiments, a configuration of the surgical robot is selected based on the simulations. For example, multiple simulations can be performed for a surgical robot in different configurations (e.g., the surgical robot having different end effectors) and using different surgical techniques. The healthcare provider can select the surgical robot configuration and surgical plan based, at least in part, on the simulations. End effectors and tools of the surgical robot, imaging equipment, and manual equipment can be selected based on the simulations.

In some embodiments, the surgical system can perform virtual simulations based on one more design parameters, including simulation time, resource usage, accuracy level, and/or data output. The simulation time can be selected so that the virtual simulation is completed within a time period (e.g., percentage of completion time for a surgical step, percentage of surgical procedure duration, user input time period, etc.). The complexity of the models can be increased or decreased to decrease or increase, respectively, the simulation time period. If the user requests a significant amount of data output (e.g., joint mechanics, loads applied to anatomical structures, multiple implants, fatigue life, etc.), high complexity models (e.g., FEA models with a large number of elements/nodes, optimization models, fluid flow models, etc.) can be generated. Resource usage parameters can be used to select features of three-dimensional models of the anatomy and implants based on available processing resources, including central processing unit (CPU) cycles, memory space, network bandwidth, or a combination thereof. For example, the resource usage parameters can be set to limit usage of such processing resource(s). The surgical system can perform one or more corrective measures to free up the amount of resources required to enable process resources to be available to the robotic apparatus to complete tasks. The corrective measures can include one or more of allocating memory space, prioritizing packets, limiting CPU usage, and/or throttling bandwidth (e.g., throttling network bandwidth). The complexity and features (e.g., surface contours, feature matching, etc.) can be selected based on the available computing resources.

The surgical system can determine the simulation time period based on an action schedule of the surgical plan, a time allocated for the at least one robotic surgical action to be planned and completed, etc. The virtual simulations can be performed while one or more instruments are at least partially positioned within a patient to complete a current surgical action. This allows simulations to be performed concurrently with surgical actions on the patient. Suturing tools, anchoring tools, bronchoscopes, endoscopes, and/or imaging equipment are at least partially positioned within the patient to obtain the intraoperative patient data.

Virtual surgical procedures can include one or more robotic assisted surgical steps, automated surgical steps, and/or physician-controlled surgical steps. Intraoperative virtual simulations can be performed at any time during a surgical procedure to plan future surgical steps or actions. The system can collect real-time surgical data, patient data, or other information continuously or periodically before, after, and/or during surgical steps. Surgical plans can be modified based on intraoperative planning, trained ML models, virtual simulations, etc., and obtained data, such as pre-operative data, intraoperative data (e.g., surgical robot data, patient data, etc.), and/or other data. In some embodiments, virtual simulations are performed based on intraoperative patient data. The virtual simulations can be used to generate one or more robotic surgical actions for an intraoperative surgical plan using a trained ML model. The surgical system can control a robotic surgical apparatus to perform the robotic surgical action according to the intraoperative surgical plan. Planned robotic surgical actions can be generated any number of times to dynamically modify the intraoperative surgical plan. The real-time planning enables one or more trained ML models to determine surgical steps based on the current status of the patient, functionality of the surgical robotic apparatus, etc. If the surgical robotic apparatus is not configured for performing surgical action(s), a user can be notified that the configuration of the surgical robotic apparatus should be modified by, for example, changing end effectors, installing new instruments, etc. Once reconfigured, the surgical robotic apparatus can continue in autonomous mode, semi-autonomous mode, or another mode.

In some embodiments, the processes described herein are performed by the modules described. In other embodiments, the processes are performed by a computer system, e.g., the example computer system 300 illustrated and described in more detail with reference to FIG. 3. Particular entities, for example, the console 108 or the robotic surgical system 160, perform some or all of the steps of the process in other embodiments. The console 108 and the robotic surgical system 160 are illustrated and described in more detail with reference to FIG. 1. Likewise, embodiments can include different and/or additional steps or can perform the steps in different orders.

FIG. 9 illustrates a surgical metaverse system 900, according to an embodiment. System 900 includes a surgical robot 902, which is a robotic system designed to assist a surgeon in performing a surgical operation on a patient. Surgical robot 902 can include a controller 904, memory 906, and at least one robotic arm 912 with an end effector 914. The surgical robot 902 may further include a user interface 910 for accepting control inputs from a user, such as a surgeon or other medical professional, and a communications interface 908 for transmitting and receiving data to and from a cloud 920 for the purpose of training an AI operating within the surgical robot or receiving remote commands from a remote user or an AI existing external to the surgical robot 902.

The surgical robot 902 may additionally comprise a plurality of sensors 916 for providing feedback to the user or an AI. Controller 904 is a computing device comprised of a processor for performing computations and communicates with a memory 906 for storing data. The controller 904 is in communication with a communications interface 908 and may further be allowed to control the at least one robotic arm 912 and end effector 914 of a surgical robot 902. The controller 904 can be a commercially available CPU or graphical processing unit (GPU) or may be a proprietary, purpose-build design. More than one controller 904 may operate in tandem and may be of different types, such as a CPU and a GPU. A GPU is not restricted to only processing graphics or image data and may be used for other computations.

Memory 906 is the electronic circuitry within a computing device that temporarily stores data for usage by the controller 904. The memory 906 may additionally comprise persistent data storage for storing data used by the controller 904. The memory 906 may be integrated into a controller 904 or may be a discrete component. The memory 906 may be integrated into a circuit, such as soldered onto a component of a single board computer (SBC), or may be a removable component, such as a discrete dynamic random-access memory (DRAM) stick, secure digital (SD) card, flash drive, solid-state drive (SSD), magnetic hard disk drive, etc. In some embodiments, memory 906 may be part of a controller 904. Multiple types of memory 906 may be used by the surgical robot 902.

Communications interface 908 allows the surgical robot 902 to communicate with external devices and may comprise a wireless antenna and transceiver or a port for receiving a cable to facilitate a wired connection. Examples of a wired connection include ethernet, USB, or a proprietary connection. A wireless communications interface 908 may include any of Wi-Fi, Bluetooth, NFC, or a cellular communications interface such as 3G, 4G, long-term evolution (LTE), or 5G. The communications interface 908 may connect a user interface 910 to the surgical robot 902 or may facilitate access to a local network or a cloud 920 network to access a remote server and/or database.

User interface 910 is a means of interacting with a surgical robot 902 and may include any of a keyboard, computer mouse, trackball, joystick, wireless or wired gamepad, sliders, scroll wheels, touch screen, or microphone for receiving voice commands. The user interface 910 may additionally comprise any method of interaction of a user with a surgical robot 902 not listed. The user interface 910 may accept direct inputs, such as from a joystick controlling the movement of a robotic arm, or indirect inputs, such as commands entered on a keyboard or touch screen, such as adjusting the sensitivity of a joystick control or the speed of a robotic arm's movement in response to a joystick. The user interface 910 may also comprise a screen for presenting information to the user, such as patient status, imaging data, and navigation data and speakers for providing auditory feedback. The user interface 910 may also utilize haptics to provide feedback to the user. In additional embodiments, the user interface 910 may comprise an augmented-reality (AR) or virtual-reality (VR) headset to enable a surgeon to view imagery from at least one imaging device 918 in real-time and may additionally comprise an overlay, such as highlighting the blood vessels comprising a path which the catheter must be advanced to access the treatment site, such as a blood clot. The user interface 910 may additionally comprise voice or eye-tracking controls. In embodiments, the controls are customized for the anatomy of the patient and the surgical procedure.

The robotic surgical embodiments herein use VR, AR, mixed reality (MR), or a combination thereof without limitation. Extended reality (XR) includes representative forms such as AR, MR, VR, and the areas interpolated among them. The levels of virtuality range from partially sensory inputs to immersive virtuality, also called VR. XR is a superset that includes the entire spectrum from "the complete real" to "the complete virtual" in the concept of reality-virtuality continuum. System 900 can extend human experiences, especially relating to the senses of existence (represented by VR) and the acquisition of cognition (represented by AR). In embodiments, extended-reality learning (XRL) is used to generate a new immersive experiential learning model that places users into realistic intentional interactions. By leveraging AR, MR, VR, branching video (BV), and AI, system 900 is able to go beyond simulation in a virtual metaverse.

Multisensory XR integrates the five traditional senses, including sight, hearing, smell, taste, and touch. Perception involves signals that go through the nervous system, as vision involves light striking the retina of the eye, smell is mediated by odor molecules, and hearing involves pressure waves. Sensory cues of multisensory XR include visual, auditory, olfactory, haptic, and environmental. Scent can be used in XR, as in biology, the olfactory system is integrated through the sensory nervous system. Multisensory experiences have elements of neuromorphic engineering, cognitive science, positive psychology, neuroenhancement, and nanoemulsion technology. In embodiments, system 900 uses OpenXR and WebXR standards. System 900 can use perception, motor control, multisensory integration, vision systems, head-eye systems, and auditory processing.

System 900 can simulate experiences that can be similar to or completely different from the real-world operating room. System 900 can use either VR headsets or multi-projected environments to generate realistic images, sounds, and other sensations that simulate a user's physical presence in a virtual surgical simulation environment. In some embodiments, a surgeon performs manual surgical simulation that surgical robot 902 later mimics. In some embodiments, a robotic surgical system performs virtual simulation in an XR surgical simulation environment.

A person using system 900 is able to look around the artificial operating room, move around in it, and interact with virtual features or items. The effect can be generated by VR headsets consisting of a head-mounted display (HMD) having a small screen in front of the eyes but can also be created through specially designed rooms with multiple large screens. VR typically incorporates auditory and video feedback but may also allow other types of sensory and force feedback through haptic technology. The system 900 uses either VR headsets or multi-projected surgical simulation environments to generate realistic images, sounds, and other sensations that simulate a user's physical presence in a virtual surgical simulation environment.

In embodiments, system 900 uses AR. AR is an interactive experience of a real-world environment where the objects (e.g., surgical tools 154) that reside in the real operating room are enhanced by computer-generated perceptual information, sometimes across multiple sensory modalities, including visual, auditory, haptic, somatosensory, and olfactory. System 900 can incorporate a combination of real and virtual operating rooms, real-time interaction, and accurate 3D registration of virtual and real objects. The overlaid sensory information can be constructive (i.e., additive to the natural environment) or destructive (i.e., masking of the natural environment). This experience is seamlessly interwoven with the physical operating room such that it is perceived as an immersive aspect of the real environment.

System 900 blends components of the digital operating room into the users' perception of the real operating room, not as a simple display of data but through the integration of immersive sensations, which are perceived as natural parts of a surgical simulation environment. For example, system 900 uses AR to enhance natural environments or situations and offer perceptually enriched experiences. With the help of advanced AR technologies (e.g., adding computer vision, incorporating AR cameras into smartphone applications, and object recognition), the information about the surrounding real operating room of the user becomes interactive and digitally manipulated. Information about the surgical simulation environment and its objects is overlaid on the real operating room. This information can be virtual. System 900 can perform AR techniques in real-time and in semantic contexts with environmental elements. Immersive perceptual information is sometimes combined with supplemental information. This combines the benefits of both AR technology and heads-up display (HUD) technology. In embodiments, system 900 uses MR, which is the merging of real and virtual operating rooms to produce new environments and visualizations, where physical and digital objects (e.g., patient anatomical features, surgical tools 154) co-exist and interact in real-time. MR is a hybrid of AR and VR.

System 900 can receive user input from an interface, sensors of a headset (e.g., a VR headset), motion sensors, etc. System 900 can control the movement of a virtual model of surgical robot 902 according to the user input. The degrees of freedom, accuracy, and operational parameters (e.g., speed of motion or range of motion) of the virtual model can match or be similar to the corresponding physical features of the robotic system. System 900 can score one or more surgical steps performed in the XR surgical simulation environment. The scoring can be displayed in real-time or near real-time and used to determine the adjusted surgical workflow.

In some embodiments, system 900 includes the system and components discussed in connection with FIGS. 4A-4C. To perform actions in the surgical metaverse, a user can operate hand-operated input devices (e.g., devices 424, 426, illustrated held by the user's left and right hands 427, 428, respectively in FIG. 4B). Referring to FIG. 4B, a viewer 430 can include left and right eye displays 434, 436 for metaverse viewing. Surgical team members can concurrently view the metaverse using viewers, VR headsets, etc. The user can view, for example, the surgical site, instruments 437, 438, or the like. The user's movements of the input devices 424, 426 can be translated in real-time to metaverse movements viewable via the viewer 430 and display (e.g., display 124 of FIG. 1) while the user can be provided with optional feedback, such as scoring of surgical steps, alerts (e.g., potential adverse events), notifications, and/or information. The information can include, without limitation, surgical or implantation plans, patient vitals, modification to surgical plans, values, scores, predictions, simulations, and other output, data, and information disclosed herein. The console 420 can be located in the surgical room or at a remote location. In some embodiments, the same console 420 is used to simulate surgical steps in the metaverse and to control the physical surgical robot.

The XR surgical simulation environment can include non-linear characteristics (e.g., micromechanics, mechanical behavior, etc.) of soft tissue and other mechanical properties applied to tissue to generate finite element models (e.g., non-linear finite element models), joint modeling (e.g., linear joint modeling, non-linear joint modeling, dynamic joint modeling, etc.), or the like. System 900 can model and simulate the dynamic behavior of non-linear anatomical structures. The simulation can model the dynamic behavior of tissue interacting with instruments, implants, etc., and can include all or some pre-operative activities, intra-operative activities, and/or post-operative activities. This enables a user to select portions of a procedure to be analyzed.

Robotic arm 912 is a mechanically actuated arm or lever with at least two degrees of freedom. Robotic arm 912 will typically include at least one end effector 914 or an imaging device 918 and may include both an end effector 914 and an imaging device 918. In embodiments, system 900 obtains one or more images and sensor data for a patient using imaging device 918 and sensors 916. The robotic arm 912 may additionally be capable of changing the end effector 914 to facilitate multiple functions and operations of a variety of tools. The robotic arm 912 may be manually controlled or operated in an autonomous or semi-autonomous mode. A surgical robot 902 may have one robotic arm 912 or multiple robotic arms 912, each of which may be operated independently by one or more users or autonomous systems or a combination of users and autonomous systems.

An end effector 914 is the end of a robotic arm 912 which is conducting work. The end effector 914 is typically a tool or device for interacting with a physical object and may be a surgical tool intended for acting upon or within a patient or may be a gripping device for securing a separate surgical tool to a robotic arm 912. The end effector 914 may be permanently affixed to the end of a robotic arm 912 or may be detachable, allowing for a system of interchangeable end effectors 914, which may alternatively be selected and swapped by a single robotic arm 912 or multiple robotic arms 912. The end effector 914 may comprise a catheter or other tool for accessing a treatment site within a patient.

Similarly, the end effector 914 may relate to a deployable device, such as a stent, prior to deployment in a patient. The end effector 914 may be constructed of materials that intentionally absorb, reflect, or are transparent to X-rays to facilitate the end effector's 914 visibility when viewed using angiography, fluoroscopy, or other imaging modalities, or alternatively allow the X-rays to pass through to prevent their interference in images. In some embodiments, the end effector 914 may be made to be selectively transparent to X-rays, such as by changing the profile of the end effector 914 or X-ray absorbing or reflective components to increase or reduce their visibility to an imaging device 918.

Sensor 916 is a measurement tool for monitoring a characteristic or metric associated with a surgical robot 902, end effector 914, or patient. A sensor 916 may be discrete or part of an array or assembly, such as integrated into a catheter. One or more of the sensors 914 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 916 may be integrated into the operation of the surgical robot 902 or may monitor the status of a patient.

In embodiments, system 900 extracts features from surgical actions performed by a user on a 3D digital twin. Generating a surgical workflow comprises generating workflow objects using a machine learning (ML) model based on the features. The ML model is trained to provide surgical workflows based on stored historical workflows. In embodiments, the ML model is trained using data obtained from the one or more sensors 916. For example, data acquired by sensors 916 is used to train a ML algorithm used by surgical robot 902 or AI to control surgical robot 902.

Sensors 916 may additionally comprise an X-ray dosimeter to monitor the intensity of X-rays being emitted toward the patient to prevent excessive doses of radiation. The sensors 916 may be utilized to reduce the intensity of the X-rays or reduce the duration or increase the interval in which the X-rays are emitted toward the patient to control the dose throughout a procedure. An imaging device 918 refers to any device capable of collecting data that can be used to create an image, or a representation of a physical structure or phenomenon. Imaging device 918 is any device capable of detecting sound or electromagnetic waves and assembling a visual representation of the detected waves. Imaging devices 918 can collect waves from any part of the electromagnetic spectrum or sounds at any range of frequencies, often as a matrix of independently acquired measurements, with each measurement representing a pixel of a two or three-dimensional image. These measurements may be taken simultaneously or in series via a scanning process or a combination of methods.

Some pixels of an image produced by an imaging device 918 may be interpolated from direct measurements representing adjacent pixels in order to increase the resolution of a generated image. Imaging devices 918 may receive or generate imaging data from a plurality of imagining devices 918. The plurality of imaging devices 918 may include, for example, cameras attached to the robotic arm 912, cameras mounted to the ceiling or other structure above the surgical theater, cameras that may be mounted on a tripod or other independent mounting device, cameras that may be body worn by the surgeon or other surgical staff, cameras that may be incorporated into a wearable device, such as an AR device like Google Glass, Microsoft HoloLens, etc., cameras that may be integrated into an endoscopic, microscopic, laparoscopic, or any camera or other imaging device 918 (e.g., ultrasound) that may be present in the surgical theater.

Imaging device 918 may include any algorithm or software module capable of determining qualitative or quantitative data from medical images, which may be, for example, a deep learning algorithm that has been trained on a data set of medical images. An imaging device 918 may further refer to a device used to acquire medical imagery by any means, including MRI, CT, X-ray, PET, ultrasound, arthrography, angiography, fluoroscopy, myelography, etc. An imaging device 918 may acquire images in real-time or be used to create composite images or models in real-time.

Cloud 920 is a distributed network of computers comprising servers and databases. Cloud 920 may be a private cloud, where access is restricted by isolating the network, such as preventing external access, or by using encryption to limit access to only authorized users. Alternatively, a cloud 920 may be a public cloud where access is widely available via the Internet. A public cloud may not be secured or may include limited security features.

In embodiments, system 900 generates controls on a GUI for the user to perform actions on a 3D digital twin using an XR surgical simulation environment. In embodiments, the controls are customized for the anatomy of the patient and the surgical procedure. For example, surgical robot network 922 is a network connected to surgical robot 902 in which surgical robot 902 receives and sends data, provides controls to a user for surgical robot 902 through user interface 910 and enables a user to use metaverse GUI 944 to design, test, and create a surgical process for a patient. Base module 924 initiates the input module 926, the setup module 928, the simulation module 930, the correlation module 932, the review module 934, and the output module 936 using a message, a software or hardware trigger, an interrupt, or another signal.

Input module 926 begins by being initiated by the base module 924. The input module 926 connects to the MRI module 948. The input module 926 sends a request to the MRI module 948 for the data stored in the MRI database 950. Then, the input module 926 is continuously polling to receive the data stored in the MRI database 950. The input module 926 receives the data stored in the MRI database 950 from the MRI module 948. Then the input module 926 stores the received data in the patient database 938. The input module 926 returns to the base module 924. Setup module 928 begins operation by being initiated by the base module 924. The setup module 928 filters the patient database 938 on the patient ID. The setup module 928 extracts the patient's imaging data stored in the patient database 938. The setup module 928 creates the patient's 3D digital twin. The setup module 928 stores the patient's digital twin in the surgery database 940. Then the setup module 928 displays the digital twin on the metaverse GUI 944.

System 900 generates a digital twin from patient images. The digital twin generated is a real-time virtual representation of the real-world operating room and surgical procedure (the physical twin) that serves as the indistinguishable digital counterpart of it for practical purposes, such as system simulation, integration, testing, monitoring, and maintenance. The operating room is outfitted with various sensors related to vital areas of functionality. These sensors produce data about different aspects of the patient and surgical performance, such as temperature, medical conditions, and more. The data from an operating room can be relayed to system 900 and applied to the digital copy.

In embodiments, the digital twin can include a digital twin prototype (DTP), a digital twin instance (DTI), or a digital twin aggregate (DTA). The DTP consists of the designs, analyses, and processes that realize the physical patient and procedures. The DTI is the digital twin of each individual instance of the patient's anatomy. The DTA is the aggregation of DTIs whose data and information can be used for virtual simulation of a surgical procedure, prognostics, and learning. In embodiments, Internet of Things (IoT) technology is used by system 900 to enable connectivity between the physical operating room and its digital counterpart. The connectivity is generated by sensors on the physical patient or in the operating room that obtain data and integrate and communicate this data through various integration technologies.

In embodiments, system 900 generates an XR surgical simulation environment by associating one or more virtual models of one or more surgical tools 154 and the surgical robot 902 with one or more images of a patient and sensor data of the patient. The XR surgical simulation environment comprises a digital twin of the anatomy of the patient for performing a virtual simulation of a surgical procedure. In embodiments, system 900 displays, via an electronic display, the 3D digital twin within the XR surgical simulation environment for viewing by a user. For example, a user can input setup options for metaverse GUI 944 to generate the XR surgical simulation environment. The setup module 928 returns to the base module 924. A simulation module 930 which begins by being initiated by the base module 924. The simulation module 930 filters the surgery database 940 on the patient ID. The simulation module 930 extracts the patient's digital twin. The simulation module 930 displays the patient's digital twin on the metaverse GUI 944. Then the simulation module 930 displays the available tools for the surgery on the metaverse GUI 944. Then the user selects a tool from the metaverse GUI 944.

In embodiments, system 900 identifies surgical actions performed by a user on a digital twin using an XR surgical simulation environment. For example, the user performs an action on the metaverse GUI 944 using the selected tool. Simulation module 930 determines if the user saved the tool and the action performed on the metaverse GUI 944. If it is determined that the user did not save the tool and the action performed, the process returns to the user selecting a tool required for the surgery.

If it is determined that the user selected to save the tool and the action performed, the simulation module 930 determines if another step is required in the surgery. If it is determined that another step is required for the surgery, then the user selects to add another step in the metaverse GUI 944, and the process returns to the user selecting a tool required for the surgery. If it is determined that another step is not required for the surgery, the simulation module 930 stores the tools and actions performed in the surgery database 940. Then the simulation module 930 returns to the base module 924.

Correlation module 932 begins operation by being initiated by the base module 924. The correlation module 932 filters the surgery database 940 based on the surgery type. For example, the correlation module 932 filters the surgery database 940 on the type of surgery that is needed by a patient, such as a Brostrom-Gould repair surgery. The Brostrom-Gould repair surgery is primarily used to repair the ATFL in the ankle. The recovery time for the procedure varies according to the patient but usually takes a minimum of 3-6 months. The surgery stabilizes the ankle, improves the ankle's mechanics, and restores function. The surgery helps a patient to experience less pain related to his or her injury and ankle sprains, as well as to avoid early arthrosis.

Correlation module 932 selects the first parameter in the surgery database 940. The correlation module 932 performs correlations on the selected parameter and the remaining parameters to determine if the parameters are highly correlated. The correlation module 932 determines if the correlation coefficient is over the predetermined threshold, for example, over a correlation coefficient of 0.75. If it is determined that the correlation coefficient is over the predetermined threshold, then the correlation module 932 extracts the best match data point from the data set. The correlation module 932 then stores the data entry for the best match data point in the recommendation database 942. If it is determined that the correlation coefficient is not over the predetermined threshold, or after the data entry for the best match data point is stored in the recommendation database 942, the correlation module 932 determines if there are more parameters remaining in the surgery database 940. If it is determined that there are more parameters remaining in the surgery database 940, the correlation module 932 selects the next parameter in the surgery database 940, and the process returns to performing correlations on the parameters. If it is determined that there are no more parameters remaining in the surgery database 940, the correlation module 932 returns to the base module 924.

Review module 934 begins by being initiated by the base module 924. The review module 934 filters the surgery database 940 based on the patient ID. The review module 934 extracts the patient data from the surgery database 940. The review module 934 selects the first step in the patient's procedure from the extracted data from the surgery database 940. The review module 934 sorts the recommendation database 942 by the highest correlated data entry. The review module 934 selects the highest correlated data entry from the recommendation database 942. The review module 934 displays the patient data and the correlated data entry on the metaverse GUI 944. The review module 934 determines if the user selected the next data entry in the recommendation database 942. In embodiments, system 900 adjusts a surgical workflow based on a comparison of the surgical workflow to stored historical workflows. For example, if it is determined that the user did not select the next correlated data entry in the recommendation database 942, the process continues to determine if the user made any adjustments to the step in the surgical workflow. In embodiments, system 900 transmits the adjusted surgical workflow to surgical robot 902 to configure the surgical robot 902 with the adjusted surgical workflow. The adjusted surgical workflow comprises the workflow objects and information describing the surgical actions. Surgical robot 902 is configured to perform surgical actions on the patient according to the adjusted surgical workflow.

If it is determined that the user selected the next data entry in the recommendation database 942, the review module 934 selects the next data entry in the recommendation database 942, and the process returns to displaying the patient data and the correlated data entry on the metaverse GUI 944. Then the review module 934 determines if the user adjusted the step for the patient. If it is determined that the user did adjust the step for the patient, the review module 934 stores the adjustment in the surgery database 940. If it is determined that the user did not adjust the step for the patient or after the adjustment is stored in the surgery database 940, the review module 934 determines if there are more steps remaining for the procedure for the patient. If it is determined that there are more steps remaining for the patient's procedure, then the review module 934 selects the next step for the patient's procedure, and the process continues to sort the recommendation database 942 on the highest correlated data entry.

If it is determined that there are no more steps remaining for the patient's procedure, then the review module 934 returns to the base module 924. In embodiments, system 900 configures surgical robot 902 with an adjusted workflow comprising workflow objects and information describing surgical actions performed on a digital twin. For example, output module 936 begins by being initiated by base module 924. Output module 936 connects to the surgical robot 902. Then, the output module 936 sends the data stored in the surgery database 940 to the surgical robot 902. The output module 936 then returns to the base module 924.

Patient database 938 can include data describing a patient ID (e.g., JS123), a first name of a patient (e.g., John), or a last name of a patient (e.g., Smith). Patient database 938 can include data describing an area in which an MRI was taken (e.g., ankle) or data files (e.g., JS-Ankle#1.JPEG). Patient database 938 can include data describing the MRI data of a patient. MRI is a medical imaging technique that uses a magnetic field and computer-generated radio waves to create detailed images of the organs and tissues in a body. Most MRI machines are large, tube-shaped magnets. When a patient lies inside an MRI machine, the magnetic field temporarily realigns water molecules in the body. Radio waves cause these aligned atoms to produce faint signals, which are used to create cross-sectional MRI images. In some embodiments, the MRI machine can also produce 3D images that can be viewed from different angles. In some embodiments, the database contains a series of cross-sectional MRI images and stores the data in the sequence in which they are captured by the imaging device. In some embodiments, the database may contain all of the historical medical images of a patient in order to create a virtual 3D representation of the patient's anatomy. In some embodiments, the database may contain all of the historical medical images of a patient in order to create a virtual 3D representation of the patient's anatomy.

In some embodiments, the patient's medical images used to create a 3D image or digital twin of the patient may be from a singular type of medical imaging, a plurality of different types of medical imaging, or any combination of types of medical imaging, including, MRI, CT, X-ray, PET, ultrasound, arthrography, angiography, fluoroscopy, myelography, etc.

Surgery database 940 can include data describing a patient ID, a type of surgery, or a virtual 3D image of the patient. Surgery database 940 can include data describing tools required for a surgery, a process required for a surgery, or data files for replays of a step as input into metaverse GUI 944. Surgery database 940 can include data describing (x, y, z) coordinates of a patient's body, tools used, or techniques used (e.g., a threading technique used in a surgery). The (x, y, z) coordinates of the anatomy specify the position of any anatomical structure in three-dimensional space using distances to three mutually perpendicular planes (or, equivalently, by a perpendicular projection onto three mutually perpendicular lines). In embodiments, n Cartesian coordinates (an element of real n-space) specify the structure in an n-dimensional Euclidean space for any dimension n.

Surgery database 940 can include data describing calculations (e.g., forces required in certain steps or techniques), materials required for certain steps or techniques, or specialists required for specific steps or techniques. Surgery database 940 can include data describing patient data of historical patients that have had procedures performed.

Recommendation database 942 contains the data entries that had highly correlated parameters that were over the predetermined threshold in the process described in the correlation module 932. The recommendation database 942 can include data describing a patient's ID, correlation coefficients, or a type of surgery. The recommendation database 942 can include data describing a sex of a patient, an age of a patient, or a location of a patient. The recommendation database 942 can include data describing a recovery time of a patient, a virtual 3D image of the patient, or tools required for a surgery. The recommendation database 942 can include data describing a process required for a surgery, data files for replays of a step as input into metaverse GUI 944, or (x, y, z) coordinates of a patient's body. The recommendation database 942 can include data describing tools used, techniques used (e.g., a threading technique used in the surgery) or calculations (e.g., forces required in certain steps or techniques). The recommendation database 942 can include data describing materials required for certain steps or techniques or specialists required for the specific steps or techniques.

The recommendation database 942 can include data describing a hospital in which a procedure takes place, a patient's primary care physician, or a surgeon or specialist performing a procedure. In embodiments, system 900 extracts a success rate of a surgical procedure from stored historical workflows. A current surgical workflow is adjusted based on the success rate. For example, recommendation database 942 includes data describing a success rate of a type of procedure, etc. In embodiments, data entries describe a patient's entire surgical procedure to be used during the review module 934. In some embodiments, the data entries may store the individual steps of the patient's surgical procedure that are highly correlated with the current patient's planned surgical procedure.

Metaverse GUI 944 is an XR-space in which users can interact with a computer-generated surgical simulation environment and other users. Metaverse GUI 944 allows a user, such as a surgeon, doctor, medical professional, etc., to view an area of a patient's body that requires surgery in a VR space. The metaverse GUI 944 allows the user to view a virtual 3D model of the operating room in order to input the movements necessary for the surgical robot 902. The metaverse GUI 944 also allows the user to select various tools, materials, and techniques that are required for the surgery and allows the user to manipulate the tools, materials, and techniques rendered over the patient's virtual 3D image to perform the processes and steps needed for the surgery in a virtual space. The user's movements and actions are saved and stored in the surgery database 940 to assist the surgeon in performing the surgery or to provide the surgical robot 902 with the approximate (x, y, z) coordinates to perform the surgery.

Metaverse GUI 944 enables users to view or replay the surgery in the virtual 3D space to alter or adjust movements or actions to perform the surgery. The metaverse GUI 944 also allows other users to join in the same virtual 3D space to allow multiple users to collaborate on the surgical process for a patient, such as to select various tools, materials, and techniques that are required for the surgery and allows the user to manipulate the tools, materials, and techniques rendered over the patient's virtual 3D image to perform the processes and steps needed for the surgery in a virtual space. In some embodiments, the metaverse GUI 944 may provide the user or surgical robot 902 with a list of materials needed, a list of tools required, a workflow process of the surgical procedure, a virtual 3D visual replay of the surgical procedure, etc.

In embodiments, system 900 generates a surgical workflow for the surgical robot 902. The surgical workflow comprises workflow objects for the surgical procedure based on surgical actions performed on a digital twin. A workflow defines an orchestrated and repeatable pattern of activity (e.g., surgical steps) enabled by the systematic organization of medical resources into processes that transform materials, provide services, or process information. System 900 defines a workflow as a sequence of operations, the work of surgical robot 902, or one or more simple or complex mechanisms. A workflow can be a building block to be combined with other surgical steps or procedures. System 900 establishes, performs, and monitors a defined sequence of processes and tasks in accordance with the workflow. A workflow can be represented as a graphical map. System 900 also includes an extensible interface so that external software applications can be integrated and provide support for workflows that provide faster response times.

A workflow can be a description of a logically necessary, partially ordered set of actions to accomplish a specific goal (e.g., the surgical procedure) given certain starting conditions. A surgical plan, when augmented with a schedule and resource allocation calculations, defines a particular instance of systematic processing in pursuit of a goal (workflow). A workflow may be viewed as an often optimal or near-optimal realization of the mechanisms required to execute the surgical plan repeatedly.

A workflow object refers to an event, task, gateway, etc., associated with the workflow. Events define the start and the end of a surgical step that the workflow specifies. Each workflow has a Start event and an End event. Optionally, a workflow can include one or more Terminate events. A task (also referred to as a workflow action) runs a single unit of work in the workflow, such as a portion of a surgical step. An action represents something that is performed during the workflow. Examples of actions are provided throughout this specification in the context of arthroscopic surgery.

In some embodiments, the user may customize the virtual surgical simulation environment to match the operating room the surgeon will perform the surgery in, allowing the user to structure or design an operating room to determine the location of certain items for when the surgery is performed, or allow the user to create a unique operating room that is personalized by the user. In some embodiments, the patient's medical images used to create a 3D image or digital twin of the patient may be from a singular type of medical imaging, a plurality of different types of medical imaging, or any combination of types of medical imaging, including MRI, CT, X-ray, PET, ultrasound, arthrography, angiography, fluoroscopy, myelography, etc.

Hospital network 946 provides medical information of a patient to the surgical robot network 922, such as electronic health records, medical images, such as MRI, CT, X-ray, PET, ultrasound, arthrography, angiography, fluoroscopy, myelography, etc., lists patient doctors and health care professionals, provides patient's current medications and prescriptions, provides patient's medical history, and provides patient's specialists, etc. MRI module 948 connects to the input module 926. MRI module 948 is continuously polling to receive a request for the data stored in the MRI database 950 from the input module 926. The MRI module 948 receives a request for the data stored in the MRI database 950 from the input module 926. Then, the MRI module 948 sends the data stored in the MRI database 950 to the input module 926 and returns to continuously poll for a request from the input module 926 for the data stored in the MRI database 950. MRI database 950 can store data describing a patient ID, a first name of a patient, a last name of a patient, an area in which an MRI was taken (e.g., ankle), or data files. MRI database 950 can also store data describing the MRI data of a patient.

In some embodiments, the patient's medical images used to create a 3D image or digital twin of the patient may be from a singular type of medical imaging, a plurality of different types of medical imaging, or any combination of types of medical imaging, including MRI, CT, X-ray, PET, ultrasound, arthrography, angiography, fluoroscopy, myelography, etc.

In some embodiments, system 900 generates an XR surgical simulation environment, including virtual models of one or more surgical tools 154, a virtual model of surgical robot 902 configured to virtually operate the one or more surgical tools 154, and a 3D digital anatomical twin of a patient. System 900 displays, via an electronic display, at least a portion of the 3D digital twin for viewing by a user controlling the virtual model of the surgical robot 902 within the XR surgical simulation environment. System 900 identifies surgical actions performed by the virtual model of the surgical robot 902 using the virtual models of the surgical tools 154. System 900 generates a surgical workflow for the surgical robot 902. The surgical workflow comprises workflow objects for the surgical procedure based on the identified surgical actions. System 900 adjusts the surgical workflow based on a comparison of the surgical workflow to one or more stored reference workflows. System 900 transmits the adjusted surgical workflow to the surgical robot 902 to perform the surgical procedure according to the adjusted surgical workflow.

In some embodiments, system 900 compares the surgical workflow to the one or more stored reference workflows by scoring one or more steps of the surgical workflow. System 900 compares the scored one or more steps of the surgical workflow with corresponding scores of reference steps in the reference workflows. System 900 selects the reference steps with scores that are higher than the corresponding scored steps of the surgical workflow to modify the surgical workflow.

In some embodiments, the virtual model of the surgical robot 902 is configured to simulate the functionality of the surgical robot 902 to be used in the procedure. In some embodiments, system 900 receives user input from the user. System 900 controls the movement of the virtual model of the surgical robot 902 based on the user input. System 900 scores the surgical steps performed in the XR surgical simulation environment, wherein the scoring is used to determine the adjusted surgical workflow. System 900 generates 3D movements of the surgical tools within the XR surgical simulation environment to simulate surgical steps performed by the one or more surgical tools 154.

Figure 10:
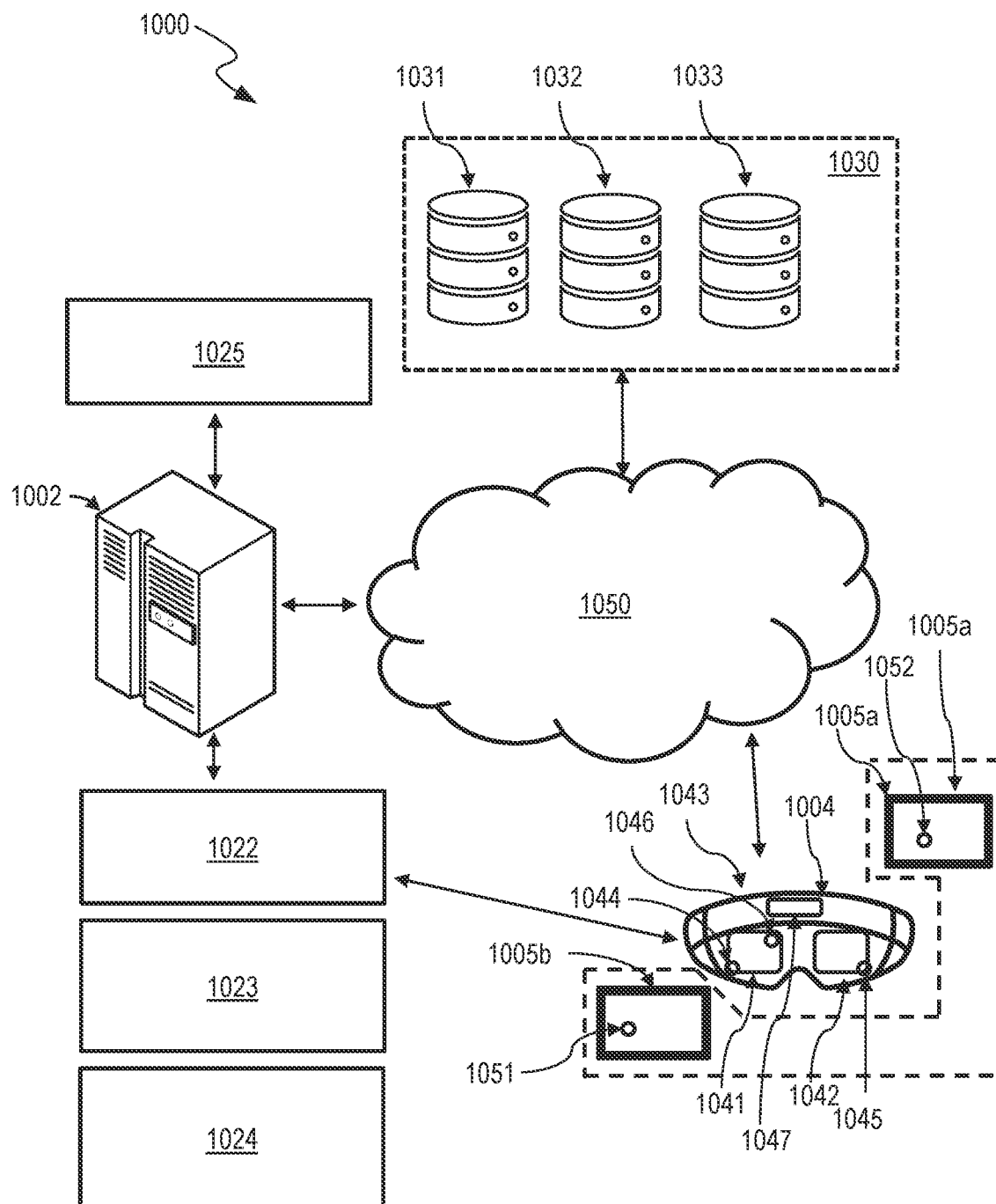
FIG. 10 illustrates an extended reality (XR) system for facilitating robotic medicine, in accordance with one or more embodiments.

FIG. 10 illustrates an XR system 1000, in accordance with one or more embodiments. System 1000 can be used to perform an XR computer-implemented method. For example, system 1000 can be used for pre-operative training, surgical planning, intra-operative assistance or monitoring, etc. For pre-operative training, system 1000 can be used to simulate surgical steps, train ML systems, and analyze or map anatomy (e.g., patient anatomy obtained via images, digital twin, etc.). An example ML system 200 is illustrated and described in more detail with reference to FIG. 2.

System 1000 can analyze user performance and then generate additional simulations based on the user performance to allow users to practice surgical procedures any number of times. For surgical planning, a user (e.g., a physician, surgeon, or other medical professional) or system 1000 can remove, add, or modify actions based on, for example, user performance, user input, predicted events, outcomes, or the like. For intra-operative assistance or monitoring, system 1000 can generate an XR environment (e.g., an AR environment or other environment) with displayed anatomical information (e.g., mappings of anatomical features), surgical plan mapping, instrument data (e.g., instrument instructions, operational parameters, etc.), sensor data, patient data (e.g., real-time vitals or patient records), and other information for assisting the user.

Mappings of anatomical features can include, without limitation, labeling that identifies anatomic elements (e.g., organs or tissues), positions of anatomical features (including underlying anatomical features not visible to the naked eye), target information (e.g., targeted tissue to be removed or target location for implanting devices), or the like. System 1000 can display, for example, mapping information in the multi-modality images 600, 610 of FIGS. 6A, 6B, respectively. For example, the anatomical features (e.g., tibia, fibula, etc.) of the joint in image 600 can be labeled as shown in FIG. 6A. The diseased tissue 630 of FIG. 6B can be labeled and identified to assist with its removal. As the tissue 630 is removed, the image can be updated to show margins to limit the removal of healthy tissue. The user can select layers of mappings (e.g., cardiovascular layers showing cardiovascular features, neurological layers showing nerve tissue, orthopedic layers identifying anatomy of joints, target layers showing targeted tissue(s) or implant sites, surgical step layers showing a post-surgical step outcome, simulation layers shown simulation outcomes, etc.) to control the displayed information.

In some embodiments, system 1000 obtains a digital anatomical model representing the anatomical features of a patient. The digital anatomical model is generated using the imaging methods described in more detail with reference to FIG. 1 and the methods described in more detail with reference to FIG. 9. System 1000 can include an AR device (e.g., wearable device 1004) that provides VR simulations for practicing surgical procedures and identifying anatomical features (e.g., tissue, organs, abnormal features, normal features, or non-targeted tissue).

In some embodiments, system 1000 generates an XR surgical simulation environment that includes the digital anatomical model. The digital anatomical model is viewable by at least one user using an AR device, such as the devices illustrated and described in more detail with reference to FIGS. 10-11. The XR surgical simulation environment is configured to enable the at least one user to virtually perform one or more surgical steps on the digital anatomical model. For example, the user can identify types of tissue (e.g., bony tissue, cartilage, skin, fat, nerve tissue), abnormal features (e.g., diseased tissue, malfunctioning organs, or normal features such as healthy tissue or organs), non-targeted tissue (e.g., nerves or healthy tissue) when viewing a digital twin or a virtual anatomical model of the patient.

A different XR platform is used, and a different XR surgical simulation environment is generated for different surgery types, e.g., cardiovascular, neurological, or orthopedic surgery. A different XR platform is used for each of the above because each platform has different modeling parameters. The modeling parameters can be retrieved from a modeling parameter library for generating a digital anatomical model based on one or more surgical steps of a surgical plan. For example, cardiovascular parameters used to generate a digital anatomical model include heart valve properties, tissue properties (e.g., elastic properties of vascular wall tissue), fluid pressures (e.g., aortic blood pressure), heart rate, dP/dt max, cardiac output, stroke volume, pulmonary artery blood pressure, pulmonary capillary wedge pressure, peripheral resistance, tension time index, left cardiac work, or renal blood flow and resistance. Neurological parameters can include parameters related to nerve tissue (e.g., signal transmission characteristics, size of nerves, etc.), mental status, cranial nerves, motor system, reflexes, sensory system, coordination, or station and gait.

Different ML models are used and trained differently for each XR surgical simulation environment generated for different surgery types. For example, ML models for orthopedic surgery are trained using training data describing joint and muscle forces, muscle and joint loads, activation patterns, muscle-tendon behavior, muscle excitations, or muscle fiber lengths. Different XR platforms are used because the error margins between anatomical features are different for different surgery types. For example, brain surgery offers less room for error than orthopedic surgery. The granularity of anatomical features is different. Therefore, different VR modeling is performed for each surgery type, and different software packages are designed.

VR training can also include identifying features (e.g., anatomical structures or delivery paths), surgical equipment, body part positions (e.g., a body part position of the patient, a body part position of the user or surgical team member positions), and other data to assist in surgical procedures. User input (e.g., labels, position notes, or the like) can be collected (e.g., voice, keyboard, XR device input, etc.) during the simulations and then used to modify planned surgical procedures, provide annotation during surgical procedures using XR environments, or the like.

In some embodiments, system 1000 receives anatomical mapping information from the at least one user via the XR device (e.g., VR device, AR device, etc.). In some embodiments, the same XR device is used to perform VR simulations to input anatomical mapping information and perform an AR-assisted surgery on the patient based on the anatomical mapping information. In other embodiments, different XR devices are used for training and performing the surgery. In some training procedures, multiple users input anatomical mapping information, which is aggregated to determine what information is correct. The aggregation can be used to determine confidence scoring for XR mapping. For example, a confidence score for AR mapping is based on a threshold percentage (e.g., at least 80%, 90%, 95%, or 99%) of the users providing the same mapping (e.g., mapping input using an XR environment).

In response to the confidence score reaching a threshold level for anatomical features associated with a procedure, the mapping can be deployed for performing the procedure on patients. In AR/VR-assisted surgical procedures, the wearable device 1004 can display information to assist the user. The displayed information can include surgical plan information (e.g., instrument information, current surgical staff, progress in the surgical procedure, or potential adverse events), patient vitals, anatomical mappings, physician notes, and other information to assist the user. The user can move, add, or eliminate displayed information to enhance the experience. The configuration of the wearable device 1004, information displayed, and feedback provided to the user can be selected based on the procedures to be performed.

In some embodiments, system 1000 performs confidence-score AR mapping to meet a confidence threshold for the one or more surgical steps to be performed on the anatomy of the patient. The confidence-score AR mapping includes selecting at least a portion of the anatomical mapping information for the AR mapping to the anatomy of the patient. The selected anatomical mapping information is mapped to the anatomical features of the patient. Via the AR device, an AR environment is displayed to the at least one user. The AR environment includes the mapping of the selected anatomical mapping information to the anatomical features.

In some embodiments, the confidence threshold (e.g., 90%, 95%, or 99%) is selected based on a surgery type of the one or more surgical steps. Image data of the patient is segmented to identify digital anatomical features associated with the surgery type. For example, the identification is performed using the ML system 200 of FIG. 2. The digital anatomical features are part of the digital anatomical model. Via a VR device, one or more anatomical identification prompts are generated for receiving the anatomical mapping information from the at least one user to label one or more discrete anatomical features viewed by the user. The surgery type can be a cardiovascular surgery, an orthopedic surgery, brain surgery, a joint replacement surgery, or an anatomical features repair surgery. The discrete anatomical features associated with the surgery type can be identified using one or more ML algorithms.

The AR environment includes the mapping of the selected anatomical mapping information to the anatomical features. In some embodiments, the computer system maps at least some of the anatomical features of the patient using a ML platform. The ML platform includes a plurality of surgery-type-specific ML modules to be applied to the image data of the patient to provide the anatomical surgery-type mapping. The surgery-type-specific ML modules can be trained using surgery-type grouped data sets, including surgery-type mappings. Surgery-type mappings can include layers based on the surgery type. For example, a cardiovascular surgery mapping can include layers showing cardiovascular features (e.g., vessels, arteries, etc.), targeted features (e.g., heart valves to be modified or replaced, locations of atherosclerosis, etc.). A neurological surgery mapping can include layers showing nerve tissue (e.g., a layer with target nerve tissue, a layer with non-targeted nerve tissue). An orthopedic surgery mapping can include layers identifying the anatomy of joints. The user can select layers, data sets, and mapping information to be added or removed from the surgery-type data. For example, each platform includes a different feature extraction module, a different ML model, and different training methods.

System 1000 includes a server (or other computer system 1002), where such system 1002 includes one or more non-transitory storage media storing program instructions to perform one or more operations of a projection module 1022, a display module 1023, or a feedback module 1024. In some embodiments, system 1000 includes wearable device 1004, where the wearable device 1004 may include one or more non-transitory storage media storing program instructions to perform one or more operations of the projection module 1022, the display module 1023, or the feedback module 1024.

Wearable device 1004 can be a VR headset, such as a head-mounted device that provides VR for the wearer. Wearable device 1004 can be used in applications, including simulators and trainers for robotic medicine. Wearable device 1004 typically includes a stereoscopic display (providing separate images for each eye), stereo sound, and sensors like accelerometers and gyroscopes for tracking the pose of the user's head to match the orientation of the virtual camera with the user's eye positions in the real world. The user is typically a medical professional, e.g., a surgeon, a nurse, a surgeon's assistant, or a doctor. Wearable device 1004 can also have eye-tracking sensors and controllers. Wearable device 1004 can use head-tracking, which changes the field of vision as a surgeon turns their head.

Wearable device 1004 can include imagers, sensors, displays, feedback devices, controllers, or the like. The wearable device 1004 can capture data, locally analyze data, and provide output to the user based on the data. A controller of the wearable device 1004 can perform local computing (e.g., edge computing) with or without communicating with a remote server and can store edge computing ML libraries locally analyzing data to provide output. This allows onboard processing to be performed to avoid or limit the impact of, for example, network communications.

System 1000 can include one or more wearable devices configured to be worn on other parts of the body. The wearable devices can include, for example, gloves (e.g., haptic feedback gloves or motion-tracking gloves), wearable glasses, loops, heart monitors, heart rate monitors, or the like. These wearable devices can communicate with components of the system 1000 via wire connections, optical connections, wireless communications, etc. The wearable device 1004 can also communicate with external sensors and equipment. Example sensors and medical equipment is illustrated and described in more detail with reference to FIG. 1. The wearable device 1004 can receive data (sensor output, equipment output, operational information for instruments, etc.) and display the received information to the user. This allows the user to view sensor data without turning their attention away from a surgical site.

System 1000 can include a set of external displays 1005 (e.g., accessories of the wearable device 1004, desktop monitors, television screens, or other external displays), where the set of external displays 1005 may be provided instructions to display visual stimuli based on measurements or instructions provided by the wearable device 1004 or the server 1002. In some embodiments, the wearable device 1004 may communicate with various other electronic devices via a network 1050, where the network 1050 may include the Internet, a local area network, a peer-to-peer network, etc.

The wearable device 1004 may send and receive messages through the network 1050 to communicate with a server 1002, where the server 1002 may include one or more non-transitory storage media storing program instructions to perform one or more operations of a statistical predictor 1025. It should further be noted that while one or more operations are described herein as being performed by particular components of the system 1000, those operations may be performed by other components of the system 1000 in some embodiments. For example, operations described in this disclosure as being performed by the server 1002 may instead be performed by the wearable device 1004, where program code or data stored on the server 1002 may be stored on the wearable device 1004 or another client computer device instead. Similarly, in some embodiments, the server 1002 may store program code or perform operations described as being performed by the wearable device 1004. For example, the server may perform operations described as being performed by the projection module 1022, the display module 1023, or the feedback module 1024. Furthermore, although some embodiments are described herein with respect to ML models, other prediction models (e.g., a statistical model) may be used instead of or in addition to ML models. For example, a statistical model may be used to replace a neural network model in one or more embodiments. An example ML system 200 is illustrated and described in more detail with reference to FIG. 2.

In some embodiments, the system 1000 may present a set of stimuli (e.g., shapes, text, or images) on a display of the wearable device 1004. The wearable device 1004 may include a case 1043, a left transparent display 1041, and a right transparent display 1042, where light may be projected from emitters of the wearable device through waveguides of the transparent displays 1041-1042 to present stimuli viewable by an eye(s) of a user wearing the wearable device 1004. The wearable device 1004 also includes a set of outward-facing sensors 1047, where the set of outward-facing sensors 1047 may provide sensor data indicating the physical space around the wearable device 1004. In some embodiments, the set of outward-facing sensors 1047 may include cameras, infrared sensors, lidar sensors, radar sensors, etc. In some embodiments, the sensors 1047 can be inward-facing to monitor the user's state (e.g., level of stress, alertness level, etc.).

In some embodiments, the sensors 1047 can be cameras that capture images of the environment, patient, equipment, user, or the like. The captured images can be used to analyze steps being performed, a patient's state, and/or the surrounding environment. This allows the system 1000 to provide comprehensive analytics during procedures. For example, output from the sensors 1047 of the wearable device 1004 can be used to analyze the concentration/focus level of the user, alertness of the user, and stress level of the user (e.g., stress level calculated based on user metrics, such as heart rate, blood pressure, or breathing pattern), and other metrics. Surgical plans can be modified based on the collective metrics to enhance the performance of the user. In some embodiments, if the user becomes unable to maintain a threshold level of focus, the system 1000 can modify surgical plans such that critical steps are performed by another user, a robotic surgery system (such as the systems illustrated and described in more detail with reference to FIGS. 4A, 4B, and 9), or using alternative techniques. This allows interoperative modification of surgical steps based on the user.

In some embodiments, sensors 1047 can track the wearer's eyes and provide feedback to the user to encourage the user to focus on targeted regions for visualization. This can help train the user to focus attention on regions or areas for each surgical step or action. The wearable device 1004 can receive and store operative plans, surgical data, and other information sufficient to allow one or more surgical steps to be performed with or without remote communications. This ensures that surgical steps can be completed if there is communication failure at the surgical suite.

In some procedures, the system 1000 can develop one or more training simulations for a user. The user can perform the simulations for manual procedures, robotically assisted procedures, or robotic procedures. The system 1000 can adaptively update the simulations based on desired procedure criteria, such as surgical time, predicted outcome, safety, outcome scores, or the like. This allows the system 1000 to develop surgical plans suitable for the procedures while training the user. In some embodiments, the wearable device 1004 can collect user input to synchronize the user's input with a surgical procedure. For example, the system 1000 can develop surgical plans with surgical steps for appropriate time periods based on threshold metrics. Example surgical plans are described in more detail with reference to FIG. 5. If the user becomes fatigued or tired, surgical steps can be shortened, reduced, or assigned to other users. Other users can use other wearable devices that are synchronized to communicate with the wearable device 1004 to provide coordinated operation between users.

In some embodiments, system 1000 receives a surgery type of the one or more surgical steps. A digital anatomical model is generated based on the surgery type. The digital anatomical model includes anatomical information associated with a portion of the anatomical features to be surgically altered during the one or more surgical steps. For example, system 1000 retrieves modeling parameters for generating the digital anatomical model based on the one or more surgical steps. The digital anatomical model is generated according to the modeling parameters. The modeling parameters can include, for example, one or more parametric modeling parameters, model properties (e.g., properties of tissue, fluids, thermal properties, etc.), fluid modeling parameters, mesh parameters (e.g., parameters for generating 3D meshes), kinematic parameters, boundary conditions, loading parameters, biomechanical parameters, fluid dynamic parameters, thermodynamic parameters, etc. The anatomical features are identified within the digital anatomical model. Anatomical characteristics are assigned to the identified anatomical features for viewing by the at least one user. The anatomical characteristics can include, for example, one or more anatomical feature statuses (e.g., unhealthy, normal, healthy), tissue properties, vitals for anatomical elements, sizes of anatomical features, etc.

In some embodiments, system 1000 retrieves modeling parameters for generating the digital anatomical model based on the one or more surgical steps. The digital anatomical model is generated according to the modeling parameters. The anatomical features are identified within the digital anatomical model. Anatomical characteristics are assigned to the identified anatomical features for viewing by the at least one user. For example, the modeling parameters define three-dimensional (3D) objects in an XR or AR environment that can be moved with a number of degrees of freedom (e.g., six degrees of freedom) using a controller (e.g., cursor). Modeling the identified anatomical features enables a user to experiment with perspective compared to traditional software or surgical practice.

The XR surgical simulation environment can include polygonal modeling, e.g., connecting points in 3D space (vertices) by line segments to form a polygonal mesh. For example, the XR surgical simulation environment includes textured polygonal meshes that are flexible and/or planar to approximate curved surfaces of simulation of surgical steps. In some embodiments, curve modeling (defining surfaces by curves that are influenced by weighted control points) is used. For example, performing the surgical steps virtually on the digital anatomical model uses digital sculpting (also known as sculpt modeling or 3D sculpting) to cut, push, pull, smooth, grab, pinch or otherwise manipulate virtual anatomical features as if they were made of real-life tissue or bone.

Generating the digital anatomical model is performed by developing a mathematical coordinate-based representation of different surfaces of the anatomical features in three dimensions by manipulating edges, vertices, and polygons in the simulated XR environment. The digital anatomical model represents the physical anatomy using a collection of points in 3D space, connected by different geometric entities such as lines and curved surfaces, etc. In embodiments, the digital anatomical model can be created by procedural modeling or scanning based on the imaging methods described in more detail with reference to FIG. 1. The digital anatomical model can also be represented as a 2D image using 3D rendering.

The AR mapping to the anatomy can include solid models that define a volume of the anatomical feature they represent, mapped using constructive solid geometry. In some embodiments, system 1000 receives information describing at least one surgical outcome for the one or more surgical steps. One or more correlations are determined between the anatomical mapping information and the at least one surgical outcome. A confidence-score AR mapping engine is updated based on the determination. The confidence-score AR mapping engine is configured to perform confidence-score AR mapping for other patients in new AR environments.

The anatomical mapping information can include shells or boundaries that represent surfaces of the anatomical features. The AR environment displayed to the at least one user can include polygonal meshes representing the physical anatomical features, subdivision surfaces, or level sets for deforming surfaces that can undergo topological changes. The AR mapping process can include transforming digital representations of the anatomical features into polygonal representations (polygon-based rendering) of the anatomical features overlaid on images of the physical anatomical features.

Furthermore, the system 1000 may present stimuli on the set of external displays 1005 during a visual testing operation. While the set of external displays 1005 is shown with two external displays, a set of external displays may include more or fewer external displays, such as only one external display or more than two external displays. For example, a set of external displays may include four external displays, eight external displays, nine external displays, or some other number of external displays. The external displays may include one or more types of electronic displays, such as computer monitors, smartphones, television screens, laptop devices, tablet devices, LED devices, LCD devices, and other types of electronic displays, etc. In some embodiments, the external display may include a projector, where the location of the external display may include a wall or screen onto which one or more stimuli is projected. In some embodiments, the external display may itself be transparent or partially transparent.

During or after a visual testing operation, the system 1000 may obtain feedback information related to the set of stimuli, where the feedback information may indicate whether or how an eye responds to one or more stimuli of the set of stimuli. For example, some embodiments may use the wearable device 1004 to collect feedback information that includes various eye-related characteristics. In some embodiments, the feedback information may include an indication of a response of an eye to the presentation of a dynamic stimulus at a first display location 1046 on a wearable device 1004. Alternatively, or in addition, the feedback information may include an indication of a lack of a response to such a stimulus. The response or lack of response may be determined based on one or more eye-related characteristics, such as an eye movement, a gaze direction, a distance in which an eye's gaze traveled in the gaze direction, a pupil size change, a user-specific input, etc. In some embodiments, the feedback information may include image data or results based on image data. For example, some embodiments may obtain an image or sequence of images (e.g., in the form of a video) of an eye captured during a testing operation as the eye responds to a stimulus.

In some embodiments, the system 1000 may track the ocular data of an eye and update associated ocular information based on feedback information indicating eye responses to stimuli. Some embodiments may use a prediction model to detect a non-responsive region of a visual field or another ocular issue of a visual field portion associated with the ocular data. In some embodiments, satisfying a set of vision criteria for a visual field location may include determining whether an eye responded to a stimulus presented at the display location mapped to the visual field location, where different presented stimuli may vary in brightness, color, shape, size, etc.

In some embodiments, the system 1000 can adjust viewing by the user based on the ocular information collected by the wearable device 1004. Any number of simulations can be performed to generate ocular information suitable for determining optimal settings for a user. The settings can change throughout the surgical procedure based on the surgical steps. For example, if the user becomes tired or fatigued, the system 1000 can adjust the visual field to stimulate the user, thereby increasing attentiveness. In some embodiments, the user can adjust the stimuli to his or her preferred preferences. Other responses can be collected and associated with the surgical procedure, specific surgical steps, or the like. Feedback scores can be generated to rank the collected set of stimuli. The score can be based on the time to complete action, biometric levels of the user (e.g., state of stress or heart rate), or other metrics.

In some embodiments, data used or updated by one or more operations described in this disclosure may be stored in a set of databases 1030. In some embodiments, the server 1002, the wearable device 1004, the set of external displays 1005, or other computer devices may access the set of databases to perform one or more operations described in this disclosure. For example, a prediction model used to determine ocular information may be obtained from a first database 1031, where the first database 1031 may be used to store prediction models or parameters of prediction models. Alternatively, or in addition, the set of databases 1030 may store feedback information collected by the wearable device 1004 or results determined from the feedback information. For example, a second database 1032 may be used to store a set of user profiles that include or link to feedback information corresponding with eye measurement data for the users identified by the set of user profiles. Alternatively, or in addition, the set of databases 1030 may store instructions indicating different types of testing procedures. For example, a third database 1033 may store a set of testing instructions that causes a first stimulus to be presented on the wearable device 1004, then causes a second stimulus to be presented on a first external display 1005*a*, and thereafter causes a third stimulus to be presented on a second external display 1005*b*.

In some embodiments, the projection module 1022 may generate a field-to-display map that maps a position or region of a visual field with a position or region of the set of external displays 1005 or of an AR interface displayed on the left transparent display 1041 or the right transparent display 1042. The field-to-display map may be stored in various forms, such as in the form of a set of multi-dimensional arrays, a function, a subroutine, etc. For example, the field-to-display map may include a first multi-dimensional array, where the first two dimensions of the first array may indicate a coordinate in a combined display space that maps 1:1 with a visual field. In some embodiments, a third dimension of the first array may identify which external display or wearable display to use when presenting a stimulus. Furthermore, a fourth and fifth dimension of the array may be used as coordinates relative to the origin of each respective external display. In some embodiments, an array or other set of numbers described in this disclosure may instead be divided into a plurality of arrays or other subsets of numbers. In some embodiments, the field-to-display map may be used in reverse, such that a display location may be mapped to a visual field location ("field location") using the field-to-display map. Some embodiments pre-generate a display-to-field map by inverting one or more of the arrays described above. Furthermore, some embodiments may use or update a map by using an array or other data structure of the map. Various other embodiments of the field-to-display map are possible, as described elsewhere in this disclosure.

In some embodiments, the projection module 1022 may obtain sensor information from the set of outward-facing sensors 1047, where the sensor information may include position measurements of the set of external displays 1005. For example, a user wearing the wearable device 1004 may rotate or translate their head, which may cause a corresponding rotation or translation of the wearable device 1004. Some embodiments may detect these changes in the physical orientation or position of the wearable device 1004 with respect to the set of external displays 1005. Some embodiments may then perform a mapping operation to determine the positions and orientations of the set of external displays based on the sensor information collected by the set of outward-facing sensors 1047.

In some embodiments, the projection module 1022 may update a field-to-display map that stores or otherwise indicates associations between field locations of a visual field and display locations of the left transparent display 1041, the right transparent display 1042, or the set of external displays 1005. For example, the set of outward-facing sensors 1047 may include one or more cameras to collect visual information from a surrounding area of the wearable device 1004, where the visual information may be used to determine a position or orientation of one or more devices of the set of external displays 1005. As the wearable device 1004 is moved, some embodiments may continuously obtain sensor information indicating changes to the external environment, including changes in the position or orientation of the set of external displays 1005 relative to the position or orientation of the wearable device 1004. For example, some embodiments may generate a point cloud representing the surfaces of objects around the wearable device 1004 and determine the positions and orientations of the set of external displays 1005 relative to the wearable device 1004 based on the point cloud. Furthermore, some embodiments may continuously update the field-to-display map as new sensor information is collected by the set of outward-facing sensors 1047.

In some embodiments, the display module 1023 may present a set of stimuli on the wearable device 1004 or the set of external displays 1005. In some embodiments, the left transparent display 1041 and right transparent display 1042 may be positioned with respect to the case 1043 to fit an orbital area on a user such that each display of the transparent displays 1041-1042 is able to collect data and present stimuli or other images to the user. The left transparent display 1041 and right transparent display 1042 may contain or be associated with an electronic display configured to present re-created images to an eye viewing the respective transparent display. In various embodiments, electronic display may include a projector, display screen, and/or hardware to present an image viewable by the eye. In some embodiments, a projector of an electronic monitor may be positioned to project images onto an eye of the subject or onto or through a screen, glass, waveguide, or other material. For example, the display module 1023 may cause a fixation point or another visual stimulus to be projected onto the first display location 1046, where the fixation point at the first display location 1046 may then be viewed by an eye of a user wearing the wearable device 1004.

In some embodiments, the display module 1023 may cause a set of stimuli to be displayed onto electronic displays other than the displays of the other external displays, such as an external display of the set of the external displays 1005. For example, after presenting a stimulus on a display of the wearable device 1004, the display module 1023 may cause a stimulus to be presented on the second external display 1005b at a second display location 1051. As used in this disclosure, an external display location may include a display location on an external display. The display module 1023 may then proceed to display additional stimuli on an additional location of the first external display 1005a, the wearable device 1004, or the second external display 1005b.

Some embodiments may determine the display location for a stimulus by first determining the location or region of a visual field. After determining the location or region of the visual field, some embodiments may then use a field-to-display map to determine which display location of the left transparent display 1041, the right transparent display 1042, or the set of external displays 1005 to use when displaying a stimulus. For example, some embodiments may determine that a previous sequence of sensor measurements indicated that a first region of a visual field has not yet been tested and select this first region for testing. Some embodiments may then use the field-to-display map to determine a third display location 1052 on the first external display 1005a and, in response to selecting the third display location 1052, display a stimulus at the third display location 1052. As described elsewhere in this disclosure, some embodiments may measure eye movements or otherwise measure responses of an eye to the stimuli presented on the set of external displays 1005 to measure a visual field of the eye. Furthermore, as described in this disclosure, a visual field location of a stimulus may include the field location mapped to or otherwise associated with the display location of the stimulus, where the mapping or association between the display and the field location is determined by a field-to-display map. Similarly, as used in this disclosure, a gaze location that is located at a field location may also be described as being located at a display location mapped to the field location.

In some embodiments, the feedback module 1024 may record feedback information indicating eye responses to the set of stimuli presented on the wearable device 1004 or the set of external displays 1005. In some embodiments, the transparent displays 1041-1042 may include a left inward-directed sensor 1044 and a right inward-directed sensor 1045, where the inward-directed sensors 1044-1045 may include eye-tracking sensors. The inward-directed sensors 1044-1045 may include cameras, infrared cameras, photodetectors, infrared sensors, etc. For example, the inward-directed sensors 1044-1045 may include cameras configured to track pupil movement and determine and track the visual axes of the subject. In some embodiments, the inward-directed sensors 1044-1045 may include infrared cameras and be positioned in lower portions relative to the transparent displays 1041-1042. The inward-directed sensors 1044-1045 may be directionally aligned to point toward a presumed pupil region for line-of-sight tracking or pupil tracking.

In some embodiments, the feedback module 1024 may use the inward-directed sensors 1044-1045 to collect feedback information indicating eye motion as an eye responds to different stimuli. For example, the feedback module 1024 may retrieve feedback information of an eye collected by the inward-directed sensors 1044-1045 as the eye responds to the presentation of a stimulus at the first display location 1046 and the second display location 1051. By collecting feedback information while stimuli are presented on both the wearable device 1004 and one or more devices of the set of external displays 1005, some embodiments may increase the boundaries of a visual field for which ocular data may be detected.

In some embodiments, the statistical predictor 1025 may retrieve stimuli information, such as stimuli locations and characteristics of the stimuli locations, where the stimuli locations may include locations on the set of external displays 1005. The statistical predictor 1025 may also retrieve training outputs indicative of the presence or absence of ocular responses or other outputs of a prediction model. The statistical predictor 1025 may then provide the set of stimuli information and training outputs to a ML model to update the parameters of the ML model to predict ocular responses based on new inputs. An example ML system 200 is illustrated and described in more detail with reference to FIG. 2. Alternatively, or in addition, the statistical predictor 1025 may use statistical models or rules to determine ocular responses and generate a visual field map representing a visual field of an eye, where one or more regions of the visual field map may be associated with a set of ocular responses or otherwise include ocular response information.

Figure 11:
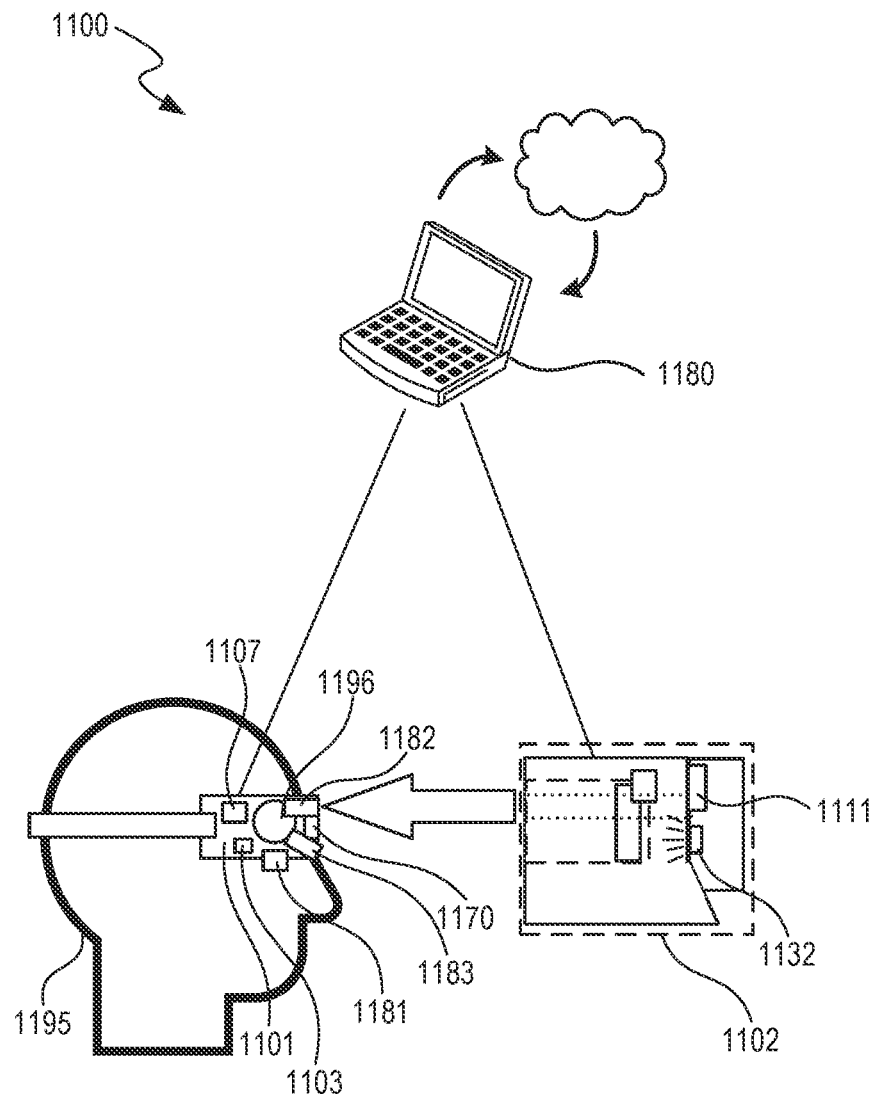
FIG. 11 illustrates an XR head mounted display (HMD) for facilitating robotic medicine, in accordance with one or more embodiments.

FIG. 11 illustrates an XR HMD 1101 for facilitating robotic medicine, in accordance with one or more embodiments. HMD 1101 can be, for example, an augmented reality device worn by a user while the user views a surgical environment. Information can be displayed at selected locations to avoid obstructing the viewing of targeted areas. Medical professional 1195 can wear HMD 1101, which can include a computing device 1107. Computing device 1107 can include a processor, microprocessor, controller, or other circuitry. In some embodiments, an eye 1196 of the medical professional may be capable of viewing images and video in XR from the operating room 1102 through lenses 1170 of the HMD 1101. The HMD 1101 may include an interior-facing camera to capture eye-related information and a set of exterior-facing cameras that include an exterior-facing camera 1182.

In some embodiments, a user initiates an XR session using computing system 1180 that is in communication with the HMD 1101. Computing system 1180 may include a stand-alone computer capable of operating without connecting to another computing device outside of a local network. Alternatively, or in addition, the computing system 1180 may include a computing system that receives program instructions or required data from an external data source not available through a local network.

In some embodiments, the computing system 1180 may initiate an XR session. Computing system 1180 may communicate with the HMD 1101 via a wireless connection or wired connection. For example, the computing system 1180 may send a wireless message to the computing device 1107 to initiate an XR session. For example, the computing system 1180 may send a command to the HMD 1101 via a Bluetooth® connection, where the command may cause the HMD 1101 to activate.

In some embodiments, the computing system 1180 may communicate with both the HMD 1101 to perform one or more operations. For example, the HMD 1101 may present an initial set of instructions to a medical professional 1195 and request a response from the medical professional 1195. After the medical professional 1195 provides a requested response (e.g., pressing a button, making a statement, etc.), the computing system 1180 may send a first set of instructions to the HMD 1101 to calibrate readings to more accurately measure eye-related data associated with the eye 1196. After the HMD 1101 sends a message to the computing system 1180 that calibration operations have been completed, the computing system 1180 may send further instructions to the HMD 1101. The computing system 1180 may determine the position of a fixation point based on eye-related readings and send a message to the HMD 1101 that causes the HMD 1101 to display a visual stimulus at the fixation point on the lenses 1170. After receiving a message from the HMD 1101 that the eye 1196 has set its gaze at the fixation point, the computing system 1180 may continue the XR session.

In some embodiments, an application executed by the computing device 1107 of the HMD 1101 may be used to control operations of components of the HMD 1101 or other electronic components. For example, the application executed by computing device 1107 may begin a visual test program and send a wireless message to a circuitry of the system 1180 using a wireless headset communication subsystem 1103. The wireless message may be based on one of various types of communication standards, such as a Bluetooth® standard, a Wi-Fi Direct standard, a NFC standard, a ZigBee® standard, a 6LoWPAN standard, etc.

In some embodiments, an application being executed by the computing device 1107 may retrieve data from the interior-facing camera 1183 and send instructions to control medical equipment based on this data. For example, the computing device 1107 may execute an application to perform a Viola-Jones object detection framework to detect an eye in a set of images using a boosted feature classifier based on video data provided by the interior-facing camera 1183. Furthermore, the application executed by the computing device 1107 may permit additional sensor data to trigger equipment in the operating room 1102, such as by receiving voice instructions captured from a microphone 1181, motion detected by the exterior-facing camera 1182, feeling a set of touches on the body of the HMD 1101, etc.

In some embodiments, a testing application executed by the computing device 1107 detects that a gaze location of medical professional 1195 is focused on a target user interface (UI) element or a target direction based on data collected by interior-facing camera 1183. For example, HMD 1101 displays a set of instructions that causes medical professional 1195 to look at a target UI location. In some embodiments, the target UI location is represented by a target region associated with the target UI location, such that a gaze location determined to be within the target region is considered to be focused on the target UI location. In response to a determination that the gaze location of eye 1196 is focused on the target UI location based on images provided by the interior-facing camera 1183, the application can activate medical equipment 1132. Furthermore, the application can send a message to robotic surgical system 1111 to turn off medical equipment 1132 based on a determination that the target UI location is no longer a focus of the user's gaze. Robotic surgical system 1111 is the same as or similar to robotic surgical system 160 illustrated and described in more detail with reference to FIG. 11. Alternatively, some embodiments may forego waiting for the medical professional 1195 to focus on a particular UI location or a particular direction before activating the medical equipment 1132.

In additional embodiments, a computer system obtains patient data of a patient. A user-mapping program is used to train an intra-operative AR mapping platform based on the obtained patient data. For example, the user-mapping program is configured to receive user input for the identification of individual anatomical features. One or more anatomical features of the patient associated with a surgical plan are identified for the patient based on the obtained patient data. The computer system performs an intra-operative AR mapping of the identified one or more anatomical features using the trained intra-operative AR mapping platform. Via an AR device, the intra-operative AR mapping is displayed to be viewed by a user.

In some embodiments, performing the intra-operative AR mapping includes obtaining a surgical plan and determining one or more anatomical features to be identified based on a surgical step of the surgical plan. The one or more anatomical features are identified. The one or more anatomical features and associated information for the surgical step are labeled. For example, one or more unidentifiable anatomical features of the patient are marked. The surgical plan is modified based on the determination of the one or more unidentifiable anatomical features. In some embodiments, an autonomous mapping platform is used to perform the intra-operative AR mapping. The autonomous mapping platform is trained by multiple users inputting anatomical data for reference patient images and validated for autonomously mapping a set of anatomical features associated with a surgery.

In some embodiments, a computer system selects one or more candidate features of a virtual anatomical model displayed in a VR environment displayed to a user. For example, the candidate features can be vascular vessels, nerves, or organ names. User input is received for the selected one or more candidate features. The computer system determines whether the user input for one or more candidate features reaches a threshold confidence score. In response to the user input reaching the threshold confidence score, the user input is identified as accurately labeling the one or more candidate features. In some embodiments, a computer system stores the user input as reference label data for the corresponding one or more candidate features. For example, the user input includes a label for each one of the respective one or more candidate features. The one or more candidate features can be unknown anatomical features, and the user input identifies the unknown features.

In some embodiments, determining whether the user input for one or more candidate features reaches the threshold confidence score is based on a comparison reference user input for similar candidate features. For example, the user input is used to train a ML model. For each of the candidate features, the user input can include at least one of a name of the candidate feature, a tissue type of the candidate feature, or user annotation. For example, a tissue type can be bone, nerve tissue, or soft tissue. The user annotation can be physician notes.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The systems discussed in connection with FIGS. 1-5, 9, and 12 can include the features of the systems discussed in connection with FIGS. 12, 20-22, 28-30. Additionally, the systems discussed in connection with FIGS. 1-5, 9, and 12 can be configured to perform methods, processes, and steps discussed in connection with FIGS. 12-32. For example, the systems 100, 400, 1000, 1100 can be configured to manage software (e.g., new software, software updates, etc.), tele-surgery, or the like. For example, the robotic surgical system (e.g., system 100, 400, 1000, 1100, 1200, or 2200) can provide a process (e.g., process 1300, 1500, 1600, 1700, 1800, or 1900) for providing one or more updates to a surgical robot (e.g., surgical robot 902, 1202 or 2202). The surgical robot can receive a notification that there is an update available, detect a new hardware component that has been attached to the surgical robot, and/or determine an update is needed. The surgical robot system can determine when to receive and install the software update. The surgical robot can determine if it is currently in use or is inactive, and if inactive the surgical robot downloads the latest update. When a medical professional begins a procedure with the surgical robot, the surgical robot receives a training status or certification status of the medical professional for the new update. If the medical professional is trained and/or certified, the medical professional may use the surgical robot with the latest update. If the medical professional is not trained and/or certified, the medical professional may use the surgical robot with a previous version or in some instances may be denied using the surgical robot. In some embodiments, the robotics surgical system can notify the medical professional that they are not trained and/or certified. The robotics surgical system can then perform training and/or certification to a medical professional. This allows the medical professional to decide whether to use a previous version or the updated version of the software. If the medical professional completes training and/or certification, the user's profile can be updated to include the training/certification completion information, thereby allowing the medical professional to use the updated software in future procedures.

In some embodiments, the robotic surgical system (e.g., system 100, 400, 1000, 1100, 1200, or 2200) can provide a process (e.g., process 2300, 2400, 2500, 2600, 2700, 3100, or 3200) for remote monitoring and technician support for safety and redundancy. The surgical robot (e.g., surgical robot 902, 1202, or 2202) can collect data representing at least one assistance parameter of the surgical robot during a surgical procedure. The data is assessed, and it is determined if non-surgical assistance is required and connecting the medical professional to a technician to resolve a potential issue. The technician may test the data representing at least one assistance parameter to resolve the potential issue the medical professional may be experiencing. The technician can modify hardware, replace hardware, modify software, or the like. In some embodiments, the robotic surgical system can determine whether new software or a software update can resolve the potential issue. For example, the robotic surgical system can determine that an update to a hardware component or the surgical robot itself can enable the surgical robot to resolve the potential issue. The robotic surgical system can then notify a remote server that the new software update is needed. When newly available software is received, the robotic surgical system can authenticate and then install the software via, for example, and over-the-air installation process, or other update or installation procedure. The newly available software can enable new functionality of the robotic surgical system. In some procedures, the robotic surgical system can automatically notify the technician when an adverse event occurs. This can reduce the response time to resolve to resolve potential issues.

Figure 12:
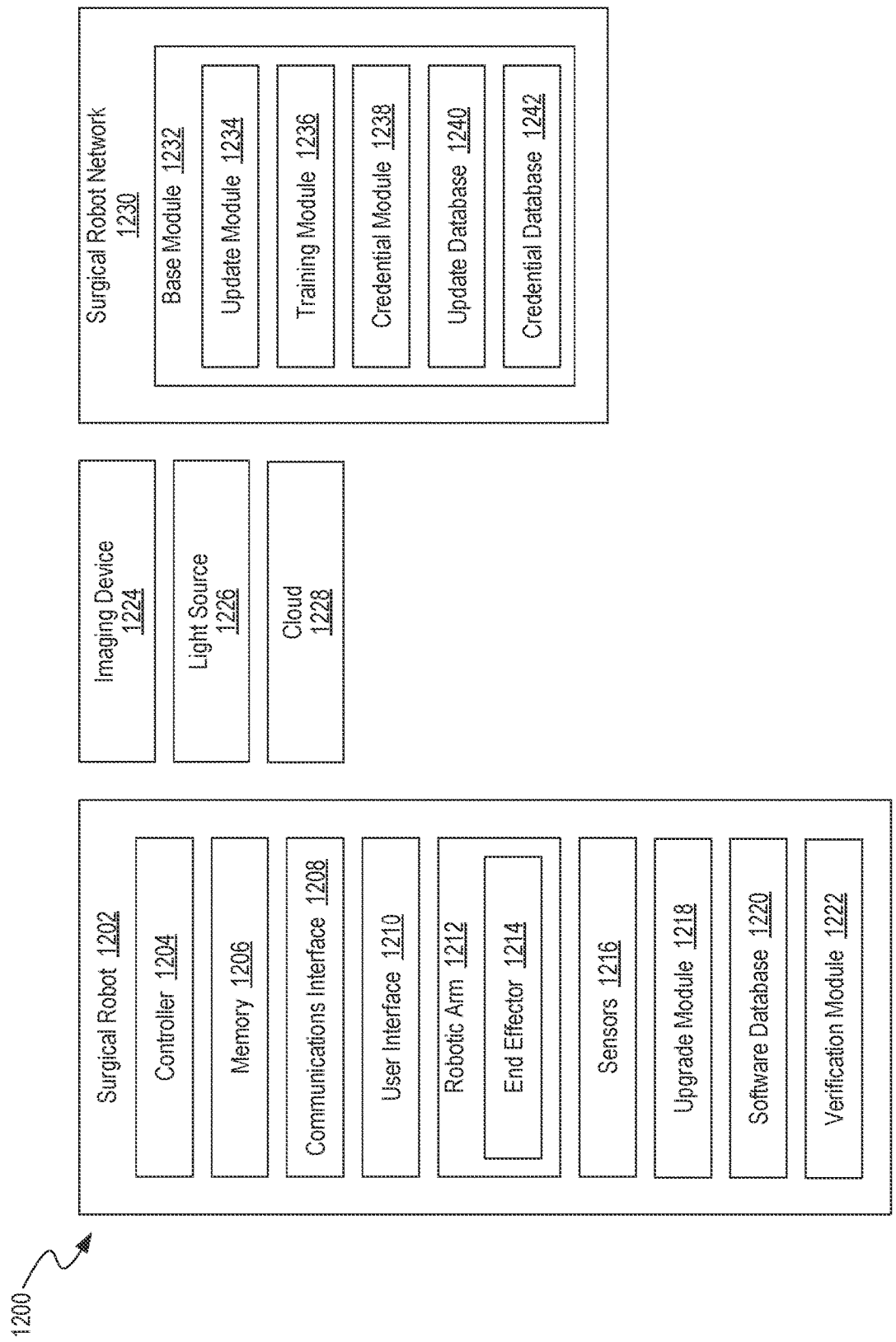
FIG. 12 is a block diagram illustrating an example robotic surgical system for providing updates to a surgical robot, in accordance with one or more embodiments.

FIG. 12 illustrates a system 1200 for providing updates to a surgical robot. This system comprises of a surgical robot 1202 which is a robotic system designed to assist a surgeon in performing a surgical operation on a patient. A surgical robot 1202 may include a controller 1204, memory 1206, and at least one robotic arm 1212 with an end effector 1214. The surgical robot 1202 may further include a user interface 1210 for accepting control inputs from a user, such as a surgeon or other medical professional and a communications interface 1208 for transmitting and receiving data to and from a cloud 1222 for the purpose of training an artificial intelligence operating within the surgical robot or receiving remote commands from a remote user or an artificial intelligence existing external to the surgical robot 1202. The surgical robot 1202 may additionally comprise a plurality of sensors 1216 for providing feedback to the user or an artificial intelligence. Further, embodiments may include a controller 1204 that is a computing device comprised of a processor for performing computations and communicates with a memory 1206 for storing data. The controller 1204 is in communication with a communications interface 1208 and may further be allowed to control the at least one robotic arm 1212 and end effector 1214 of a surgical robot 1202. The controller may be a commercially available central processing unit (CPU) or graphical processing unit (GPU) or may be a proprietary, purpose-build design. More than one controller 1204 may operate in tandem and may be of different types, such as a CPU and a GPU. A GPU is not restricted to only processing graphics or image data and may be used for other computations. Further, embodiments may include a memory 1206 which is the electronic circuitry within a computing device that temporarily stores data for usage by the controller 1204.

The memory 1206 may additionally comprise persistent data storage for storing data used by the controller 1204. The memory 1206 may be integrated into a controller 1204 or may be a discrete component. The memory 1206 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, memory 1206 may be part of a controller 1204. Multiple types of memory 1206 may be used by the surgical robot 1202. Further, embodiments may include a communications interface 1208 which allows the surgical robot 1202 to communicate with external devices and may comprise a wireless antenna and transceiver or a port for receiving a cable to facilitate a wired connection. Examples of a wired connection include ethernet, universal serial bus (USB) or a proprietary connection. A wireless communications interface 1208 may include any of Wi-Fi, Bluetooth, near field communications (NFC) or a cellular communications interface such as 3G, 4G, LTE, or 5G.

The communications interface 1208 may connect a user interface 1210 to the surgical robot 1202 or may facilitate access to a local network or a cloud 1222 network to access a remote server and/or database. Further, embodiments may include a user interface 1210 that is a means of interacting with a surgical robot 1202 and may include any of a keyboard, computer mouse, trackball, joystick, wireless or wired gamepad, sliders, scroll wheels, touch screen or microphone for receiving voice commands. The user interface 1210 may additionally comprise any method of interaction of a user with a surgical robot 1202 not listed. The user interface 1210 may accept direct inputs, such as from a joystick controlling the movement of a robotic arm or indirect inputs such as commands entered on a keyboard or touch screen such as adjusting the sensitivity of a joystick control or the speed of a robotic arm's 1212 movement in response to a joystick. The user interface 1210 may also comprise a screen for presenting information to the user such as patient status, imaging data, and navigation data and speakers for providing auditory feedback. The user interface 1210 may also utilize haptics to provide feedback to the user. In additional embodiments, the user interface 1210 may comprise an augmented reality (AR) or virtual reality (VR) headset to enable a surgeon to view imagery from at least one imaging device 1218 in real-time and may additionally comprise an overlay, such as highlighting the blood vessels comprising a path which the catheter must be advanced to access the treatment site, such as a blood clot. The user interface 1210 may additionally comprise voice or eye tracking controls. Further, embodiments may include a robotic arm 1212 which is a mechanically actuated arm or lever with at least two degrees of freedom.

A robotic arm 1212 can include at least one end effector 1214 or an imaging device 1218 and may include both an end effector 1214 and an imaging device 1218. The robotic arm 1212 may additionally be capable of changing the end effector 1214 to facilitate multiple functions and operation of a variety of tools. The robotic arm 1214 may be manually controlled or operated in an autonomous or semi-autonomous mode. A surgical robot 1202 may have one robotic arm 1212 or multiple robotic arms 1212, each of which may be operated independently by one or more users or autonomous systems or a combination of users and autonomous systems. Further, embodiments may include an end effector 1214 which is the end of a robotic arm 1212 which is conducting work. The end effector 1214 is typically a tool or device for interacting with a physical object and may be a surgical tool intended for acting upon or within a patient or may be a gripping device for securing a separate surgical tool to a robotic arm 1212. The end effector 1214 may be permanently affixed to the end of a robotic arm 1212 or may be detachable allowing for a system of interchangeable end effectors 1214 which may alternatively be selected and swapped by a single robotic arm 1212 or multiple robotic arms 1212. The end effector 1214 may comprise a catheter or other tool for accessing a treatment site within a patient. Similarly, the end effector 1214 may relate to a deployable device, such as a stent, prior to deployment in a patient. The end effector 1214 may be constructed of materials which intentionally absorb, reflect, or are transparent to X-Rays to facilitate the end effector's 1214 visibility when viewed using angiography, fluoroscopy, or other imaging modalities, or alternatively allow the X-Rays to pass through to prevent their interference in images.

In some embodiments, the end effector 1214 may be made to be selectively transparent to X-Rays such as by changing the profile of the end effector 1214 or X-Ray absorbing or reflective components to increase or reduce their visibility to an imaging device 1218. Further, embodiments may include a sensor 1216 which is a measurement tool for monitoring a characteristic or metric associated with a surgical robot 1202, end effector 1214 or patient. A sensor 1216 may be discrete or part of an array or assembly, such as integrated into a catheter. One or more of the sensors 1216 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 1216 may be integrated into the operation of the surgical robot 1202 or may monitor the status of a patient. The data acquired by the sensors 1216 may be used to train a machine learning algorithm used by the surgical robot 1202 or artificial intelligence to control the surgical robot 1202.

The sensors 1216 may additionally comprise an X-Ray dosimeter to monitor the intensity of X-Rays being emitted toward the patient to prevent excessive doses of radiation. The sensors 1216 may be utilized to reduce the intensity of the X-Rays or reduce the duration or increase the interval in which the X-Rays are emitted toward the patient to control the dose throughout a procedure. Further, embodiments may include an upgrade module 1218 which begins with the upgrade module 1218 continuously polling for a notification from the update module 1234. The upgrade module 1218 receives the notification from the update module 1234. The upgrade module 1218 determines if the surgical robot 1202 is currently active. If it is determined that the surgical robot 1202 is currently active the upgrade module 1218 continuously polls for the surgical robot 1202 to be inactive. The upgrade module 1218 determines the surgical robot 1202 is inactive. If it is determined that the surgical robot 1202 is inactive the upgrade module 1218 sends a request for the update to the update module 1234. The upgrade module 1218 receives the update from the update module 1234. The upgrade module 1218 downloads the update from the update module 1234. The upgrade module 1218 stores the update in the software database 1220 and the process returns to continuously polling for a notification from the update module 1234. In some embodiments, the upgrade module 1218 determines whether to start the updating process based on, for example, a schedule for the surgical robot 1202, whether the update will be performed pre-operatively or intra-operatively, etc. For example, if the surgical robot 1202 is scheduled to perform a surgical procedure prior to a predicted update completion time, the upgrade module 1218 can wait until an appropriate length of time of planned inactivity for the surgical robot prior to begin the upgrade process. If the surgical robot 1202 has partially completed a surgical procedure on a patient, the upgrade module 1218 can determine whether to perform an intra-operative software installation or post-operative installation. To perform an intra-operative software installation, the system upgrade module 1218 can determine an installation time based on the surgical plan (e.g., installation that will not affect the timing of the surgical steps) to reduce the likelihood of surgical complications.

Further, embodiments may include a software database 1220 which contains the list of updates and versions of the updates that the surgical robot 1202 has downloaded from the surgical robot network 1232. The database contains the date that the download occurred, the update ID, and the version of the update that was downloaded. The database is used during the process described in the verification module 1222 in which the surgical robot 1202 sends the latest update and version to the surgical robot network 1232 to confirm that the user is authorized to perform procedures using the latest update. In some embodiments, the database may contain the type of update, such as a hardware or software update, the characteristic of the update, such as the component that is being updated or a process or procedure that is being updated, the data file containing the update, etc. In some embodiments, the database may contain the procedure the update is associated with, such as anchor placement for a Brostrom Gould procedure, incision location for a back discectomy, etc. Further, embodiments may include a verification module 1222 which begins by continuously polling for a request from the credential module 1238. The verification module 1222 receives the request from the credential module 1238. The verification module 1222 extracts the most recent update from the software database 1220. The verification module 1222 sends the most recent update to the credential module 1238. The verification module 1222 determines if the surgical robot 1202 received confirmation from the credential module 1238 that the user is authorized to perform the procedure with the most recent update. If it is determined that the user is authorized to perform the procedure with the most recent update the verification module 1222 uses the most recent update for the procedure. If it is determined that the user is not authorized to perform the procedure using the most recent update the verification module 1222 determines if the surgical robot 1202 received a request to use the previous version. If it is determined that the surgical robot 1202 received a request to use the previous version the verification module 1222 uses the previous update. If it is determined that the surgical robot 1202 did not receive a request to use the previous update the verification module 1222 sends a notification that the user is not authorized to perform the procedure using the surgical robot 1202. The verification module 1222 allows the user to perform the procedure using either the most recent update or the previous update and the process returns to continuously polling for a request from the credential module 1238.

The software database 1220 can also store authorization information, such as the authorization input (e.g., authorization input 493 discussed in connection with 304), or other information. For example, the software database can store training information for user, credentials for user, and other information associated with usage of surgical equipment. The system can retrieve the information to determine whether a user should be granted permission rights to operate equipment. In some embodiments, a user can input authorization input into a user device to be granted permission rights, as discussed in FIGS. 4A and 4C.

Further, embodiments may include an imaging device 1224 which refers to any device capable of collecting data which can be used to create an image, or a representation of a physical structure or phenomena. An imaging device 1224 may include any device capable of detecting sound or electromagnetic waves and assembling a visual representation of the detected waves. imaging devices 1224 may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device 1224 may be interpolated from direct measurements representing adjacent pixels in order to increase the resolution of a generated image. Imaging devices 1224 may receive or generate imaging data from a plurality of imagining devices 1224. The plurality of imaging devices 1224 may include, for example, cameras attached to the robotic arm 1212, cameras mounted to the ceiling or other structure above the surgical theater, cameras that may be mounted on a tripod or other independent mounting device, cameras that may be body worn by the surgeon or other surgical staff, cameras that may be incorporated into a wearable device, such as an augmented reality device like Google Glass, Microsoft HoloLens, etc., cameras that may be integrated into an endoscopic, microscopic, laparoscopic, or any camera or other imaging device 1218 (e.g. ultrasound) that may be present in the surgical theater. The imaging device 1224 may include any algorithm or software module capable of determining qualitative or quantitative data from medical images, which may be, for example, a deep learning algorithm that has been trained on a data set of medical images. An imaging device 1224 may further refer to a device used to acquire medical imagery by any means including magnetic resonance imaging (MRI), computed tomography (CT), X-Ray, positron emission tomography (PET), ultrasound, arthrography, angiography, fluoroscopy, myelography, etc.

An imaging device 1224 may acquire images in real-time or be used to create composite images or models in real-time. Further, embodiments may include a light source 1226 such as surgical lights also referred to as operating light, refers to an instrument that performs illumination of a local area or cavity of the patient. The light source 1226 plays an important role in illumination before, during, and after a medical procedure. The light source 1226 may be categorized by lamp type as conventional (incandescent) and LED (light-emitting diode). The light source 1226 may be categorized by mounting configuration as ceiling-mounted, wall-mounted, or floor stand. The light source 1226 may be categorized by type as tungsten, quartz, and/or xenon halogens and light-emitting diodes (LEDs). The light source 1226 may include sterilizable handles which allow the surgeon to adjust light positions. Some important factors affecting the light source 1226 may be illumination, shadow management (cast shadows and contour shadows), the volume of light, heat management, fail-safe surgical lighting. The light source 1226 can be integrated into the embodiments in a variety of manners.

Further, embodiments may include a cloud 1228 which is a distributed network of computers comprising servers and databases. A cloud 1228 may be a private cloud 1228, where access is restricted by isolating the network such as preventing external access, or by using encryption to limit access to only authorized users. Alternatively, a cloud 1228 may be a public cloud 1228 where access is widely available via the internet. A public cloud 1228 may not be secured or may be include limited security features. Further, embodiments may include a surgical robot network 1230 which may be a network connected to the surgical robot 1202 in which the surgical robot may receive and send data, provide controls to a user for the surgical robot 1202 through a user interface 1210, and allow a user to send data to the surgical robot 1202 related to a designed, tested, or created surgical process for a patient. Further, embodiments may include a base module 1232 which initiates the update module 1234, the training module 1236, and the credential module 1238. Further, embodiments may include an update module 1234 which begins by being initiated by the base module 1232. The update module 1234 queries the update database 1240 for a new software/hardware update. The update module 1234 extracts the new software/hardware update from the update database 1240. The update module 1234 connects to the surgical robot 1202. The update module 1234 sends a notification to the upgrade module 1218. The update module 1234 is continuously polling to receive a request for the software/hardware update from the upgrade module 1218. The update module 1234 receives a request for the update from the upgrade module 1218. The update module 1234 sends the update to the upgrade module 1218. The update module 1234 stores the update and the robot ID in the credential database 1242. The update module 1234 returns to the base module 1232. Further, embodiments may include a training module 1236 which begins by being initiated by the base module 1232. The training module 1236 filters the credential database 1242 on the newest update. The training module 1236 filters the credential database 1242 on uncertified users. The training module 1236 extracts the first uncertified user from the credential database 1242. The training module 1236 sends a notification to the user to schedule training for certification for the new update. The training module 1236 determines if there are more uncertified users in the credential database 1242. If it is determined that the credential database 1242 contains more uncertified users the training module 1236 extracts the next uncertified user from the credential database 1242 and the process returns to sending a notification to the uncertified user to schedule training for certification on the new update. If it is determined that there are no more uncertified users in the credential database 1242 the training module 1236 returns to the base module 1232. Further, embodiments may include a credential module 1238 which begins by being initiated by the base module 1232. The user logs in to the surgical robot network 1230. The credential module 1238 connects to the surgical robot 1202. The credential module 1238 sends a request to the verification module 1222 for the current update the surgical robot 1202 is using. The credential module 1238 receives the current update from the verification module 1222 that the surgical robot 1202 is using. The credential module 1238 compares the user to the credential database 1242. The credential module 1238 determines if the user is authorized to use the current update the surgical robot 1202 is using. If it is determined that the user is authorized to use the current version the surgical robot 1202 is operating with the credential module 1238 sends a notification to the verification module 1222 that the user is authorized. If it is determined that the user is not authorized to use the current version the surgical robot 1202 is operating with the credential module 1238 sends a request to the verification module 1222 to use the previous update. Then the user performs the surgical procedure using the surgical robot 1202. The credential module 1238 returns to the base module 1232.

Further, embodiments may include an update database 1240 which may contain the software and hardware updates that are sent to the surgical robots 1202 and may be created by a user and stored on the surgical robot network 1230. The database contains the date the update was uploaded to the surgical robot network 1230, the update ID, the type of update, such as a hardware or software update, the characteristic of the update, such as the component that is being updated or a process or procedure that is being updated, the version of the update, and the data file containing the update that allows the surgical robots 1202 to download the update. In some embodiments, the updates may be software processes for the surgical robot 1202 to perform new surgical procedures, such as a new suture pattern, insert an anchor at different location on the ankle, make an incision at a different location for a back procedure, clean damaged tissue, etc. In some embodiments, the software updates may be for specific actions in a surgical procedure, a series of actions in a surgical procedure, or an entire surgical procedure allowing the surgical robot 1202 to perform surgical maneuvers, actions, procedures, etc. that it was not capable of prior to the update.

In some embodiments, the software updates may be backend software updates, such as updates for the surgical robots 1202 operating systems, optimizing current software systems, control systems, interfaces, etc. In some embodiments, the hardware updates may be for the installation of a new component that also requires new software to operate the new hardware or perform actions or procedures with the new hardware component. In some embodiments, the hardware updates may be for a new end effector 1214, robotic arm 1212, sensors 1216, controllers 1204, mobility systems, such as the manner in which the surgical robot 1202 may move around an operating room, imaging devices 1224 that may be incorporated in the surgical robot 1202, light sources 1226 that may be incorporated in the surgical robot 1202, etc. In some embodiments, the updates may require a medical professional to perform training on the update to familiarize themselves with the new features or become certified in operating the surgical robot 1202 with the enhance capabilities. In some embodiments, the updates may not require a medical professional to perform training on the update, such as software updates the improve the operating system, changes in the underlying code in which certain maneuvers or functions use that do not change the way in which the medical professional operates or handles the surgical robot 1202. In some embodiments, the updates may come from a 3rd party source or through another database in the surgical robot network 1202 in which a plurality of users can upload updates that are then tested, vetted, and approved to be added to the update database 1240 where they can be downloaded by the surgical robots 1202. In some embodiments, the surgical robot network 1232 may be a hospital network that operates a plurality of the surgical robots 1202 and the users can access an app store the includes a plurality of updates, both software and hardware, to allow their surgical robots to download certain updates to perform certain actions, procedures, processes, etc. that are useful for the medical professionals.

Further, embodiments may include a credential database 1242 which is created in the process described in the update module 1234 and the training module 1236 and is used during the process described in the credential module 1238 which allows medical professionals to be authorized to perform procedures with the surgical robot 1202 as long as they have had the proper training on the latest software or hardware updates. The database contains the date of the update, the update ID, the version of the update, and then for each update the name of the medical professional, if the training by the medical professional is complete or incomplete, and the if the medical professional is certified to perform actions or procedures with the latest update. In some embodiments, the database may contain additional information about the medical professional, such as the hospital the medical professional is based out of, their contact information, such as phone number, email address, office location, etc., the medical professional's education background, the medical professional's professional background or work experience, the date the medical professional completed training or when training is scheduled to be completed, the medical professional's specialty or area of medicine, etc. The database is used as a means of verification for the surgical robot 1202 to confirm the medical professional is certified in the operating the surgical robot 1202 with the latest updates. In some embodiments, the medical professional's calendar or schedule may be included in the database to allow the medical professional to schedule the appropriate training needed for a procedure that may be coming up on their schedule.

Functioning of the upgrade module 1218 will now be explained with reference to FIG. 13. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 13:
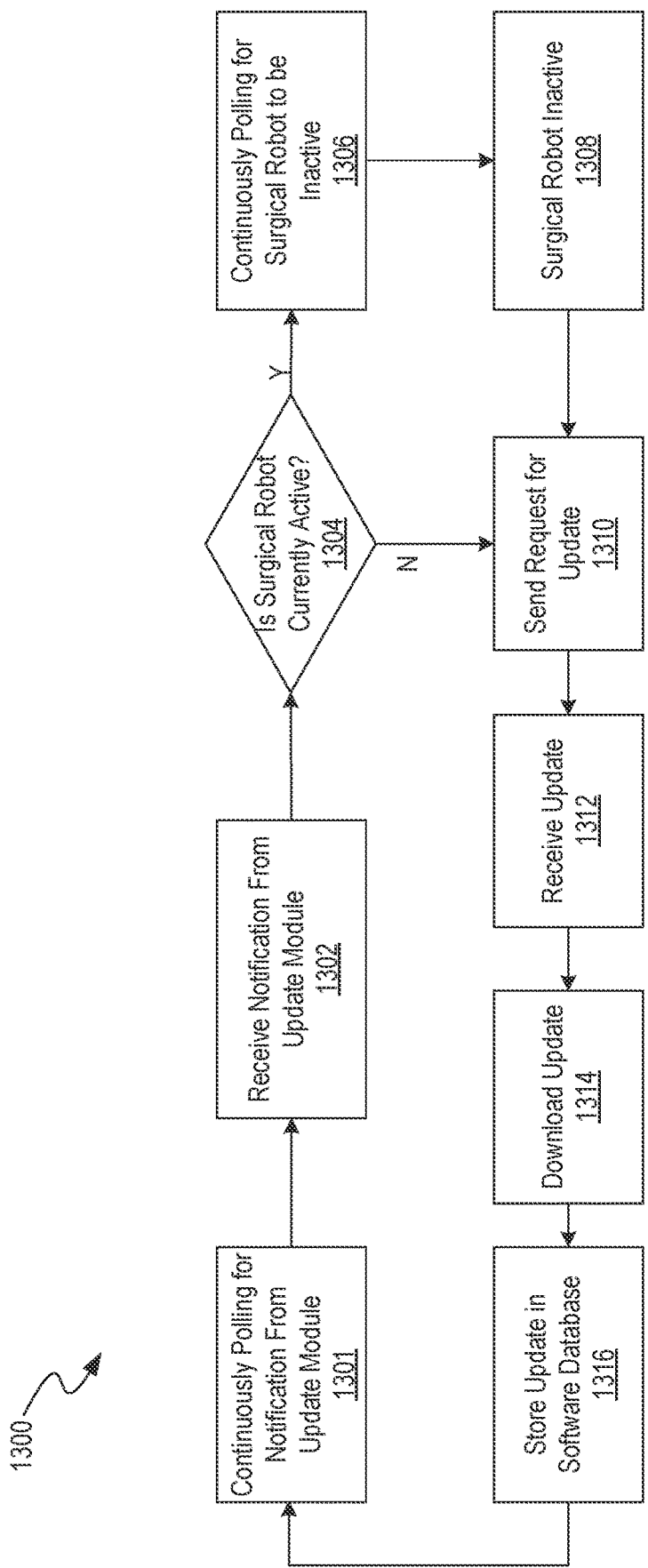
FIG. 13 is a flow diagram illustrating an example process for an upgrade module, in accordance with one or more embodiments.

FIG. 13 displays the upgrade module 1218. The process 1300 begins with the upgrade module 1218 continuously polling, at step 1301, for a notification from the update module 1234. For example, the upgrade module 1218 is continuously polling for a notification for a new update for the surgical robot 1202 from the update module 1234. The upgrade module 1218 receives, at step 1302, the notification from the update module 1234. For example, the upgrade module 1218 receives a notification from the update module 1234 that there is a new update for the surgical robot 1202. In some embodiments, if a new hardware component is attached to the surgical robot then the surgical robot may send a notification or request to the update module 1234 to download the accompanying software to utilize the new hardware component. The upgrade module 1218 determines, at step 1304, if the surgical robot 1202 is currently active. For example, the upgrade module 1218 may determine if the surgical robot 1202 is currently in use by a medical professional or is currently performing a procedure. For example, the upgrade module 1218 may compare the current time and date to a schedule or calendar for the surgical robot's 1202 scheduled procedures and if it is determined that the surgical robot 1202 is currently scheduled for a procedure then the surgical robot 1202 is currently in use and is active. If it is determined that the surgical robot 1202 is currently active the upgrade module 1218 continuously polls, at step 1306, for the surgical robot 1202 to be inactive. For example, the upgrade module 1218 may compare the current time and date to a schedule or calendar for the surgical robot's 1202 scheduled procedures and if it is determined that the surgical robot 1202 is currently scheduled for a procedure then the surgical robot 1202 is currently in use and is active. The upgrade module 1218 determines, at step 1308, the surgical robot 1202 is inactive. For example, the upgrade module 1218 may determine the surgical robot 1202 is inactive by comparing the current time and date to a schedule or calendar for the surgical robot's 1202 scheduled procedures and if it is determined that the surgical robot 1202 is currently not scheduled for a procedure then the surgical robot 1202 is currently inactive. In some embodiments, the upgrade module 1218 may determine if components of the surgical robot 1202 are online or active, such as an end effector 1214 is moving or changing position, a sensor 1216 is collecting data, the communication interface 1208 is interacting with the surgical robot network 1232 and receiving instructions or data, etc. If it is determined that the surgical robot 1202 is inactive the upgrade module 1218 sends, at step 1310, a request for the update to the update module 1234. For example, once it is determined that the surgical robot 1202 is inactive the upgrade module 1218 sends a request to the update module 1234 to send the latest update. The upgrade module 1218 receives, at step 1312, the update from the update module 1234. For example, the update module sends the update data entry from the update database 1240 to the upgrade module 1218, which may include the date the update was uploaded to the surgical robot network 1230, the update ID, the type of update, such as a hardware or software update, the characteristic of the update, such as the component that is being updated or a process or procedure that is being updated, the version of the update, and the data file containing the update that allows the surgical robots 1202 to download the update.

The upgrade module 1218 downloads/installs, at step 1314, the update from the update module 1234. For example, the upgrade module 1218 downloads the update received from the update module 1234. Downloading is the transmission of a file or data from one computer to another over a network, usually from a larger server to a user device, such as a surgical robot 1202. In some embodiments, the updates may be software processes for the surgical robot 1202 to perform new surgical procedures, such as a new suture pattern, insert an anchor at different location on the ankle, make an incision at a different location for a back procedure, clean damaged tissue, etc. In some embodiments, the software updates may be for specific actions in a surgical procedure, a series of actions in a surgical procedure, or an entire surgical procedure allowing the surgical robot 1202 to perform surgical maneuvers, actions, procedures, etc. that it wasn't capable of prior to the update. In some embodiments, the software updates may be backend software updates, such as updates for the surgical robots 1202 operating systems, optimizing current software systems, control systems, interfaces, etc. In some embodiments, the hardware updates may be for the installation of a new component that also requires new software to operate the new hardware or perform actions or procedures with the new hardware component. In some embodiments, the hardware updates may be for a new end effector 1214, robotic arm 1212, sensors 1216, controllers 1204, mobility systems, such as the manner in which the surgical robot 1202 may move around an operating room, imaging devices 1224 that may be incorporated in the surgical robot 1202, light sources 1226 that may be incorporated in the surgical robot 1202, etc. In some embodiments, the updates may require a medical professional to perform training on the update to familiarize themselves with the new features or become certified in operating the surgical robot 1202 with the enhance capabilities. In some embodiments, the updates may not require a medical professional to perform training on the update, such as software updates the improve the operating system, changes in the underlying code in which certain maneuvers or functions use that do not change the way in which the medical professional operates or handles the surgical robot 1202. The upgrade module 1218 stores, at step 1316, the update in the software database 1220 and the process returns to continuously polling for a notification from the update module 1234. For example, the upgrade module 1218 stores the data associated with the update in the software database 1220, such as the date that the download occurred, the update ID, and the version of the update that was downloaded.

Functioning of the software database 1220 will now be explained with reference to FIG. 14 and table 1400. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 14 displays the software database 1220. The database contains the list of updates and versions of the updates that the surgical robot 1202 has downloaded from the surgical robot network 1232. The database contains the date that the download occurred, the update ID, and the version of the update that was downloaded. The database is used during the process described in the verification module 1222 in which the surgical robot 1202 sends the latest update and version to the surgical robot network 1232 to confirm that the user is authorized to perform procedures using the latest update. In some embodiments, the database may contain the type of update, such as a hardware or software update, the characteristic of the update, such as the component that is being updated or a process or procedure that is being updated, the data file containing the update, etc. In some embodiments, the database may contain the procedure the update is associated with, such as anchor placement for a Brostrom Gould procedure, incision location for a back discectomy, etc.

Functioning of the verification module 1222 will now be explained with reference to FIG. 15. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 15:
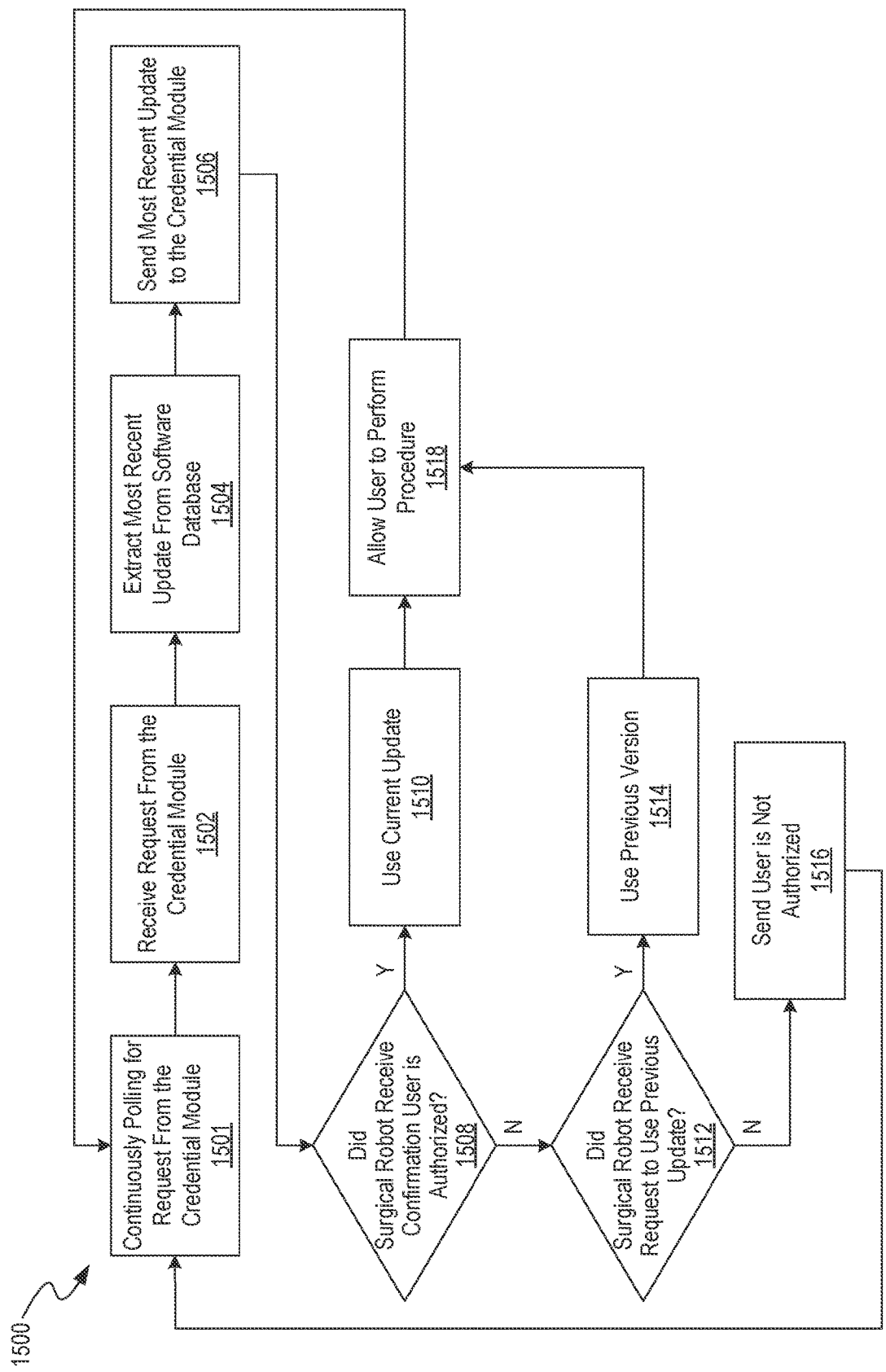
FIG. 15 is a flow diagram illustrating an example process for a verification module, in accordance with one or more embodiments.

FIG. 15 displays the verification module 1222. The process 1500 begins with the verification module 1222 continuously polling, at step 1501, for a request from the credential module 1238. For example, the verification module 1222 is continuously polling for a request from the credential module 1238 for the latest update that the surgical robot 1202 has installed. In some embodiments, the verification module 1222 may determine if the surgical robot 1202 is active or inactive prior to engaging in with credential module 1238. The verification module 1222 receives, at step 1502, the request from the credential module 1238. For example, the verification module 1222 receives a request from the credential module 1238 to send the current update or version that the surgical robot 1202 has installed in order to confirm that the medical professional that is operating the surgical robot 1202 or working alongside the surgical robot 1202 is certified using the latest update that the surgical robot 1202 is operating. The verification module 1222 extracts, at step 1504, the most recent update from the software database 1220. For example, the verification module 1222 extracts the most recent update from the software database 1220, such as the date that the download occurred, the update ID, and the version of the update that was downloaded. The verification module 1222 sends, at step 1506, the most recent update to the credential module 1238. For example, the verification module 1222 sends the extracted most recent update stored in the software database 1220 to the credential module 1238, such as the date that the download occurred, the update ID, and the version of the update that was downloaded.

The verification module 1222 determines, at step 1508, if the surgical robot 1202 received confirmation from the credential module 1238 that the user is authorized to perform the procedure with the most recent update. For example, the verification module 1222 determines if the credential module 1238 send a notification or signal that confirms that the medical professional is certified in the latest update or if the medical professional is not certified in the latest update. If it is determined that the user is authorized to perform the procedure with the most recent update the verification module 1222 uses, at step 1510, the most recent update for the procedure. For example, if the medical professional is certified and has completed the training on the newest update the medical professional is authorized to perform the procedure using the surgical robot 1202 latest update. If it is determined that the user is not authorized to perform the procedure using the most recent update the verification module 1222 determines, at step 1512, if the surgical robot 1202 received a request to use the previous version. For example, if the medical professional is not certified or trained in the latest update for the surgical robot 1202 the verification module 1222 determines if the credential module 1238 sent a notification or signal to use the previous version or update or a previous version of one of the updates installed on the surgical robot 1202. If it is determined that the surgical robot 1202 received a request to use the previous version the verification module 1222 uses, at step 1514, the previous update. For example, if there was an update to the user interface 1210 of the surgical robot 1202 the verification module 1222 would use the previous user interface 1210 since the medical professional is certified using that user interface 1210. Additionally, if the update was for a new anchor placement in a Brostrom Gould procedure then the credential module 1238 would send a signal or notification to the verification module 1222 that the user is not certified in the new procedure and the surgical robot 1202 would perform the previous procedure or in this case the previous anchor location. If it is determined that the surgical robot 1202 did not receive a request to use the previous update the verification module 1222 sends, at step 1516, a notification that the user is not authorized to perform the procedure using the surgical robot 1202 and the process returns to continuously polling for a request from the credential module 1238. For example, if the user is not certified in using a new hardware component, such as an end effector 1214 or robotic arm 1212 then the verification module 1222 may determine that the procedure cannot be completed since the old end effector 1214 or robotic arm 1212 is no longer in use by the surgical robot 1202 and the medical professional would be denied from accessing the surgical robot 1202. The verification module 1222 allows, at step 1518, the user to perform the procedure using either the most recent update or the previous update and the process returns to continuously polling for a request from the credential module 1238. For example, the medical professional may perform the procedure with the surgical robot 1202 either using the newest update or a previous update.

Functioning of the base module 1232 will now be explained with reference to FIG. 13. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 16 displays the base module 1232. The process 1600 begins with the base module 1232 initiating, at step 1601, the update module 1234. For example, the update module 1234 queries the update database 1240 for a new software/hardware update. The update module 1234 extracts the new software/hardware update from the update database 1240. The update module 1234 connects to the surgical robot 1202. The update module 1234 sends a notification to the upgrade module 1218. The update module 1234 is continuously polling to receive a request for the software/hardware update from the upgrade module 1218. The update module 1234 receives a request for the update from the upgrade module 1218. The update module 1234 sends the update to the upgrade module 1218. The update module 1234 stores the update and the robot ID in the credential database 1242. The update module 1234 returns to the base module 1232. The base module 1232 initiates, at step 1602, the training module 1236. For example, the training module 1236 begins by being initiated by the base module 1232. The training module 1236 filters the credential database 1242 on the newest update. The training module 1236 filters the credential database 1242 on uncertified users (e.g., surgical robot operators, such as an operator in surgery room, remote operator/consultant, etc.). The training module 1236 extracts the first uncertified user from the credential database 1242. The training module 1236 sends a notification to the user to schedule training for certification for the new update. The training module 1236 determines if there are more uncertified users in the credential database 1242. If it is determined that the credential database 1242 contains more uncertified users the training module 1236 extracts the next uncertified user from the credential database 1242 and the process returns to sending a notification to the uncertified user to schedule training for certification on the new update. If it is determined that there are no more uncertified users in the credential database 1242 the training module 1236 returns to the base module 1232.

The base module 1232 initiates, at step 1604, the credential module 1238. For example, the credential module 1238 begins by being initiated by the base module 1232. The user logs in to the surgical robot network 1230. The credential module 1238 connects to the surgical robot 1202. The credential module 1238 sends a request to the verification module 1222 for the current update the surgical robot 1202 is using. The credential module 1238 receives the current update from the verification module 1222 that the surgical robot 1202 is using. The credential module 1238 compares the user to the credential database 1242. The credential module 1238 determines if the user is authorized to use the current update the surgical robot 1202 is using. If it is determined that the user is authorized to use the current version the surgical robot 1202 is operating with the credential module 1238 sends a notification to the verification module 1222 that the user is authorized. If it is determined that the user is not authorized to use the current version the surgical robot 1202 is operating with the credential module 1238 sends a request to the verification module 1222 to use the previous update. Then the user performs the surgical procedure using the surgical robot 1202. The credential module 1238 returns to the base module 1232.

Functioning of the update module 1234 will now be explained with reference to FIG. 16. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 17 displays the update module 1234. The process 1700 begins with the update module 1234 being initiated, at step 1701, by the base module 1232. In some embodiments, the update module 1234 may be continuously running in the background to provided updates to the surgical robot 1202 without the need of being initiated by the base module 1232. The update module 1234 queries, at step 1702, the update database 1240 for a new software/hardware update. For example, the update module 1234 queries the update database 1240 for a new update or a new entry, such as a new update for the surgical robot 1202. The update module 1234 may use the date stored in the update database 1240 to determine if the update has been previously sent to the surgical robot 1202 or the update database 1240 may contain the robot IDs that have previously downloaded the update. The update module 1234 extracts, at step 1704, the new software/hardware update from the update database 1240. For example, the update module 1234 extracts the new update data entry from the update database 1240 including the date the update was uploaded to the surgical robot network 1230, the update ID, the type of update, such as a hardware or software update, the characteristic of the update, such as the component that is being updated or a process or procedure that is being updated, the version of the update, and the data file containing the update that allows the surgical robots 1202 to download the update. The update module 1234 connects, at step 1706, to the surgical robot 1202. For example, the update module 1234 may connect to the surgical robot 1202 or the upgrade module 1218 through the communication interface 1208. The update module 1234 sends, at step 1708, a notification to the upgrade module 1218. For example, the update module 1234 may send a notification or a signal to the surgical robot 1202 that there is a new update that must be installed. The update module 1234 is continuously polling, at step 1710, to receive a request for the software/hardware update from the upgrade module 1218. For example, the upgrade module 1218 will send a request for the update when the surgical robot 1202 is not active. This will prevent the surgical robot 1202 from attempting to download software or hardware updates while the surgical robot 1202 is being used, such as performing a surgical procedure.

The update module 1234 receives, at step 1712, a request for the update from the upgrade module 1218. For example, the update module 1234 receives a request from the upgrade module 1218 that the surgical robot 1202 is inactive and ready to receive the update data to allow the surgical robot 1202 to download the newest update. The update module 1234 sends, at step 1714, the update to the upgrade module 1218. For example, the update module sends the update data entry from the update database 1240 to the upgrade module 1218, which may include the date the update was uploaded to the surgical robot network 1230, the update ID, the type of update, such as a hardware or software update, the characteristic of the update, such as the component that is being updated or a process or procedure that is being updated, the version of the update, and the data file containing the update that allows the surgical robots 1202 to download the update. The update module 1234 stores, at step 1716, the update and the robot ID in the credential database 1242. For example, the update module 1234 may store the update and the robot ID in the credential database 1242 to ensure that any user that tries to perform a procedure with the surgical robot 1202 has completed the necessary training and is certified to operate the surgical robot 1202 that contains the latest update. The update module 1234 returns, at step 1718, to the base module 1232.

Functioning of the training module 1236 will now be explained with reference to FIG. 17. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 18:
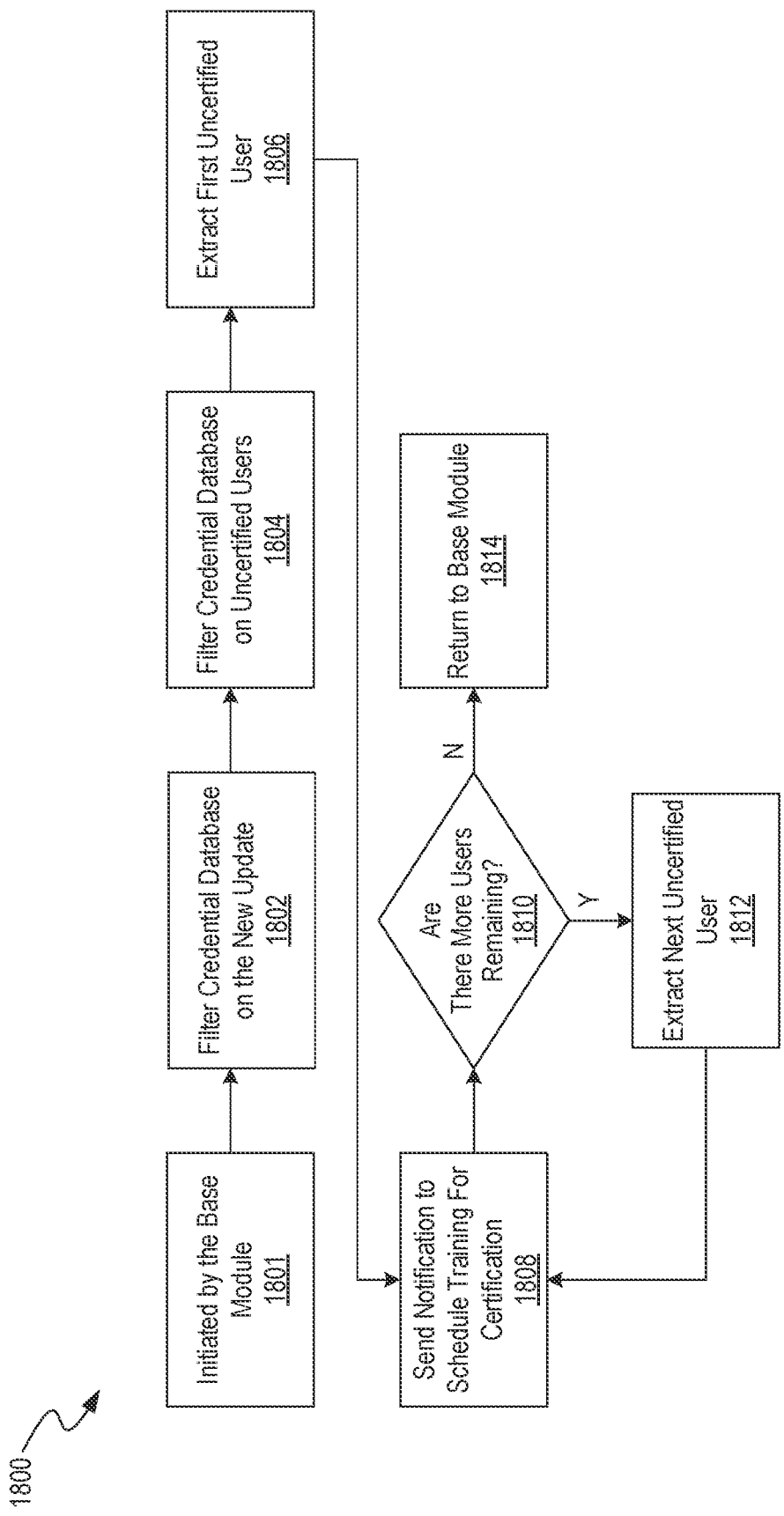
FIG. 18 is a flow diagram illustrating an example process for a training module, in accordance with one or more embodiments.

FIG. 18 displays the training module 1236. The process 1800 begins with the training module 1236 being initiated, at step 1801, by the base module 1232. In some embodiments, the training module 1236 may be continuously running in the background to notify and schedule training with the medical professionals without the need of being initiated by the base module 1232. The training module 1236 filters, at step 1802, the credential database 1242 on the newest update. For example, the training module 1236 filters the credential database 1242 on the newest update that was provided to the surgical robot 1202, such as update ID SP7896 which is an update for new suture pattern for the surgical robot 1202 to perform. The newest update can include/indicate technician changes to the surgical robot, replacement of component, maintenance of the surgical robot, etc.

The training module 1236 filters, at step 1804, the credential database 1242 on uncertified users. For example, the credential database 1242 is filtered on users or medical professionals that are currently not certified to operate the surgical robot's 1202 newest update. In some embodiments, the training module 1236 may filter only on uncertified medical professionals or medical professionals that have not completed training regardless of the date of the update to ensure that medical professionals are up to date on training for all of the updates that have been downloaded by the surgical robot 1202.

The training module 1236 extracts, at step 1806, the first uncertified user from the credential database 1242. For example, the training module 1236 may extract the medical professional (e.g., surgical robot operator), their contact information, and the update version from the credential database 1242. The training module 1236 sends, at step 1808, a notification to the user (e.g., surgical robot operator, such as operator in surgery room, remote operator/consultant, etc.) to schedule training for certification for the new update. For example, the training module 1236 may send a notification to the medical professional to schedule training on the newest update that was provided to the surgical robot 1202. In some embodiments, the training module 1236 may compare the update that the medical professional is not trained on to the medical professional's calendar or schedule to determine if there is a potential conflict, such as the update is for a Brostrom Gould procedure, and the medical professional is scheduled to perform a Brostrom Gould procedure in two days. The training module 1236 may leave a plurality of notifications to inform the medical professional of the new update and the potential conflict for the medical professional. In some embodiments, the training module 1236 may determine a time slot on the medical professional's calendar or schedule and schedule the training for the medical professional prior to the procedure that will have conflict and notify the medical professional of the scheduled training. In some embodiments, the training may include the medical professional to perform the actions or procedures of the surgical robot 1202 to prepare the medical professional to complete the procedure without the use of the surgical robot 1202 in an emergency situation. In some embodiments, once the medical professional has completed and passed the training the training module 1236 updates the credential database 1242 and stores that the medical professional has completed training and is certified to use the updates that the surgical robot 1202 has downloaded.

In some embodiments, the medical professional may be required to complete patient side training in which the medical professional is exposed to the steps of the operative procedure, such as what to do on the console controlling the surgical robot 1202, and also necessitates the development of skills unique to the medical professional, such as troubleshooting to ensure the process is performed smoothly. The medical professional develops an understanding of the ergonomics and restriction of access created by the robotic arms. No metrics such as number of procedure or duration of patient side assistance are available. It is plausible that patient side skills are acquired relatively quickly, and that establishing a sign off of competency would enable progression to console in a relatively short duration. In some embodiments, the medical professional may be required to complete patient positioning and port placement training. Patient positioning and port placement play a key role in the ergonomics of the procedure. Proper patient positioning not only ensures that each member of the surgical team, such as the patient side assistant, scrub nurse, anesthetist, etc. gets adequate access to the patient, but also maintains an optimal spatial configuration between the patient cart of the surgical robot 1202 and the target organ in question. Similarly correct port placement enables access to target organs, allowing for the required triangulation, without any extracorporeal or intracorporeal instrument clashes. Simulation of this can be learnt in sham operating theaters placing ports into mannequins and testing for access and instrument clash and emergency undocking procedures. In some embodiments, the medical professional may be required to achieve basic laparoscopic skills. Basic laparoscopic skills required for a robotic surgeon include laparoscopic access and creation of pneumoperitoneum, take down of adhesions that prevent port insertion, application of clips, suction and retraction. These basic skills can be acquired in a dry lab and fine-tuned during bedside training. The acquisition of basic laparoscopic skills has its own learning curve but has been shown to ease the development of robotic skills on the console. Intensive training in basic laparoscopic skills reduces the time taken to perform the task robotically as well as reduced the number of errors. A potential explanation for this benefit of basic laparoscopic skills is the development of a robust and safe method of instrument position and use. As laparoscopic instruments do not allow much freedom, there are limited ways of achieving a set task, such as needle positioning. The procedural skills so developed tend to be the most ergonomic and safe way of performing the task. The increased maneuverability of the robotic platform in a sense allows development of many ways of achieving a task in a dry lab. All methods may not necessarily be the most ergonomic, and the skills developed in this setting may not be generalizable during a difficult operation. Hence, developing the correct basic laparoscopic skills provides a cognitive imprint that helps develop the correct robotic skills on the console, which can bail the surgeon out in difficult robotic cases.

Development of basic laparoscopic skills also improves spatial awareness, for example of organs as well as instruments, the ability to delicately handle tissues and the ability to safely maneuver and operate in three-dimensional space. In some embodiments, the medical professional may be required to complete console training on the surgical robot 1202. In some embodiments, the robotic system is a master slave system, and the console is the interface controlling mechanical movement. Similar to any advanced technological training, knowledge and working of the console is of paramount importance. Certification in these online modules is essential prior to embarking on any console training. Most modules such as describe each component of the system and also provide information on troubleshooting. Proficiency in these basic console skills, such as camera, pedal, finger control, etc. can be achieved in a relatively straightforward manner in a dry lab or virtual reality (VR) simulated environment. Individual and team reaction to system errors can be simulated, repeated and assessed. Advanced console skills, such as excision, suturing and use of diathermy, need to be developed in a mentored simulation environment, either undertaken in a VR simulator, dry lab or a wet lab, for example live animal, cadaveric animal, human models, etc. With the evolution of competency-based training and a focus on patient safety in modern surgical practice, simulation provides not only a platform for initial skill development, but also skill assessment. In some embodiments, the medical professional may be required to complete training on virtual reality simulators. Types of simulators, features and validation VR simulation is increasingly used in medical training and is considered a first and essential step in robotic surgical training. An advantage of VR systems software is the assessment and measurement of progress. Simulated exercises start from basic console control and increase in difficulty to complex tasks. Current simulators have been evaluated to have face validity, for example looks like what it simulates, content validity, such as accurately simulates the test condition, and construct validity, for example can differentiate between novice and expert. These enable the trainee to register procedure specific movements required using tailored videos. The trainee sits at the console grasping the pincer grip and watches a video of the procedure, for example a robotic prostatectomy, being performed, while the console arms move in accordance with the operating surgeon. Once the movements are registered, the trainee can mimic the movements of the surgeon and perform the procedure in real time. The movement of the trainee can be tracked and evaluated by a board software.

Another important aspect of VR simulation-based training is its role in the maintenance/retention of acquired robotic skills. For example, a warmup practice session on the VR simulator may improve task performance and reduce errors in the dry lab not only for basic but also for complicated skills such as robotic suturing. In some embodiments, the medical professional may be required to complete dry lab training. Dry lab simulation is cost effective and can reliably simulate cutting, suturing and grasping exercises. Dry lab training simulates real time challenges and is a good interface to learn initial console troubleshooting, especially with regard to camera and clutch control, position of hands etc. The consumables for dry lab exercises can be as simple as routine beads, needles, sutures, etc. to sophisticated vascular and bowel models. Dry lab exercises are however limited in that it is difficult to maintain a standardized record or method of assessment, something that is essential in the early stage. Objective assessments made by a keen observing trainer may be required in order for the trainee to have any benefit from the system. In some embodiments, the medical professional may be required to complete wet lab training. Handling of tissues and understanding the reaction of tissues to instrument touch cannot be learnt in dry labs. Further, use of diathermy and vascular control can only be learnt in wet labs. Experience in the wet lab soon teaches the medical professional to recognize the consistency of tissues based solely on visual clues. Robotic wet labs provide excellent training ground for near live surgical exposure. Wet labs can provide three different types of training material. Frozen animal parts, frozen human body parts and live animals with the cost increasing proportionately. Animal and human body parts are excellent training material to learn handling of tissues, dissection, excision, diathermy and suturing techniques. Embalmed body parts allow vascular identification and dissection but alas do not provide a learning ground for vascular control. Live anesthetized or euthanized animal models are expensive and limited with regard to number of times they can be used but have an advantage of bleeding simulation. In some embodiments, the medical professional may be required to complete training in the operating room. The medical professional may enter into an agreement with a mentor who will oversee the training. The modular process begins with the medical professional performing the simplest part of the procedure, and progressively taking on increasingly difficult bits as the mentor sees fit. The transition of mentor from preceptor, who will step in when required, to proctor, who supervises and allows the trainee sufficient opportunity to operate, usually indicates that the medical professional is progressing. Dual console control allows the mentor to step in and take over immediately without the medical professional having to leave the console, potentially providing the medical professional with more operating time on the console. In some embodiments, the training in the operating room may be completed through tele-mentoring in which the mentor can view the same images as the operating surgeon and provide expert guidance in real time.

In some embodiments, the medical professional may be required to complete training in non-technical skills development for robotic surgery. The presence of the robot in the operating room poses a unique challenge to team communication and risk management and hence development of non-technical skills is of paramount importance. Non-technical skills such as teamwork, leadership, situational awareness, and decision-making have all been shown to have a significant impact on surgical success and can be developed easily in a simulated environment. The training module 1236 determines, at step 1810, if there are more uncertified users in the credential database 1242. For example, the training module 1236 goes through each medical professional that is either uncertified or has not completed training in the credential database 1242 to ensure that each medical professional is notified of the update, schedules the training, performs the training and is certified to operate the surgical robot 1202 with the latest updates. If it is determined that the credential database 1242 contains more uncertified users the training module 1236 extracts, at step 1812, the next uncertified user from the credential database 1242 and the process returns to sending a notification to the uncertified user to schedule training for certification on the new update. Once the uncertified users become certified, the certification status is updated for the user in the credential database 1242 so the user can operate the surgical robot after the installation of the update. If it is determined that there are no more uncertified users in the credential database 1242 the training module 1236 returns, at step 1814, to the base module 1232.

Functioning of the credential module 1238 will now be explained with reference to FIG. 19 and process 1900. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 19:
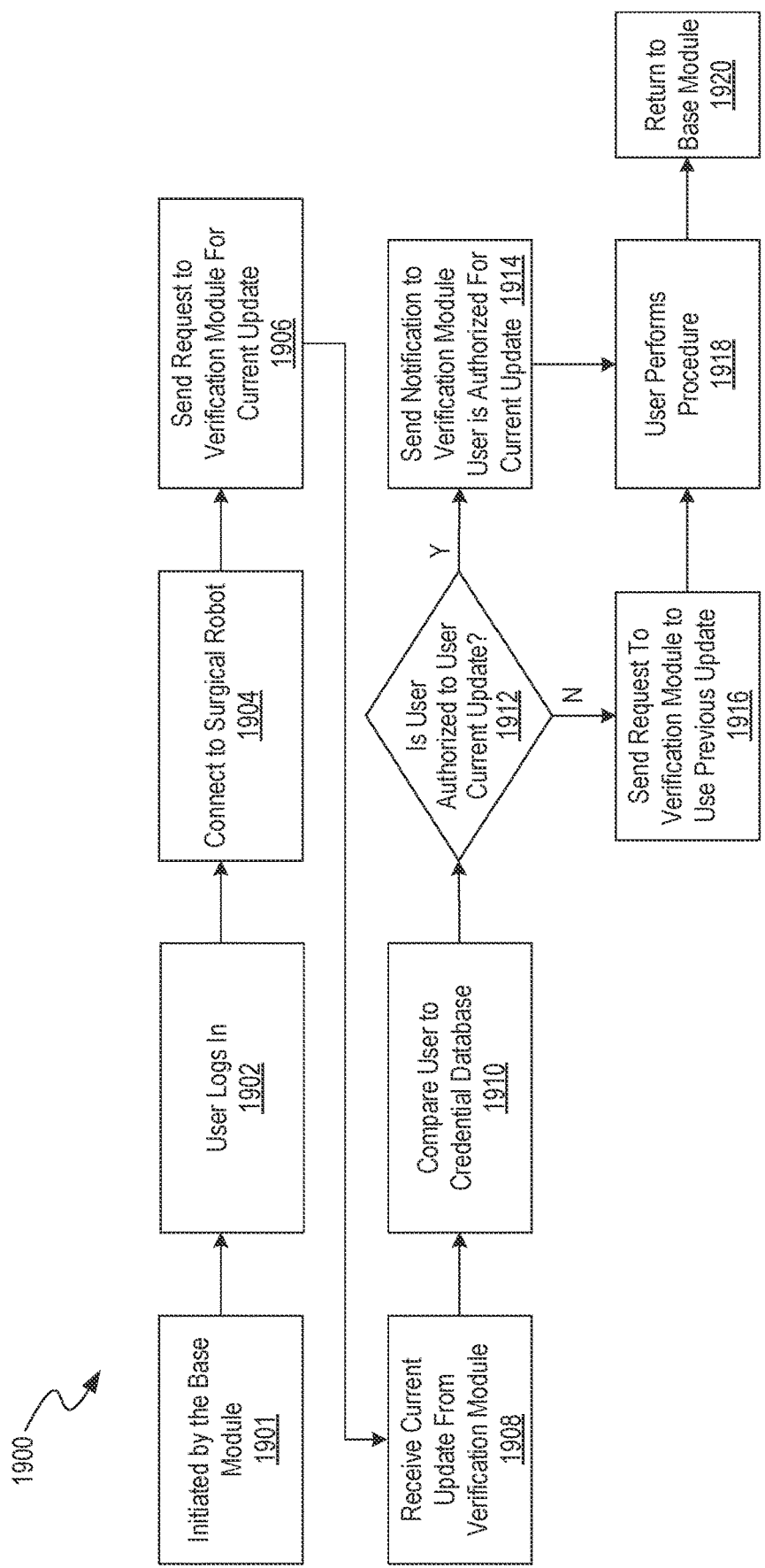
FIG. 19 is a flow diagram illustrating an example process for a credential module, in accordance with one or more embodiments.

FIG. 19 displays the credential module 1238. The process 1900 begins with the credential module 1238 being initiated, at step 1901, by the base module 1232. In some embodiments, the credential module 1238 may be initiated by a user logging into their account to perform a procedure with the use of the surgical robot 1202 without the need of being initiated by the base module 1232. The user logs in, at step 1902, to the surgical robot network 1230. For example, the user may be a medical professional that logs into the surgical robot network 1232 through the use of a username and password. In some embodiments, the medical professional may log in using an e-mail address and pin number or a number of authentication means. The credential module 1238 connects, at step 1904, to the surgical robot 1202. For example, the credential module 1238 may connect to the verification module 1222 through the communication interface 1208 allowing the user to interact with the surgical robot 1202 through the surgical robot network 1232. The credential module 1238 sends, at step 1906, a request to the verification module 1222 for the current update the surgical robot 1202 is using. For example, the credential module 1238 sends a request to the verification module 1222 to receive the current update or version that the surgical robot 1202 has installed in order to confirm that the medical professional that is operating the surgical robot 1202 or working alongside the surgical robot 1202 is certified using the latest update that the surgical robot 1202 is operating.

The credential module 1238 receives, at step 1908, the current update from the verification module 1222 that the surgical robot 1202 is using. For example, the credential module 1238 receives the current update from the verification module 1222, such as update ID SP7896 version 10.003. The credential module 1238 compares, at step 1910, the user to the credential database 1242. For example, the credential module 1238 may compare the received update and version along with the medical professional's name, ID, username, etc. to determine if the medical professional has completed the training and is certified to operate the surgical robot 1202 using the latest update. The credential module 1238 determines, at step 1912, if the user is authorized to use the current update the surgical robot 1202 is using. For example, the credential module 1238 may filter the credential database on the update ID and the version and the medical professional's name and extract the training status and certification status of the medical professional. If the medical professional has completed training and is certified the credential module 1238 will send a notification or signal to the verification module 1222 that the user is certified and can perform the procedure using the latest update. If it is determined that the medical professional is not certified the credential module 1238 will send a notification or signal to the verification module 1222 to use the previous update and version that the medical professional is certified with to perform the procedure. For example, if there was an update to the user interface 1210 of the surgical robot 1202 the verification module 1222 would use the previous user interface 1210 since the medical professional is certified using that user interface 1210.

Additionally, if the update was for a new anchor placement in a Brostrom Gould procedure then the credential module 1238 would send a signal or notification to the verification module 1222 that the user is not certified in the new procedure and the surgical robot 1202 would perform the previous procedure or in this case the previous anchor location. In some embodiments, if the user is not certified in using a new hardware component, such as an end effector 1214 or robotic arm 1212 then the verification module 1222 may determine that the procedure can not be completed since the old end effector 1214 or robotic arm 1212 is no longer in use by the surgical robot 1202 and the medical professional would be denied from accessing the surgical robot 1202. If it is determined that the user is authorized to use the current version the surgical robot 1202 is operating with the credential module 1238 sends, at step 1914, a notification to the verification module 1222 that the user is authorized. For example, the credential module 1238 may filter the credential database on the update ID and the version and the medical professional's name and extract the training status and certification status of the medical professional. If the medical professional has completed training and is certified the credential module 1238 will send a notification or signal to the verification module 1222 that the user is certified and can perform the procedure using the latest update.

If it is determined that the user is not authorized to use the current version the surgical robot 1202 is operating with the credential module 1238 sends, at step 1916, a request to the verification module 1222 to use the previous update. If it is determined that the medical professional is not certified the credential module 1238 will send a notification or signal to the verification module 1222 to use the previous update and version that the medical professional is certified with to perform the procedure. For example, if there was an update to the user interface 1210 of the surgical robot 1202 the verification module 1222 would use the previous user interface 1210 since the medical professional is certified using that user interface 1210. Additionally, if the update was for a new anchor placement in a Brostrom Gould procedure then the credential module 1238 would send a signal or notification to the verification module 1222 that the user is not certified in the new procedure and the surgical robot 1202 would perform the previous procedure or in this case the previous anchor location. In some embodiments, if the user is not certified in using a new hardware component, such as an end effector 1214 or robotic arm 1212 then the verification module 1222 may determine that the procedure cannot be completed since the old end effector 1214 or robotic arm 1212 is no longer in use by the surgical robot 1202 and the medical professional would be denied from accessing the surgical robot 1202. Then the user performs, at step 1918, the surgical procedure using the surgical robot 1202. For example, the medical professional may perform the procedure with the use of the surgical robot 1202 either using the latest update or previous version. The credential module 1238 returns, at step 1920, to the base module 1232.

Functioning of the update database 1240 will now be explained with reference to FIG. 20 and table 2000. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 20 displays the update database 1240. The database contains the software and hardware updates that are sent to the surgical robots 1202 and may be created by a user and stored on the surgical robot network 1230. The database contains the date the update was uploaded to the surgical robot network 1230, the update ID, the type of update, such as a hardware or software update, the characteristic of the update, such as the component that is being updated or a process or procedure that is being updated, the version of the update, and the data file containing the update that allows the surgical robots 1202 to download the update. In some embodiments, the updates may be software processes for the surgical robot 1202 to perform new surgical procedures, such as a new suture pattern, insert an anchor at different location on the ankle, make an incision at a different location for a back procedure, clean damaged tissue, etc.

In some embodiments, the software updates may be for specific actions in a surgical procedure, a series of actions in a surgical procedure, or an entire surgical procedure allowing the surgical robot 1202 to perform surgical maneuvers, actions, procedures, etc. that it wasn't capable of prior to the update. In some embodiments, the software updates may be backend software updates, such as updates for the surgical robots 1202 operating systems, optimizing current software systems, control systems, interfaces, etc. In some embodiments, the hardware updates may be for the installation of a new component that also requires new software to operate the new hardware or perform actions or procedures with the new hardware component. In some embodiments, the hardware updates may be for a new end effector 1214, robotic arm 1212, sensors 1216, controllers 1204, mobility systems, such as the manner in which the surgical robot 1202 may move around an operating room, imaging devices 1224 that may be incorporated in the surgical robot 1202, light sources 1226 that may be incorporated in the surgical robot 1202, etc. In some embodiments, the updates may require a medical professional to perform training on the update to familiarize themselves with the new features or become certified in operating the surgical robot 1202 with the enhance capabilities. In some embodiments, the updates may not require a medical professional to perform training on the update, such as software updates the improve the operating system, changes in the underlying code in which certain maneuvers or functions use that do not change the way in which the medical professional operates or handles the surgical robot 1202. In some embodiments, the updates may come from a 3rd party source or through another database in the surgical robot network 1202 in which a plurality of users can upload updates that are then tested, vetted, and approved to be added to the update database 1240 where they can be downloaded by the surgical robots 1202.

In some embodiments, the surgical robot network 1232 may be a hospital network that operates a plurality of the surgical robots 1202 and the users can access an app store the includes a plurality of updates, both software and hardware, to allow their surgical robots to download certain updates to perform certain actions, procedures, processes, etc. that are useful for the medical professionals. In some embodiments, the updates provided to the surgical robot 1202 may be to further autonomy of the surgical procedures that the surgical robot 1202 performs, such as making incisions, perform actions such as inserting sutures, removing damaged tissue, reconnecting certain ligaments or tissue, and suturing the incision, etc.

Functioning of the credential database 1242 will now be explained with reference to FIG. 21 and table 2100. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 21 is a table 2100 illustrating an example credential database, in accordance with one or more embodiments. FIG. 21 displays the credential database 1242. The database is created in the process described in the update module 1234 and the training module 1236 and is used during the process described in the credential module 1238 which allows medical professionals to be authorized to perform procedures with the surgical robot 1202 as long as they have had the proper training on the latest software or hardware updates. The database contains the date of the update, the update ID, the version of the update, and then for each update the name of the medical professional, if the training by the medical professional is complete or incomplete, and the if the medical professional is certified to perform actions or procedures with the latest update. In some embodiments, the database may contain additional information about the medical professional, such as the hospital the medical professional is based out of, their contact information, such as phone number, email address, office location, etc., the medical professional's education background, the medical professional's professional background or work experience, the date the medical professional completed training or when training is scheduled to be completed, the medical professional's specialty or area of medicine, etc. The database is used as a means of verification for the surgical robot 1202 to confirm the medical professional is certified in the operating the surgical robot 1202 with the latest updates. In some embodiments, the medical professional's calendar or schedule may include in the database to allow the medical professional to schedule the appropriate training needed for a procedure that may be coming up on their schedule.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 22:
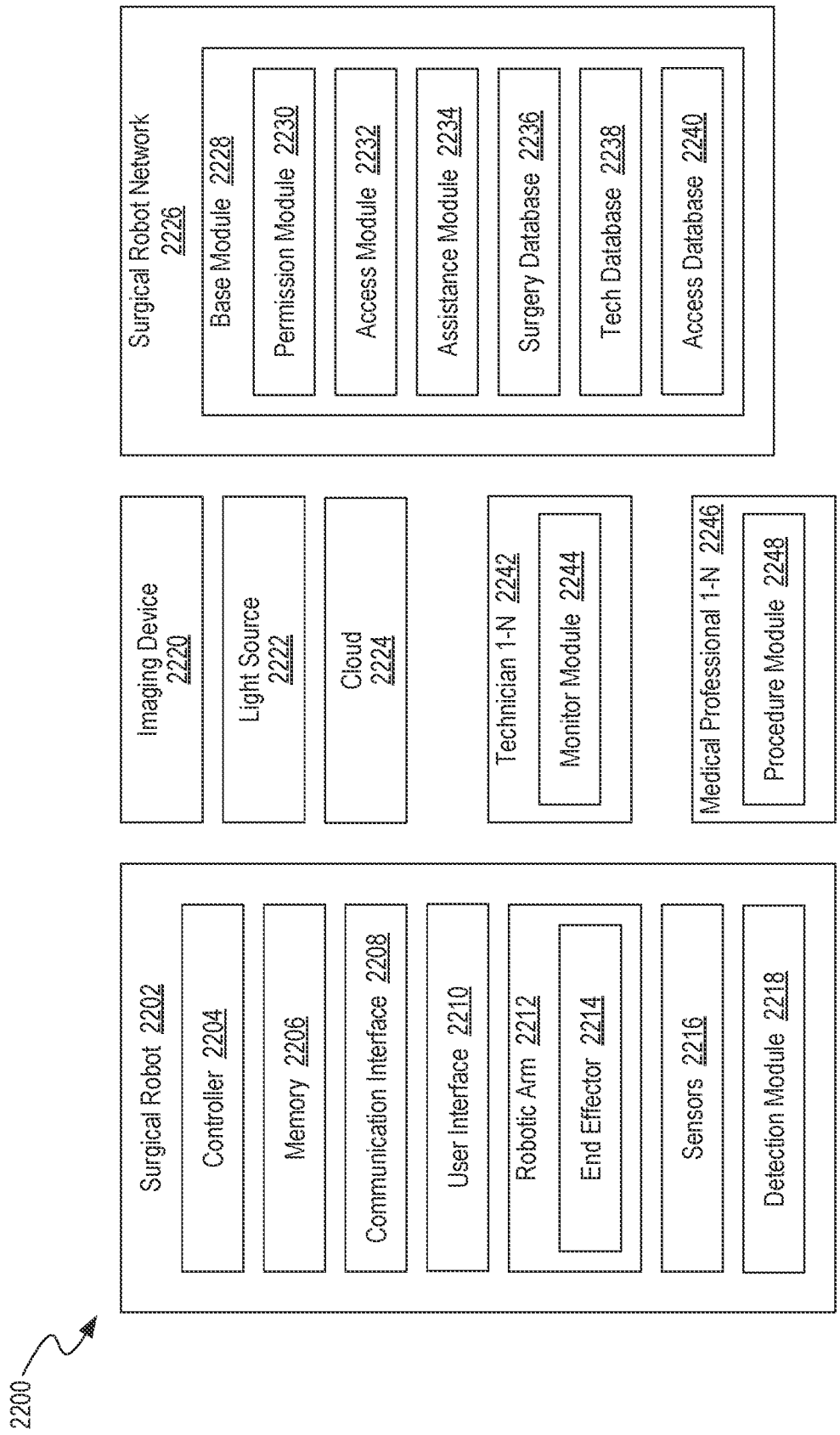
FIG. 22 is a block diagram illustrating an example robotic surgical system for remotely monitoring a surgical robot, in accordance with one or more embodiments.

FIG. 22 illustrates a process 2200 of remotely monitoring a surgical robot. This process comprises of a surgical robot 2202 which is a robotic system designed to assist a surgeon in performing a surgical operation on a patient. A surgical robot 2202 may include a controller 2204, memory 2206, and at least one robotic arm 2212 with an end effector 2214. The surgical robot 2202 may further include a user interface 2210 for accepting control inputs from a user, such as a surgeon or other medical professional and a communications interface 2208 for transmitting and receiving data to and from a cloud 2222 for the purpose of training an artificial intelligence operating within the surgical robot or receiving remote commands from a remote user or an artificial intelligence existing external to the surgical robot 2202. The surgical robot 2202 may additionally comprise a plurality of sensors 2216 for providing feedback to the user or an artificial intelligence.

Further, embodiments may include a controller 2204 which is a computing device comprised of a processor for performing computations and communicates with a memory 2206 for storing data. The controller 2204 is in communication with a communications interface 2208 and may further be allowed to control the at least one robotic arm 2212 and end effector 2214 of a surgical robot 2202. The controller may be a commercially available central processing unit (CPU) or graphical processing unit (GPU) or may be a proprietary, purpose-build design. More than one controller 2204 may operate in tandem and may be of different types, such as a CPU and a GPU. A GPU is not restricted to only processing graphics or image data and may be used for other computations. Further, embodiments may include a memory 2206 which is the electronic circuitry within a computing device that temporarily stores data for usage by the controller 2204. The memory 2206 may additionally comprise persistent data storage for storing data used by the controller 2204. The memory 2206 may be integrated into a controller 2204 or may be a discrete component. The memory 2206 may be integrated into a circuit, such as soldered on component of a single board computer (SBC) or may a removable component such as a discrete dynamic random-access memory (DRAM) stick, secure digital (SD) card, flash drive, solid state drive (SSD), magnetic hard disk drive (SSD), etc. In some embodiments, memory 2206 may be part of a controller 2204. Multiple types of memory 2206 may be used by the surgical robot 2202.

Further, embodiments may include a communications interface 2208 which allows the surgical robot 2202 to communicate with external devices and may comprise a wireless antenna and transceiver or a port for receiving a cable to facilitate a wired connection. Examples of a wired connection include ethernet, universal serial bus (USB) or a proprietary connection. A wireless communications interface 2208 may include any of Wi-Fi, Bluetooth, near field communications (NFC) or a cellular communications interface such as 3G, 4G, LTE, or 5G. The communications interface 2208 may connect a user interface 2210 to the surgical robot 2202 or may facilitate access to a local network or a cloud 2222 network to access a remote server and/or database. Further, embodiments may include a user interface 2210 which is a means of interacting with a surgical robot 2202 and may include any of a keyboard, computer mouse, trackball, joystick, wireless or wired gamepad, sliders, scroll wheels, touch screen or microphone for receiving voice commands. The user interface 2210 may additionally comprise any method of interaction of a user with a surgical robot 2202 not listed. The user interface 2210 may accept direct inputs, such as from a joystick controlling the movement of a robotic arm or indirect inputs such as commands entered on a keyboard or touch screen such as adjusting the sensitivity of a joystick control or the speed of a robotic arm's 2212 movement in response to a joystick.

The user interface 2210 may also comprise a screen for presenting information to the user such as patient status, imaging data, and navigation data and speakers for providing auditory feedback. The user interface 2210 may also utilize haptics to provide feedback to the user. In additional embodiments, the user interface 2210 may comprise an augmented reality (AR) or virtual reality (VR) headset to enable a surgeon to view imagery from at least one imaging device 2218 in real-time and may additionally comprise an overlay, such as highlighting the blood vessels comprising a path which the catheter must be advanced to access the treatment site, such as a blood clot. The user interface 2210 may additionally comprise voice or eye tracking controls. Further, embodiments may include a robotic arm 2212 which is a mechanically actuated arm or lever with at least two degrees of freedom. A robotic arm 2212 will typically include at least one end effector 2214 or an imaging device 2218 and may include both an end effector 2214 and an imaging device 2218. The robotic arm 2212 may additionally be capable of changing the end effector 2214 to facilitate multiple functions and operation of a variety of tools. The robotic arm 2214 may be manually controlled or operated in an autonomous or semi-autonomous mode. A surgical robot 2202 may have one robotic arm 2212 or multiple robotic arms 2212, each of which may be operated independently by one or more users or autonomous systems or a combination of users and autonomous systems. Further, embodiments may include an end effector 2214 which is the end of a robotic arm 2212 which is conducting work. The end effector 2214 is typically a tool or device for interacting with a physical object and may be a surgical tool intended for acting upon or within a patient or may be a gripping device for securing a separate surgical tool to a robotic arm 2212.

The end effector 2214 may be permanently affixed to the end of a robotic arm 2212 or may be detachable allowing for a system of interchangeable end effectors 2214 which may alternatively be selected and swapped by a single robotic arm 2212 or multiple robotic arms 2212. The end effector 2214 may comprise a catheter or other tool for accessing a treatment site within a patient. Similarly, the end effector 2214 may relate to a deployable device, such as a stent, prior to deployment in a patient. The end effector 2214 may be constructed of materials which intentionally absorb, reflect, or are transparent to X-Rays to facilitate the end effector's 2214 visibility when viewed using angiography, fluoroscopy, or other imaging modalities, or alternatively allow the X-Rays to pass through to prevent their interference in images. In some embodiments, the end effector 2214 may be made to be selectively transparent to X-Rays such as by changing the profile of the end effector 2214 or X-Ray absorbing or reflective components to increase or reduce their visibility to an imaging device 2218.

Further, embodiments may include a sensor 2216 which is a measurement tool for monitoring a characteristic or metric associated with a surgical robot 2202, end effector 2214 or patient. A sensor 2216 may be discrete or part of an array or assembly, such as integrated into a catheter. One or more of the sensors 2216 may include an electrophysiologic sensor, a temperature sensor, a thermal gradient sensor, a barometer, an altimeter, an accelerometer, a gyroscope, a humidity sensor, a magnetometer, an inclinometer, an oximeter, a colorimetric monitor, a sweat analyte sensor, a galvanic skin response sensor, an interfacial pressure sensor, a flow sensor, a stretch sensor, a microphone, any combination thereof, etc. The sensors 2216 may be integrated into the operation of the surgical robot 2202 or may monitor the status of a patient. The data acquired by the sensors 2216 may be used to train a machine learning algorithm used by the surgical robot 2202 or artificial intelligence to control the surgical robot 2202. The sensors 2216 may additionally comprise an X-Ray dosimeter to monitor the intensity of X-Rays being emitted toward the patient to prevent excessive doses of radiation. The sensors 2216 may be utilized to reduce the intensity of the X-Rays or reduce the duration or increase the interval in which the X-Rays are emitted toward the patient to control the dose throughout a procedure.

Further, embodiments may include a detection module 2218 which begins by connecting to the surgical robot network 2226. The detection module 2218 is continuously polling to receive a signal to begin the error detection process for the surgical procedure from the assistance module 2234. The detection module 2218 receives the signal to begin the error detection process for the surgical procedure from the assistance module 2234. The detection module 2218 collects the data on the surgical robot 2202. The detection module 2218 determines if there was an error detected. If it is determined that there was no error detected the detection module 2218 determines if the medical professional requested assistance. If it is determined that there was an error detected or that the medical professional requested assistance the detection module 2218 sends an error detection signal to the assistance module 2234. Then the detection module 2218 determines if the surgical procedure is complete. If it is determined that the surgical procedure is not complete the detection module 2218 returns to collecting data on the surgical robot 2202 and if it is determined that the surgical procedure is complete the detection module 2218 ends. The detection module 2218 can performing one or more of the steps using one or more machine-learning algorithms. For example, the detection module 2218 can include an ML system (e.g., ML system 200 of FIG. 2 or other ML systems disclosed herein) configured to detect errors in real or near-real time. The ML system of the detection module 2218 can determine the equipment associated with the error based on, for example, user input (e.g., user observations), operational data of the surgical robot, data for patient monitoring equipment, etc.

Further, embodiments may include an imaging device 2220 which refers to any device capable of collecting data which can be used to create an image, or a representation of a physical structure or phenomena. An imaging device 2220 may include any device capable of detecting sound or electromagnetic waves and assembling a visual representation of the detected waves imaging devices 2220 may collect waves from any part of the electromagnetic spectrum or sounds at any range of frequencies, often as a matrix of independently acquired measurements which each representing a pixel of a two or three-dimensional image. These measurements may be taken simultaneously or in series via a scanning process or a combination of methods. Some pixels of an image produced by an imaging device 2220 may be interpolated from direct measurements representing adjacent pixels in order to increase the resolution of a generated image. Imaging devices 2220 may receive or generate imaging data from a plurality of imagining devices 2220. The plurality of imaging devices 2220 may include, for example, cameras attached to the robotic arm 2212, cameras mounted to the ceiling or other structure above the surgical theater, cameras that may be mounted on a tripod or other independent mounting device, cameras that may be body worn by the surgeon or other surgical staff, cameras that may be incorporated into a wearable device, such as an augmented reality device like Google Glass, Microsoft HoloLens, etc., cameras that may be integrated into an endoscopic, microscopic, laparoscopic, or any camera or other imaging device 2220 (e.g. ultrasound) that may be present in the surgical theater. The imaging device 2220 may include any algorithm or software module capable of determining qualitative or quantitative data from medical images, which may be, for example, a deep learning algorithm that has been trained on a data set of medical images. An imaging device 2220 may further refer to a device used to acquire medical imagery by any means including magnetic resonance imaging (MRI), computed tomography (CT), X-Ray, positron emission tomography (PET), ultrasound, arthrography, angiography, fluoroscopy, myelography, etc.

An imaging device 2220 may acquire images in real-time or be used to create composite images or models in real-time. Further, embodiments may include a light source 2222 such as surgical lights also referred to as operating light, refers to an instrument that performs illumination of a local area or cavity of the patient. The light source 2222 plays an important role in illumination before, during, and after a medical procedure. The light source 2222 may be categorized by lamp type as conventional (incandescent) and LED (light-emitting diode). The light source 2222 may be categorized by mounting configuration as ceiling-mounted, wall-mounted, or floor stand. The light source 2222 may be categorized by type as tungsten, quartz, and/or xenon halogens and light-emitting diodes (LEDs). The light source 2222 may include sterilizable handles which allow the surgeon to adjust light positions. Some important factors affecting the light source 2222 may be illumination, shadow management (cast shadows and contour shadows), the volume of light, heat management, fail-safe surgical lighting. The light source 2222 can be integrated into the embodiments in a variety of manners.

Further, embodiments may include a cloud 2224 which is a distributed network of computers comprising servers and databases. A cloud 2224 may be a private cloud 2224, where access is restricted by isolating the network such as preventing external access, or by using encryption to limit access to only authorized users. Alternatively, a cloud 2224 may be a public cloud 2224 where access is widely available via the internet. A public cloud 2224 may not be secured or may be include limited security features. Further, embodiments may include a surgical robot network 2224 which may be a network connected to the surgical robot 2202 in which the surgical robot may receive and send data, provide controls to a user for the surgical robot 2202 through a user interface 2210, and allow a user to send data to the surgical robot 2202 related to a designed, tested, or created surgical process for a patient. Further, embodiments may include a base module 2228 which begins by connecting to the procedure module 2248. The base module 2228 is continuously polling for the surgical procedure data from the procedure module 2248. The base module 2228 receives the surgical procedure data from the procedure module 2248. The base module 2228 stores the surgical procedure data from the procedure module 2248 in the surgery database 2236. The base module 2228 initiates the permission module 2230. The base module 2228 initiates the access module 2232.

The base module 2228 initiates the assistance module 2234. Further, embodiments may include a permission module 2230 which begins by being initiated by the base module 2228. The permission module 2230 queries the surgery database 2236 for the new data entry. The permission module 2230 extracts the new data entry from the surgery database 2236. The permission module 2230 filters the tech database 2238 on available technicians at the time and date of the surgical procedure from the data entry extracted from the surgery database 2236. The technician may be available at the surgery suite, available remotely, etc. The permission module 2230 assigns a technician to the surgical procedure extracted from the surgery database 2236. The permission module 2230 sends the assignment to the technician through the monitor module 2244. The permission module 2230 stores the technician in the access database 2240. The permission module 2230 returns to the base module 2228. Further, embodiments may include an access module 2232 which begins by being initiated by the base module 2228. The access module 2232 is continuously polling for a request to access the surgical robot 2202 from the medical professional through the procedure module 2248. The access module 2232 receives a request to access the surgical robot 2202 from the medical professional through the procedure module 2248. The access module 2232 compares the medical professional to the access database 2240. The access module 2232 extracts the access areas for the medical professional. The access module 2232 provides access to the surgical robot 2202 for the medical professional. The access module 2232 sends that access has been granted to the medical professional through the procedure module 2248. The access module 2232 is continuously polling for a request to access the surgical robot 2202 from the technician through the monitor module 2244. The access module 2232 receives a request to access the surgical robot 2202 from the technician through the monitor module 2244.

The access module 2232 compares the technician to the access database 2240. The access module 2232 extracts the access areas for the technician. The access module 2232 provides access to the surgical robot 2202 for the technician. The access module 2232 sends that access has been granted to the technician through the monitor module 2244. The access module 2232 is continuously polling for the surgical procedure to be initiated by the medical professional through the procedure module 2248. The access module 2232 receives that the surgical procedure has been initiated by the medical professional from the procedure module 2248. The access module 2232 sends a notification to the technician that the surgical procedure has been initiated by the medical professional through the monitor module 2244. The access module 2232 returns to the base module 2228. Further, embodiments may include an assistance module 2234 which begins by being initiated by the base module 2228. The assistance module 2234 sends a begin error detection signal to the detection module 2218. The assistance module 2234 is continuously polling for an error detected signal from the detection module 2218. The assistance module 2234 determines if an error detected signal was received from the detection module 2218. If it is determined that the assistance module 2234 received an error detected signal from the detection module 2218 the assistance module 2234 sends the error detected signal to the technician through the monitor module 2244. If it is determined that the assistance module 2234 did not receive an error detected signal from the detection module 2218 the assistance module 2234 determines if the surgical procedure is completed. If it is determined that the surgical procedure is not completed the assistance module 2234 returns to continuously polling for an error detected signal from the detection module 2218. If it is determined that the surgical procedure is completed the assistance module 2234 returns to the base module 2228.

Further, embodiments may include a surgery database 2236 which contains the surgical procedure data from the medical professional during the process described in the base module 2228. The database contains the date of the surgical procedure, the time of the surgical procedure, the patient, the procedure being performed, the surgeon that will be performing the surgical procedure, the emergency surgeon, the medical observers of the surgical procedure, and the technician of the surgical robot during the surgical procedure and the emergency technician who are both assigned the surgical procedure during the permission module 2228. Further, embodiments may include a tech database 2238 which contains the list of the technicians that can monitor the surgical robots 2202 during a surgical procedure and the times that they are scheduled to monitor the surgical robots during certain surgical procedures. The database contains the name of the technician, the technician's ID or unique identifier, the date that the technician is scheduled to monitor a surgical robot 2202, and the start time and the estimated end time that the technician will be monitoring a surgical robot 2202 for a surgical procedure. Further, embodiments may include an access database 2240 which contains access permissions for all the parties involved in a surgical procedure including the areas, components, or elements that the party is able to access and the ones that they do not have access to. The database contains the patient's name, the surgical procedure being performed, the participants of the surgical procedure, the involvement of the participants, such as surgeon, technician, etc., then a plurality of areas, components, or elements of the surgical robot 2202 and surgical procedure that provide access to specific participants and deny access to other participants, such as control of the surgical robot 2202, access to the surgical robot 2202 robotic arms 2212, end effectors 2214, user interface 2210, communication interface 2208, controllers 2204, the code of the surgical robot 2202, the patient's electronic health records or EHR, the imaging devices 2220 and devices recording the surgical procedure, updates on the procedure, etc. Further, embodiments may include a plurality of technicians 1-N 2242 which is worker in a field of technology, such as surgical robots 2202, who is proficient in the relevant skill and technique with a relatively practical understanding of theoretical principles. The technician may use a system monitor of a surgical robot 2202 to monitor the performance of surgical robot 2202.

A system monitor may be a hardware or software component used to monitor system resources and performance in a computer system, such as a surgical robot 2202. In some embodiments, the technician may monitor the performance and status of a surgical robot 2202 during a surgical procedure in which the technician is granted access to the specific surgical robot 2202 being used in the procedure but is not capable of accessing patient data, such as data from an electronic health record. Further, embodiments may include a monitor module 2244 which begins by connecting to the surgical robot network 2226. The monitor module 2244 is continuously polling for the assignment from the permission module 2230. The monitor module 2244 receives the assignment from the permission module 2230. The monitor module 2244 sends a request for access to the surgical robot 2202 to the access module 2232. The monitor module 2244 receives access to the surgical robot 2202 from the access module 2232. The monitor module 2244 is continuously polling for the surgical procedure to be initiated by the medical professional from the access module 2232. The monitor module 2244 receives that the surgical procedure has been initiated by the medical professional from the access module 2232. The monitor module 2244 connects to the surgical robot 2202. The technician monitors the parameters (e.g., operational data) of the surgical robot 2202. The monitor module 2244 determines if an error detected signal was received from the assistance module 2234. If it is determined that the monitor module 2244 received an error detected signal from the assistance module 2234 the technician resolves the error that was detected. If it is determined that the monitor module 2244 did not receive an error detected signal from the assistance module 2234 the monitor module 2244 determines if the surgical procedure is complete. If it is determined that the surgical procedure is not complete the monitor module 2244 returns to the technician monitoring the parameters of the surgical robot 2202. If it is determined that the surgical procedure is complete the monitor module 2244 ends.

Further, embodiments may include a plurality of medical professionals 1-N 2246 which may approve a connection to the surgical robot network 2228 to diagnosis and create a medical procedure for a patient through telemedicine. The medical professional may connect and control the surgical robot 2202 through a connection with surgical robot network 2226 to perform the procedure. The medical professional may request assistance on the surgical robot 2202 user interface 2210 to notify a technician of a possible technical issue during a surgical procedure. Medical professionals may be a person that provides medical care and services within the scope of their license such as a physician, physician assistant, nurse practitioner, registered nurses, surgeons, specialists, medical experts, etc. Further, embodiments may include a procedure module 2248 which begins by connecting to the surgical robot network 2226. The procedure module 2248 sends the surgical procedure data to the base module 2228. The procedure module 2248 sends a request to access the surgical robot 2202 to the access module 2232. The procedure module 2248 receives access to the surgical robot 2202 from the access module 2232. The procedure module 2248 connects to the surgical robot 2202. The procedure module 2248 sends that the surgical procedure has been initiated by the medical professional to the access module 2232. The medical professional performs the surgical procedure on the patient by controlling the surgical robot 2202. The procedure module 2248 determines if the medical professional requested assistance. If it is determined that the medical professional requested assistance the procedure module 2248 sends assistance has been requested to the detection module 2218. The procedure module 2248 is continuously polling for the resolution to the requested assistance by the medical professional. The procedure module 2248 receives the resolution to the requested assistance by the medical professional. The procedure module 2248 determines if the surgical procedure is completed. If it is determined that the surgical procedure is not completed the procedure module 2248 returns to the medical professional performing the surgical procedure. If it is determined that the surgical procedure is completed the procedure module 2248 ends.

Functioning of the detection module 2218 will now be explained with reference to FIG. 23. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 23:
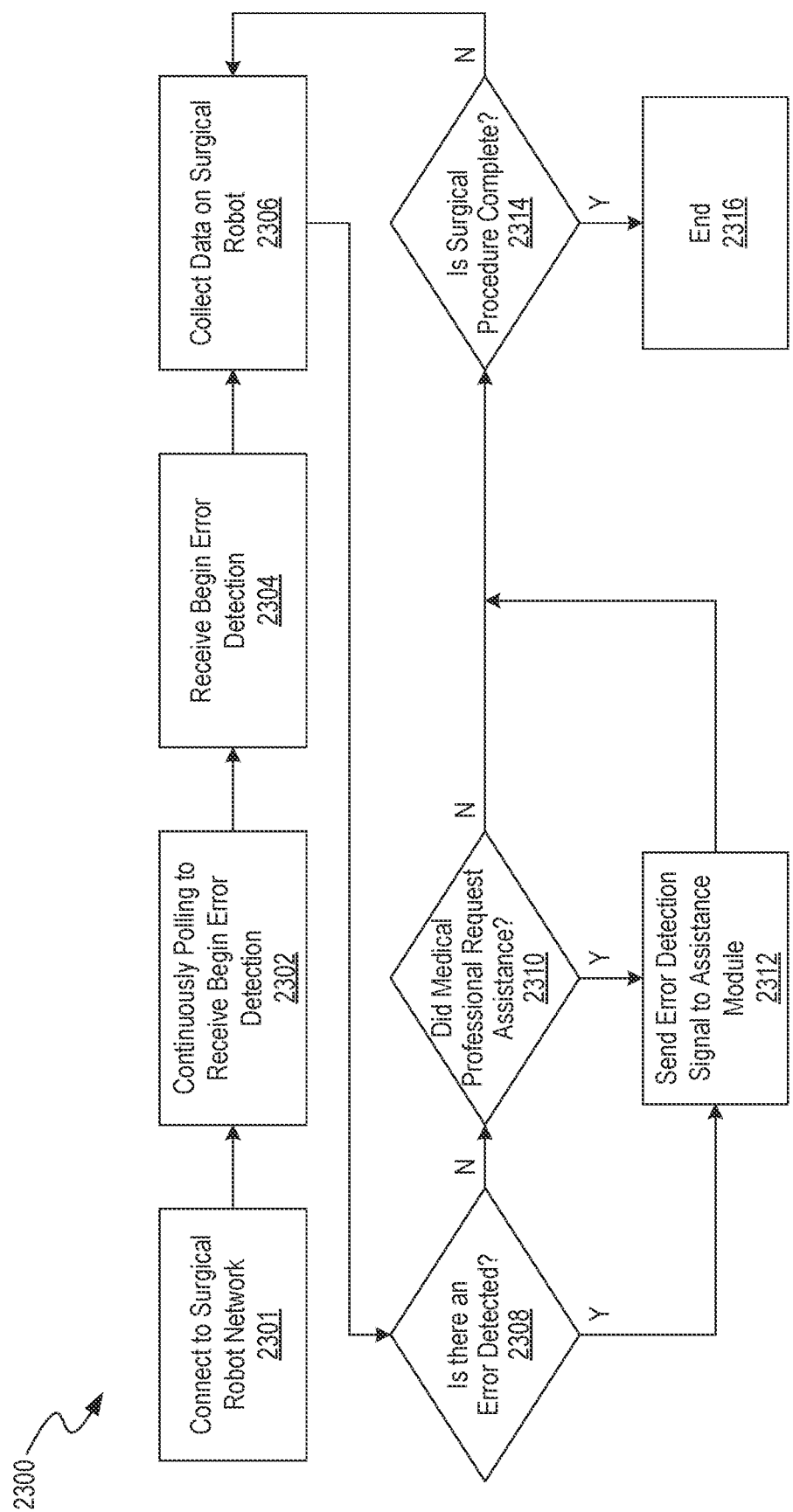
FIG. 23 is a flow diagram illustrating an example process for a detection module, in accordance with one or more embodiments.

FIG. 23 displays the detection module 2218. The process 2300 begins with the detection module 2218 connecting, at step 2301, to the surgical robot network 2226. For example, the detection module 2218 may connect to the surgical robot 2226 and send and receive data from the permission module 2230, access module 2232 and assistance module 2234. In some embodiments, the detection module 2218 may connect to the procedure module 2248 and monitor module 2244. The detection module 2218 is continuously polling, at step 2302, to receive a signal to begin the error detection process for the surgical procedure from the assistance module 2234. For example, the detection module 2218 is continuously polling to receive a signal from the assistance module 2234 to begin error detection. For example, the error detection may be to initiate the system monitor which is hardware or software component used to monitor system resources and performance in a computer system. In some embodiments, the monitor system may provide the technician with a display that presents operational data to the technician, such as free space on one or more hard drives, the temperature of the CPU and other important components, and networking information including the system IP address, current rates of upload and download, error notifications, power supply, software monitoring, etc. The detection module 2218 receives, at step 2304, the signal to begin the error detection process for the surgical procedure from the assistance module 2234. For example, the detection module 2218 receives a signal from the assistance module 2234 to begin error detection. For example, the error detection may be to initiate the system monitor which is hardware or software component used to monitor system resources and performance in a computer system. In some embodiments, the monitor system may provide the technician with a display that presents operational data to the technician, such as free space on one or more hard drives, the temperature of the CPU and other important components, and networking information including the system IP address, current rates of upload and download, error notifications, power supply, software monitoring, etc.

The detection module 2218 collects, at step 2306, the data on the surgical robot 2202. For example, the detection module 2218 collects data (e.g., operational data) on the surgical robot 2202, such as history of maintenance, servicing information, equipment performance data (e.g., cutting speed of a saw, RPMs of a drill, image quality from a camera, free space on one or more hard drives, the temperature of the CPU and other important components, and networking information including the system IP address, current rates of upload and download, error notifications, power supply, software monitoring, etc.). In some embodiments, the detection module 2218 may create a surgical robot 2202 report for the technician that includes the total number of procedures performed by the surgical robot 2202, the number of malfunctions, the list of instruments, the robotic arms 2212 used, the console performance, the performance of the imaging devices 2218, the percentage of the instruments malfunctioning, the number of patients injured during the surgical procedure, etc. The detection module 2218 determines, at step 2308, if there was an error detected. For example, the detection module 2218 may identify an error notification from the system monitor that an aspect, feature, function, component, element, etc. is not performing or behaving properly (e.g., operating below a performance threshold) resulting in an error notification from the system. The error can be based on an error confidence score, comparisons to other failed features, historical errors, operating performance of a component of the surgical robot, etc.

In some embodiments, the notification may be displayed on the user interface 2210 to notify the technician. If it is determined that there was no error detected the detection module 2218 determines, at step 2310, if the medical professional requested assistance. For example, if there is no error detected from the system monitor, the detection module 2218 determines if a request was received from the procedure module 2248 which would inform the system that the medical professional is experiencing an issue with the surgical robot 2202. If it is determined that there was an error detected or that the medical professional requested assistance the detection module 2218 sends, at step 2312, an error detection signal to the assistance module 2234. For example, if the detection module 2218 determines there is an error signal the technician may access the area of concern on the surgical robot 2202, such as connectivity of the surgeon, and analyze the connection speeds of the surgical robot 2202 and the medical professional to identify where the error is coming from, and if the medical professional is the one experiencing the connection issues notify the emergency surgeon to take over control of the surgical robot 2202 until the surgeon can reconnect to the surgical robot 2202.

In some embodiments, the error signal may be generated through machine learning in which the monitor module uses the surgical robot 2202 report to identify potential errors that will occur in the surgical procedure. For example, the surgical robot 2202 report may contain the total number of procedures performed by the surgical robot 2202, the number of malfunctions, the list of instruments, the robotic arms 2212 used, the console performance, the performance of the imaging devices 2218, the percentage of the instruments malfunctioning, the number of patients injured during the surgical procedure, etc. A machine learning algorithm may be used to determine the correlations between the patients, type of surgery, actions performed by the surgical robot 2202, and the parameters (e.g., operational data) listed in the surgical robot 2202 report to find correlations in the data. If the data is highly correlated the machine learning algorithm may recommend altering the surgical procedure plan, use a different robotic arm 2212, use a different end effector 2214, place the surgical robot 2202 in a different position for a certain action, etc. For example, if it is highly correlated that the robotic arm 2212 will malfunction on an anchor placement for a Brostrom Gould procedure if the surgical robot 2202 is positioned at the patient's waist, the recommendation may be to place the surgical robot 2202 by the patient's ankle or legs to allow the robot arm 2212 an improved angle to place the anchor. Once the error is resolved the detection module 2218 may allow the medical professional to continue with the surgical procedure. Then the detection module 2218 determines, at step 2314, if the surgical procedure is complete. If it is determined that the surgical procedure is not complete the detection module 2218 returns to collecting data on the surgical robot 2202. For example, the medical professional may input on the user interface 2210 or send a signal through the procedure module 2248 that the surgical procedure is complete. If it is determined that the surgical procedure is complete the detection module 2218 ends, at step 2316.

Functioning of the base module 2228 will now be explained with reference to FIG. 24 and process 2400. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments. In some implementations, the errors are identified via machine learning algorithms.

Figure 24:
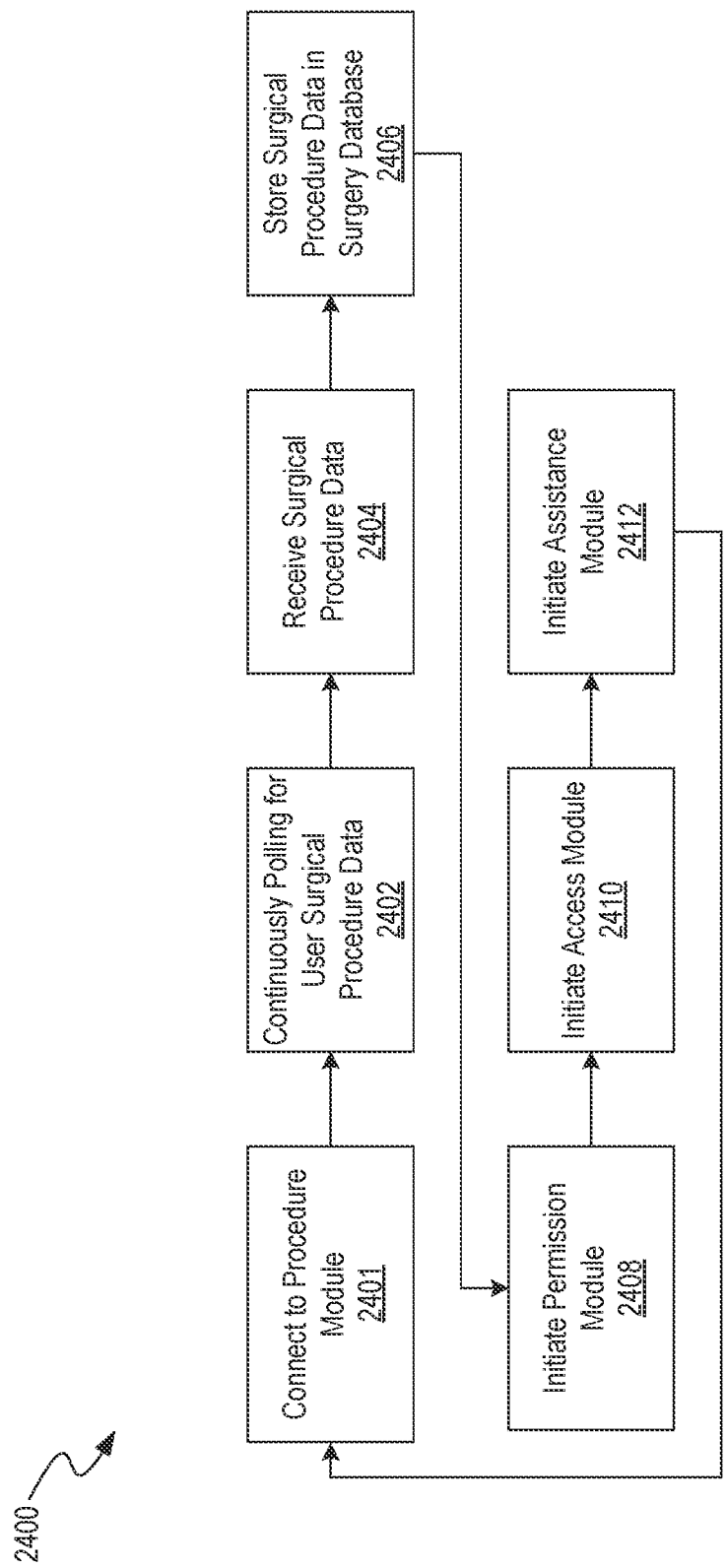
FIG. 24 is a flow diagram illustrating an example process for a base module, in accordance with one or more embodiments.

FIG. 24 displays the base module 2228. The process 2400 begins with the base module 2228 connecting, at step 2401, to the procedure module 2248. For example, the base module 2228 connects to the medical professional through the procedure module 2248. In some embodiments, the medical professional may access the base module 2228 through logging into the surgical robot network 2226 with the use of a username and password combination or other digital authentication to verify themselves. The base module 2228 manages access control of various users via at least one of several means known to the art, including, for example mandatory access control, discretionary access control, role-based access control, rule-based access control, attribute based access control, or some combination thereof. The base module 2228 is continuously polling, at step 2402, for the surgical procedure data from the procedure module 2248. For example, the base module 2228 is continuously polling to receive the surgical procedure data such as, the patient's name, the surgical procedure being performed, the surgeon scheduled to perform the surgical procedure, the emergency surgeon scheduled to perform the surgical procedure in the event the original surgeon is incapable of performing the surgical procedure, the medical observers, if any, that will be observing the surgical procedure, etc. In some embodiments, the received surgical procedure data, may include the patient's personal information such as their place of residency, age, height, weight, insurance provider, primary care physician, etc.

In some embodiments, the data may include the patient's electronic health records or EHR, family history, medication history, allergies, previous surgical procedures, etc. In some embodiments, the data may include the steps for the surgical procedure or the surgical procedure plan, the tools or instruments that will be used in the procedure, the anesthesia or medications that the will patient will receive prior to the procedure, the actions to be performed by the surgical robot 2202, the actions to be performed by the medical professional or surgeon, the estimated time the surgical procedure will take to be performed, etc. In some embodiments, the data on the medical professionals such as the surgeon and emergency surgeon may include the surgeon's credentials, performance history, specialty, consultation notes, etc. The base module 2228 receives, at step 2404, the surgical procedure data from the procedure module 2248. For example, the base module 2228 receives the surgical procedure data (e.g., operational data) such as, the patient's name, the surgical procedure being performed, the surgeon scheduled to perform the surgical procedure, the emergency surgeon scheduled to perform the surgical procedure in the event the original surgeon is incapable of performing the surgical procedure, the medical observers, if any, that will be observing the surgical procedure, history of maintenance, servicing information, equipment performance data (e.g., cutting speed of a saw, RPMs of a drill, image quality from a camera, etc.). In some embodiments, the received surgical procedure data, may include the patient's personal information such as their place of residency, age, height, weight, insurance provider, primary care physician, etc. In some embodiments, the data may include the patient's electronic health records or EHR, family history, medication history, allergies, previous surgical procedures, etc. In some embodiments, the data may include the steps for the surgical procedure or the surgical procedure plan, the tools or instruments that will be used in the procedure, the anesthesia or medications that the will patient will receive prior to the procedure, the actions to be performed by the surgical robot 2202, the actions to be performed by the medical professional or surgeon, the estimated time the surgical procedure will take to be performed, etc.

In some embodiments, the data on the medical professionals such as the surgeon and emergency surgeon may include the surgeon's credentials, performance history, specialty, consultation notes, etc. The base module 2228 stores, at step 2406, the surgical procedure data from the procedure module 2248 in the surgery database 2236. For example, the base module 2228 stores the surgical procedure data in the surgery database 2236, such as, the patient's name, the surgical procedure being performed, the surgeon scheduled to perform the surgical procedure, the emergency surgeon scheduled to perform the surgical procedure in the event the original surgeon is incapable of performing the surgical procedure, the medical observers, if any, that will be observing the surgical procedure, etc. In some embodiments, the received surgical procedure data, may include the patient's personal information such as their place of residency, age, height, weight, insurance provider, primary care physician, etc. In some embodiments, the data may include the patient's electronic health records or EHR, family history, medication history, allergies, previous surgical procedures, etc.

In some embodiments, the data may include the steps for the surgical procedure or the surgical procedure plan, the tools or instruments that will be used in the procedure, the anesthesia or medications that the will patient will receive prior to the procedure, the actions to be performed by the surgical robot 2202, the actions to be performed by the medical professional or surgeon, the estimated time the surgical procedure will take to be performed, etc. In some embodiments, the data on the medical professionals such as the surgeon and emergency surgeon may include the surgeon's credentials, performance history, specialty, consultation notes, etc. The base module 2228 initiates, at step 2408, the permission module 2230. For example, the permission module 2230 begins by being initiated by the base module 2228. The permission module 2230 queries the surgery database 2236 for the new data entry. The permission module 2230 extracts the new data entry from the surgery database 2236. The permission module 2230 filters the tech database 2238 on available technicians at the time and date of the surgical procedure from the data entry extracted from the surgery database 2236. The permission module 2230 assigns a technician to the surgical procedure extracted from the surgery database 2236. The permission module 2230 sends the assignment to the technician through the monitor module 2244. The permission module 2230 stores the technician in the access database 2240. The permission module 2230 returns to the base module 2228. The base module 2228 initiates, at step 2410, the access module 2232. For example, the access module 2232 begins by being initiated by the base module 2228. The access module 2232 is continuously polling for a request to access the surgical robot 2202 from the medical professional through the procedure module 2248.

The access module 2232 receives a request to access the surgical robot 2202 from the medical professional through the procedure module 2248. The access module 2232 compares the medical professional to the access database 2240. The access module 2232 extracts the access areas for the medical professional. The access module 2232 provides access to the surgical robot 2202 for the medical professional. The access module 2232 sends that access has been granted to the medical professional through the procedure module 2248. The access module 2232 is continuously polling for a request to access the surgical robot 2202 from the technician through the monitor module 2244. The access module 2232 receives a request to access the surgical robot 2202 from the technician through the monitor module 2244. The access module 2232 compares the technician to the access database 2240. The access module 2232 extracts the access areas for the technician. The access module 2232 provides access to the surgical robot 2202 for the technician. The access module 2232 sends that access has been granted to the technician through the monitor module 2244. The access module 2232 is continuously polling for the surgical procedure to be initiated by the medical professional through the procedure module 2248. The access module 2232 receives that the surgical procedure has been initiated by the medical professional from the procedure module 2248. The access module 2232 sends a notification to the technician that the surgical procedure has been initiated by the medical professional through the monitor module 2244. The access module 2232 returns to the base module 2228.

The base module 2228 initiates, at step 2412, the assistance module 2234. For example, the assistance module 2234 begins by being initiated by the base module 2228. The assistance module 2234 sends a begin error detection signal to the detection module 2218. The assistance module 2234 is continuously polling for an error detected signal from the detection module 2218. The assistance module 2234 determines if an error detected signal was received from the detection module 2218. If it is determined that the assistance module 2234 received an error detected signal from the detection module 2218 the assistance module 2234 sends the error detected signal to the technician through the monitor module 2244. If it is determined that the assistance module 2234 did not receive an error detected signal from the detection module 2218 the assistance module 2234 determines if the surgical procedure is completed. If it is determined that the surgical procedure is not completed the assistance module 2234 returns to continuously polling for an error detected signal from the detection module 2218. If it is determined that the surgical procedure is completed the assistance module 2234 returns to the base module 2228.

Functioning of the permission module 2230 will now be explained with reference to FIG. 25 and process 2500. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 25:
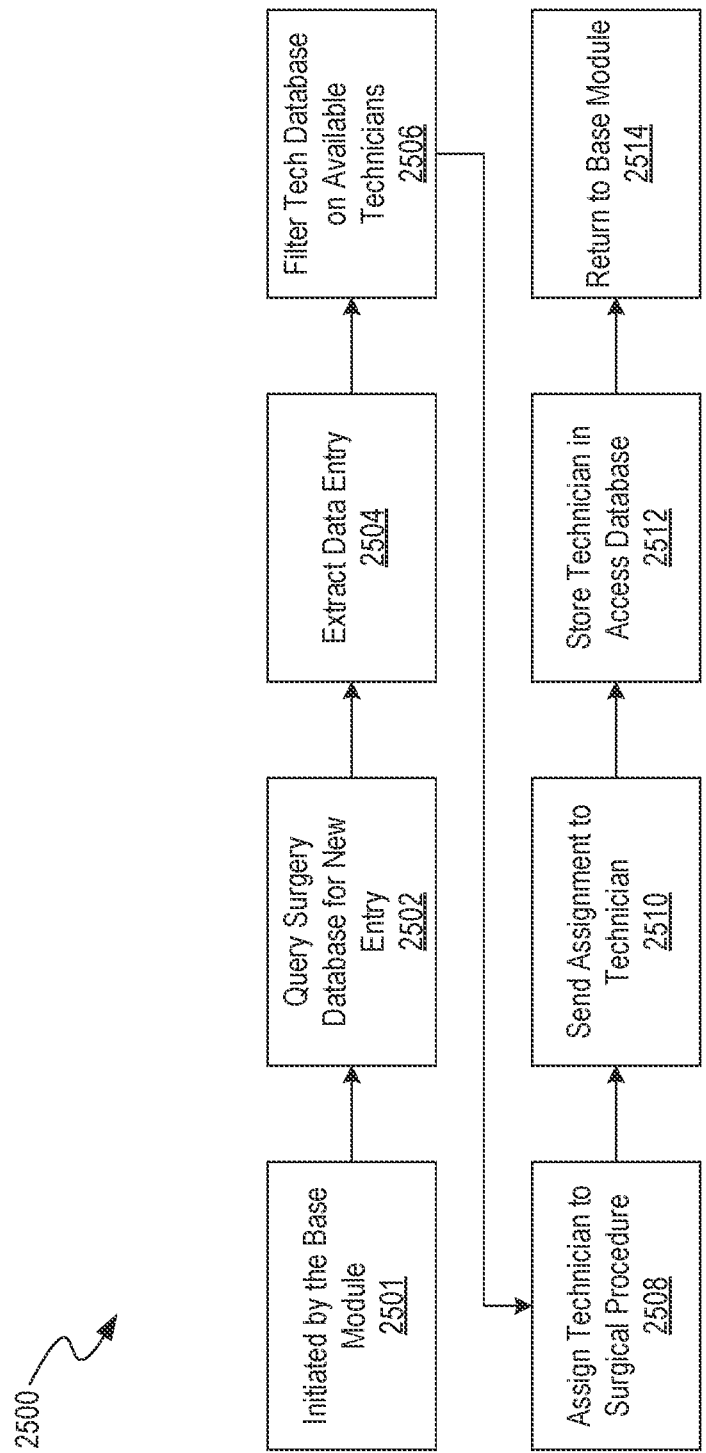
FIG. 25 is a flow diagram illustrating an example process for a permission module, in accordance with one or more embodiments.

FIG. 25 displays the permission module 2230. The process 2500 begins with the permission module 2230 being initiated, at step 2501, by the base module 2228. For example, once the base module 2228 receives and stores the surgical procedure data from the procedure module 2248 in the surgery database 2236 the base module 2228 initiates the permission module 2230 to find an available technician to monitor the surgical robot 2202 during the surgical procedure and assign the available technician. In some embodiments, the permission module 2230 may assign an emergency technician to replace the technician in the event the technician is unable to monitor the surgical robot 2202, assign an emergency technician that is physically present at the medical facility the surgical procedure is taking place, etc. The permission module 2230 queries, at step 2502, the surgery database 2236 for the new data entry. For example, the permission module 2230 sends a query to the surgery database 2236 for the new data entry, such as the new surgical procedure data that was stored in the surgery database 2236 during the process described in the base module 2228.

The permission module 2230 extracts, at step 2504, the new data entry from the surgery database 2236. For example, the permission module 2230 extracts the date and time the surgery will be performed from the surgery database 2230. In some embodiments, the type of surgery being performed may be extracted if there is a need for a more experienced technician to be monitoring the surgical robot 2202 system. For example, this may not be required for typical procedures, but in the event that there is a unique, difficult, or rare surgical procedure being performed it may be desired to have an extremely experienced, highly credentialed technician overseeing the surgical robot 2202 system. The permission module 2230 filters, at step 2506, the tech database 2238 on available technicians at the time and date of the surgical procedure from the data entry extracted from the surgery database 2236. For example, the permission module 2230 filters the tech database 2238 on the date and time the surgical procedure will be performed to identify the technicians that will be available during the surgical procedure. In some embodiments, the tech database 2238 may be further filtered for specific characteristics of the technician, such as location, credentials, education history, work experience, hours already worked prior to the surgery to prevent a fatigued technician from being assigned to the surgical procedure, etc.

The permission module 2230 assigns, at step 2508, a technician to the surgical procedure extracted from the surgery database 2236. For example, the permission module 2230 assigns the technician to the surgical procedure. In some embodiments, the permission module 2230 may store the assigned technician, and emergency technician, in the surgery database 2236. The permission module 2230 sends, at step 2510, the assignment to the technician through the monitor module 2244. For example, the permission module 2230 sends a notification to the technician of the assignment. In some embodiments, the notification may be a calendar invite to the technician's calendar or schedule. In some embodiments, the technician may have the option to accept or decline the assignment. In some embodiments, the technician may request a change of time the surgical procedure may take place based on maintenance schedules, software updates, etc. In some embodiments, the technician may receive information based on the surgical robot 2202 being used, such as collected operational data, history of maintenance, servicing information, failed component information, the manufacturer, type, and/or model, etc. The permission module 2230 stores, at step 2512, the technician in the access database 2240. For example, the access database 2240 stores the technician in the access database 2240, which contains access permissions for all the parties involved in a surgical procedure including the areas, components, or elements that the party is able to access and the ones that they do not have access to. The permission module 2230 returns, at step 2514, to the base module 2228.

Functioning of the access module 2232 will now be explained with reference to FIG. 26 and process 2600. One skilled in the art will appreciate that, for this and other processes and methods disclosed, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 26:
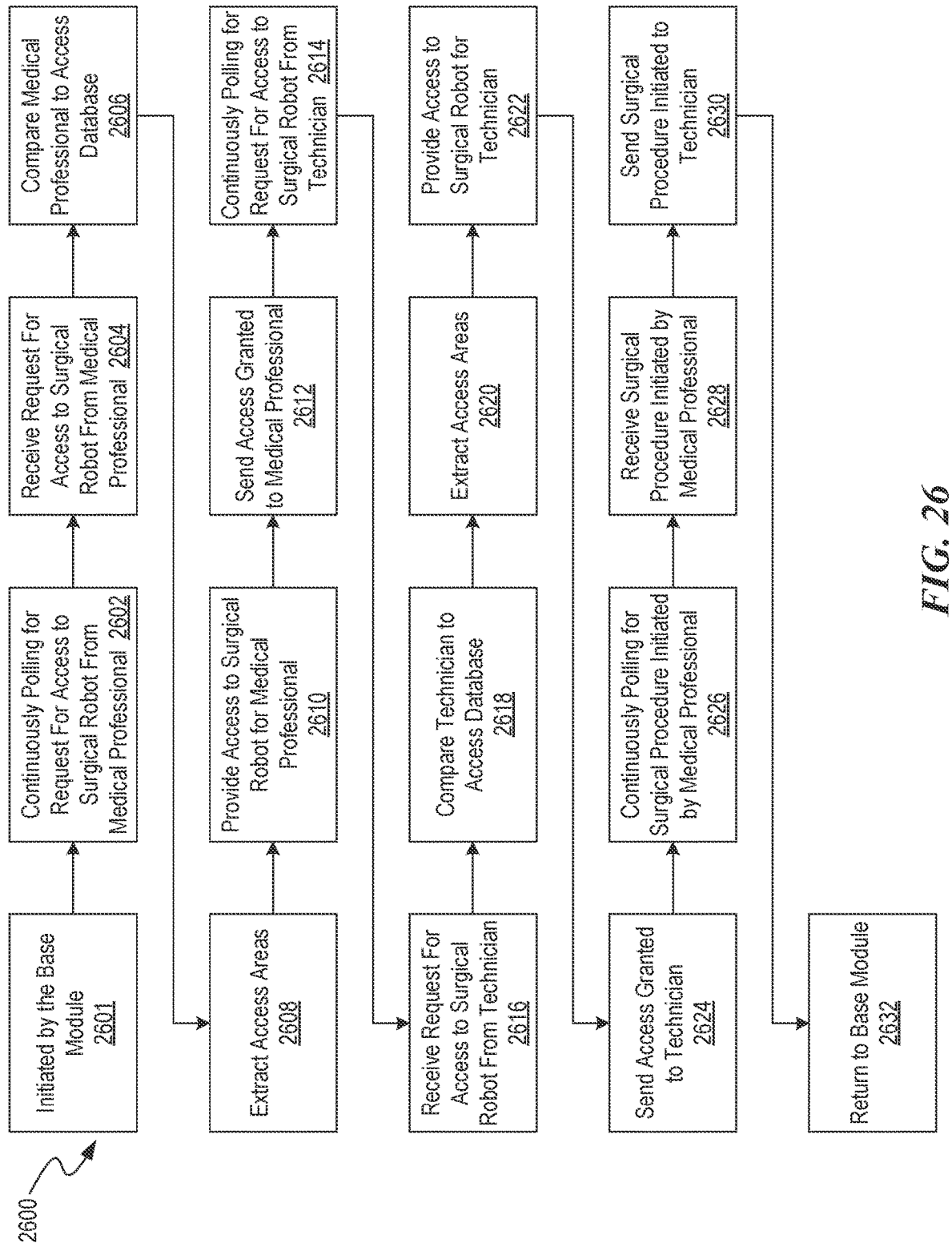
FIG. 26 is a flow diagram illustrating an example process for an access module, in accordance with one or more embodiments.

FIG. 26 displays the access module 2232. The process 2600 begins with the access module 2232 being initiated, at step 2601, by the base module 2228. The access module 2232 is continuously polling, at step 2602, for a request to access the surgical robot 2202 from the medical professional through the procedure module 2248. For example, the access module 2232 is continuously polling for the medical professional to send a request to access the surgical robot 2202 being used in the surgical procedure. In some embodiments, the surgery database 2236 may contain the data on the surgical robot 2202 being used in the surgical procedure such as the manufacturer, type, model, ID, etc. In some embodiments, the medical professional may send their verification and the access module 2232 compares the medical professional verification to the surgery database 2236 to determine which surgical robot 2202 the medical professional is requesting access to. The access module 2232 receives, at step 2604, a request to access the surgical robot 2202 from the medical professional through the procedure module 2248. For example, the access module 2232 receives the request from the medical professional to send access to the surgical robot 2202 being used in the surgical procedure. In some embodiments, the surgery database 2236 may contain the data on the surgical robot 2202 being used in the surgical procedure such as the manufacturer, type, model, ID, etc.

In some embodiments, the medical professional may send their verification and the access module 2232 compares the medical professional verification to the surgery database 2236 to determine which surgical robot 2202 the medical professional is requesting access to. The access module 2232 compares, at step 2606, the medical professional to the access database 2240. For example, the access module 2232 compares the medical professional to the access database 2240 to determine the aspects, features, controls, components, elements, etc. of the surgical robot 2202 or surgical procedure that the medical professional has access to. The access module 2232 extracts, at step 2608, the access areas for the medical professional. For example, the access module 2232 extracts the aspects, features, controls, components, elements, etc. of the surgical robot 2202 or surgical procedure that the medical professional has access to. In some embodiments, the access module 2232 may send a list of the aspects, features, controls, components, elements, etc. that the medical professional is allowed to access to the procedure module 2248. In some embodiments, the access module 2232 may receive a request from the medical professional through the procedure module 2248 for additional access, limit access to the medical observers, family or friends, etc. The access module 2232 provides, at step 2610, access to the surgical robot 2202 for the medical professional. For example, the access module 2232 provides a communication channel from the procedure module 2248 to the surgical robot 2202 to allow the medical professional to access the surgical robot 2202.

In some embodiments, the actions of the medical professional may be monitored by the access module 2232 and if the medical professional tries to access an aspect, feature, component, element, etc. of the surgical robot 2202 or surgical procedure that they do not have access to the data and the access module 2232 may send a notification to the medical professional that access has been denied. The access module 2232 sends, at step 2612, that access has been granted to the medical professional through the procedure module 2248. For example, the access module 2232 may send a notification to the medical professional that they have been granted access to the surgical robot 2202 and the notification may contain a list of the aspects, features, functions, components, elements, etc. that the medical professional has access to. In some embodiments, the medical professional may receive a list of the access permissions granted to other parties, such as medical observers, family members of the patient, friends of the patient, and may adjust or change the permissions granted to the other parties, expect the technicians, depending on the surgical procedure being performed. The access module 2232 is continuously polling, at step 2614, for a request to access the surgical robot 2202 from the technician through the monitor module 2244. For example, the access module 2232 is continuously polling for the technician to send a request to access the surgical robot 2202 being used in the surgical procedure.

In some embodiments, the surgery database 2236 may contain the data on the surgical robot 2202 being used in the surgical procedure such as the manufacturer, type, model, ID, etc. In some embodiments, the technician may send their verification and the access module 2232 compares the technician verification to the surgery database 2236 to determine which surgical robot 2202 the technician is requesting access to. The access module 2232 receives, at step 2616, a request to access the surgical robot 2202 from the technician through the monitor module 2244. For example, the access module 2232 receives the request from the technician to send access to the surgical robot 2202 being used in the surgical procedure. In some embodiments, the surgery database 2236 may contain the data on the surgical robot 2202 being used in the surgical procedure such as the manufacturer, type, model, ID, etc. In some embodiments, the technician may send their access credentials (e.g., username, password, identification information, verification information, private key, public key, identification number, etc.) and the access module 2232 compares the technician access credentials to the surgery database 2236 to determine which surgical robot 2202 the technician is requesting access to. The access module 2232 compares, at step 2618, the technician to the access database 2240. For example, the access module 2232 compares the technician to the access database 2240 to determine the aspects, features, controls, components, elements, etc. of the surgical robot 2202 or surgical procedure that the technician has access to. The access module 2232 extracts, at step 2620, the access areas for the technician. For example, the access module 2232 extracts the aspects, features, controls, components, elements, etc. of the surgical robot 2202 or surgical procedure that the technician has access to. In some embodiments, the access module 2232 may send a list of the aspects, features, controls, components, elements, etc. that the technician is allowed to access to the procedure module 2248.

In some embodiments, the access module 2232 may receive a request from the technician through the monitor module 2244 for additional access, limit access to the medical observers, family or friends, etc. The access module 2232 provides, at step 2622, access to the surgical robot 2202 for the technician. For example, the access module 2232 provides a communication channel (e.g., secure, encrypted, etc.) from the monitor module 2244 to the surgical robot 2202 to allow the technician to access the surgical robot 2202. In some embodiments, the actions of the technician may be monitored by the access module 2232 and if the technician tries to access an aspect, feature, component, element, etc. of the surgical robot 2202 or surgical procedure that they do not have access to the data and the access module 2232 may send a notification to the technician that access has been denied. The access module 2232 sends, at step 2624, that access has been granted to the technician through the monitor module 2244. For example, the access module 2232 may send a notification to the technician that they have been granted access to the surgical robot 2202 and the notification may contain a list of the aspects, features, functions, components, elements, etc. that the technician has access to. In some embodiments, the technician may receive a system report from the surgical robot 2202 that may include operating status, historical performance, connection strength, signal strength, etc. The access module 2232 is continuously polling, at step 2626, for the surgical procedure to be initiated by the medical professional through the procedure module 2248. For example, the access module 2232 is continuously polling to receive a notification from the procedure module 2248 that the medical professional has initiated the surgical procedure.

In some embodiments, the medical professional may have to wait to receive a signal from the technician that a pre-surgery diagnostic has been performed and that the surgical robot 2202 is operating at a level that is acceptable to perform the surgical procedure. The access module 2232 receives, at step 2628, that the surgical procedure has been initiated by the medical professional from the procedure module 2248. For example, the access module 2232 receives a notification from the procedure module 2248 that the medical professional has initiated the surgical procedure. In some embodiments, the medical professional may have to wait to receive a signal from the technician that a pre-surgery diagnostic has been performed and that the surgical robot 2202 is operating at a level that is acceptable to perform the surgical procedure. The access module 2232 sends, at step 2630, a notification to the technician that the surgical procedure has been initiated by the medical professional through the monitor module 2244. For example, the access module 2232 sends a notification to the technician through the monitor module 2244 that the medical professional has begun the surgery. In some embodiments, the medical professional may not be allowed to begin the surgery until the technician performs a pre-surgery diagnostic on the surgical robot 2202 to ensure that the surgical robot 2202 is operating properly to perform the surgical procedure. The access module 2232 returns, at step 2632, to the base module 2228.

Functioning of the assistance module 2234 will now be explained with reference to FIG. 27 and process 2700. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 27:
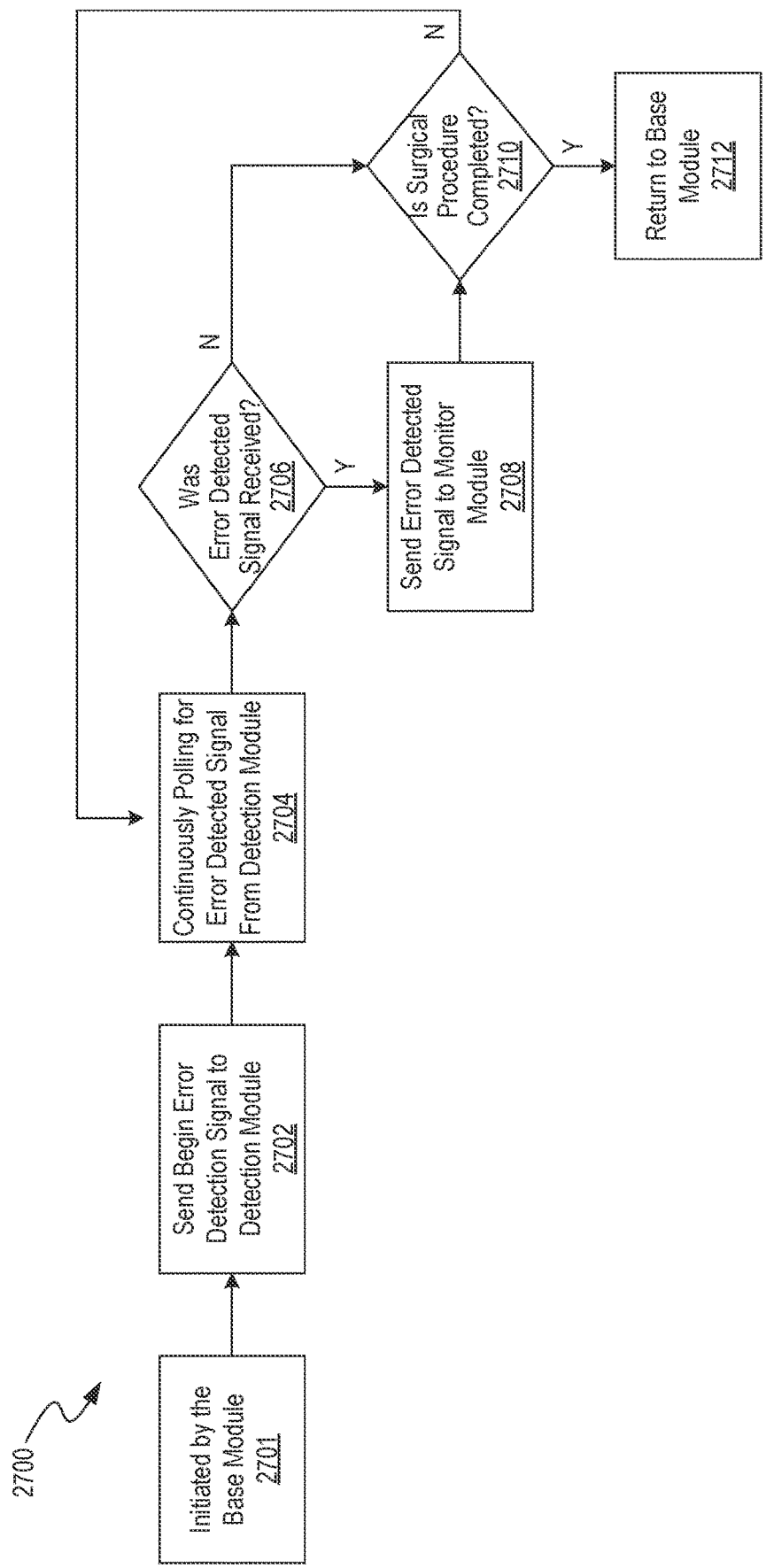
FIG. 27 is a flow diagram illustrating an example process for an assistance module, in accordance with one or more embodiments.

FIG. 27 displays the assistance module 2234. The process 2700 begins with the assistance module 2234 being initiated, at step 2701, by the base module 2228. For example, once the medical professional initiates the surgical procedure and the technician is notified that the surgical procedure has begun the access module 2232 returns to the base module 2228 and the base module 2228 initiates the assistance module 2234 to send any potential errors, troubleshooting issues, request from the medical professional, etc. to the technician for the technician to resolve. The assistance module 2234 sends, at step 2702, a begin error detection signal to the detection module 2218. For example, the assistance module 2234 sends a signal to the surgical robot 2202 to begin error detection. For example, the error detection may be to initiate the system monitor which is hardware or software component used to monitor system resources and performance in a computer system.

In some embodiments, the monitor system may provide the technician with a display that presents data to the technician, such as free space on one or more hard drives, the temperature of the CPU and other important components, and networking information including the system IP address, current rates of upload and download, error notifications, power supply, software monitoring, etc. The assistance module 2234 is continuously polling, at step 2704, for an error detected signal from the detection module 2218. The surgical robot network 2226 can monitor, via sensors, components of the surgical robot during the surgical procedure. If the components are operating below a performance threshold, the surgical robot network generates an error notification that identifies the components for maintenance/repair. For example, the detection module 2218 may send a signal to the assistance module 2234 that an error has been detected on the surgical robot 2202, such as a connection issue in which the signal strength of the connection between the surgical robot 2202 and the medical professional has dropped dramatically or has dropped below a performance threshold (e.g., a value of signal strength) that will begin effecting performance of the medical professional's controls of the surgical robot 2202. The assistance module 2234 determines, at step 2706, if an error detected signal was received from the detection module 2218. For example, the assistance module 2234 determines if an error signal was received from the detection module 2218 and if so the error signal is sent to the technician through the monitor module 2244. In some embodiments, the error signal may be an error identified by the surgical robot 2202 system monitor or may be a request from the medical professional that a component, element, feature, function, etc. of the surgical robot 2202 is not performing correctly. If it is determined that the assistance module 2234 received an error detected signal from the detection module 2218 the assistance module 2234 sends, at step 2708, the error detected signal to the technician through the monitor module 2244. For example, the detection module 2218 may send a signal to the assistance module 2234 that an error has been detected on the surgical robot 2202, such as a connection issue in which the signal strength of the connection between the surgical robot 2202 and the medical professional has dropped dramatically or has dropped below a rate that will begin effecting performance of the medical professional's controls of the surgical robot 2202, and the signal is sent to the monitor module 2244 to notify the technician. If it is determined that the assistance module 2234 did not receive an error detected signal from the detection module 2218 the assistance module 2234 determines, at step 2710, if the surgical procedure is completed. If it is determined that the surgical procedure is not completed the assistance module 2234 returns to continuously polling for an error detected signal from the detection module 2218. If it is determined that the surgical procedure is completed the assistance module 2234 returns, at step 2712, to the base module 2228. For example, the assistance module 2234 may receive a notification from the medical professional through the procedure module 2248 or the surgical robot 2202 that the surgical procedure has been completed and the assistance module 2234 may notify the technician through the monitor module 2244 and the assistance module 2234 returns to the base module 2228.

Functioning of the surgery database 2236 will now be explained with reference to FIG. 28 and table 2800. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 28 displays the surgery database 2236. The database contains the surgical procedure data from the medical professional during the process described in the base module 2228. The database contains the date of the surgical procedure, the time of the surgical procedure, the patient, the procedure being performed, the surgeon that will be performing the surgical procedure, the emergency surgeon, the medical observers of the surgical procedure, and the technician of the surgical robot during the surgical procedure and the emergency technician who are both assigned the surgical procedure during the permission module 2228. In some embodiments, the database may include the patient's personal information such as their place of residency, age, height, weight, insurance provider, primary care physician, etc. In some embodiments, the patient data may include the patient's electronic health records or EHR, family history, medication history, allergies, previous surgical procedures, etc.

In some embodiments, the procedure data may include the steps for the surgical procedure or the surgical procedure plan, the tools or instruments that will be used in the procedure, the anesthesia or medications that the will patient will receive prior to the procedure, the actions to be performed by the surgical robot 2202, the actions to be performed by the medical professional or surgeon, the estimated time the surgical procedure will take to be performed, etc. In some embodiments, the data on the medical professionals such as the surgeon and emergency surgeon may include the surgeon's credentials, performance history, specialty, consultation notes, etc. In some embodiments, the medical observers 1-N may include students, professors, colleagues, or other medical professionals that are viewing the surgery or operation for training or assessment purposes. In some embodiments, the technician and emergency technician may be added to the database through the process described in the permission module 2230. In some embodiments, the emergency surgeon may be a medical professional that is capable of completing the surgical procedure in the case the assigned surgeon becomes unable to perform the surgical procedure, for example, if the surgeon is performing the surgery remotely the emergency surgeon may be physically present at the medical facility where the surgery is taking place in the emergency that the surgeon has technical issues, is assessing the surgeon, is providing training for the surgeon, etc. In some embodiments, the emergency technician may be a technician capable of replacing the technician in an emergency situation, such as if the technician is remotely monitoring the surgical robot 2202 and experiences a technical issues, for example loss of power, the emergency technician may be also remotely monitoring the surgical robot 2202 or may be physically present at the medical facility. In some embodiments, the surgeon may be present at the medical facility and the technician may be monitoring the surgical robot 2202 remotely. In some embodiments, the surgeon may be performing the surgical procedure remotely while the technician is physically present at the medical facility.

Functioning of the tech database 2238 will now be explained with reference to FIG. 29 and table 2900. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 29 displays the tech database 2238. The database contains the list of the technicians that can monitor the surgical robots 2202 during a surgical procedure and the times that they are scheduled to monitor the surgical robots during certain surgical procedures. The database contains the name of the technician, the technician's ID or unique identifier, the date that the technician is scheduled to monitor a surgical robot 2202, and the start time and the estimated end time that the technician will be monitoring a surgical robot 2202 for a surgical procedure. For example, the database contains the work schedule or calendar for the technicians that are capable of monitoring the surgical robots 2202 and provide assistance for the medical professionals if needed or resolve any technical issues, such as but not limited to, error codes, malfunctions, resets, reboots, patching or installing software, troubleshooting or bug fixing, monitor connection statuses, etc. In some embodiments, the database may include credentials for the technician, such as educational history, work experience, training credentials, for example completed training courses, models of the surgical robot 2202 that the technician is allowed to monitor through completing the proper training, etc. In some embodiments, the database may contain the skills or capabilities of the technician, such as resolving connection issues, troubleshooting surgical robot 2202 issues, patching software bugs, etc. In some embodiments, the database may include maintenance personnel that are present at the medical facility to provide hands on maintenance of the surgical robot 2202 through communication with the assigned technician. In some embodiments, the database may contain the technician's supervisor or superior in the situation that the technician needs assistance. In some embodiments, the supervisor or superior may be required to monitor the work, troubleshooting, error detection, etc. that the technicians are performing during a surgical procedure.

Functioning of the access database 2240 will now be explained with reference to FIG. 30 and table 3000. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

FIG. 30 displays the access database 2240. The database contains access permissions for all the parties involved in a surgical procedure including the areas, components, or elements that the party is able to access and the ones that they do not have access to. The database contains the patient's name, the surgical procedure being performed, the participants of the surgical procedure, the involvement of the participants, such as surgeon, technician, etc., then a plurality of areas, components, or elements of the surgical robot 2202 and surgical procedure that provide access to specific participants and deny access to other participants, such as control of the surgical robot 2202, access to the surgical robot 2202 robotic arms 2212, end effectors 2214, user interface 2210, communication interface 2208, controllers 2204, the code of the surgical robot 2202, the patient's electronic health records or EHR, the imaging devices 2220 and devices recording the surgical procedure, updates on the procedure, etc. The database may be used to provide access to aspects of the patient's surgical procedure depending on participant's involvement or relationship to the patient and limit or restrict access to other aspects of the surgical procedure.

In some embodiments, the imaging devices 2220 may be cameras or video recording devices that may display actions of the surgical robot 2202 or the surgical procedure, such as cameras in the operating room, cameras on end effectors 2214, cameras on robotic arms 2212, cameras used for the surgical procedure, such as endoscopes, cameras for cardiology, transplant surgery, gastrointestinal surgery, colon and rectal surgery, orthopedic surgery, etc. In some embodiments, the procedure updates may be digital updates that family and friends of the patient may receive during the surgical procedure to be informed of the progress of the surgery, such as steps or actions completed by the medical professional or surgical robot 2202. In some embodiments, the technician may have additional control of the surgical robot 2202, such as the software code of the surgical robot 2202, controllers 2204, communication interface 2208, etc. to fix any issues that may present themselves during a surgical procedure. In some embodiments, the technician may be restricted from viewing any patient data. In some embodiments, the technician may have a separate user interface 2210 that is different from the user interface 2210 that the medical professional is interacting with. For example, the technician's user interface 2210 may include receiving error codes, access to data files and structures, the software code or program that is currently being used or performed, etc. In some embodiments, the data in the database may be stored in a blockchain to prevent the data from being altered or changed, and create a historical record of additions to the database.

Functioning of the monitor module 2244 will now be explained with reference to FIG. 31 and process 3100. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 31:
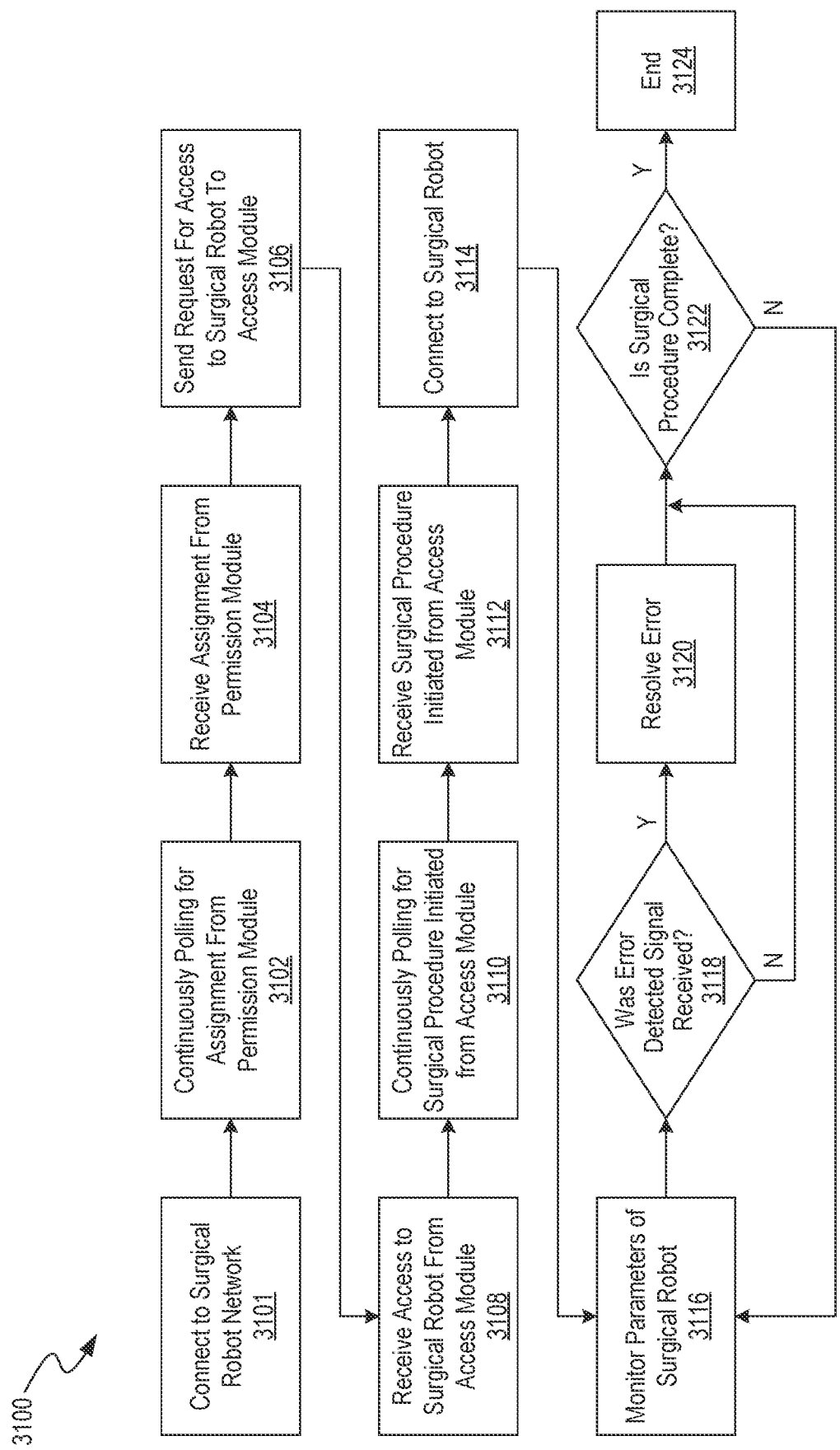
FIG. 31 is a flow diagram illustrating an example process for a monitor module, in accordance with one or more embodiments.

FIG. 31 displays the monitor module 2244. The process 3100 begins with the monitor module 2244 connecting, at step 3101, to the surgical robot network 2228. For example, the monitor module 2244 may connect to the surgical robot network 2228 to receive and send data to and from the permission module 2230, access module 2232, and assistance module 2234 as well as connect to the surgical robot 2202. In some embodiments, the technician may connect to the medical professional by connecting the monitor module 2244 to the procedure module 2248 to have a direct line of communication with medical professional during the surgical procedure. The monitor module 2244 is continuously polling, at step 3102, for the assignment from the permission module 2230. For example, the monitor module 2244 is continuously polling to receive a notification from the permission module 2230 for the assignment, such as which surgical procedure the technician has been assigned to monitor for technical issues. In some embodiments, the notification may be a calendar invite to the technician's calendar or schedule. In some embodiments, the technician may have the option to accept or decline the assignment. In some embodiments, the technician may request a change of time the surgical procedure may take place based on maintenance schedules, software updates, etc. In some embodiments, the technician may receive information based on the surgical robot 2202 being used, such as the manufacturer, type, and/or model, etc.

The monitor module 2244 receives, at step 3104, the assignment from the permission module 2230. For example, the monitor module 2244 receives a notification from the permission module 2230 for the assignment, such as which surgical procedure the technician has been assigned to monitor for technical issues. In some embodiments, the notification may be a calendar invite to the technician's calendar or schedule. In some embodiments, the technician may have the option to accept or decline the assignment. In some embodiments, the technician may request a change of time the surgical procedure may take place based on maintenance schedules, software updates, etc. In some embodiments, the technician may receive information based on the surgical robot 2202 being used, such as the manufacturer, type, and/or model, etc. The monitor module 2244 sends, at step 3106, a request for access to the surgical robot 2202 to the access module 2232. For example, the monitor module 2244 sends a request from the technician to receive access to the surgical robot 2202 being used in the surgical procedure. In some embodiments, the technician may send a verification to the access module 2232 which compares the technician verification to the surgery database 2236 to determine which surgical robot 2202 the technician is requesting access to. The monitor module 2244 receives, at step 3108, access to the surgical robot 2202 from the access module 2232. For example, the monitor module 2244 is provided a communication channel from the monitor module 2244 to the surgical robot 2202 to allow the technician to access the surgical robot 2202.

In some embodiments, the actions of the technician may be monitored and if the technician tries to access an aspect, feature, component, element, etc. of the surgical robot 2202 or surgical procedure that they do not have access to the access module 2232 may send a notification to the technician that access has been denied. In some embodiments, the technician may request access to additional features or functions of the surgical robot 2202. In some embodiments, the technician may be provided with a surgical robot 2202 report which may contain a list of previous errors and the resolution used for the errors to enhance the performance of the technician during the monitoring of the surgical robot 2202. In some embodiments, the technician may receive a system report from the surgical robot 2202 that may include operating status, historical performance, connection strength, signal strength, etc. The monitor module 2244 is continuously polling, at step 3110, for the surgical procedure to be initiated by the medical professional from the access module 2232. For example, the monitor module 2244 is continuously polling to receive a notification that the medical professional has begun the surgery. In some embodiments, the medical professional may not be allowed to begin the surgery until the technician performs a pre-surgery diagnostic on the surgical robot 2202 to ensure that the surgical robot 2202 is operating properly to perform the surgical procedure. The monitor module 2244 receives, at step 3112, that the surgical procedure has been initiated by the medical professional from the access module 2232. For example, the monitor module 2244 receives a notification that the medical professional has begun the surgery.

In some embodiments, the medical professional may not be allowed to begin the surgery until the technician performs a pre-surgery diagnostic on the surgical robot 2202 to ensure that the surgical robot 2202 is operating properly to perform the surgical procedure. In some embodiments, the technician may have access to the user interface 2210 of the surgical robot 2202 to view when the surgical procedure has begun. In some embodiments, the technician may have their own user interface 2210 to view the system monitor of the surgical robot 2202, such as a display that presents data to the technician, such as free space on one or more hard drives, the temperature of the CPU and other important components, and networking information including the system IP address, current rates of upload and download, error notifications, power supply, software monitoring, etc. The monitor module 2244 connects, at step 3114, to the surgical robot 2202. For example, the monitor module 2244 connects to the surgical robot 2202 through the surgical robot network 2228 that allows the technician to access certain features, functions, controls, aspects, etc. of the surgical robot 2202 during the surgical procedure. The technician monitors, at step 3116, the parameters of the surgical robot 2202. For example, the technician monitors operational data, such as the hardware and software performance of the surgical robot 2202 during the surgical procedure, such as free space on one or more hard drives, the temperature of the CPU and other important components, and networking information including the system IP address, current rates of upload and download, error notifications, power supply, software monitoring, potential malfunctions, instrumentation performance, robotic arm 2212 performance, end effector 2214 performance, console performance, operating performance of the imaging devices 2218, etc. The monitor module 2244 determines, at step 3118, if an error detected signal was received from the assistance module 2234. For example, the monitor module 2244 may receive an error detected signal from the assistance module 2234 which may be an error identified by the surgical robot 2202 system monitor or may be a request from the medical professional that a component, element, feature, function, etc. of the surgical robot 2202 is not performing correctly (e.g., operating below a performance threshold). If it is determined that the monitor module 2244 received an error detected signal from the assistance module 2234 the technician resolves, at step 3120, the error that was detected. For example, if the monitor module 2244 receives an error signal the technician may access the area of concern on the surgical robot 2202, such as connectivity of the surgeon, and analyze the connection speeds of the surgical robot 2202 and the medical professional to identify where the error is coming from, and if the medical professional is the one experiencing the connection issues notify the emergency surgeon to take over control of the surgical robot 2202 until the surgeon can reconnect to the surgical robot 2202.

In some embodiments, the error signal may be generated through machine learning in which the monitor module uses the surgical robot 2202 report to identify potential errors that will occur in the surgical procedure. For example, the surgical robot 2202 report may contain the total number of procedures performed by the surgical robot 2202, the number of malfunctions, the list of instruments, the robotic arms 2212 used, the console performance, the performance of the imaging devices 2218, the percentage of the instruments malfunctioning, the number of patients injured during the surgical procedure, etc. A machine learning algorithm may be used to determine the correlations between the patients, type of surgery, actions performed by the surgical robot 2202, and the parameters listed in the surgical robot 2202 report to find correlations in the data. If the data is highly correlated the machine learning algorithm may recommend altering the surgical procedure plan, use a different robotic arm 2212, use a different end effector 2214, place the surgical robot 2202 in a different position for a certain action, etc. For example, if it is highly correlated that the robotic arm 2212 will malfunction on an anchor placement for a Brostrom Gould procedure if the surgical robot 2202 is positioned at the patient's waist, the recommendation may be to place the surgical robot 2202 by the patient's ankle or legs to allow the robot arm 2212 an improved angle to place the anchor. If it is determined that the monitor module 2244 did not receive an error detected signal from the assistance module 2234 the monitor module 2244 determines, at step 3122, if the surgical procedure is complete. If it is determined that the surgical procedure is not complete the monitor module 2244 returns to the technician monitoring the parameters of the surgical robot 2202. For example, if no error detected signal was received the process returns to the technician monitoring the surgical robot 2202. If it is determined that the surgical procedure is complete the monitor module 2244 ends, at step 3124. For example, the monitor module 2244 may receive a signal from the assistance module 2234, the procedure module 2248, or the surgical robot 2202 that the surgical procedure has been completed.

Functioning of the procedure module 2248 will now be explained with reference to FIG. 32 and process 3200. One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 32:
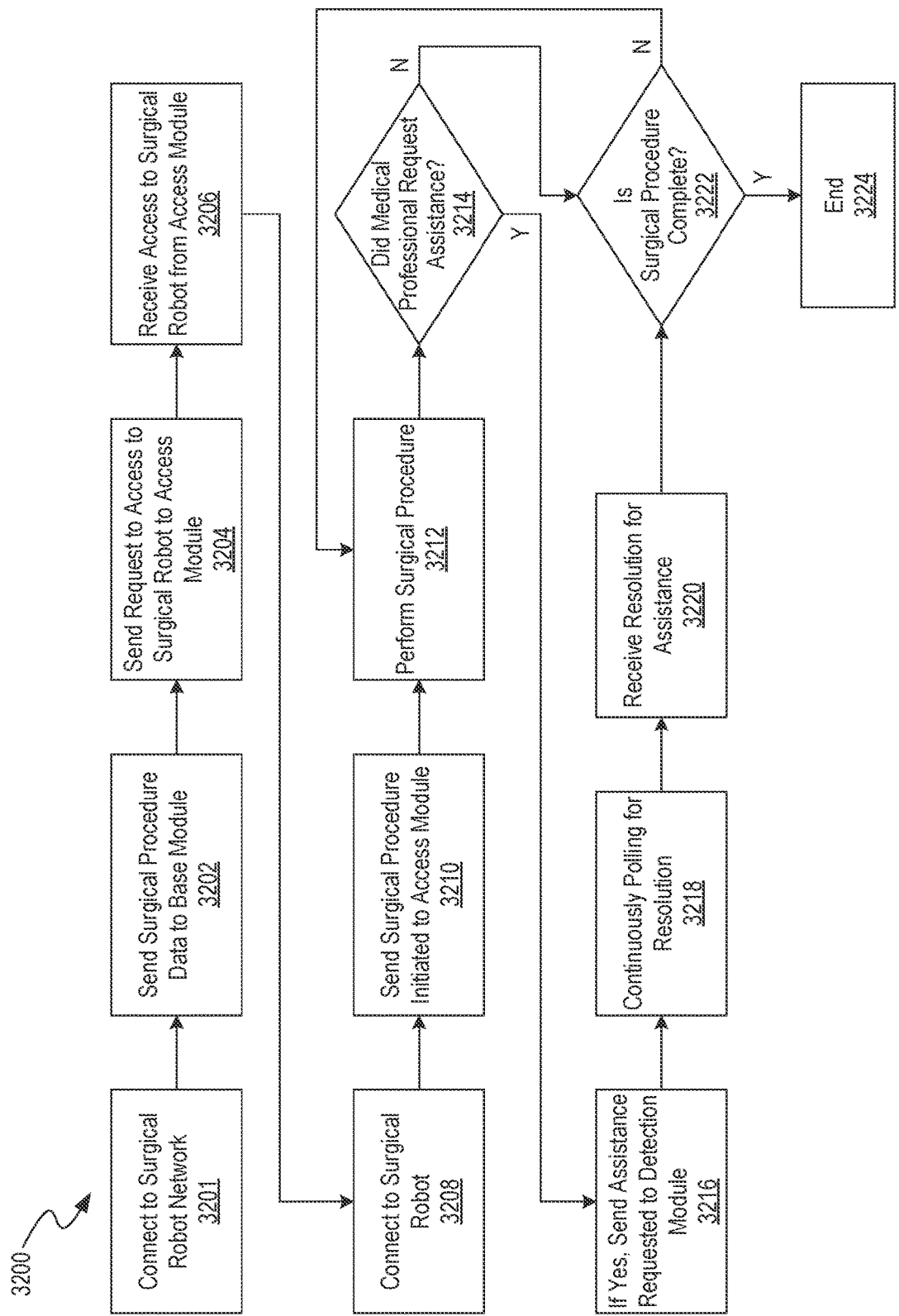
FIG. 32 is a flow diagram illustrating an example process for a procedure module, in accordance with one or more embodiments.

FIG. 32 displays the procedure module 2248. The process 3200 begins with the procedure module 2248 connecting, at step 3201, to the surgical robot network 2226. For example, the medical professional connects to the surgical robot network 2226 through the procedure module 2248 connecting to the base module 2228. In some embodiments, the medical professional may access the base module 2228 through logging into the surgical robot network 2226 with the use of a username and password combination or other digital authentication to verify themselves, such as, for example, Knowledge-based authentication, two-factor authentication, credit bureau based authentication, Database Methods, Online Verification, Biometric Verification, etc. Knowledge-based authentication (KBA) verifies a person's identity by requiring a response to security questions. Two-factor or Multi-Factor Authentication requires a user to enter a code sent to their email or mobile phone. Using 2FA or MFA, you can easily verify a user's email address and phone number.

The procedure module 2248 sends, at step 3202, the surgical procedure data to the base module 2228. For example, the procedure module 2248 sends the surgical procedure data such as, the patient's name, the surgical procedure being performed, the surgeon scheduled to perform the surgical procedure, the emergency surgeon scheduled to perform the surgical procedure in the event the original surgeon is incapable of performing the surgical procedure, the medical observers, if any, that will be observing the surgical procedure, etc. In some embodiments, the surgical procedure data may include the patient's personal information such as their place of residency, age, height, weight, insurance provider, primary care physician, etc. In some embodiments, the data may include the patient's electronic health records or EHR, family history, medication history, allergies, previous surgical procedures, etc. In some embodiments, the data may include the steps for the surgical procedure or the surgical procedure plan, the tools or instruments that will be used in the procedure, the anesthesia or medications that the will patient will receive prior to the procedure, the actions to be performed by the surgical robot 2202, the actions to be performed by the medical professional or surgeon, the estimated time the surgical procedure will take to be performed, etc. In some embodiments, the data on the medical professionals such as the surgeon and emergency surgeon may include the surgeon's credentials, performance history, specialty, consultation notes, etc.

The procedure module 2248 sends, at step 3204, a request to access the surgical robot 2202 to the access module 2232. For example, the procedure module 2248 sends a request from the medical professional to receive access to the surgical robot 2202 being used in the surgical procedure. In some embodiments, the surgery database 2236 may contain the data on the surgical robot 2202 being used in the surgical procedure such as the manufacturer, type, model, ID, etc. In some embodiments, the medical professional may send a verification to determine which surgical robot 2202 the medical professional is requesting access to. The procedure module 2248 receives, at step 3206, access to the surgical robot 2202 from the access module 2232. For example, the procedure module 2248 is provided a communication channel from the procedure module 2248 to the surgical robot 2202 to allow the medical professional to access the surgical robot 2202. In some embodiments, the actions of the medical professional may be monitored and if the medical professional tries to access an aspect, feature, component, element, etc. of the surgical robot 2202 or surgical procedure that they do not have access to the data and receive a notification to the medical professional that access has been denied. The procedure module 2248 connects, at step 3208, to the surgical robot 2202. For example, the procedure module 2248 connects to the surgical robot 2202 through the surgical robot network 2228 that allows the medical professional to access certain features, functions, controls, aspects, etc. of the surgical robot 2202 during the surgical procedure.

The procedure module 2248 sends, at step 3210, that the surgical procedure has been initiated by the medical professional to the access module 2232. For example, once the medical professional is ready to begin the surgical procedure the medical professional may input in the procedure module 2248 or surgical robot 2202 user interface 2210 that they are beginning the surgical procedure. The medical professional performs, at step 3212, the surgical procedure on the patient by controlling the surgical robot 2202. For example, the medical professional may perform the procedure with the use of the surgical robot 2202 with the features, functions, components, elements, aspects, etc. that the medical professional has been granted access to. The procedure module 2248 determines, at step 3214, if the medical professional requested assistance. For example, the medical professional may request assistance of the technician by inputting a request in the user interface 2210 of the surgical robot 2202. For example, the medical professional may request assistance in the event that there is lag between the medical professional and surgical robot 2202, if a robotic arm 2212 or end effector 2214 is not performing as desired, etc. If it is determined that the medical professional requested assistance the procedure module 2248 sends, at step 3216, assistance has been requested to the detection module 2218. For example, once the medical professional requests assistance the technician is notified of the potential error from the procedure module 2248 sending the request to the detection module 2218 which sends a signal to the assistance module 2234 which notifies the technician through the monitor module 2244.

In some embodiments, the procedure module 2248 may send the request directly to the monitor module 2244. The procedure module 2248 is continuously polling, at step 3218, for the resolution to the requested assistance by the medical professional. For example, once the request has been resolved the procedure module 2248 may receive a signal or notification from the monitor module 2244, surgical robot network 2226 or user interface 2210 on the surgical robot 2202. The technician can send, via a device, a resolution notification that the error/issue is resolved. The procedure module 2248 receives, at step 3220, the resolution to the requested assistance by the medical professional. For example, once the request has been resolved the procedure module 2248 may receive a signal or notification from the monitor module 2244, surgical robot network 2226 or user interface 2210 on the surgical robot 2202. The procedure module 2248 determines, at step 3222, if the surgical procedure is completed. The surgical robot 2202 can confirm the component was properly replace by running tests on the replaced component.

If it is determined that the surgical procedure is not completed the procedure module 2248 returns to the medical professional performing the surgical procedure. For example, the medical professional continues the procedure until completion. If it is determined that the surgical procedure is completed the procedure module 2248 ends, at step 3224. For example, the medical professional may input on the user interface 2210 of the surgical robot 2202 or through the procedure module 2248 that they are complete with the surgical procedure and the technician is notified that the surgical procedure is completed.

The functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

The description and drawings herein are illustrative and are not to be construed as limiting. Numerous specific details are described to provide a thorough understanding of the disclosure. However, in certain instances, well-known details are not described in order to avoid obscuring the description. Further, various modifications can be made without deviating from the scope of the embodiments.

The terms used in this specification generally have their ordinary meanings in the art, within the context of the disclosure, and in the specific context where each term is used. Certain terms that are used to describe the disclosure are discussed above, or elsewhere in the specification, to provide additional guidance to the practitioner regarding the description of the disclosure. For convenience, certain terms can be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms can on occasion be used interchangeably.

Consequently, alternative language and synonyms can be used for any one or more of the terms discussed herein, and no special significance is to be placed upon whether or not a term is elaborated or discussed herein. Synonyms for certain terms are provided. A recital of one or more synonyms does not exclude the use of other synonyms. The use of examples anywhere in this specification, including examples of any term discussed herein, is illustrative only and is not intended to further limit the scope and meaning of the disclosure or of any exemplified term. Likewise, the disclosure is not limited to various embodiments given in this specification.

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter. For example, U.S. patent application Ser. No. 17/547,678, filed Dec. 10, 2021, is incorporated herein by reference in its entirety.

It is to be understood that the embodiments and variations shown and described herein are merely illustrative of the principles of this invention and that various modifications can be implemented by those skilled in the art.

What is claimed is:

1. A method performed by a robotic surgical system, comprising:
   detecting, during a surgical procedure, at least one error in an operation of a surgical robot that includes multiple end effectors for performing at least a portion of the surgical procedure;
   in response to detecting the at least one error, determining one or more components of the surgical robot associated with the at least one error based on operational data of the surgical robot;
   selecting at least one technician to resolve the at least one error based on the one or more components;
   sending, to a device associated with the at least one technician, a notification that provides access to a communication channel to the surgical robot to allow the at least one technician to access the surgical robot remotely;
   receiving, from the device associate with the at least one technician or the surgical robot, a resolution notification that the at least one error was resolved; and
   in response to receiving the resolution notification, proceeding with the surgical procedure.

2. The method of claim 1, comprising:
   receiving, from the at least one technician, a request to access the surgical robot, wherein the request includes at least one access credential of the at least one technician;
   comparing the at least one access credential to a surgery database to determine the at least one technician is authorized to access the one or more components associated with the at least one error; and
   sending, to the at least one technician, information associated the one or more components associated with the at least one error.

3. The method of claim 1, comprising:
   monitoring the one or more components of the surgical robot during the surgical procedure;
   determining the one or more components are operating below a performance threshold;
   in response to determining the one or more components are operating below the performance threshold, generating at least one error notification that identifies the one or more components; and
   sending, to the device associate with the at least one technician, the at least one error notification.

4. The method of claim 1,
   wherein the at least one error is identified by at least one machine-learning algorithm, wherein the at least one machine-learning algorithm is trained based on at least one dataset associated with previously identified errors.

5. The method of claim 1, comprising:
   receiving an update notification that a software update is available for the surgical robot;
   determining that the surgical robot is inactive;

in response to determining that the surgical robot is inactive, installing the software update to the surgical robot;

in response to installing the software update, sending, to at least one operator of the surgical robot, a training notification for the at least one operator to become certified to operate the surgical robot after installation of the software update.

6. The method of claim 5, comprising:

receiving, from an operator, a request to operate the surgical robot;

identifying a certification status of the operator for the surgical robot; and in response to the certification status not including the software update, granting the operator access to a previous software version of the surgical robot, wherein the previous software version is different than the software update.

7. The method of claim 5, comprising:

identifying one or more operators that need to be certified for operating the surgical robot after the installation of the software update; and in response to the one or more operators becoming certified, updating a certification status of the one or more operators for operating the surgical robot after the installation of the software update.

8. A system comprising:

one or more processors; and one or more memories storing instructions that, when executed by the one or more processors, cause the system to perform a process performed by a robotic surgical system, the process comprising:

detecting, during a surgical procedure, at least one error in an operation of a surgical robot that includes multiple end effectors for performing at least a portion of the surgical procedure;

in response to detecting the at least one error, determining one or more components of the surgical robot associated with the at least one error based on operational data of the surgical robot;

selecting at least one technician to resolve the at least one error based on the one or more components;

sending, to a device associated with the at least one technician, a notification that provides access to a communication channel to the surgical robot to allow the at least one technician to access the surgical robot remotely;

receiving, from the device associate with the at least one technician or the surgical robot, a resolution notification that the at least one error was resolved; and in response to receiving the resolution notification, proceeding with the surgical procedure.

9. The system according to claim 8, wherein the process further comprises:

receiving, from the at least one technician, a request to access the surgical robot, wherein the request includes at least one access credential of the at least one technician;

comparing the at least one access credential to a surgery database to determine the at least one technician is authorized to access the one or more components associated with the at least one error; and sending, to the at least one technician, information associated the one or more components associated with the at least one error.

10. The system according to claim 8, wherein the process further comprises:

monitoring the one or more components of the surgical robot during the surgical procedure;

determining the one or more components are operating below a performance threshold;

in response to determining the one or more components are operating below the performance threshold, generating at least one error notification that identifies the one or more components; and sending, to the device associate with the at least one technician, the at least one error notification.

11. The system according to claim 8, wherein the at least one error is identified by at least one machine-learning algorithm, wherein the at least one machine-learning algorithm is trained based on at least one dataset associated with previously identified errors.

12. The system according to claim 8, wherein the process further comprises:

receiving an update notification that a software update is available for the surgical robot;

determining that the surgical robot is inactive;

in response to determining that the surgical robot is inactive, installing the software update to the surgical robot;

in response to installing the software update, sending, to at least one operator of the surgical robot, a training notification for the at least one operator to become certified to operate the surgical robot after installation of the software update.

13. The system according to claim 12, wherein the process further comprises:

receiving, from an operator, a request to operate the surgical robot;

identifying a certification status of the operator for the surgical robot; and in response to the certification status not including the software update, granting the operator access to a previous software version of the surgical robot, wherein the previous software version is different than the software update.

14. The system according to claim 12, wherein the process further comprises:

identifying one or more operators that need to be certified for operating the surgical robot after the installation of the software update; and in response to the one or more operators becoming certified, updating a certification status of the one or more operators for operating the surgical robot after the installation of the software update.

15. A non-transitory computer-readable medium storing instructions that, when executed by a computing system, cause the computing system to perform operations performed by a robotic surgical system, the operations comprising:

detecting, during a surgical procedure, at least one error in an operation of a surgical robot that includes multiple end effectors for performing at least a portion of the surgical procedure;

in response to detecting the at least one error, determining one or more components of the surgical robot associated with the at least one error based on operational data of the surgical robot;

selecting at least one technician to resolve the at least one error based on the one or more components;

sending, to a device associated with the at least one technician, a notification that provides access to a communication channel to the surgical robot to allow the at least one technician to access the surgical robot remotely;

receiving, from the device associate with the at least one technician or the surgical robot, a resolution notification that the at least one error was resolved; and in response to receiving the resolution notification, proceeding with the surgical procedure.

16. The non-transitory computer-readable medium of claim 15, wherein the operations further comprise:

receiving, from the at least one technician, a request to access the surgical robot, wherein the request includes at least one access credential of the at least one technician;

comparing the at least one access credential to a surgery database to determine the at least one technician is authorized to access the one or more components associated with the at least one error; and sending, to the at least one technician, information associated the one or more components associated with the at least one error.

17. The non-transitory computer-readable medium of claim 15, wherein the operations further comprise:

monitoring the one or more components of the surgical robot during the surgical procedure;

determining the one or more components are operating below a performance threshold;

in response to determining the one or more components are operating below the performance threshold, generating at least one error notification that identifies the one or more components; and sending, to the device associate with the at least one technician, the at least one error notification.

18. The non-transitory computer-readable medium of claim 15, wherein the at least one error is identified by at least one machine-learning algorithm, wherein the at least one machine-learning algorithm is trained based on at least one dataset associated with previously identified errors.

19. The non-transitory computer-readable medium of claim 15, wherein the operations further comprise:

receiving an update notification that a software update is available for the surgical robot;

determining that the surgical robot is inactive;

in response to determining that the surgical robot is inactive, installing the software update to the surgical robot;

in response to installing the software update, sending, to at least one operator of the surgical robot, a training notification for the at least one operator to become certified to operate the surgical robot after installation of the software update.

20. The non-transitory computer-readable medium of claim 19, wherein the operations further comprise:

receiving, from an operator, a request to operate the surgical robot;

identifying a certification status of the operator for the surgical robot; and in response to the certification status not including the software update, granting the operator access to a previous software version of the surgical robot, wherein the previous software version is different than the software update.

\* \* \* \* \*